US006410718B1

(12) United States Patent
Bloksberg et al.

(10) Patent No.: US 6,410,718 B1
(45) Date of Patent: Jun. 25, 2002

(54) MATERIALS AND METHODS FOR THE MODIFICATION OF PLANT LIGNIN CONTENT

(75) Inventors: Leonard N. Bloksberg; Ilkka Havukkala, both of Remuera (NZ)

(73) Assignees: Genesis Research & Development Corporation Ltd.; Fletcher Challenge Forests Ltd., both of (NZ)

( * ) Notice: Subject to any disclaimer, the term of this patent is extended or adjusted under 35 U.S.C. 154(b) by 0 days.

(21) Appl. No.: 09/615,192

(22) Filed: Jul. 12, 2000

Related U.S. Application Data

(63) Continuation-in-part of application No. 09/169,789, filed on Oct. 9, 1998, which is a continuation-in-part of application No. 08/975,316, filed on Nov. 21, 1997, now Pat. No. 5,952,486, which is a continuation-in-part of application No. 08/713,000, filed on Sep. 11, 1996, now Pat. No. 5,850,020.
(60) Provisional application No. 60/143,811, filed on Jul. 14, 1999.

(51) Int. Cl.[7] .................... C07H 21/02; C07H 21/04; C12N 15/82; C12N 15/00; C12N 15/09

(52) U.S. Cl. ................. 536/23.6; 536/23.1; 536/24.1; 435/320.1; 435/468

(58) Field of Search .................. 435/417, 468, 435/320.1; 536/23.6, 24.1, 23.1, 23.2

(56) References Cited

U.S. PATENT DOCUMENTS

| | | | |
|---|---|---|---|
| 5,850,020 A | 12/1998 | Bloksberg et al. | |
| 5,952,486 A | 9/1999 | Bloksberg et al. | |

FOREIGN PATENT DOCUMENTS

| | | | | |
|---|---|---|---|---|
| EP | 0513884 | 11/1992 | ........... | C12N/15/11 |
| EP | 0516958 | 12/1992 | ........... | C12N/15/54 |
| EP | 0632128 | 1/1995 | ........... | C12N/15/53 |
| EP | 0716147 | 6/1996 | ........... | C12N/15/82 |
| JP | 9173069 | 7/1997 | ............ | A01H/1/00 |
| NZ | 328434 | 5/1998 | | |
| WO | 9008828 | 8/1990 | ........... | C12N/15/82 |
| WO | 9305159 | 3/1993 | ........... | C12N/15/53 |
| WO | 9305160 | 3/1993 | ........... | C12N/15/54 |
| WO | 9315599 | 8/1993 | ........... | C12N/15/00 |
| WO | 9324638 | 12/1993 | ........... | C12N/15/82 |
| WO | 9408036 | 4/1994 | ........... | C12N/21/04 |
| WO | 9421794 | 9/1994 | ........... | C12N/15/29 |
| WO | 9423044 | 10/1994 | ........... | C12N/15/82 |
| WO | 9507993 | 3/1995 | ........... | C12N/15/82 |
| WO | 9527790 | 10/1995 | ........... | C12N/15/53 |
| WO | 9620595 | 7/1996 | .......... | A01N/35/02 |
| WO | 9723599 | 7/1997 | | |
| WO | 9745549 | 12/1997 | ........... | C12N/15/82 |
| WO | 9811205 | 3/1998 | | |
| WO | 9839454 | 9/1998 | ........... | C12N/15/53 |
| WO | 0022099 | 4/2000 | | |

OTHER PUBLICATIONS

Hu et al. Compartmentalized expression of two structurally and functionally distinct 4–coumarate: CoA ligase genes in aspen (*populus tremuloides*) Proc. Natl. Acad. Sci. U.S.A. 95 (9), 5407–5412 1998.*
yahiaoui et al. Comparative Efficiency Of Different Constructs For Down Regulation Of Tobacco Cinnamyl Alcohol Dehydrogenase vol. 49, No. 2 pp. 295–306 1998.*
GenBank Accession No. AW191302; Bossinger, G.; submitted Nov. 23, 1999.
GenBank Accession No. AJ244010; Rech, P., et al.; submitted Jul. 21, 1999.
GenBank Accession No. AF239686; Kumar, A., et al.; submitted Feb. 28, 2000.
GenBank Accession No. BE454671; Wing, R. A.; submitted Jul. 26, 2000.
GenBank Accession No. AF041049; Hu, W.J., et al.; submitted Jan. 6, 1998.
GenBank Accession No. AF008183; Allina, S.M., et al.; submitted Jun. 12, 1997.
GenBank Accession No. AF052223; Heath, R.L., et al.; submitted Mar. 5, 1998.
GenBank Accession No. AW244908; Walbot, V., et al.; submitted Feb. 28, 2000.
Lee, Diane et al., "Antisense Suppression of 4–Coumarate: Coenzyme A Ligase Activity in Arabidopsis Leads to Altered Lignin Subunit Composition," *The Plant Cell*, vol. 9, No. 11, pp. 1985–1998 (Nov. 1997).
Kajita, Shinya et al., "Alterations in the Biosynthesis of Lignin in Transgenic Plants with Chimeric Genes for 4–Coumarate:Coenzyme A Ligase," *Plant Cell Physiol.* vol. 37, No. 7, pp. 957–965 (Oct. 1996).
Hauffe, Karl D. et al., "Combinatorial interactions between positive and negative cis–acting elements control spatial patterns of 4CL–1 expression in transgenic tobacco," *The Plant Journal*, vol. 4, No. 2, pp. 235–253 (Aug. 1993).
PCT Written Opinion; In re Fletcher Challenge Forests, Ltd. International Application No. PCT/NZ99/00168, filed 06 Oct. 1999.
Hu, Wen–Jing et al., "Repression of lignin biosynthesis promotes cellulose accumulation and growth in transgenic trees," Nature Biotechnology, vol. 17, No. 8, pp. 808–812 (Aug. 1999).

(List continued on next page.)

*Primary Examiner*—Remy Yucel
*Assistant Examiner*—Konstantina Katcheres
(74) *Attorney, Agent, or Firm*—Ann W. Speckman; Janet Sleath

(57) ABSTRACT

Novel isolated polynucleotides and polypeptides associated with the lignin biosynthetic pathway are provided, together with constructs including such sequences. Methods for the modulation of lignin content, lignin structure and lignin composition in target organisms are also disclosed, the methods comprising incorporating one or more of the polynucleotides of the present invention into the genome of a target organism.

6 Claims, 3 Drawing Sheets

OTHER PUBLICATIONS

Neustaedter, David A. et al., "Anovel Parsley 4CLI cis–element is required for developmentqally regulated expression and protein–DNA complex formation,"The Plant Journal, vol. 18, No. 1, pp. 77–88 (Apr. 1999).

Hauffe, Karl D. et al., "A Parsley 4CL–1 Promoter Fragment Specifies Complex Expression Patterns in Transgenic Tobacco," *The Plant Cell*, vol. 3, No. 2, pp. 435–443 (May 1991).

Leonard Nathan Bloksberg, Studies on the Biology of Phenylalanine Ammonia Lyase and Plant Pathogen Interaction, *Genetics*, Abstract iii, Dec. 1991.

D. Palitha Dharmawardhana et al., A β–Glucosidase from Lodgepole Pine Xylem Specific for the Lignin Precursor Coniferin, *Plant Physiol*, 107:331–339, 1995.

G. Schmid et al., Enzymic synthesis of lignin precursors. Purification and properties of UDP glucose: coniferyl–alcohol glucosyltransferase from cambial sap of spruce (*Picea abies* L.), *Eur J. Biochem* 123: 363–70, 1982.

U. N. Dwivedi et al., Modification of lignin biosynthesis in transgenic Nicotiana through expression of an antisense O–methyltransferase gene from Populus, *Plant Molecular Biology* 26:61–71, 1994.

Carolyn Napoli et al., Introduction of a Chimeric Chalcone Synthase Gene into Petunia Results in Reversible Co–Suppression of Homologous Genes in trans, *The Plant Cell* 2: 279–289, Apr. 1990.

Ross Whetten et al., Lignin Biosynthesis, *The Plant Cell* 7: 1001–1013, Jul. 1995.

J. Prima–Pettenati et al., Molecular cloning and expression of a *Eucalyptus gunnii* cDNA clone encoding cinnamyl alcohol dehydrogenase, *Plant Mol Biol* 21: 1085–95, 1993.

C. Feuillet et al., Tissue– and cell–specific expression of cinnamyl alcohol dehydrogenase promoter in transgenic poplar plants, *Plant Mol Biol* 27: 651–667, 1995.

H. Wengenmayer et al., Enzymic synthesis of lignin precursors. Purification and properties of a cinnamoyl–CoA: NADPH reductase from cell suspension cultures of soybean (Glycinemax), *Eur J. Biochem* 65: 529–536, 1976.

T. Ludertiz et al., Enzymatic synthesis of lignin precursors. Comparison of cinnamoyl–CoA reductase and cinnamyl alcohol: NADP+ dehydrogenase from spruce S(*Picea abies* L.) and soybean )Glycine max L.), *Eur. J. Biochem* 119: 115–124, 1981.

F. Sarni et al., Purification and properties of cinnamoyl–CoA reductase and cinnamyl alcohol dehydrogenase from poplar stems (*Populus X euramericana*) *Eur J. Biochem* 139: 259–265, 1984.

R.C. Bugos, et al., Characterization of bispecific caffeic acid/5–hydroxyferulic acid O–methyltransferase from aspen, *Phytochemistry* 31: 1495–1498, 1992.

C. Hermann et al., Enzymatic synthesis of lignin: purification to homogeneity of the three O–methyltransferases of tobacco and production of specific antibodies, *Arch Biochem Biophys* 253: 367–376, 1987.

J. Van Doorsselaere et al., One–step purification and characterization of a lignin–specific O–methyltransferase from poplar, *Gene* 133: 213–317, 1993.

R.C. Bugos et al., cDNA cloning, sequence analysis and seasonal expression of lignin–bispecific caffeic acid 5–hydroxyferulic acid O–methyltransferase of aspen, *Plant Mol Biol* 17: 1203–1215, 1991.

P. Collazo et al., Structure and expression of the lignin O–methyltransferase gene from *Zea mays* L., *Plant Mol Biol* 20: 857–867, 1992.

W. Hosel et al., Characterization of beta–glucosidase isoenzymes possible involved in lignification from chick pea (*Cicer arietinum* L.) cell suspension cultures, *Eur J Biochem* 84: 487–492, 1978.

Dixon, R. A. et al., Metabolic engineering: prospects for crop improvement through genetic manipulation of phenylpropanoid biosynthesis and defense responses—a review, *Gene Papers* 179: 61–71, 1996.

Hotze, M. et al., Cinnamate 4–hydroxylase from *Catharanthus roseus*, and a strategy for the functional expression of plant cytochrome $P_{450}$ proteins as translational fusions with $P_{450}$ reductase in *Escherichia coli*, *FEBS letters* 374: 345–350 ,1995.

Hotze, M., et al., *C. roseus* mRNA for cinnamate 4–hydroxylase (CYP73), *EMBL Sequence Database, Rel. 39*, Apr. 15, 1994, Accession No. Z32563. (XP–002054206).

Mizutani, M. et al., Molecular Cloning and Sequencing of a cDNA Encoding Mung Bean Cytochrome P450 Possessing Cinnamate 4–Hydroxylase Activity, *Biochemical and Biophysical Research Communications* 190:3, 875–880, 1993.

Kawai, S., et al., Populus kitakamiensis cyp 73a gene for cinnamic acid 4–hydroxylase complete cds. *EMBL Sequence Database, Rel. 46*, Dec. 30, 1995, Accession No. D82812 (XP002054135).

Sewalt et al., Reduced Lignin Content and Altered Lignin Composition in Transgenic Tobacco Down–Regulated in Expression of L–Phenylalanine Ammonia–Lyase or Cinnamate 4–Hydroxylase, *Plant Physiol.* 115: 41–50, 1997.

Boudet, A.M., et al., Transley Review No. 80 Biochemistry and molecular biology of lignification, *New Phytoolgist* 129: 203–236, 1995.

Boudet, A.M. et al., Lignin genetic engineering, *Molecular Breeding* 2: 25–39, 1996.

Shiokawa, T., et al., Expression analysis of a cinnamic acid 4–hydroxylase gene from a hybrid aspen, *Populus kitakamiensis*. Chemical Abstracts 125:13, 1996.

Poeydomenge, O., et al., A cDNA Encoding S–Adenosyl–L–Methionine:Caffeic Acid 3–0–Methyl–transferase from Eucalyptus, *Plant Physiol* 105: 749–750, 1994.

Mason, M.E., et al., Pinus elliotti PEC18 mRNA partial sequence, *EMBL Sequence Database, Rel. 47* May 31, 1996, Accession No. U55006 (XP 002054138).

Wagner, A., et al., Pinus radiata cinnamyl alcohol dehydrogenase (CAD) mRNA, complete cds, *EMBL Sequence Database, Rel. 48* Jul. 28, 1996, Accession No. U62394 (XP002054137).

Van Doorsselaere, J., et al., A novel lignin in poplar trees with a reduced caffeic acid/5–hydroxyferulic acid O–methyltransferase activity, *Plant Journal* 8:6, 855–864, 1995.

Ni, Weiting et al., Reduced lignin in transgenic plants containing a caffeic acid O=methyltransferase antisense gene, *Transgenic Research* 3: 120–126, 1994.

Halpin, C. et al., Manipulation of lignin quality by down–regulation of cinnamyl alcohol dehydrogenase, *Plant Journal* 63:3, 339–350, 1994.

In re Genesis Research & Development Corp. and Fletcher Challenge Forests Ltd; PCT International Search Report: Int'l No. PCT/NZ99/00168 filed Oct. 6, 1999 (7 sheets).

GenBank (no EST GSS HTS STS); Accession No. Z49263 (Sep. 25, 1997).

EMBL (no EST GSS HTG STS); Accession No. L07634 (Jan. 7, 1993).
GenBank (no EST GSS HTG STS); Accession No. X92437 (Jul. 17, 1998).
EMBL (no EST GSS HTG STS); Accession No. D87520 (Sep. 8, 1996).
EMBL (no EST GSS HTG STS); Accession No. U29243 (Jul. 9, 1995).
GenBank (no EST GSS HTG STS); Accession No. U12013 (Mar. 23, 1996).
GenBank (no EST GSS HTG STS); Accession No. U12012 (Mar. 23, 1996).
GenBank (no EST GSS HTG STS); Accession No. U39405 (Feb. 7, 1997).
GenBank (no EST GSS HTG STS); Accession No. U39404 (Feb. 7, 1997).
GenBank (no EST GSS HTG STS); Accession No. AF008183 (Feb. 26, 1998).
Swiss–Prot; Accession No. P14912 (Apr. 1, 1990).
Swiss–Prot: Accession No. P14913 (Apr. 1, 1990).
GenPept: Accession No. BAA07828 (Dec. 8, 1994).
GenPept: Accession No. AAB18638 (Mar. 7, 1996).
GenPept: Accession No. AAC39366 (Jun. 12, 1997).
GenPept: Accession No. AAB18638 (Mar. 7, 1996).
GenPept: Accession No. AAC39365 (Jun. 12, 1997).
GenBank (no EST GSS HTG STS); Accession No. U38416 (Aug. 12, 1996).
GenPept; Accession No. AAA62426 (1994).
Swiss–Prot; Accession No. P93711 (Jul. 15, 1998).
EMBL (no EST GSS HTG STS); Accession No. X52623 (Jul. 9, 1990).
GenBank (no EST GSS HTG STS); Accession No. L43362 (Jul. 7, 1995).
GenPept; Accession No. AAA92669 (Jul. 7, 1994).
GenPept: Accession No. AAB18637 (Mar. 7, 1996).
Swiss–Prot: Accession No. P93711 (Jul. 15, 1998).
EMBL (no EST GSS HTG STS); Accession No. X52623 (Jul. 9, 1990).
GenBank (no EST GSS HTG STS); Accession No. L43362 (Jul. 7, 1995).
GenPept; Accession No. AAA92669 (Jul. 7, 1994).
GenPept; Accession No. AAB18637 (Mar. 7, 1996).
Swiss–Prot: Accession No. P13687 (Jul. 1, 1993).
PIR; Accession No. PQ0773 (Jul. 14, 1994).
In re Bloksberg, et al., "Materials and Methods for the Modification of Plant Lignin Content, Patent Application No. 09/211,710; Filed Dec. 14, 1998; Allowed Claims.
Wagner, A. et al., "Isolation and Characterization of a Cinnamyl–Alcohol Dehydrogenase Gene from Pinus Radiata", *Queenstown Molecular Biology Meeting*, New Zealand Forest Research Institute (Aug. 1996).
Atanassova, R. et al. Altered lignin composition in transgenic tobacco expressing O–methyltransferase sequence in sense and antisense orientation, *Plant Jnl.* 8: 465–477, 1995.
Chabbert et al., Manipulation of lignin quality in transgenic poplar, *Biotechnol. Pulp. Pap. Ind. Proc. Int. Conf.* $6^{th}$ pp. 319–322, 1995.
Baucher, M. et al., Higher extractability of lignin in poplar by reducing cinnamyl alcohol dehydrogenase activity, *Somatic Cell Geneicts and Molecular Genetics of Trees*, ISBN 0–7923–4179–1, pp. 153–158, 1996.
Boudet A. M. et al., La lignification domestiquee *BioFutur* 158:27–31, 1996.

Boudet A. M. Genes involved in monolignol biosynthesis and their manipulation for tailoring new lignins *Am. Chem Soc. Abstracts of Paper at National Meeting*, No. 1, 1996.
Elkind Y. et al., Abnormal plant development and down–regulation of phenylpropanoid biosynthesis in transgenic tobacco containing a heterologous phenylalanine ammonia–lyase gene *Proc. Natl. Acad. Sci. USA* 87:9057–9061, 1990.
Bate, N.J. et al., Quantitative relationship between phenylalanine ammonia–lyase levels and phenylpropanoid accumulation in transgenic tobacco identifies a rate–determining step in natural product biosynthesis, *Proc. Natl. Acad. Sci. USA* 91:7608–7612, 1994.
Kajita S. et al., Alterations in the biosynthesis of lignin in transgenic plants with chimeric genes for 4–coumarate: Coenzyme A ligase *Plant Cell. Physiol.* 37:957–965, 1996.
Erickson et al., Laccase as a target for decreasing the lignin content in transgenic trees through antisense genetic engineering, *Biotechnol. Pulp Pap. Ind. Proc.* $6^{th}$ *Intl. Conf.* pp. 310–314, 1996.
Lagrimini, L.M., Wound–induced deposition of polyphenols in transgenic plants overexpressing peroxidase *Plant Physiol.* 96:577–583, 1991.
Liu, T.Y. et al. Lignin contect and composition in tobacco plants with over and under expressed peroxidase, *Supplement to Plant Physiol.* 102:103, 1993.
McIntyre, C.L. et al. Strategies for the suppression of peroxidase gene expression in tobacco. II. In vivo suppression of peroxidase activity in transgenic tobacco using ribozyme and antisense constructs *Transgenic Research* 5:263–270, 1996.
Sikorski, R.S. et al., Yeast centromere vector pRS415 with LEU2 marker, complete sequence, EMBL Accession NO. U03449, Jan. 8, 1984.
Yu, L.X. et al. Lycopersicon chilense unknown protein (LC15) mRNA, complete cds, EMBL Accession No. U19099, Oct. 3, 1995.
Grima–Pettenati, J. et al., E. gunnii OMT mRNA for O–methyltransferase, EMBL Accession No. X74814, Dec. 31, 1993.
Poeydomenge O. et al. a cDNA encoding S–adenosyl–L–methionine:caffeic acid 3–O–methyltransferase from eucalyptus, *Plant Physiol.* 105:749–750, 1994.
Raynal et al. A. thaliana transcribed sequence; clone PAP790; 5' end similar to cinnamyl alcohol dehydrogenase; *Stylosanthes hmilis*, EMBL Accession No. Z46703, Nov. 18, 1994.
Goffner D. et al., E. gunnii mRNA for cinnamyl alcohol dehydrogenase, EMBL Accession No. X88797, Dec. 31, 1995.
Newman T., et al., 10030 *Arabidopsis thaliana* cDNA clone 143C13T7, EMBL Accession No. T46767, Feb. 11, 1995.
Zhang, X.H. et al., *Pinus taedae* phenylalanine ammonia–lyase (lpPAL) gene complete cds, EMBL Accession No. U39792, Jan. 1, 1996.
Voo, K.S. et al. *Pinus taeda* PT4CL2 4–coumarate–CoA ligase enzyme, mRNA complete cds, EMBL Accession No. U12013, Jul. 27, 1994.
Zhang X.H. et al., *Pinus taeda* xylem 4–coumarate:CoA ligase (lp4CL–1) gene, complete cds, EMBL Accession No. U39405, Jan. 1, 1996.
Davies, K.M. et al. Malus sp. mRNA for anthocyanin hydroxylase, EMBL Accession No. X71360, Apr. 27, 1993.

Hrmova M. et al., *Hordeum vulgare* beta–d–glucan exohydrolase, isoenzyme exoII, mRNA, complete cds, EMBL Accession No. U46003, Feb. 29, 1996.

Willekens, H.D. N. plumbaginifolia mRNA for catalase (cat3 gene), EMBL Accession No. Z36977, Sep. 7, 1994.

Ritter D. et al., *Gossypium hirsutum* peroxidase mRNA, complete cds, EMBL Accession No. L08199, Dec. 24, 1992.

Meyer K. et al., *Arabidopsis thaliana* ferulate–5–hydroxylase (FAH1) mRNA, completed cds, EMBL Accession No. U38416, Aug. 13, 1996.

Meyer K. et al., Ferulate–5–hydroxylase from *Arabidopsis thaliana* defines a new family of cytochrome P450–dependent monooxygenases *Proc. Natl. Acad. Sci. USA* 93:6869–6874, 1996.

Sewalt, V.J.H., et al. Reduced lignin content and altered lignin composition in transgenic tobacco down–regulated in expression of L–phenylalanine ammonia–lyase or cinnamate 4–hydroxylase *Plant Physiol.* 115:41–50, 1997.

Rech, P. et al., *E. gunii* mRNA for caffeoyl–CoA O–methyltransferase, EMBL Accession No. Y12228, Apr. 8, 1997.

Bachem, C.W.B., et al. Antisense expression of polyphenol oxidase genes inhibits enzymatic browning in potato tubers, *Biotechnology* 12:1101–1105, 1994.

Udagama–Randeniya, P.V. et al., Coniferyl alcohol oxidase: A catechol oxidase? *Trees* 10:102–108, 1995.

Dharmawardhana, D.P. et al., A beta–glycosidase from lodgepole pine xylem specific for the lignin precursor coniferin *Plant Physiol* 107:331–339, 1995.

Database Dissabs, AN97:45741 Dissabs Order No. AARNN14739, Dharmawardhana, D.P. et al. A biochemical and molecular study of lignin biosynthesis (*Pinus contorta*, glucosidase, conferin, xylem).

Bao W. et al. A laccase associated with lignification in loblolly pine xylem *Science* 260:672–674, 1993.

Shiokawa, T. et al., Expression analysis of a cinnamic acid 4–hydroxylase gene from a hybrid aspen, *Populus kitakamiensis, Chem. Abstracts*, vol. 125, No. 13, abstract No. 163462, Sep. 23, 1996.

* cited by examiner

SEQUENCE LISTING

```
<160> NUMBER OF SEQ ID NOS:  405

<210> SEQ ID NO 1
<211> LENGTH: 535
<212> TYPE: DNA
<213> ORGANISM: Eucalyptus grandis
<220> FEATURE:
<221> NAME/KEY: unsure
<222> LOCATION: (110)...(110)

<400> SEQUENCE: 1
cttcgcgcta ccgcatactc caccaccgcg tgcagaagat gagctcggag g gtgggaagg     60 aggattgcct cggttgggct gcccgggacc cttctgggtt cctctccccn t acaaattca   120 cccgcaggcc gtgggaagcg aagacgtctc gattaagatc acgcactgtg g agtgtgcta   180 cgcagatgtg gcttggacta ggaatgtgca gggacactcc aagtatcctc t ggtgccggg   240 gcacgagata gttggaattg tgaaacaggt tggctccagt gtccaacgct t caaagttgg   300 cgatcatgtg ggggtgggaa cttatgtcaa ttcatgcaga gagtgcgagt a ttgcaatga   360 caggctagaa gtccaatgtg aaaagtcggt tatgactttt gatggaattg a tgcagatgg   420 tacagtgaca aagggaggat attctagtca cattgtcgtc catgaaaggt a ttgcgtcag   480 gattccagaa aactacccga tggatctagc agcgcattgc tctgtgctgg a tcac        535

<210> SEQ ID NO 2
<211> LENGTH: 671
<212> TYPE: DNA
<213> ORGANISM: Pinus radiata

<400> SEQUENCE: 2
gcgcctgcag gtcgacacta gtggatccaa agaattcggc acgaggttgc a ggtcgggga     60 tgatttgaat cacagaaacc tcagcgattt tgccaagaaa tatggcaaaa t ctttctgct   120 caagatgggc cagaggaatc ttgtggtagt ttcatctccc gatctcgcca a ggaggtcct   180 gcacacccag ggcgtcgagt ttgggtctcg aacccggaac gtggtgttcg a tatcttcac   240 gggcaagggg caggacatgg tgttcaccgt ctatggagat cactggagaa a gatgcgcag   300 gatcatgact gtgcctttct ttacgaataa agttgtccag cactacagat t cgcgtggga   360 agacgagatc agccgcgtgg tcgcggatgt gaaatcccgc gccgagtctt c cacctcggg   420
```

| | |
|---|---|
| cattgtcatc cgtagcgcct ccagctcatg atgtataata ttatgtatag g atgatgttc | 480 |
| gacaggagat tcgaatccga ggacgacccg cttttcctca agctcaaggc c ctcaacgga | 540 |
| gagcgaagtc gattggccca gagctttgag tacaattatg gggatttcat t cccagtctt | 600 |
| aggcccttcc tcagaggtta tcacagaatc tgcaatgaga ttaaagagaa a cggctctct | 660 |
| cttttcaagg a | 671 |

<210> SEQ ID NO 3
<211> LENGTH: 940
<212> TYPE: DNA
<213> ORGANISM: Pinus radiata
<220> FEATURE:
<221> NAME/KEY: unsure
<222> LOCATION: (463)...(463)

<400> SEQUENCE: 3

| | |
|---|---|
| cttcaggaca agggagagat caatgaggat aatgttttgt acatcgttga g aacatcaac | 60 |
| gttgcagcaa ttgagacaac gctgtggtcg atggaatggg gaatagcgga g ctggtgaac | 120 |
| caccaggaca ttcagagcaa ggtgcgcgca gagctggacg ctgttcttgg a ccaggcgtg | 180 |
| cagataacgg aaccagacac gacaaggttg ccctaccttc aggcggttgt g aaggaaacc | 240 |
| cttcgtctcc gcatggcgat cccgttgctc gtccccaca tgaatctcca c gacgccaag | 300 |
| ctcgggggct acgatattcc ggcagagagc aagatcctgg tgaacgcctg g tggttggcc | 360 |
| aacaaccccg ccaactggaa gaaccccgag gagttccgcc cgagcggtt c ttcgaggag | 420 |
| gagaagcaca ccgaagccaa tggcaacgac ttcaaattcc tgnccttcgg t gtggggagg | 480 |
| aggagctgcc cgggaatcat tctggcgctg ctctcctcgc actctccatc g gaagacttg | 540 |
| ttcagaactt ccaccttctg ccgccgcccg ggcagagcaa agtggatgtc a ctgagaagg | 600 |
| gcgggcaatt cagccttcac attctcaacc attctctcat cgtcgccaag c ccatagctt | 660 |
| ctgcttaatc ccaacttgtc agtgactggt atataaatgc gcgcacctga a caaaaaaca | 720 |
| ctccatctat catgactgtg tgtgcgtgtc cactgtcgag tctactaaga g ctcatagca | 780 |
| cttcaaaagt ttgctaggat ttcaataaca gacaccgtca attatgtcat g tttcaataa | 840 |
| aagtttgcat aaattaaatg atatttcaat atactatttt gactctccac c aattgggga | 900 |
| attttactgc taaaaaaaaa aaaaaaaaaa aaaaaaaaaa | 940 |

<210> SEQ ID NO 4
<211> LENGTH: 949
<212> TYPE: DNA
<213> ORGANISM: Pinus radiata
<220> FEATURE:
<221> NAME/KEY: unsure
<222> LOCATION: (1)...(949)
<223> OTHER INFORMATION: n at all occurrences indicates unsure

<400> SEQUENCE: 4

| | |
|---|---|
| nngctcnacc gacggtggac ggtccgctac tcagtaactg agtgggatcc c ccgggctga | 60 |
| caggcaattc gatttagctc actcattagg caccccaggc tttacacttt a tgcttccgg | 120 |
| ctcgtatgtt gtgtggaatt gtgagcggat aacaatttca cacaggaaac a gctatgacc | 180 |
| atgattacgc caagcgcgca attaaccctc actaaaggga caaaagctg g agctccacc | 240 |
| gcggtggcgg ccgctctaga actagtggat ccaaagaatt cggcacgaga c ccagtgacc | 300 |
| ttcaggcctg agagatttct tgaggaagat gttgatatta agggccatga t tacaggcta | 360 |
| ctgccattgg tgcagggcgc aggatctgcc ctggtgcaca attgggtatt a atttagttc | 420 |

-continued

| | |
|---|---|
| agtctatgtt gggacacctg cttcatcatt tcgtatgggc acctcctgag g gaatgaagg | 480 |
| cagaagacat agatctcaca gagaatccag ggcttgttac tttcatggcc a agcctgtgc | 540 |
| aggccattgc tattcctcga ttgcctgatc atctctacaa gcgacagcca c tcaattgat | 600 |
| caattgatct gatagtaagt ttgaattttg ttttgataca aaacgaaata a cgtgcagtt | 660 |
| tctccttttc catagtcaac atgcagcttt cttctctga agcgcatgca g ctttcttc | 720 |
| tctgaagccc aacttctagc aagcaataac tgtatatttt agaacaaata c ctattcctc | 780 |
| aaattgagwa tttctctgta ggggnngnta attgtgcaat ttgcaagnaa t agtaaagtt | 840 |
| tantttaggg nattttaata gtcctangta ananngggna atgntagngg g cattnagaa | 900 |
| anccctaata gntgttggng gnngntaggn tttttnacca aaaaaaaaa | 949 |

<210> SEQ ID NO 5
<211> LENGTH: 959
<212> TYPE: DNA
<213> ORGANISM: Pinus radiata
<220> FEATURE:
<221> NAME/KEY: unsure
<222> LOCATION: (697)...(697)

<400> SEQUENCE: 5

| | |
|---|---|
| gaattcggca cgagaaagcc ctagaatttt ttcagcatgc tatacagcc c cagcgacaa | 60 |
| ctttaactgc aataactgtg gaagcgtaca aaagtttgt cctagtttct c tcattcaga | 120 |
| ctggtcaggt tccagcattt ccaaaataca cacctgctgt tgtccaaaga a atttgaaat | 180 |
| cttgcactca gccctacatt gatttagcaa acaactacag tagtgggaaa a tttctgtat | 240 |
| tggaagcttg tgtcaacacg aacacagaga agttcaagaa tgatagtaat t tggggttag | 300 |
| tcaagcaagt tttgtcatct ctttataaac ggaatattca gagattgaca c agacatatc | 360 |
| tgaccctctc tcttcaagac atagcaagta cggtacagtt ggagactgct a agcaggctg | 420 |
| aactccatgt tctgcagatg attcaagatg gtgagatttt tgcaaccata a atcagaaag | 480 |
| atgggatggt gagcttcaat gaggatcctg aacagtacaa aacatgtcag a tgactgaat | 540 |
| atatagatac tgcaattcgg agaatcatgg cactatcaaa gaagctcacc a cagtagatg | 600 |
| agcagatttc gtgtgatcat tcctacctga gtaaggtggg gagagagcgt t caagatttg | 660 |
| acatagatga ttttgatact gttccccaga agttcanaaa tatgtaacaa a tgatgtaaa | 720 |
| tcatcttcaa gactcgctta tattcattac tttctatgtg aattgatagt c tgttaacaa | 780 |
| tagtactgtg gctgagtcca gaaaggatct ctcggtatta tcacttgaca t gccatcaaa | 840 |
| aaaatctcaa atttctcgat gtctagtctt gattttgatt atgaatgcga c ttttagttg | 900 |
| tgacatttga gcacctcgag tgaactacaa agttgcatgt taaaaaaaaa a aaaaaaa | 959 |

<210> SEQ ID NO 6
<211> LENGTH: 1026
<212> TYPE: DNA
<213> ORGANISM: Pinus radiata

<400> SEQUENCE: 6

| | |
|---|---|
| gaattcggca cgagctttga ggcaacctac attcattgaa tcccaggatt t cttcttgtc | 60 |
| caaacaggtt taaggaaatg gcaggcacaa gtgttgctgc agcagaggtg a aggctcaga | 120 |
| caacccaagc agaggagccg gttaaggttg tccgccatca agaagtggga c acaaaagtc | 180 |
| ttttgcagag cgatgccctc tatcagtata tattggaaac gagcgtgtac c ctcgtgagc | 240 |
| ccgagccaat gaaggagctc cgcgaagtga ctgccaagca tccctggaac c tcatgacta | 300 |

-continued

```
cttctgccga tgagggtcaa tttctgggcc tcctgctgaa gctcattaac g ccaagaaca    360
ccatggagat tggggtgtac actggttact cgcttctcag cacagccctt g cattgcccg    420
atgatggaaa gattctagcc atggacatca acagagagaa ctatgatatc g gattgccta    480
ttattgagaa agcaggagtt gcccacaaga ttgacttcag agagggccct g ctctgccag    540
ttctggacga actgcttaag aatgaggaca tgcatggatc gttcgatttt g tgttcgtgg    600
atgcggacaa agacaactat ctaaactacc acaagcgtct gatcgatctg g tgaaggttg    660
gaggtctgat tgcatatgac aacaccctgt ggaacggatc tgtggtggct c cacccgatg    720
ctcccctgag gaaatatgtg agatattaca gagatttcgt gatggagcta a caaggccc    780
ttgctgtcga tccccgcatt gagatcagcc aaatcccagt cggtgacggc g tcacccttt    840
gcaggcgtgt ctattgaaaa caatccttgt ttctgctcgt ctattgcaag c ataaaggct    900
ctctgattat aaggagaacg ctataatata tggggttgaa gccatttgtt t tgtttagtg    960
tattgataat aaagtagtac agcatatgca agtttgtat caaaaaaaaa a aaaaaaaa   1020
aaaaaa                                                              1026
```

<210> SEQ ID NO 7
<211> LENGTH: 1454
<212> TYPE: DNA
<213> ORGANISM: Pinus radiata

<400> SEQUENCE: 7

```
gaattcggca cgaggccaac tgcaagcaat acagtacaag agccagacga t cgaatcctg     60
tgaagtggtt ctgaagtgat gggaagcttg gaatctgaaa aaactgttac a ggatatgca    120
gctcgggact ccagtggcca cttgtcccct tacacttaca atctcagaaa g aaaggacct    180
gaggatgtaa ttgtaaaggt catttactgc ggaatctgcc actctgattt a gttcaaatg    240
cgtaatgaaa tggacatgtc tcattaccca atggtccctg gcatgaagt g gtggggatt    300
gtaacagaga ttggcagcga ggtgaagaaa ttcaaagtgg agagcatgt a ggggttggt    360
tgcattgttg ggtcctgtcg cagttgcggt aattgcaatc agagcatgga a caatactgc    420
agcaagagga tttggaccta caatgatgtg aaccatgacg gcacacctac t cagggcgga    480
tttgcaagca gtatggtggt tgatcagatg twtgtggttc gaatcccgga g aatcttcct    540
ctggaacaag cggcccctct gttatgtgca ggggttacag ttttcagccc a atgaagcat    600
ttcgccatga cagagcccgg gaagaaatgt gggattttgg gttaggagg c gtggggcac    660
atgggtgtca agattgccaa agcctttgga ctccacgtga cggttatcag t tcgtctgat    720
aaaaagaaag aagaagccat ggaagtcctc ggcgccgatg cttatcttgt t agcaaggat    780
actgaaaaga tgatggaagc agcagagagc ctagattaca taatggacac c attccagtt    840
gctcatcctc tggaaccata tcttgcccct ctgaagacaa atggaaagct a gtgatgctg    900
ggcgttgttc cagagtcgtt gcacttcgtg actcctctct taatacttgg g agaaggagc    960
atagctggaa gtttcattgg cagcatggag gaaacacagg aaactctaga t ttctgtgca   1020
gagaagaagg tatcatcgat gattgaggtt gtgggcctgg actacatcaa c acggccatg   1080
gaaaggttgg agaagaacga tgtccgttac agatttgtgg tggatgttgc t agaagcaag   1140
ttggataatt agtctgcaat caatcaatca gatcaatgcc tgcatgcaag a tgaatagat   1200
ctggactagt agcttaacat gaagggaaa ttaaattttt atttaggaac t cgatactgg   1260
tttttgttac tttagttag cttttgtgag gttgaaacaa ttcagatgtt t tttaactt    1320
gtatatgtaa agatcaattt ctcgtgacag taaataataa ccaatgtctt ctgccaaat    1380
```

<210> SEQ ID NO 8
<211> LENGTH: 740
<212> TYPE: DNA
<213> ORGANISM: Pinus radiata

<400> SEQUENCE: 8

```
gaattcggca cgagaccatt tccagctaat attggcatag caattggtca t tctatctttt      60
gtcaaaggag atcaaacaaa ttttgaaatt ggacctaatg gtgtggaggc t agtcagcta     120
tacccagatg tgaaatatac cactgtcgat gagtacctca gcaaatttgt g tgaagtatg     180
cgagattctc ttccacatgc ttcagagata cataacagtt tcaatcaatg t ttgtcctag     240
gcatttgcca aattgtgggt tataatcctt cgtaggtgtt tggcagaaca g aacctcctg     300
tttagtatag tatgacgagc taggcactgc agatccttca cactttttctc t tccataaga    360
aacaaatact cacctgtggt ttgttttctt tctttctgga actttggtat g caataatg     420
tctttggaaa ccgcttagtg tggaatgcta agtactagtg tccagagttc t aagggagtt    480
ccaaaatcat ggctgatgtg aactggttgt tccagagggt gtttacaacc a acagttgtt    540
cagtgaataa ttttgttaga gtgtttagat ccatctttac aaggctattg a gtaaggttg    600
gtgttagtga acgaatgat gtcaaatctt gatgggctga ctgactctct t gtgatgtca     660
aatcttgatg gattgtgtct ttttcaatgg taaaaaaaaa aaaaaaaaaa a aaaaaaaa     720
aaaaaaaaaa aaaaaaaaaa                                                740
```

<210> SEQ ID NO 9
<211> LENGTH: 624
<212> TYPE: DNA
<213> ORGANISM: Pinus radiata

<400> SEQUENCE: 9

```
gaattcctgc agcccggggg atccactagt tctagagcgg ccgccaccgc g gtggagctc      60
gcgcgcctgc aggtcgacac tagtggatcc aaagaattcg gcacgaggcc c gacggccac    120
tgttggacg ccatggaagc tctccggaaa gccgggattc tggaaccgtt t aaactgcag    180
cccaaggaag gactggctct cgtcaacggc acagcggtgg gatccgccgt g gccggtcc     240
gtctgtgttg acgccaacgt gctgggcgtg ctggctgaga ttctgtctgc g ctctctgc    300
gaggtgatgc aagggaaacc ggagttcgta gatccgttaa cccaccagtt g aagcccac    360
ccagggcaga tcgaagccgc ggccgtcatg gagttcctcc tcgacggtag c gactcgtg    420
aaagaagcag cgcggcttca cgagaaagac ccgttgagca aaccgaaaca a gaccctac    480
gctctgcgaa catcgccaca gtggttgggg cctccgatcg aagtcatccg c gctgyact    540
cactccatcg agcgggagat caattccgtc aacgacaatc cgttaatcga t gtctccagg    600
gacatggctg tccacggcgg caac                                           624
```

<210> SEQ ID NO 10
<211> LENGTH: 278
<212> TYPE: DNA
<213> ORGANISM: Pinus radiata

<400> SEQUENCE: 10

```
gaattcctgc agcccggggg atccactagt tctagagcgg ccgccaccgc g gtggagctc      60
```

-continued

| | | | |
|---|---|---|---|
| cagtacctgg | ccaaccccgt | cacgactcac gtccagagcg ccgaacaaca c aaccaggat | 120 |
| gtcaattccc | tcggcttgat | ctccgccaga aagactgccg aggccgttga g atttaaag | 180 |
| ctgatgttcg | ctacatatct | ggtggcctta tgccaggcga tcgatctccg g cacctggaa | 240 |
| gaaaacatgc | gatccgttgt | gaagcacgta gtcttgca | 278 |

<210> SEQ ID NO 11
<211> LENGTH: 765
<212> TYPE: DNA
<213> ORGANISM: Pinus radiata

<400> SEQUENCE: 11

| | | | |
|---|---|---|---|
| gagctcctgc | aagtcatcga | tcatcagccc gttttctcgt acatcgacga t cccacaaat | 60 |
| ccatcatacg | cgcttatgct | ccaactcaga gaagtgctcg tagatgaggc t ctcaaatca | 120 |
| tcttgcccag | acgggaatga | cgaatccgat cacaatttgc agcccgctga g agcgctgga | 180 |
| gctgctggaa | tattacccaa | ttgggtgttt agcaggatcc ccatatttca a gaggagttg | 240 |
| aaggcccgtt | tagaggaaga | ggttccgaag gcgagggaac gattcgataa t gggacttc | 300 |
| ccaattgcaa | acagaataaa | caagtgcagg acatatccca tttacagatt c gtgagatca | 360 |
| gagttgggaa | ccgatttgct | aacagggccc aagtggagaa gccccggcga a gatatagaa | 420 |
| aaggtatttg | agggcatttg | ccaagggaaa attggaaacg tgatcctcaa a tgtctggac | 480 |
| gcttggggtg | ggtgcgctgg | accattcact ccacgtgcat atcctgcgtc t cctgcagcg | 540 |
| ttcaatgcct | catattgggc | atggtttgat agcaccaaat caccctctgc a acgagcggc | 600 |
| agaggtttct | ggagcgccca | acaacaacaa gttctttgat ttaactgact c ttaagcatt | 660 |
| cctaaacagc | ttgttcttcg | caataacgaa tctttcatct tcgttacttt g taaagatg | 720 |
| gggttccaac | aaaatagaag | aaatatttc gatccaaaaa aaaaa | 765 |

<210> SEQ ID NO 12
<211> LENGTH: 453
<212> TYPE: DNA
<213> ORGANISM: Pinus radiata

<400> SEQUENCE: 12

| | | | |
|---|---|---|---|
| tgattatgcg | gatccttggg | cagggatacg gcatgacaga agcaggcccg g tgctggcaa | 60 |
| tgaacctagc | cttcgcaaag | aatcctttcc ccgccaaatc tggctcctgc g gaacagtcg | 120 |
| tccggaacgc | tcaaataaag | atcctcgatt acaggaactg gcgagtctct c ccgcacaat | 180 |
| caagccggcg | aaatctgcat | ccgcggaccc gaaataatga aaggatatat t aacgacccg | 240 |
| gaatccacgg | ccgctacaat | cgatgaagaa ggctggctcc acacaggcga c gtcgggtac | 300 |
| attgacgatg | acgaagaaat | cttcatagtc gacagagtaa aggagattat c aatataaag | 360 |
| gcttccaggt | ggatcctgct | aatcgaattc ctgcagcccg ggggtccact a gttctagag | 420 |
| cggccgccac | cgcggtggag | ctccagcttt tgt | 453 |

<210> SEQ ID NO 13
<211> LENGTH: 278
<212> TYPE: DNA
<213> ORGANISM: Pinus radiata

<400> SEQUENCE: 13

| | | | |
|---|---|---|---|
| tcttcgaatt | ctcttcacg | actgcttcgt taatggctgc gatggctcga t attgttaga | 60 |
| tgataactca | acgttcaccg | gagaaaagac tgcaggccca aatgttaatt c tgcgagagg | 120 |

-continued

| attcgacgta atagacacca tcaaaactca agttgaggca gcctgcagtg g tgtcgtgtc | 180 |
| agttgccgac attctcgcca ttgctgcacg cgattcagtc gtccaactgg g gggcccaac | 240 |
| atggacggta cttctgggag aaaagacgga tccgatca | 278 |

<210> SEQ ID NO 14
<211> LENGTH: 23
<212> TYPE: DNA
<213> ORGANISM: Pinus radiata

<400> SEQUENCE: 14

| cttcgaattc wyttycayga ytg | 23 |

<210> SEQ ID NO 15
<211> LENGTH: 22
<212> TYPE: DNA
<213> ORGANISM: Pinus radiata

<400> SEQUENCE: 15

| gatcggatcc rtcyykycty cc | 22 |

<210> SEQ ID NO 16
<211> LENGTH: 472
<212> TYPE: DNA
<213> ORGANISM: Eucalyptus grandis

<400> SEQUENCE: 16

| aattcggcac gagacgacct cttgtatcgg acccggatcc gctatcgtta a cgtacacac | 60 |
| gttctagtgc tgaatggaga tggagagcac caccggcacc ggcaacggcc t tcacagcct | 120 |
| ctgcgccgcc gggagccacc atgccgaccc actgaactgg ggggcggcgg c agcagccct | 180 |
| cacagggagc cacctcgacg aggtgaagcg gatggtcgag gagtaccgga g gccggcggt | 240 |
| gcgcctcggc ggggagtccc tcacgatagc ccaggtggcg gcgtggcga g tcaggaggg | 300 |
| ggtaggggtc gagctctcgg aggcggcccg tcccagggtc aaggccagca g cgactgggt | 360 |
| catggagagc atgaacaagg gaactgacag ctacgggtc accaccgggt t cggcggcaa | 420 |
| cttctcaaac cggaggccga agcaaggcgg tccttttcag aaggaactta t a | 472 |

<210> SEQ ID NO 17
<211> LENGTH: 622
<212> TYPE: DNA
<213> ORGANISM: Eucalyptus grandis

<400> SEQUENCE: 17

| ccaaagctcc tagtgcctca tgagtctgct gaggattgca caattggcgg g ttcgacgtg | 60 |
| ccccgaggca ccatgatcct ggttaatgcg tgggcaattc aaagagaccc a aaagtgtgg | 120 |
| gacgatccca caaattttaa accggagagg tacgagggat tggaaggtga t catgcctac | 180 |
| cgactattgc cgtttgggat ggggaggaga agttgtcctg gtgctggcct t gccaataga | 240 |
| gtggtgagct tggtcctggc ggcgcttatt cagtgcttcg aatgggaacg a gttggcgaa | 300 |
| gaattggtgg acttgtccga ggggacggga ctcacaatgc caaagagaga g ccattggag | 360 |
| gccttgtgca aagcgcgtga atgcatgata gctaatgttc ttgcgcacct t taagaaggt | 420 |
| cgttgtctaa tgaatttaca ttggtgatgt atctccaatg ttttttgaata a tcaaataga | 480 |
| ctgaaaatag gccagtgcag ctttaggaat gatcgtgagc atcaatagca t cctgaggag | 540 |
| gccaatgcag ctttaggcct ttctcttagg agaaaaatga tggtttatat a ggtactggc | 600 |
| aacattgttc aaaaaaaaaa aa | 622 |

<210> SEQ ID NO 18
<211> LENGTH: 414
<212> TYPE: DNA
<213> ORGANISM: Eucalyptus grandis

<400> SEQUENCE: 18

```
cacgctcgac gaattcggta ccccgggttc gaaatcgata agcttggatc c aaagcaaca      60
cattgaactc tctctctctc tctctctctc tctctctctc tcccccaccc c cccttccca     120
accccaccca catacagaca agtagatacg cgcacacaga agaagaaaag a tgggggttt     180
caatgcagtc aatcgcacta gcgacggttc tggccgtcct aacgacatgg g cgtggaggg     240
cggtgaactg gtgtggctg aggccgaaga ggctcgagag gcttctgaga c agcaaggtc     300
tctccggcaa gtcctacacc ttcctggtcg gcgacctcaa ggagaacctg c ggatgctca     360
aggaagccaa gtccaagccc atcgccgtct ccgatgacat caagcctcgt c tct          414
```

<210> SEQ ID NO 19
<211> LENGTH: 469
<212> TYPE: DNA
<213> ORGANISM: Eucalyptus grandis

<400> SEQUENCE: 19

```
gaattcggca cgagtgtctc tctctctctc tctctctgta aaccaccatg c tcttcctca      60
ctcatctcct agcagttcta ggggttgtgt tgctcctgct aattctatgg a gggcaagat     120
cttctccgaa caaacccaaa ggtactgcct taccccggga gctgccgggc g catggccga     180
tcataggcca catccacttg ctgggcggcg agacccgct ggccaggacc c tggccgcca     240
tggcggacaa gcagggcccg atgtttcgga tccgtctcgg agtccacccg g cgaccatca     300
taagcagccg tgaggcggtc cgggagtgct tcaccaccca cgacaaggac c tcgcttctc     360
gccccaaatc caaggcggga atccacttgg gctacgggta tgccggtttt g gcttcgtag     420
aatacgggga cttttggcgc gagatgagga agatcaccat gctcgagct               469
```

<210> SEQ ID NO 20
<211> LENGTH: 341
<212> TYPE: DNA
<213> ORGANISM: Eucalyptus grandis

<400> SEQUENCE: 20

```
cgggctcgtg gctcggctcc ggcgcaacgc ccttcccacc gggcccgagg g gcctcccgg      60
tcatcgggaa catgctcatg atgggcgagc tcacccaccg cggcctcgcg a gtctggcga     120
agaagtatgg cgggatcttc cacctccgca tgggcttcct gcacatggtt g ccgtgtcgt     180
cccccgacgt ggcccgccag gtcctccagg tccacgacgg gatcttctcg a accggcctg     240
ccaccatcgc gatcagctac ctcacgtatg accgggccga catggccttc g cgcactacg     300
gcccgttctg gcggcagatg cggaagctgt gcgtgatgaa a                         341
```

<210> SEQ ID NO 21
<211> LENGTH: 387
<212> TYPE: DNA
<213> ORGANISM: Eucalyptus grandis

<400> SEQUENCE: 21

```
gaattcggca cgagcgggct cgtggctcgg ctccggcgca acgcccttcc c accgggccc      60
gaggggcctc ccggtcatcg ggaacatgct catgatgggc gagctcaccc a ccgcggcct     120
```

-continued

| | |
|---|---|
| cgcgagtctg gcgaagaagt atggcgggat cttccacctc cgcatgggct t cctgcacat | 180 |
| ggttgccgtg tcgtccccccg acgtggcccg ccaggtcctc caggtccacg a cgggatcttt | 240 |
| ctcgaaccgg cctgccacca tcgcgatcag ctacctcacg tatgaccggg c cgacatggc | 300 |
| cttcgcgcac tacggcccgt tctggcggca gatgcggaag ctgtgcgtga t gaaagctct | 360 |
| tcagcggaag cgggctgagt cgtggga | 387 |

<210> SEQ ID NO 22
<211> LENGTH: 443
<212> TYPE: DNA
<213> ORGANISM: Eucalyptus grandis

<400> SEQUENCE: 22

| | |
|---|---|
| cacgagctcg tgagccttcc cggagacaag gccatcttac ttcgcaacaa a ttgcgtccg | 60 |
| cactcctttc tcaagaaacc tagtcatcca agaagcagag cattgcaact g caaacagcc | 120 |
| aaagcccaaa ctcgtacaga aggagagaga gagagagaat agaagcatga g tgcatgcac | 180 |
| gaaccaagca atcacgacgg ccagtgaaga tgaaagagttc ttgttcgcca t ggaaatgaa | 240 |
| tgctctgata gcactcccct tggtcttgaa ggccaccatc gaactgggga t cctcgaaat | 300 |
| actggccgag tgcgggccta tggctccact ttcgcctgct cagattgcct c ccgtctctc | 360 |
| cgcaaagaac ccggaagccc ccgtaaccct tgaccggatc ctccggtttc t cgccagcta | 420 |
| ctccatcctc tcttgcactc tcg | 443 |

<210> SEQ ID NO 23
<211> LENGTH: 607
<212> TYPE: DNA
<213> ORGANISM: Eucalyptus grandis

<400> SEQUENCE: 23

| | |
|---|---|
| gaattcggca cgagccaacc ctggaccagg tacttttggc aggcggtcca t tgcccttca | 60 |
| aaccggtcca aaccggacca tcactgtcct tatatacgtt gcatcatgcc t gctcataga | 120 |
| acttaggtca actgcaacat ttcttgatca caacatatta caatattcct a agcagagag | 180 |
| agagagagag agagagagag agagagagag agagagagag agtttgaa tcaatggcca c cgccggaga | 240 |
| ggagagccag acccaagccg ggaggcacca ggaggttggc cacaagtctc t ccttcagag | 300 |
| tgatgctctt taccaatata ttttggagac cagcgtgtac ccaagagagc t gagcccat | 360 |
| gaaggagctc aggaaaataa cagcaaaaca tccatggaac ataatgacaa c atcagcaga | 420 |
| cgaagggcag ttcttgaaca tgcttctcaa gctcatcaaa gccaagaaca c catggagat | 480 |
| tggtgtcttc actggctact ctctcctcgc caccgctctt gctcttcctg a tgacggaaa | 540 |
| gatttttggct atggacatta acagagagag ctatgaactt ggcctgccgg c atccaaaaa | 600 |
| gccggtg | 607 |

<210> SEQ ID NO 24
<211> LENGTH: 421
<212> TYPE: DNA
<213> ORGANISM: Eucalyptus grandis

<400> SEQUENCE: 24

| | |
|---|---|
| gaattcggca cgagccgttt tatttcctct gatttccttt gctcgagtct c gcggaagag | 60 |
| agagaagaga ggagaggaga gaatgggttc gaccggatcc gagacccaga t gaccccgac | 120 |
| ccaagtctcg gacgaggagg cgaacctctt cgccatgcag ctggcgagcg c ctccgtgct | 180 |
| ccccatggtc ctcaaggccg ccatcgagct cgacctcctc gagatcatgg c caaggccgg | 240 |

-continued

| | |
|---|---|
| gccgggcgcg ttcctctccc cggggggaagt cgcggcccag ctcccgaccc a gaaccccga | 300 |
| ggcacccgta atgctcgacc ggatcttccg gctgctggcc agctactccg t gctcacgtg | 360 |
| cacccgccgc gacctccccg atggcaaggt cgagcggctc tacggcttag c gccggtgtg | 420 |
| c | 421 |

<210> SEQ ID NO 25
<211> LENGTH: 760
<212> TYPE: DNA
<213> ORGANISM: Eucalyptus grandis

<400> SEQUENCE: 25

| | |
|---|---|
| ggaagaagcc gagcaaacga attgcagacg ccattgaaaa aagacacgaa a gagatcaag | 60 |
| aaggagctta agaagcatca tcaatggcag ccaacgcaga gcctcagcag a cccaaccag | 120 |
| cgaagcattc ggaagtcggc cacaagagcc tcttgcagag cgatgctctc t accagtata | 180 |
| tattggagac cagcgtctac ccaagagagc cagagcccat gaaggagctc a gggaaataa | 240 |
| cagccaaaca tccatggaac ctgatgacca catcggcgga tgaagggcag t tcctgaaca | 300 |
| tgctcctcaa gctcatcaac gccaagaaca ccatggagat cggcgtctac a ccggctact | 360 |
| ctctcctcgc aaccgccctt gctcttcccg atgacggaaa gatcttggcc a tggccatca | 420 |
| ataggggagaa cttcgagatc gggctgcccg tcatccagaa ggccggcctt g cccacaaga | 480 |
| tcgatttcag agaaggccct gccctgccgc tccttgatca gctcgtgcaa g atgagaaga | 540 |
| accatggaac gtacgacttc ttctcaatcc ttaatcgttc atttgaatac a aatacatgc | 600 |
| tcaatggttc aaagacaaca taagacagaa gatggaaaaa atagaaagga a ggaaagtat | 660 |
| taagggtagt ttctcatttc atcaatgctt gattttgaga tctcctttct g gtgcgatca | 720 |
| gctgacccgg cggcacaggt gatgccatcc ccgacgggaa | 760 |

<210> SEQ ID NO 26
<211> LENGTH: 508
<212> TYPE: DNA
<213> ORGANISM: Eucalyptus grandis

<400> SEQUENCE: 26

| | |
|---|---|
| gaattcggta cccggggtcg aaatcgataa gcttggatcc aaagaattcg g cacgagatc | 60 |
| actaaccatc tgcctttctt catcttcttt cttctgcttc tcctccgttt c ctcgtttcg | 120 |
| atatcgtgaa aggagtccgt cgacgacaat ggccgagaag agcaaggtcc t gatcatcgg | 180 |
| agggacgggc tacgtcggca agttcatcgt ggaagcgagt gcaaaagcag g catcccac | 240 |
| gttcgcgctg gttaggcaga gcacggtctc cgaccccgtc aagggccagc t cgtcgagag | 300 |
| cttcaagaac ttgggcgtca ctctgctcat cggtgatctg tacgatcatg a gagcttggt | 360 |
| gaaggcaatc aagcaagccg acgtggtgat atcgacagtg gggcacatgc a aatggcgga | 420 |
| tcagaccaaa gaatcgtcga cgccattaaa ggaagctggc aacgttaagg t ttgttggtt | 480 |
| ggttcatttg atctggtttg gggggtc | 508 |

<210> SEQ ID NO 27
<211> LENGTH: 495
<212> TYPE: DNA
<213> ORGANISM: Eucalyptus grandis

<400> SEQUENCE: 27

| | |
|---|---|
| gaattcggca cgaggttaat ggcagtgcag cctcaacacc acccaccttc c tccatctct | 60 |
| ctcctcccct tcttctttctc tgacttcaat ggcagccgac tccatgcttg c gttcagtat | 120 |

```
aagaggaagg tgggcagcc taaagggca ctgcgggtca ctgcatcaag c aataagaag    180 atcctcatca tgggaggcac ccgtttcatc ggtgtgtttt tgtcgagact a cttgtcaaa    240 gaaggtcatc aggtcacttt gtttaccaga ggaaaagcac ccatcactca a caattgcct    300 ggtgagtcgg acaaggactt cgctgatttt tcatccaaga tcctgcattt g aaaggagac    360 agaaaggatt ttgattttgt taaatctagt cttgctgcag aaggctttga c gttgtttat    420 gacattaacg gcgagaggcg gatgaagtcg caccaatttt ggatgcctgc c aaaccttga    480 accagtcaac tactg                                                       495

<210> SEQ ID NO 28
<211> LENGTH: 472
<212> TYPE: DNA
<213> ORGANISM: Eucalyptus grandis

<400> SEQUENCE: 28
gaattcggca cgagcataag ctctcccgta atcctcacat cacatggcga a gagcaaggt     60 cctcgtcgtt ggcggcactg gctacctcgg gcggaggttc gtgagggcga g cctggacca    120 gggccacccc acgtacgtcc tccagcgtcc ggagaccggc ctcgacattg a aagctcca    180 gacgctactg cgcttcaaga ggcgtggcgc ccaactcgtc gaggcctcgt t ctcagacct    240 gaggagcctc gtcgacgctg tgaggcgggt cgatgtcgtc gtctgtgcca t gtcggggt    300 ccacttccgg agccacaaca tcctgatgca gctcaagctc gtggaggcta t caagaagc    360 tggaaatgtc aagcggtttt tgccgtcaga gttcggaatg acccggccc t catgggtca    420 tgcaattgag ccgggaaggg tcacgttcga tgagaaatgg aggtgagaaa a g            472

<210> SEQ ID NO 29
<211> LENGTH: 396
<212> TYPE: DNA
<213> ORGANISM: Eucalyptus grandis

<400> SEQUENCE: 29
gaattcggca cgaggaggca cctcctcgaa acgaagaaga agaaggacga a ggacgaagg     60 agacgaaggc gagaatgagc gcggcgggcg gtgccgggaa ggtcgtgtgc g tgaccgggg    120 cgtccggtta catcgcctcg tggctcgtca agctcctcct ccagcgcggc t acaccgtca    180 aggccaccgt ccgcgatccg aatgatccaa aaaagactga acatttgctt g gacttgatg    240 gagcgaaaga tagacttcaa ctgttcaaag caaacctgct ggaagagggt t catttgatc    300 ctattgttga gggttgtgca ggcgttttt c aaactgcctc tccctttat c atgatgtca    360 aggatccgca ggcagaatta cttgatccgg ctgtaa                                396

<210> SEQ ID NO 30
<211> LENGTH: 592
<212> TYPE: DNA
<213> ORGANISM: Eucalyptus grandis

<400> SEQUENCE: 30
gaattcggca cgaggttgaa cctcccgtcc tcggctctgc tcggctcgtc a ccctcttcg     60 cgctcccgca tactccacca ccgcgtacag aagatgagct cggagggtgg g aaggaggat    120 tgcctcggtt gggctgcccg ggaccctct gggttcctct ccccctacaa a ttcacccgc    180 agggcgtgg gaagcgaaga cgtctcgatt aagatcacgc actgtggagt g tgctacgca    240 gatgtggctt ggactaggaa tgtgcaggga cactccaagt atcctctggt g ccagggcac    300
```

```
gagatagttg gaattgtgaa acaggttggc tccagtgtcc aacgcttcaa a gttggcgat      360 catgtggggg tgggaactta tgtcaattca tgcagagagt gcgagtattg c aatgacagg      420 ctagaagtcc aatgtgaaaa gtcggttatg acttttgatg gaattgatgc a gatggtaca      480 gtgacaaagg gaggatattc tagtcacatt gtcgtccatg aaaggtattg c gtcaggatt      540 ccagaaaact acccgatgga tctagcagcg catttgctct gtgctggatc a c            592
```

```
<210> SEQ ID NO 31
<211> LENGTH: 468
<212> TYPE: DNA
<213> ORGANISM: Eucalyptus grandis

<400> SEQUENCE: 31
gaattcggca cgagaactca tcttgaaatg tcattggagt catcatcctc t agtgagaag      60 aaacaaatgg gttccgccgg attcgaatcg gccacaaagc cgcacgccgt t tgcattccc     120 taccctgcac aaagccacat ggcgccatg ctcaagctag caaagctcct c catcacaag      180 ggcttccaca tctccttcgt caacaccgag ttcaaccacc ggcggctcgc c agggctcga     240 ggccccgagt tcacaaatgg aatgctgagc gactttcagt tcctgacaat c cccgatggt     300 cttcctcctt cggacttgga tgcgatccaa gacatcaaga tgctctgcga a tcgtccagg     360 aactatatgg tcagccccat caacgatctt gtatcgagcc tgggctcgaa c ccgagcgtc     420 cctccggtga cttgcatcaa tctcggatgg tttcatgaca ctcgtgac               468
```

```
<210> SEQ ID NO 32
<211> LENGTH: 405
<212> TYPE: DNA
<213> ORGANISM: Eucalyptus grandis

<400> SEQUENCE: 32
ctttactccg ccaagaagat ccaatcgcag ttttcgcaat tggcccatta c acaaatgcg      60 gtccatcttc atcgggaagt ctcttggcag aagaccggag ttgcatttcc t ggctggaca     120 agcaagcccc taactcagtg gtctatgtga gtccttggga catcgcctct g tgaacgagt     180 cggaattttc cgaaatagct ttaggtttag ccgatagcca gcagccattc t tgtgggtgg     240 ttcgacccgg gtcagtgagc ggctcggaac tcttagagaa tttgcccggt t gctttctgg     300 aggcattaca ggagaggggg aagattgtga atgggcgcc tcaacatgaa g tgctggctc      360 atcgggctgt cggagcgttt tggactcaca atggatggaa ctcca                    405
```

```
<210> SEQ ID NO 33
<211> LENGTH: 380
<212> TYPE: DNA
<213> ORGANISM: Eucalyptus grandis

<400> SEQUENCE: 33
ggcaaacacg cccgttttcg ttttactaag agaagatggt gagcgttgtg g ctggtagag      60 tcgagagctt gtcgagcagt ggcattcagt cgatcccgca ggagtatgtg a ggccgaagg     120 aggagctcac aagcattggc gacatcttcg aggaggagaa gaagcatgag g gccctcagg     180 tcccgaccat cgacctcgag gacatagcgt ctaaagaccc cgtggtgagg g agaggtgcc     240 acgaggagct caggaaggct gccaccgact ggggcgtcat gcacctcgtc a accatggga     300 tccccaacga cctgattgag cgtgtaaaga aggctggcga ggtgttcttc a acctcccga     360
```

```
tcgaggagaa ggacaagcat                                              380

<210> SEQ ID NO 34
<211> LENGTH: 305
<212> TYPE: DNA
<213> ORGANISM: Eucalyptus grandis

<400> SEQUENCE: 34
ttgtacccga agatctccgg gaccgttcga cggcgacatc gccgtcggcc g ggaacccgt    60 cgaggccgcc gccggaggcc ggggagaagc tggagtagcc gccgtagccg g agaaggcgc  120 cgtcgtggtc ggcggcggcg cgtggtgga cctcatcgcc gtccatgctg a aggcgtcga  180 aggaagcgga catggctggg ggatcgatcg accgatccga tcggccggag g atttcgaga  240 tcggagatgg agagatggaa atgaaagaga gagagagaga gagatccggt g gactggtgg  300 tgttt                                                               305

<210> SEQ ID NO 35
<211> LENGTH: 693
<212> TYPE: DNA
<213> ORGANISM: Eucalyptus grandis

<400> SEQUENCE: 35
gaattcggca cgagctaaga gaggagagga gaggagcaag atggcactag c aggagctgc    60 actgtcagga accgtggtga gctccccctt tgtgaggatg cagcctgtga a cagactcag   120 ggcattcccc aatgtgggtc aggccctgtt tggtgtcaac tctggccgtg g cagagtgac   180 tgccatggcc gcttacaagg tcaccctgct caccctgaa ggcaaagtcg a actcgacgt   240 ccccgacgat gtttacatct tggactacgc cgaggagcaa ggcatcgact t gccctactc   300 ctgccgtgcc ggctcttgct cctcctgcgc gggcaaggtc gtggcgggga g cgtcgacca   360 gagcgacggc agcttcctgg atgatgatca gattgaggaa ggttgggtcc t cacttgtgt   420 cgcctacccct aagtctgagg tcaccattga gacccacaag gaagaggagc t cactgcttg   480 aagctctcct atatttgctt ttgcataaat cagtctcact ctacgcaact t tctccactc   540 tctcccccct tcactacatg tttgttagtt cctttagtct cttccttttt t actgtacga   600 gggatgattt gatgttattc tgagtctaat gtaatggctt ttcttttttcc t atttctgta   660 tgaggaaata aaactcatgc tctaaaaaaa aaa                                693

<210> SEQ ID NO 36
<211> LENGTH: 418
<212> TYPE: DNA
<213> ORGANISM: Eucalyptus grandis

<400> SEQUENCE: 36
aggactttat tataagcatt gtaaaaagag tcaaactaat acatcgcaag a attgggtta    60 tccaataatc tacaaaaaga aaaagtttg atgcattgag atggtaactg c ttaattcaa   120 atgccttagt ttgaaaaatt aaccaactat taaaattaat gatgatgaat a tggattatg   180 tgtgaaaaac tatatagact taaaattgac tcagaagaca ttcttttctt c ttattttat   240 gatatgatga attcggtcta aacaggcaaa tggtgtcaaa cggaagtcg g caaaactct   300 tcctcggcag tgactaccgg gcgggcgatg atgcggatcc gggggccggg t cgctggaga   360 acatcccgca cggaccggtc cacgtttggt gcggtgacaa caggcagccc a acctgga    418

<210> SEQ ID NO 37
```

<211> LENGTH: 777
<212> TYPE: DNA
<213> ORGANISM: Eucalyptus grandis

<400> SEQUENCE: 37

| | |
|---|---|
| gaattcggca cgagcataca actacactgc gacgccgccg cagaacgcga g cgtgccgac | 60 |
| catgaacggc accaaggtct accggttgcc gtataacgct acgtccagc t cgttttaca | 120 |
| ggacaccggg ataatcgcgc cggagaccca ccccatccat ctgcacggat t caacttctt | 180 |
| cggtgtgggc aaaggagtgg ggaattatga cccaaagaag gatcccaaga a gttcaatct | 240 |
| ggttgaccca gtggagagga acaccattgg aatcccatct ggtggatgga t agccatcag | 300 |
| attcacagca gacaatccag gagtttggtt cctgcactgc catctggaag t gcacacaac | 360 |
| ttggggactg aagatggcat tcttggtgga caatgggaag gggcctaaag a gaccctgct | 420 |
| tccacctcca gtgatcttc caaaatgttg atcatttgat catgaggacg a caagcgatt | 480 |
| actaatgaca ccaagttagt ggaatcttct ctttgaaaaa gaagaagaag a gcaagaaga | 540 |
| ataagaaaga tgaggagaga agccatgaaa gatttgacca agaagagaga g ggcaataaa | 600 |
| ccaaagagac ccttgagatc acgacatccc gcaattgttt ctagagtaat a gaaggattt | 660 |
| actccgacac tgctacaata aattaaggaa gacaaggaat ttggttttt t cattggagg | 720 |
| agtgtaattt gtttttggc aagctcatca catgaatcac atggaaaaaa a aaaaaa | 777 |

<210> SEQ ID NO 38
<211> LENGTH: 344
<212> TYPE: DNA
<213> ORGANISM: Eucalyptus grandis

<400> SEQUENCE: 38

| | |
|---|---|
| atatgttcag aatttcaaat gtgggaatgt caacctcctt gaacttcaga a ttcagggcc | 60 |
| atacgttgaa gctagtcgag gttgaaggat ctcacaccgt ccagaacatg t atgattcaa | 120 |
| tcgatgttca cgtgggccaa tccatggctg tcttagtgac cttaaatcag c ctccaaagg | 180 |
| actactacat tgtcgcatcc acccggttca ccaagacggt tctcaatgca a ctgcagtgc | 240 |
| tacactacac caactcgctt accccagttt ccgggccact accagctggt c caacttacc | 300 |
| aaaaacattg gtccatgaag caagcaagaa caatcaggtg gaac | 344 |

<210> SEQ ID NO 39
<211> LENGTH: 341
<212> TYPE: DNA
<213> ORGANISM: Eucalyptus grandis

<400> SEQUENCE: 39

| | |
|---|---|
| gccgcaactg caattctctt cgtaaaacat gacggctgtc ggcaaaacct c tttcctctt | 60 |
| gggagctctc ctcctcttct ctgtggcggt gacattggca gatgcaaaag t ttactacca | 120 |
| tgattttgtc gttcaagcga ccaaggtgaa gaggctgtgc acgacccaca a caccatcac | 180 |
| ggtgaacggg caattcccgg gtccgacttt ggaagttaac gacggcgaca c cctcgttgt | 240 |
| caatgtcgtc aacaaagctc gctacaacgt caccattcac tggcacggcg t ccggcaggt | 300 |
| gagatctggt tgggctgatg gggcggaatt tgtgactcaa t | 341 |

<210> SEQ ID NO 40
<211> LENGTH: 358
<212> TYPE: DNA
<213> ORGANISM: Eucalyptus grandis

<400> SEQUENCE: 40

```
gaattcggca cgagatatgt tcagaatttc aaatgtggga atgtcaacct c cttgaactt    60 cagaattcag ggccatacgt tgaagctagt cgaggttgaa ggatctcaca c cgtccagaa   120 catgtatgat tcaatcgatg ttcacgtggg ccaatccatg gctgtcttag t gacctaaaa   180 tcagcctcca aaggactact acattgtcgc atccacccgg ttcaccaaga c ggttctcaa   240 tgcaactgca gtgctacact acaccaactc gcttacccca gtttccgggc c actaccagc   300 tggtccaact taccaaaaac attggtccat gaagcaagca agaacaatca g gtggaac     358

<210> SEQ ID NO 41
<211> LENGTH: 409
<212> TYPE: DNA
<213> ORGANISM: Eucalyptus grandis

<400> SEQUENCE: 41
atcaagagtt tgagtctaaa ccttgtctaa tcctctctcg catagtcatt t ggagacgaa    60 tgctgatcgg ccgcagctgc attctcttcg taaaacatga cggctgtcgg c aaaacctct   120 ttcctcttgg gagctctcct cctcttctct gtggcggtga cattggcaga t gcaaaagtt   180 tactaccatg attttgtcgt tcaagcgacc aaggtgaaga ggctgtgcac g acccacaac   240 accatcacgg tgaacgggca attcccgggt ccgactttgg aagttaacga c ggcgacacc   300 ctcgttgtca atgtcgtcaa caaagctcgc tacaacgtca ccattcactg g cacggcgtc   360 cggcaggtga gatctggttg ggctgatggg gcggaatttg tgactcaat              409

<210> SEQ ID NO 42
<211> LENGTH: 515
<212> TYPE: DNA
<213> ORGANISM: Eucalyptus grandis

<400> SEQUENCE: 42
ctctctctct ctctctctct gtgtgttcat tctcgttgag ctcgtggtcg c ctcccgcca    60 tggatccgca caagtaccgt ccatccagtg ctttcaacac ttctttctgg a ctacgaact   120 ctggtgctcc tgtctggaac aataactctt cgttgactgt tggaagcaga g gtccaattc   180 ttcttgagga ttatcacctc gtggagaaac ttgccaactt tgataggag a ggattccag   240 agcgtgtggt gcatgccaga ggagccagtg caaagggatt ctttgaggtc a ctcatgaca   300 tttcccagct tacctgtgct gatttccttc gggcaccagg agttcaaaca c ccgtgattg   360 tccgtttctc cactgtcatc cacgaaaggg gcagccctga aaccctgagg g accctcgag   420 gttttgctgt gaagttctac acaagagagg gtaactttga tctggtggga a acaatttcc   480 ctgtcttctt tgtccgtaat gggataaaatt ccccg                            515

<210> SEQ ID NO 43
<211> LENGTH: 471
<212> TYPE: DNA
<213> ORGANISM: Eucalyptus grandis

<400> SEQUENCE: 43
gaattcggca cgaggctccc tctcgtactg ccatactcct gggacgggat t cggataggg    60 atttgcggcg atccatttct cgattcaagg ggaagaatca tggggaagtc c tacccgacc   120 gtaagccagg agtacaagaa ggctgtcgag aaatgcaaga agaagttgag a ggcctcatc   180 gctgagaaga gctgcgctcc gctcatgctc cgcatcgcgt ggcactccgc c ggtaccttc   240 gatgtgaaga cgaagaccgg aggcccgttc gggaccatga agcacgccgc g gagctcagc   300
```

-continued

```
cacggggcca acagcgggct cgacgttgcc gatcaggtct tgcagccgat c aaggatcag    360 ttccccgtca tcacttatgc tgatttctac cagctggctg cgtcgttgc t gtggaagtt    420 actggtggac ctgaagttgc ttttcacccg aagagaggc aaaccacaac c              471
```

<210> SEQ ID NO 44
<211> LENGTH: 487
<212> TYPE: DNA
<213> ORGANISM: Eucalyptus grandis

<400> SEQUENCE: 44

```
gaattcggca cgagctccca cttctgtctc gccaccatta ctagcttcaa a gcccagatc    60 tcagtttcgt gctctcttcg tcatctctgc ctcttgccat ggatccgtac a agtatcgcc   120 cgtccagcgc ttacgattcc agcttttgga caaccaacta cggtgctccc g tctggaaca  180 atgactcatc gctgactgtt ggaactagag gtccgattct cctggaggac t accatctga  240 ttgagaaact tgccaacttc gagagagaga ggattcctga gcgggtggtc c atgcacggg  300 gagccagcgc gaaagggttc ttcgaggtca cccacgacat ctctcacttg a cctgtgctg  360 atttcctccg ggctcctgga gtccagacgc ccgtaatcgt ccgtttctcc a ccgtcatcc  420 acgagcgcgg cagcccgaac ctcagggacc ctcgtggttt tgcagtgaag t tctacacca  480 gagaggg                                                             487
```

<210> SEQ ID NO 45
<211> LENGTH: 684
<212> TYPE: DNA
<213> ORGANISM: Pinus radiata

<400> SEQUENCE: 45

```
gaattcctgc agcccggggg atccactagt tctagagcgg ccgccaccgc g gtggagctc    60 gcgcgcctgc aggtcgacac tagtggatcc aaagaattcg gcacgaggcc c gacggccac   120 ttgttggacg ccatggaagc tctccggaaa gccgggattc tggaaccgtt t aaactgcag   180 cccaaggaag gactggctct cgtcaacggc acagcgtgg gatccgccgt g gccgcgtcc   240 gtctgttttg acgccaacgt gctgggcgtg ctggctgaga ttctgtctgc g ctcttctgc   300 gaggtgatgc aagggaaacc ggagttcgta gatccgttaa cccaccagtt g aagcaccac   360 ccagggcaga tcgaagccgc ggccgtcatg gagttcctcc tcgacggtag c gactacgtg   420 aaagaagcag cgcggcttca cgagaaagac ccgttgagca accgaaaca a gaccgctac    480 gctctgcgaa catcgccaca gtggttgggg cctccgatcg aagtcatccg c gctgctact   540 cactccatcg agcgggagat caattccgtc aacgacaatc cgttaatcga t gtctccagg   600 gacatggctc tccacggcgg caacttccag ggaacaccca tcggagtttc c atggacaac   660 atgcgaatct ctttggcagc cgtc                                           684
```

<210> SEQ ID NO 46
<211> LENGTH: 418
<212> TYPE: DNA
<213> ORGANISM: Pinus radiata

<400> SEQUENCE: 46

```
gaattcggca cgaggacaag gtcataggcc ctctcttcaa atgcttggat g gtggaaag    60 gaactcctgg cccattctga aataaataat cttccaagat cgcctttata c aacgactgc   120 tatgatttga gtcctcggat ctttttgttg atgcagttgt ttaccgatct g gaatttgat   180 tggtcataaa gcttgatttt gttttctttt cttttgtttt atactgctgg a tttgcatcc   240
```

```
cattggattt gccagaaata tgtaaggtg gcagatcatt tgggtgatct g aaacatgta    300 aaagtggcgg atcatttggg tagcatgcag atcagttggg tgatcgtgta c tgctttcac   360 tattacttac atatttaaag atcgggaata aaaacatgat tttaattgaa a aaaaaaa    418
```

<210> SEQ ID NO 47
<211> LENGTH: 479
<212> TYPE: DNA
<213> ORGANISM: Pinus radiata

<400> SEQUENCE: 47

```
gatatcccaa cgaccgaaaa cctgtatttt cagggcgcca tggggatccg g aattcggca    60 cgagcaagga agaaaatatg gttgcagcag cagaaattac gcaggccaat g aagttcaag   120 ttaaaagcac tgggctgtgc acggacttcg gctcgtctgg cagcgatcca c tgaactggg   180 ttcgagcagc aaggccatg gaaggaagtc actttgaaga agtgaaagcg a tggtggatt   240 cgtatttggg agccaaggag atttccattg aagggaaatc tctgacaatc t cagacgttg   300 ctgccgttgc tcgaagatcg caagtgaaag tgaaattgga tgctgcggct g ccaaatcta   360 gggtcgagga gagttcaaac tgggttctca cccagatgac caagggacg g atacctatg   420 gtgtcactac tggtttcgga gccacttctc acaggagaac gaaccaggga g ccgagctt   479
```

<210> SEQ ID NO 48
<211> LENGTH: 1785
<212> TYPE: DNA
<213> ORGANISM: Pinus radiata

<400> SEQUENCE: 48

```
tatcgataag cttgatatcg aattcctgca gcccggggga tccactagtt c tagagcggc    60 cgccaccgcg gtggagctcg cgcgcctgca ggtcgacact agtggatcca a agaattcgg   120 cacgaggttg caggtcgggg atgatttgaa tcacagaaac ctcagcgatt t gccaagaa   180 atatggcaaa atctttctgc tcaagatggg ccagaggaat cttgtggtag t ttcatctcc   240 cgatctcgcc aaggaggtcc tgcacaccca gggcgtcgag tttgggtctc g aacccggaa   300 cgtggtgttc gatatcttca cgggcaaggg gcaggacatg gtgttcaccg t ctatggaga   360 tcactggaga aagatgcgca ggatcatgac tgtgcctttc tttacgaata a agttgtcca   420 gcactacaga ttcgcgtggg aagacgagat cagccgcgtg gtcgcggatg t gaaatcccg   480 cgccgagtct tccacctcgg gcattgtcat ccgtaggcgc ctccagctca t gatgtataa   540 tattatgtat aggatgatgt tcgacaggag attcgaatcc gaggacgacc c gcttttcct   600 caagctcaag gccctcaacg gagagcgaag tcgattggcc cagagctttg a gtacaatta   660 tggggatttc attcccattc ttaggcccttt cctcagaggt tatctcagaa t ctgcaatga   720 gattaaagag aaacggctct ctcttttcaa ggactacttc gtggaagagc g caagaagct   780 caacagtacc aagactagta ccaacaccgg gggagctcaa gtgtgcaatg g accatattt   840 tagatgctca ggacaaggga gagatcaatg aggataatgt tttgtacatc g ttgagaaca   900 tcaacgttgc agcaattgag acaacgctgt ggtcgatgga atgggaata g cggagctgg   960 tgaaccacca ggacattcag agcaaggtgc gcgcagagct ggacgctgtt c ttggaccag  1020 gcgtgcagat aacggaacca gacacgacaa ggttgcccta ccttcaggcg g ttgtgaagg  1080 aaacccttcg tctccgcatg gcgatcccgt tgctcgtccc ccacatgaat c tccacgacg  1140 ccaagctcgg gggctacgat attccggcag agagcaagat cctggtgaac g cctggtggt  1200
```

-continued

| | | | | |
|---|---|---|---|---|
| tggccaacaa | ccccgccaac | tggaagaacc | ccgaggagtt | ccgccccgag c ggttcttcg | 1260 |
| aggaggagaa | gcacaccgaa | gccaatggca | acgacttcaa | attcctgcct t cggtgtggg | 1320 |
| gaggaggagc | tgcccgggaa | tcattctggc | gctgcctctc | ctcgcactct c catcggaag | 1380 |
| acttgttcag | aacttccacc | ttctgccgcc | gcccgggcag | agcaaagtgg a tgtcactga | 1440 |
| gaagggcggg | cagttcagcc | ttcacattct | caaccattct | ctcatcgtcg c caagcccat | 1500 |
| agcttctgct | taatcccaac | ttgtcagtga | ctggtatata | aatgcgcgca c ctgaacaaa | 1560 |
| aaacactcca | tctatcatga | ctgtgtgtgc | gtgtccactg | tcgagtctac t aagagctca | 1620 |
| tagcacttca | aaagtttgct | aggatttcaa | taacagacac | cgtcaattat g tcatgtttc | 1680 |
| aataaaagtt | tgcataaatt | aaatgatatt | tcaatatact | attttgactc t ccaccaatt | 1740 |
| ggggaatttt | actgctaaaa | aaaaaaaaaa | aaaaaaaaaa | aaaaa | 1785 |

<210> SEQ ID NO 49
<211> LENGTH: 475
<212> TYPE: DNA
<213> ORGANISM: Pinus radiata

<400> SEQUENCE: 49

| | | | | |
|---|---|---|---|---|
| gaattcggca | cgagatttcc | atggacgatt | ccgtttggct | tcaattcgtt t cctctggct | 60 |
| gtcctcgtcc | tcgttttcct | tgttcttcct | ccgacttttt | ctctggaagc t atggcgtaa | 120 |
| taggaacctg | ccgccaggac | ccccggcatg | gccgatcgta | gggaacgtcc t tcagattgg | 180 |
| attttccagc | ggcgcgttcg | agacctcagt | gaagaaattc | catgagagat a cggtccaat | 240 |
| attcactgtg | tggctcggtt | cccgccctct | gctgatgatc | accgaccgcg a gcttgccca | 300 |
| cgaggcgctc | gtacagaagg | gctccgtctt | cgctgaccgc | ccgccgccc t cggatgca | 360 |
| gaaaatcttc | agtagcaacc | agcacaacat | cacttcggct | gaatacggcc c gctgtggcg | 420 |
| gagccttcgc | aggaatctgg | ttaaagaagc | cctgagactt | cggcgatgaa g gctt | 475 |

<210> SEQ ID NO 50
<211> LENGTH: 801
<212> TYPE: DNA
<213> ORGANISM: Pinus radiata

<400> SEQUENCE: 50

| | | | | |
|---|---|---|---|---|
| gctccaccga | cggtggacgg | tccgctactc | agtaactgag | tgggatcccc c gggctgaca | 60 |
| ggcaattcga | tttagctcac | tcattaggca | ccccaggctt | tacactttat g cttccggct | 120 |
| cgtatgttgt | gtggaattgt | gagcggataa | caatttcaca | caggaaacag c tatgaccat | 180 |
| gattacgcca | agcgcgcaat | taaccctcac | taaagggaac | aaaagctgga g ctccaccgc | 240 |
| ggtggcggcc | gctctagaac | tagtggatcc | aaagaattcg | gcacgagacc c agtgaccct | 300 |
| caggcctgag | agatttcttg | aggaagatgt | tgatattaag | ggccatgatt a caggctact | 360 |
| gccattcggt | gcagggcgca | ggatctgccc | tggtgcacaa | ttgggtatta a tttagttca | 420 |
| gtctatgttg | ggacacctgc | ttcatcattt | cgtatgggca | cctcctgagg g aatgaaggc | 480 |
| agaagacata | gatctcacag | agaatccagg | gcttgttact | tcatggcca a gcctgtgca | 540 |
| ggccattgct | attcctcgat | tgcctgatca | tctctacaag | cgacagccac t caattgatc | 600 |
| aattgatctg | atagtaagtt | tgaattttgt | tttgatacaa | aacgaaataa c gtgcagttt | 660 |
| ctccttttcc | atagtcaaca | tgcagctttc | tttctctgaa | gcgcatgcag c tttctttct | 720 |
| ctgaagccca | acttctagca | agcaataact | gtatatttta | gaacaaatac c tattcctca | 780 |
| aattgagtat | ttctctgtag | g | | | 801 |

<210> SEQ ID NO 51
<211> LENGTH: 744
<212> TYPE: DNA
<213> ORGANISM: Pinus radiata

<400> SEQUENCE: 51

| | | | | | |
|---|---|---|---|---|---|
| gggcccccct | tcgaggtgga | cactagtgga | tccaaagaat | tcggcacgag g | ttttatctg | 60 |
| aaggacgctg | tgcttgaagg | ctcccagcca | ttcaccaaag | cccatggaat g | aatgcgttc | 120 |
| gagtacccgg | ccatcgatca | gagattcaac | aagattttca | acagggctat g | tctgagaat | 180 |
| tctaccatgt | tgatgaacaa | gattttggat | acttacgagg | gttttaagga g | gttcaggag | 240 |
| ttggtggatg | tgggaggagg | tattgggtcg | actctcaatc | tcatagtgtc t | aggtatccc | 300 |
| cacatttcag | gaatcaactt | cgacttgtcc | catgtgctgg | ccgatgctcc t | cactaccca | 360 |
| gctgtgaaac | atgtgggtgg | agacatgttt | gatagtgtac | caagtggcca a | gctattttt | 420 |
| atgaagtgga | ttctgcatga | ttggagcgat | gatcattgca | ggaagctttt g | aagaattgt | 480 |
| cacaaggcgt | tgccagagaa | ggggaaggtg | attgcggtgg | acaccattct c | ccagtggct | 540 |
| gcagagacat | ctccttatgc | tcgtcaggga | tttcatacag | atttactgat g | ttggcatac | 600 |
| aacccagggg | gcaaggaacg | cacagagcaa | gaatttcaag | atttagctaa g | gagacggga | 660 |
| tttgcaggtg | gtgttgaacc | tgtatgttgt | gtcaatggaa | tgtgggtaat g | gaattcctg | 720 |
| cagcccgggg | gatccactag | ttct | | | | 744 |

<210> SEQ ID NO 52
<211> LENGTH: 426
<212> TYPE: DNA
<213> ORGANISM: Pinus radiata

<400> SEQUENCE: 52

| | | | | | |
|---|---|---|---|---|---|
| gtggccctgg | aagtagtgtg | cgcgacatgg | attccttgaa | tttgaacgag t | ttatgttgt | 60 |
| ggtttctctc | ttggcttgct | ctctacattg | gatttcgtta | tgttttgaga t | cgaacttga | 120 |
| agctcaagaa | gaggcgcctc | ccgccgggcc | atcgggatg | gccagtggtg g | gaagtctgc | 180 |
| cattgctggg | agcgatgcct | cacgttactc | tctacaacat | gtataagaaa t | atggccccg | 240 |
| ttgtctatct | caaactgggg | acgtccgaca | tggttgtggc | ctccacgccc g | ctgcagcta | 300 |
| aggcgtttct | gaagactttg | gatataaact | tctccaaccg | gccgggaaat g | caggagcca | 360 |
| cgtacatcgc | ctacgattct | caggacatgg | tgtgggcagc | gtatggagga c | ggtggaaga | 420 |
| tggagc | | | | | | 426 |

<210> SEQ ID NO 53
<211> LENGTH: 562
<212> TYPE: DNA
<213> ORGANISM: Pinus radiata

<400> SEQUENCE: 53

| | | | | | |
|---|---|---|---|---|---|
| cagttcgaaa | ttaacctcac | taaagggaac | aaaagctgga | gttcgcgcgc c | tgcaggtcg | 60 |
| acactagtgg | atccaaagaa | ttcggcacga | gctttgaggc | aacctacatt c | attgaatcc | 120 |
| caggatttct | tcttgtccaa | acaggtttaa | ggaaatggca | ggcacaagtg t | tgctgcagc | 180 |
| agaggtgaag | gctcagacaa | cccaagcaga | ggagccggtt | aaggttgtcc g | ccatcaaga | 240 |
| agtgggacac | aaaagtcttt | tgcagagcga | tgccctctat | cagtatatat t | ggaaacgag | 300 |
| cgtgtaccct | cgtgagcccg | agccaatgaa | ggagctccgc | gaagtgactg c | caagcatcc | 360 |

-continued ctggaacctc atgactactt ctgccgatga gggtcaattt ctgggcctcc t gctgaagct    420 cattaacgcc aagaacacca tggagattgg ggtgtacact ggttactcgc t tctcagcac    480 agcccttgca ttgcccgatg atggaaagat tctagccatg acatcaaca g agagaacta    540 tgatatcgga ttgcctataa tt                                              562

<210> SEQ ID NO 54
<211> LENGTH: 1074
<212> TYPE: DNA
<213> ORGANISM: Pinus radiata

<400> SEQUENCE: 54
tcgtgccgct cgatcctcac aggcccttt tatttccctg gtgaacgata c gatgggctc     60 gcacgctgag aatggcaacg gggtggaggt tgttgatcca acggacttaa c tgacatcga   120 gaatgggaaa ccaggttatg acaagcgtac gctgcctgcg gactggaagt t tggagtgaa   180 gcttcaaaac gttatggaag aatccattta caagtacatg ctggaaacat t cacccgcca   240 tcgagaggac gaggcgtcca aggagctctg gaacgaaca tggaacctga c acagagagg    300 ggagatgatg acattgccag atcaggtgca gttcctgcgc ttgatggtaa a gatgtcagg   360 tgctaaaaag gcattggaga tcggagtttt cactggctat tcattgctca a tatcgctct   420 cgctcttcct tctgatggca aggtggtagc tgtggatcca ggagatgacc c caaatttgg   480 ctggccctgc ttcgttaagg ctggagttgc agacaaagtg gagatcaaga a aactacagg   540 gttggactat ttgattccc ttattcaaaa ggggagaag gattgcttcg a ctttgcatt   600 cgtggacgca gacaaagtga actacgtgaa ctatcatcca cggctgatga a gttagtgcg   660 cgtgggggggc gtcataattt acgacgacac cctctggttt ggtctggtgg g aggaaagga   720 tccccacaac ctgcttaaga atgattacat gaggacttct ctggagggta t caaggccat   780 caactccatg gtagccaacg accccaactt ggaggtcgcc acagtcttta t gggatatgg   840 tgtcactgtt tgttaccgca ctgcttagtt agctagtcct ccgtcattct g ctatgtatg   900 tatatgataa tggcgtcgat ttctgatata ggtggttttt caatgtttct a tcgtcatgt   960 tttctgttta gccagaatgt ttcgatcgtc atggtttctg ttaaagccag a ataaaatta  1020 gccgcttgca gttcaaaaaa aaaaaaaaaa aaaaactcga gactagttct c ttc         1074

<210> SEQ ID NO 55
<211> LENGTH: 1075
<212> TYPE: DNA
<213> ORGANISM: Pinus radiata

<400> SEQUENCE: 55
tcggagctct cgaatcctca caggcccttt ttatttccct ggtgaacgat a cgatgggct    60 cgcacgctga gaatggcaac ggggtggagg ttgttgatcc aacggactta a ctgacatcg   120 aagaatggga aaccaggtta tgacaagcgt cgctgcctgc ggactggaag t ttggagtga   180 agcttcaaaa cgttatggaa gaatccattt acaagtacat gctggaaaca t tcacccgcc   240 atcgagagga cgaggcgtcc aaggagctct ggaacgaac atggaacctg a cacagagag   300 gggagatgat gacattgcca gatcaggtgc agttcctgcg cttgatggta a agatgtcag   360 gtgctaaaaa ggcattggag atcggagttt tcactggcta ttcattgctc a atatcgctc   420 tcgctcttcc ttctgatggc aaggtggtag ctgtggatcc aggagatgac c ccaaatttg   480 gctggccctg cttcgttaag gctggagttg cagacaaagt ggagatcaag a aaactacag   540 ggttggacta tttggattcc cttattcaaa aggggagaa ggattgcttc g actttgcat   600

```
tcgtggacgc agacaaagtg aactacgtga actatcatcc acggctgatg a agttagtgc    660 gcgtgggggg cgtcataatt tacgacgaca ccctctggtt tggtctggtg g gaggaaagg   720 atccccacaa cctgcttaag aatgattaca tgaggacttc tctggagggt a tcaaggcca   780 tcaactccat ggtagccaac gaccccaact tggaggtcgc cacagtcttt a tgggatatg   840 gtgtcactgt ttgttaccgc actgcttagt tagctagtcc tccgtcattc t gctatgtat   900 gtatatgata tggcgtcga tttctgatat aggtggtttt tcaatgtttc t atcgtcatg    960 ttttctgttt agccagaatg tttcgatcgt catggttttct gttaaagcca g aataaaatt   1020 agccgcttgc agttcaaaaa aaaaaaaaaa aaaaaactcg agactagttc t cttc        1075
```

<210> SEQ ID NO 56
<211> LENGTH: 1961
<212> TYPE: DNA
<213> ORGANISM: Pinus radiata

<400> SEQUENCE: 56

```
gtttttccgcc attttttcgcc tgtttctgcg gagaatttga tcaggttcgg a ttgggattg    60 aatcaattga aaggttttta ttttcagtat ttcgatcgcc atggccaacg g aatcaagaa   120 ggtcgagcat ctgtacagat cgaagcttcc cgatatcgag atctccgacc a tctgcctct   180 tcattcgtat tgctttgaga gagtagcgga attcgcagac agaccctgtc t gatcgatgg   240 ggcgacagac agaacttatt gcttttcaga ggtggaactg attctcgca a ggtcgctgc    300 cggtctggcg aagctcgggt tgcagcaggg gcaggttgtc atgcttctcc t tccgaattg   360 catcgaattt gctttgtgt tcatgggggc ctctgtccgg ggcgccattg t gaccacggc   420 caatcctttc tacaagccgg gcgagatcgc caaacaggcc aaggccgcgg g cgcgcgcga   480 tcatagttac cctggcagct tatgtggaga actggccga tctgcagagc c acgatgtgc    540 tcgtcatcac aatcgatgat gctcccaagg aaggttgcca acatatttcc g ttctgaccg   600 aagccgacga aacccaatgc ccggccgtga caatccaccc ggacgatgtc g tggcgttgc   660 cctattcttc cggaaccacg gggctcccca agggcgtgat gttaacgcac a aaggcctgg   720 tgtccagcgt tgcccagcag gtcgatggtg aaaatcccaa tctgtatttc c attccgatg   780 acgtgatact ctgtgtcttg cctctttttcc acatctattc tctcaattcg g ttctcctct   840 gcgcgctcag agccggggct gcgacccctga ttatgcagaa attcaacctc a cgacctgtc   900 tggagctgat tcagaaatac aaggttaccg ttgccccaat tgtgcctcca a ttgtcctgg   960 acatcacaaa gagccccatc gtttcccagt acgatgtctc ggccgtccgg a taatcatgt  1020 ccggcgctgc gcctctcggg aaggaactcg aagatgccct cagagagcgt t tcccaagg   1080 ccattttcgg gcagggctac ggcatgacag aagcaggccc ggtgctggca a tgaacctag   1140 ccttcgcaaa gaatcctttc cccgtcaaat ctggctcctg cggaacagtc g tccggaacg   1200 ctcaaataaa gatcctcgat acagaaactg gcgagtctct cccgcacaat c aagccggcg   1260 aaatctgcat ccgcggaccc gaaataatga aggatatat taacgacccg g aatccacgg   1320 ccgctacaat cgatgaagaa ggctggctcc acacaggcga cgtcgggtac a ttgacgatg   1380 acgaagaaat cttcatagtc gacagagtaa aggagattat caaatataag g cttccagg    1440 tggctcctgc tgagctggaa gctttacttg ttgctcatcc gtcaatcgct g acgcagcag   1500 tcgttcctca aaagcacgag gaggcgggcg aggttccggt ggcgttcgtg g tgaagtcgt   1560 cggaaatcag cgagcaggaa atcaaggaat tcgtggcaaa gcaggtgatt t tctacaaga   1620
```

| | | | | |
|---|---|---|---|---|
| aaatacacag | agtttacttt | gtggatgcga | ttcctaagtc gccgtccggc | a agattctga | 1680 |
| gaaaggattt | gagaagcaga | ctggcagcaa | atgaaaatg aatttccata | t gattctaag | 1740 |
| attcctttgc | cgataattat | aggattcctt | tctgttcact tctatttata | t aataaagtg | 1800 |
| gtgcagagta | agcgccctat | aaggagagag | agagcttatc aattgtatca | t atggattgt | 1860 |
| caacgcccta | cactcttgcg | atcgctttca | atatgcatat tactataaac | g atatatgtt | 1920 |
| ttttttataa | atttactgca | cttctcgttc | aaaaaaaaaa a | | 1961 |

<210> SEQ ID NO 57
<211> LENGTH: 1010
<212> TYPE: DNA
<213> ORGANISM: Pinus radiata

<400> SEQUENCE: 57

| | | | | |
|---|---|---|---|---|
| gacaaacttg | gtcgtttgtt | taggttttgc | tgcaggtgaa cactaatatg | g aaggccaga | 60 |
| ttgcagcatt | aagcaaagaa | gatgagttca | ttttcacag ccctttttcct | g cagtacctg | 120 |
| ttccagagaa | tataagtctt | ttccagtttg | ttctggaagg tgctgagaaa | t accgtgata | 180 |
| aggtggccct | cgtggaggcc | tccacaggga | aggagtacaa ctatggtcag | g tgatttcgc | 240 |
| tcacaaggaa | tgttgcagct | gggctcgtgg | acaaaggcat tcaaaagggc | g atgttgtat | 300 |
| ttgttctgct | tccaaatatg | gcagaatacc | ccattattgt gctgggaata | a tgttggccg | 360 |
| gcgcagtgtt | ttctggggca | aatccttctg | cacacatcaa tgaagttgaa | a aacatatcc | 420 |
| aggattctgg | agcaaagatt | gttgtgacag | ttgggtctgc ttatgagaag | g tgaggcaag | 480 |
| tgaaactgcc | tgttattatt | gcagataacg | agcatgtcat gaacacaatt | c cattgcagg | 540 |
| aaattttga | gagaaactat | gaggccgcag | ggccttttgt acaaatttgt | c aggatgatc | 600 |
| tgtgtgcact | cccttattcc | tctggcacca | caggggcctc taaaggtgtc | a tgctcactc | 660 |
| acagaaatct | gattgcaaat | ctgtgctcta | gcttgtttga tgtccatgaa | t ctcttgtag | 720 |
| gaaatttcac | cacgttgggg | ctgatgccat | tctttcacat atatggcatc | a cgggcatct | 780 |
| gttgcgccac | tcttcgcaac | ggaggcaagg | tcgtggtcat gtccagattc | g atctccgac | 840 |
| actttatcag | ttcttttgatt | acttatgagg | tcaacttcgc gcctattgtc | c cgcctataa | 900 |
| tgctctccct | ccggtttaaa | aatcctatcg | ttaacgagtt cgatctcagc | c gcttgaaac | 960 |
| tccaaagctg | ttcatgactg | cggctgctcc | actggcgccg gatctactgc | | 1010 |

<210> SEQ ID NO 58
<211> LENGTH: 741
<212> TYPE: DNA
<213> ORGANISM: Pinus radiata

<400> SEQUENCE: 58

| | | | | |
|---|---|---|---|---|
| gaattcggca | cgagaccatt | tccagctaat | attggcatag caattggtca | t tctatcttt | 60 |
| gtcaaaggag | atcaaacaaa | ttttgaaatt | ggacctaatg gtgtggaggc | t agtcagcta | 120 |
| tacccagatg | tgaaatatac | cactgtcgat | gagtacctca gcaaatttgt | g tgaagtatg | 180 |
| cgagattctc | ttccacatgc | ttcagagata | cataacagtt tcaatcaatg | t ttgtcctag | 240 |
| gcatttgcca | aattgtgggt | tataatcctt | cgtaggtgtt tggcagaaca | g aacctcctg | 300 |
| tttagtatag | tatgacgagc | taggcactgc | agatccttca cacttttctc | t tccataaga | 360 |
| aacaaatact | cacctgtggt | ttgttttctt | tctttctgga actttggtat | g gcaataatg | 420 |
| tctttggaaa | ccgcttagtg | tggaatgcta | agtactagtg tccagagttc | t aagggagtt | 480 |
| ccaaaatcat | ggctgatgtg | aactggttgt | tccagagggt gtttacaacc | a acagttgtt | 540 |

```
cagtgaataa ttttgttaga gtgtttagat ccatctttac aaggctattg a gtaaggttg    600 gtgttagtga acggaatgat gtcaaatctt gatgggctga ctgactctct t gtgatgtca    660 aatcttgatg gattgtgtct ttttcaatgg taaaaaaaaa aaaaaaaaaa a aaaaaaaa    720 aaaaaaaaaa aaaaaaaaaa a                                              741
```

<210> SEQ ID NO 59
<211> LENGTH: 643
<212> TYPE: DNA
<213> ORGANISM: Pinus radiata

<400> SEQUENCE: 59

```
ctcatctcgg agttgcaggc tgcagctttt ggcccaaagc atgatatcag a tcaaacgac    60 gcagatgaag caaacggatc aaacagtttg cgttactgga gcagcgggtt t cattgcctc   120 atggcttgtc aagatgctcc tcatcagagg ttacactgtc agagcagcag t tcggaccaa   180 cccagctgat gataggtgga agtatgagca tctgcgagag ttggaaggag c aaaagagag   240 gcttgagctt gtgaaagctg atattctcca ttaccagagc ttactcacag t catcagagg   300 ttgccacggt gtctttcaca tggcttcagt tctcaatgat gaccctgagc a agtgataga   360 accagcagtc aagggacga ggaatgtgat ggaggcctgc gcagaaactg g ggtgaagcg   420 cgttgttttt acttcttcca tcggcgcagt ttacatgaat cctcatagag a cccgctcgc   480 gattgtccat gatgactgct ggagcgattt gactactgcg tacaaaccaa g aattggtat   540 tgctatgcaa aaaccttggc agagaaatct gcatgggata ttgctaaggg a aggaattta   600 gagcttgcag tgataaatcc aggcctggcc ttaggtccct tga                      643
```

<210> SEQ ID NO 60
<211> LENGTH: 441
<212> TYPE: DNA
<213> ORGANISM: Pinus radiata

<400> SEQUENCE: 60

```
gaattcggca cgagaatttt tctgtggtaa gcatatctat ggctcaaacc a gagagaagg    60 acgatgtcag cataacaaac tccaaaggat tggtatgcgt gacaggagcg g ctggttact   120 tggcatcttg gcttatcaag cgtctcctcc agtgtggtta ccaagtgaga g gaactgtgc   180 gggatcctgg caatgagaaa agatggctc atttatggaa gttagatggg g cgaaagaga   240 gactgcaact aatgaaagct gatttaatgg acgagggcag cttcgatgag g tcatcagag   300 gctgccatgg tgttttcac acagcgtctc cagtcgtggg tgtcaaatca g atcccaaga   360 tatggtatgc tctggccaag actttagcag aaaagcagc atgggatttt g cccaagaaa   420 accatctgga catggttgca g                                              441
```

<210> SEQ ID NO 61
<211> LENGTH: 913
<212> TYPE: DNA
<213> ORGANISM: Pinus radiata

<400> SEQUENCE: 61

```
gaattcggca cgaggaaaac atcatccagg cattttggaa atttagctcg c cggttgatt    60 caggatcctg caatggcttt tggcgaagag cagactgcct tgccacaaga a acgcctttg   120 aatcctccgg tccatcgagg aacagtgtgc gttacaggag ctgctgggtt c atagggtca   180 tggctcatca tgcgattgct tgagcgagga tatagtgtta gagcaactgt g cgagacact   240
```

-continued

```
ggtaatcctg taaagacaaa gcatctgttg gatctgccgg gggcaaatga g agattgact      300 ctctggaaag cagatttgga tgatgaagga agctttgatg ctgccattga t gggtgtgag      360 ggtgttttcc atgttgccac tcccatggat ttcgagtccg aggatcccga g aatgagata      420 attaagccaa caatcaacgg ggtcttgaat gttatgagat cgtgtgcaaa a gccaagtcc      480 gtgaagcgag ttgttttcac gtcatctgct gggactgtga attttacaga t gatttccaa      540 acaccaggca aagtttttga cgaatcatgc tggaccaacg tggatctttg c agaaaagtt      600 aaaatgacag gatggatgta ctttgtatcg aagacattag cagagaaagc t gcttgggat      660 tttgcagagg agaacaagat cgatctcatt actgttatcc ccacattggt c gttggacca      720 ttcattatgc agaccatgcc accgagcatg atcacagcct ggcactgtt a acgcggaat      780 gaaccccact acatgatact gagacaggta cagctggttc acttggatga t ctctgtatg      840 tcacatatct ttgtatatga acatcctgaa gcaagggca gatacatctc t tccacatgt      900 gatgctaccc att                                                          913

<210> SEQ ID NO 62
<211> LENGTH: 680
<212> TYPE: DNA
<213> ORGANISM: Pinus radiata

<400> SEQUENCE: 62
gaattcggca cgagatcaat ttttgcatat tattaaaaag taagtgtatt c gttctctat      60 attgatcagt cacagagtca tggccagttg tggttccgag aaagtaagag g gttgaatgg      120 agatgaagca tgcgaagaga acaagagagt ggtttgtgta actggggcaa a tgggtacat      180 cggctcttgg ctggtcatga gattactgga acatggctat tatgttcatg g aactgttag      240 ggacccagaa gacacaggga aggttgggca tttgctgcgg ctcccagggg c aagtgagaa      300 gctaaagctg ttcaaggcag agcttaacga cgaaatggcc tttgatgatg c tgtgagcgg      360 ttgtcaaggg gttttccacg ttgccaagcc tgttaatctg gactcaaacg c tcttcaggg      420 ggaggttgtt ggtcctgcgg tgaggggaac agtaaatctg cttcgagcct g cgaacgatc      480 gggcactgtg aaacgagtga tacatacctc gtccgtttca gcagtgagat t cactgggaa      540 acctgacccc cctgatactg tgctggatga atctcattgg acttcggtcg a gtattgcag      600 aaagacaaag atggtcggat ggatgtacta catcgccaac acttatgcag a agagggagc      660 ccataagttc ggatcagaga                                                   680

<210> SEQ ID NO 63
<211> LENGTH: 492
<212> TYPE: DNA
<213> ORGANISM: Pinus radiata

<400> SEQUENCE: 63
gaattcggca cgaggctggt tcaagtgtca gcccaatggc ctcccctaca g agaatcccc      60 agatttcaga agagctgcta aatcatgaga tccatcaagg aagtacagta t gtgtgacag      120 gagctgctgg cttcatagga tcatggctcg tcatgcgttt gcttgagcga g gatatactg      180 ttagaggaac tgtgcgagac actggtaatc cggtgaagac gaagcatcta t tggatctgc      240 ctggggcgaa tgagaggtta actctctgga aagcagattt ggatgatgaa g gaagctttg      300 acgccgccat tgatggttgt gagggagttt tccatgttgc cactcccatg g attttgaat      360 ccgaggaccc cgagaacgag ataattaaac ccgctgtcaa tgggatgttg a atgttttga      420 gatcgtgtgg gaaaaccaag tctatgaagc gagttgtttt cacgtcgtct g ctgggactc      480
```

```
tgcttttac gg                                                         492
```

<210> SEQ ID NO 64
<211> LENGTH: 524
<212> TYPE: DNA
<213> ORGANISM: Pinus radiata

<400> SEQUENCE: 64

```
gaattcggca cgagcttgtt caaagtcaca tatcttattt tctttgtgat a tctgcaatt    60
tccaagcttt tcgtctacct ccctgaaaag atgagcgagg tatgcgtgac a ggaggcaca   120
ggcttcatag ctgcttatct cattcgtagt cttctccaga aggttacaga a gttcgcact   180
acagttcgca acccagataa tgtggagaag tttagttatc tgtgggatct g cctggtgca   240
aacgaaagac tcaacatcgt gagagcagat ttgctagagg aaggcagttt t gatgcagca   300
gtagatggtg tagatggagt attccatact gcatcacctg tcttagtccc a tataacgag   360
cgcttgaagg aaaccctaat agatccttgt gtgaagggca ctatcaatgt c ctcaggtcc   420
tgttcaagat caccttcagt aaagcgggtg gtgcttacat cctcctgctc a tcaataccg   480
atacgactat aatagcttag agcgttccct gctggactga gtca           524
```

<210> SEQ ID NO 65
<211> LENGTH: 417
<212> TYPE: DNA
<213> ORGANISM: Pinus radiata

<400> SEQUENCE: 65

```
tcctaattgt tcgatcctcc cttttaaagc ccttccctgg ccttcattcc a ggtcacaga    60
gttgttcatg cagtgctagc aggaggagca gcgttgcaat tggggaaaat t ccaaaatca   120
ataacgagag gacagaagta agtttgtgga aatagcaacc atgccggtgt t tccttctgg   180
tctggacccc tctgaggaca atggcaagct cgtttgtgtc atggatgcgt c cagttatgt   240
aggtttgtgg attgttcagg gccttcttca acgaggctat tcagtgcatg c cacggtgca   300
gagagacgct ggcgaggttg agtctctcag aaaattgcat ggggatcgat t gcagatctt   360
ctatgcagat gtcttggatt atcacagcat tactgatgcg ctcaagggct g ttctgg      417
```

<210> SEQ ID NO 66
<211> LENGTH: 511
<212> TYPE: DNA
<213> ORGANISM: Pinus radiata

<400> SEQUENCE: 66

```
atgacacgaa tttgtgcctc tctctgacca gagcttgaag ctctgtcttc t ctgatatcg    60
cttcattcca tcatccagga gcttctgtta tatccatttc tcaaaatgg a tgcctacct   120
tgaagaaaat ggatacggcg cttccaattc tcggaaatta atgtgcctta c cggggctg   180
gagtttcctg gggattcata tcgcaagaat gctgctcggc cggggttact c agtccgttt   240
cgcaattccg gtaacgccag aagaggcagg ctcacttatg gaatccgaag a agcattatc   300
ggggaagctg gagatatgcc aagccgatct cttggattat cgcagcgttt t cggcaacat   360
caatggttgc tccggagtct tccacgtccc tgcgccctgt gatcatctgg a tggattaca   420
ggagtatccg gtatgattag tttaatagat tgacgggta tcctgtatga a ttagtttat   480
gaatttaagg ttttcttaga atttggatac t                          511
```

<210> SEQ ID NO 67

<211> LENGTH: 609
<212> TYPE: DNA
<213> ORGANISM: Pinus radiata

<400> SEQUENCE: 67

```
cattgatagt tgatggaaga ccatcagtaa agcatgaaaa agaaattgtt c caaggtgaa      60
gaagtcagtt gctccagcag aacctttta gcaattgttt ttgtatcctt t ttgccttg      120
aatatgtaat ccataaactt atgcaggaag tgcctcgtgc cgaattcggc a cgagaatca    180
ctgaccttca catatttatt ccaattctaa tatctctact cgctgtctac c tgattttc    240
agtggcgaac caacttgaca gggttggaca tggccaacag cagcaagatt c tgattattg    300
gaggaacagg ctacattggt cgtcatataa ccaaagccag ccttgctctt g gtcatccca    360
cattccttct tgtcagagag acctccgctt ctaatcctga aaggctaag c ttctggaat    420
ccttcaaggc ctcaggtgct attatactcc atggatcttt ggaggaccat g caagtcttg   480
tggaggcaat caagaaagtt gatgtagtta tctcggctgt caagggacca c agctgacgg   540
ttcaaacagg atatttatcc agggtattta aagggagggt tggaacccat c aagaaggggt  600
tttggccaa                                                               609
```

<210> SEQ ID NO 68
<211> LENGTH: 474
<212> TYPE: DNA
<213> ORGANISM: Pinus radiata

<400> SEQUENCE: 68

```
gcaagatagg ttttattctt ctggagttgg gtgaggcttg gaaatttaag t aaaagggt      60
gcatagcaat taagcagttg cagccatggc ggtctgtgga actgaagtag c tcatactgt    120
gctctatgta gctgcagaca tggtggaaaa caacacgtct attgtgacca c ctctatggc   180
tgcagcaaat tgtgagatgg agaagcctct tctaaattcc tctgccacct c aagaatact   240
ggtgatggga gccacaggtt acattggccg ttttgttgcc caagaagctg t tgctgctgg   300
tcatcctacc tatgctctta tacgcccgtt tgctgcttgt gacctggcca a agcacagcg   360
cgtccaacaa ttgaaggatg ccggggtcca tatcctttat gggtctttga g tgatcacaa   420
cctcttagta aatacattga aggacatggg ccgttgttat ctctaccatt g gag          474
```

<210> SEQ ID NO 69
<211> LENGTH: 474
<212> TYPE: DNA
<213> ORGANISM: Pinus radiata

<400> SEQUENCE: 69

```
gcaagatagg ttttattctt ctggagttgg gtgaggcttg gaaatttaag t aaaagggt      60
gcatagcaat taagcagttg cagccatggc ggtctgtgga actgaagtag c tcatactgt    120
gctctatgta gctgcagaca tggtggaaaa caacacgtct attgtgacca c ctctatggc   180
tgcagcaaat tgtgagatgg agaagcctct tctaaattcc tctgccacct c aagaatact   240
ggtgatggga gccacaggtt acattggccg ttttgttgcc caagaagctg t tgctgctgg   300
tcatcctacc tatgctctta tacgcccgtt tgctgcttgt gacctggcca a agcacagcg   360
cgtccaacaa ttgaaggatg ccggggtcca tatcctttat gggtctttga g tgatcacaa   420
cctcttagta aatacattga aggacatggg ccgttgttat ctctaccatt g gag          474
```

<210> SEQ ID NO 70

<211> LENGTH: 608
<212> TYPE: DNA
<213> ORGANISM: Pinus radiata

<400> SEQUENCE: 70

| | | | | | |
|---|---|---|---|---|---|
| cattgatagt | tgatggaaga | ccatcagtaa | agcatgaaaa | agaaattgtt c | caaggtgaa 60 |
| gaagtcagtt | gctccagcag | aacctttta | gcaattgttt | ttgtatcctt t | ttgcctttg 120 |
| aatatgtaat | ccataaactt | atgcaggaag | tgcctcgtgc | cgaattcggc a | cgagaatca 180 |
| ctgaccttca | aatatttatt | ccaattctaa | tatctctact | cgctgtctac c | tgattttc 240 |
| agtggcgaac | caacttgaca | gggttggaca | tggccaacag | cagcaagatt c | tgattattg 300 |
| gaggaacagg | ctacattggt | cgtcatataa | ccaaagccag | ccttgctctt g | gtcatccca 360 |
| cattccttct | tgtcagagag | acctccgctt | ctaatcctga | aaggctaag c | ttctggaat 420 |
| ccttcaaggc | ctcaggtgct | attatactcc | atggatcttt | ggaggaccat g | caagtcttg 480 |
| tggaggcaat | caagaaagtt | gatgtagtta | tctcggctgt | caagggacca c | agctgacgg 540 |
| atcaaacagg | atatttatcc | agggtattta | agggaggtt | ggaacccatc a | agaagggtt 600 |
| ttggccaa | | | | | 608 |

<210> SEQ ID NO 71
<211> LENGTH: 1474
<212> TYPE: DNA
<213> ORGANISM: Pinus radiata

<400> SEQUENCE: 71

| | | | | | |
|---|---|---|---|---|---|
| gaattcggca | cgagaaaacg | tccatagctt | ccttgccaac | tgcaagcaat a | cagtacaag 60 |
| agccagacga | tcgaatcctg | tgaagtggtt | ctgaagtgat | gggaagcttg g | aatctgaaa 120 |
| aaactgttac | aggatatgca | gctcgggact | ccagtggcca | cttgtcccct t | acacttaca 180 |
| atctcagaaa | gaaaggacct | gaggatgtaa | ttgtaaaggt | catttactgc g | gaatctgcc 240 |
| actctgattt | agttcaaatg | cgtaatgaaa | tggacatgtc | tcattaccca a | tggtccctg 300 |
| ggcatgaagt | ggtgggattt | gtaacagaga | ttggcagcga | ggtgaagaaa t | caaagtgg 360 |
| gagagcatgt | aggggttggt | tgcattgttg | ggtcctgtcg | cagttgcggt a | attgcaatc 420 |
| agagcatgga | acaatactgc | agcaagagga | tttggaccta | caatgatgtg a | accatgacg 480 |
| gcacacctac | tcagggcgga | tttgcaagca | gtatggtggt | tgatcagatg t | ttgtggttc 540 |
| gaatcccgga | gaatcttcct | ctggaacaag | cggcccctct | gttatgtgca g | gggttacag 600 |
| ttttcagccc | aatgaagcat | ttcgccatga | cagagcccgg | gaagaaatgt g | gattttgg 660 |
| gtttaggagg | cgtgggggcac | atgggtgtca | agattgccaa | agcctttgga c | tccacgtga 720 |
| cggttatcag | ttcgtctgat | aaaaagaaag | aagaagccat | ggaagtcctc g | gcgccgatg 780 |
| cttatcttgt | tagcaaggat | actgaaaaga | tgatggaagc | agcagagagc c | tagattaca 840 |
| taatggacac | cattccagtt | gctcatcctc | tggaaccata | tcttgccctt c | tgaagacaa 900 |
| atggaaagct | agtgatgctg | ggcgttgttc | cagagccgtt | gcacttcgtg a | ctcctctct 960 |
| taatacttgg | gagaaggagc | atagctggaa | gtttcattgg | cagcatggag g | aaacacagg 1020 |
| aaactctaga | tttctgtgca | gagaagaagg | tatcatcgat | gattgaggtt g | tgggcctgg 1080 |
| actacatcaa | cacggccatg | gaaaggttgg | agaagaacga | tgtccgttac a | gatttgtgg 1140 |
| tggatgttgc | tagaagcaag | ttggataatt | agtctgcaat | caatcaatca g | atcaatgcc 1200 |
| tgcatgcaag | atgaatagat | ctggactagt | agcttaacat | gaaagggaaa t | taaatttt 1260 |
| atttaggaac | tcgatactgg | tttttgttac | tttagtttag | cttttgtgag g | ttgaaacaa 1320 |

```
ttcagatgtt ttttttaactt gtatatgtaa agatcaattt ctcgtgacag t aaataataa    1380 tccaatgtct tctgccaaat taatatatgt attcgtattt ttatatgaaa a aaaaaaaaa    1440 aaaaaaaaaa aaaaaaaaa aaaaaaaaaa aaaa                                   1474
```

<210> SEQ ID NO 72
<211> LENGTH: 1038
<212> TYPE: DNA
<213> ORGANISM: Pinus radiata

<400> SEQUENCE: 72

```
gaattcggca cgagagaggg ttatatatct tgattctgac ctgattgtcg t cgacgacat      60 tgccaagctc tgggccacgg atttggaatc tcgtgtcctc ggggcaccag a gtactgcaa    120 ggcgaatttc acaaagtatt tcaccgataa tttctggtgg gatcccgcat t atccaagac   180 cttttgaggga aaaaaaccct gctacttcaa cacaggcgta atggtgatcg a tcttgaaaa    240 atggcgggca ggggaattca caagaaagat cgaaatctgg atggacatac a gaaggaacg    300 ccgtatctat gagctcggat cattaccgcc attttttactg gtatttgctg g tttggttaa    360 gcaagtcgat catcgttgga atcagcacgg tttaggcgga gataatttgc a aggcctttg    420 ccgagatctt caccctggac ctgtcagttt gttgcattgg agtggtaagg g caaaccttg   480 gctacgcctg gaatgccaag cggacttgcc ctctggatac tttatgggct c cttatgatc    540 tttatcgatc aacgtattac ctaaatgggg gagagagcct ctctcctcgg g gtgcttttt    600 atcgaattaa acctgatttg ataaaatgcc aaatagaact ttacgcctat g catctttca    660 gttttgaatt tcaattctgg taacgaatag aagaaaacaa tagcacagcc a caggcagga    720 caaatccatc atgagggacc aatcgtttga atttagtatt aataaggttg t tccatataa    780 cgcctgtgaa gaatgatatt gtggactgat ctatttatat ttgtactgcc a tgccatcct    840 cagccagcag agaggcaagc aatgccgctg caagtcatgt agggaaggcg t tgtgaactc    900 aatttttcggc gactgtacag gatgtaaatt tttggaacat taatatcatt a tgataagtt    960 cctgaaccaa caactgtata ataccttata aatgtatctg caactccatt t ttgcataaa   1020 aaaaaaaaaa aaaaaaaa                                                   1038
```

<210> SEQ ID NO 73
<211> LENGTH: 372
<212> TYPE: DNA
<213> ORGANISM: Pinus radiata

<400> SEQUENCE: 73

```
ctagggtctt tgggggggttc ctgatgccca attgttgctg tgcttggcat g aacccaaaa     60 catgcaagag atctgtagtc agtagtcttg ttggatctat agcttttaga a aagagtcac    120 gtccttttag ggtaacatca ttccaaccat atccagttcc accaccggct a caccttcaa    180 cgggaggagg agcaagatat tcagcattgc tttgggcacc agatggatag g cattatttt    240 ccatcggaat tcagccgagc tcgccccctc agtccaatcg tcgtgaaaat c cctcaaaat    300 tgggcaattc tggctcgaaa tcgccaaatt atgggctaca acaggattaa a attgcacag    360 aaatctgcca gt                                                          372
```

<210> SEQ ID NO 74
<211> LENGTH: 545
<212> TYPE: DNA
<213> ORGANISM: Pinus radiata -continued

```
<400> SEQUENCE: 74
aaagaattcg gcacgagggc aatccgagcc tagccaacca acttggcagc a aggagcaca      60
gggagttggc gagagaagct gttaggaaat ctttggtatt gttgaaaaat g ggaagtcag     120
ccaacaagcc tttgctccct tggagaaga atgcttccaa ggttcttgtt g caggaaccc     180
atcctgataa tctgggttat cagtgtggtg gatggacgat ggaatggcaa g gattaagtg     240
gaaacataac cgtaggaact acaattctgg aagctatcaa actagctgtc a gcccctcta     300
ctgaagtggt ttatgagcaa atccagatg ctaactatgt caaggacaa g ggttttcat      360
atgccattgt ggttgtgggt gaggcaccat acgcagaaac gtttggagac a atcttaatt     420
tgaccattcc cctaggcgga ggggacacga ttaagacgg ctgtggctcc t tgaaatgcc     480
ttgtaatctt gatatctgga aggccacttg ttattgaacc ttatcttcca t tggtggatc     540
gtttt                                                                  545

<210> SEQ ID NO 75
<211> LENGTH: 463
<212> TYPE: DNA
<213> ORGANISM: Pinus radiata

<400> SEQUENCE: 75
gcaggtcgac actagtggat ccaaagaatt cggcacgaga aaaaacaaat g ttagctagc     60
ctagtgatga gctttacgta tacctggcct tttatacatg gatctgagtt t ttatgcagg    120
tgtagagcct tttgttactc tgtatcactg ggacttgcca caagctctgg a ggacgaata    180
cggtggattt cgtagcaaaa aagttgtgga tgactttggc atattctcag a agaatgctt    240
tcgtgctttt ggagaccgtg tgaagtactg gtaactgtt aacgaaccgt t gatcttctc     300
atattttct tacgatgtgg ggcttcacgc accgggccgc tgttcgcctg g atttggaaa    360
ctgcactgcg ggaaattcag cgacagagcc ttatattgta gcccataaca t gcttcttgc    420
acatagtacc gctgttaaaa atatatagca taaatacca ggg                        463

<210> SEQ ID NO 76
<211> LENGTH: 435
<212> TYPE: DNA
<213> ORGANISM: Pinus radiata

<400> SEQUENCE: 76
acactagtgg atccaaagaa ttcggcacga ggctaccatc ttccctcata a tattgggct     60
tggagctacc agggatcctg atctggctag aagaataggg gctgctacgg c tttggaagt    120
tcgagctact ggcattcaat acacatttgc tccatgtgtt gctgtttgca g agatcctcg    180
atggggccgc tgctatgaga gctacagtga ggatccaaaa attgtcaagg c catgactga    240
gattatcgtt ggcctgcaag ggaatcctcc tgctaattct acaaaagggg g gcctttat     300
agctggacag tcaaatgttg cagcttgtgc taagcatttt gtgggttatg g tggaacaac    360
caaaggtatc gatgagaata atactgttat caactatcaa gggttatttc a acattccaa    420
attaccccca atttt                                                      435

<210> SEQ ID NO 77
<211> LENGTH: 451
<212> TYPE: DNA
<213> ORGANISM: Pinus radiata

<400> SEQUENCE: 77
gaattcggca cgagcctaga attctatggt gaaaattgtt gggacaaggc t gcccaagtt     60
```

```
tacaaaggaa cagtcccaaa tggttaaagg ttcaatagac tatctaggcg t taaccaata      120 cactgcttat tacatgtatg atcctaaaca acctaaacaa aatgtaacag a ttaccagac     180 tggactggaa tacaggcttt gcatatgctc gcaatggagt gcctattgga c caagggcga    240 actccaattg gctttacatt gtgccttggg gtctatacaa ggccgtcaca t acgtaaaag    300 aacactatgg aaatccaact atgattctct ctgaaaatgg aatggacgac c tggaaacgt    360 gacacttcca gcaggactgc atgataccat caggggtaac tactataaaa g ctatttgca   420 aaatttgatt aatgcacgtg aatgaccggg g                                     451
```

<210> SEQ ID NO 78
<211> LENGTH: 374
<212> TYPE: DNA
<213> ORGANISM: Pinus radiata

<400> SEQUENCE: 78

```
ctgctctgca agcagtacta tgcacagcaa ggcctgctta actgaaaaca g agcgctgag     60 cttgaggaaa cgctcaagca ttgctgaggc caccgtttat ctaaatagcg c aacataggg   120 cttcagaaaa atggcaatgg cacaagcatt cagaggccgt gtcttgcaag c tgcccgttt    180 gctccgccgc aacattctgc cggaggataa aagctttgga tccgctgctt c tcctagacg   240 agctcttagc ctgctctcat caaaagcctt catctctttc tctgttgaac g gcatcggct   300 agctgctaca aattcaacaa ttgtgttgca atctcgaaac ttttctgcaa a aggtaaaaa   360 gacaggacaa tctg                                                        374
```

<210> SEQ ID NO 79
<211> LENGTH: 457
<212> TYPE: DNA
<213> ORGANISM: Pinus radiata

<400> SEQUENCE: 79

```
gaagaatgga agagattaat ggtgataacg cagtaaggag gagctgcttt c ctccaggtt     60 tcatgtttgg gatagcaact tctgcttatc agtgtgaagg agctgccaac g aaggtggaa   120 aaggcccaag catctgggac tcattttcac gaacaccagg caaaattctt g atggaagca   180 acggtgatgt agcagtggat cagtatcatc gttataaggc agatgtaaaa c tgatgaaag   240 atatgggcgt ggctacctac agattctcga tttcatggcc tcgtatattt c caaagggaa   300 aaggagagat caatgaggaa ggagtagcct attacaataa cctcatcaat g aactcctcc   360 agaatggaat ccaagcgtct gtcaactttg tttcactggg atactcccca g tctctggag   420 gatgaatatg gcggatttct gaggccaacc attgtga                              457
```

<210> SEQ ID NO 80
<211> LENGTH: 346
<212> TYPE: DNA
<213> ORGANISM: Pinus radiata

<400> SEQUENCE: 80

```
ggtgtgatgg caggaattcc agtcctaagg ccatttttgca tctgtttgct t tcagtctac    60 atgctgcaca ttgtagctgc agtagcttca ccaaggctag gtagaagcag c ttcccaagg   120 ggtttcaaat ttggtgcagg gtcatctgct tatcaggcgg aaggagctgc t catgagggt   180 ggcaaaggcc caagcatttg ggatacattc tcccacactc caggtaaaat c gctgatggg   240 aatattggga tgttgcagta gatcaatacc accgttataa ggaagatgtg c agcttctca   300
```

-continued

| aatacatggg aatggacgtc tatcgtttct ctatctcctg gtcacg | 346 |

<210> SEQ ID NO 81
<211> LENGTH: 957
<212> TYPE: DNA
<213> ORGANISM: Pinus radiata

<400> SEQUENCE: 81

| gaattcggca cgagaaagcc ctagaatttt ttcagcatgc tatcacagcc c cagcgacaa | 60 |
| ctttaactgc aataactgtg gaagcgtaca aaaagtttgt cctagtttct c tcattcaga | 120 |
| ctggtcaggt tccagcattt ccaaaataca cacctgctgt tgtccaaaga a atttgaaat | 180 |
| cttgcactca gccctacatt gatttagcaa acaactacag tagtgggaaa a tttctgtat | 240 |
| tggaagcttg tgtcaacacg aacacagaga agttcaagaa tgatagtaat t tggggttag | 300 |
| tcaagcaagt tttgtcatct ctttataaac ggaatattca gagattgaca c agacatatc | 360 |
| tgaccctctc tcttcaagac atagcaagta cggtacagtt ggagactgct a agcaggctg | 420 |
| aactccatgt tctgcagatg attcaagatg gtgagatttt tgcaaccata a atcagaaag | 480 |
| atgggatggt gagcttcaat gaggatcctg aacagtacaa aacatgtcag a tgactgaat | 540 |
| atatagatac tgcaattcgg agaatcatgg cactatcaaa gaagctcacc a cagtagatg | 600 |
| agcagatttc gtgtgatcat tcctacctga gtaaggtggg gagagagcgt t caagatttg | 660 |
| acatagatga ttttgatact gttccccaga agttcacaaa tatgtaacaa a tgatgtaaa | 720 |
| tcatcttcaa gactcgctta tattcattac tttctatgtg aattgatagt c tgttaacaa | 780 |
| tagtactgtg gctgagtcca gaaaggatct ctcggtatta tcacttgaca t gccatcaaa | 840 |
| aaaatctcaa atttctcgat gtctagtctt gattttgatt atgaatgcga c ttttagttg | 900 |
| tgacatttga gcacctcgag tgaactacaa agttgcatgt taaaaaaaaa a aaaaaa | 957 |

<210> SEQ ID NO 82
<211> LENGTH: 489
<212> TYPE: DNA
<213> ORGANISM: Pinus radiata

<400> SEQUENCE: 82

| gcaggtcgac actagtggat ccaaagaatt cggcacgaga taagactaat t ttccagaca | 60 |
| atcctccatt cccattcaat tacactggta ctccacccaa taatacacag g ctgtgaatg | 120 |
| ggactagagt aaaagtcctt cccttttaaca caactgttca attgattctt c aagacacca | 180 |
| gcatcttcag cacagacagc caccctgtcc atctccatgg tttcaatttc t tgtggtgg | 240 |
| gccaaggtgt tggaaactac aatgaatcaa cagatgcacc aaattttaac c tcattgacc | 300 |
| ctgtcgagag aaacactgtg ggagttccca aaggaggttg ggctgctata a gatttcgtg | 360 |
| cagacaatcc aggggtttgg ttcatgcact gtcatttgga ggttcacaca t cgtggggac | 420 |
| tgaaaatggc gtgggtagta agaacggaa aagggcccat cgatttttcca c ccgggtggg | 480 |
| taccagtaa | 489 |

<210> SEQ ID NO 83
<211> LENGTH: 471
<212> TYPE: DNA
<213> ORGANISM: Pinus radiata

<400> SEQUENCE: 83

| gaattcggca cgagaaaacc ttttcagacg aatgttctga tgctcggccc c ggccagaca | 60 |
| acagacatac ttctcactgc caatcaggct acaggtagat actacatggc t gctcgagca | 120 |

```
tattccaacg ggcaaggagt tcccttcgat aacaccacta ccactgccat t ttagaatac       180 gagggaagct ctaagacttc aactccagtc atgcctaatc ttccattcta t aacgacacc       240 aacagtgcta ctagcttcgc taatggtctt agaagcttgg gctcacacga c cacccagtc       300 ttcgttcctc agagtgtgga ggagaatctg ttctacacca tcggtttggg g ttgatcaaa       360 tgtccggggc agtcttgtgg aggtccaacg gatcaagatt tgcagcaagt a tgaatacat       420 atcatttgtc ccgcaaccac ttcttccaat ccttcaagct cagcattttg g                 471
```

<210> SEQ ID NO 84
<211> LENGTH: 338
<212> TYPE: DNA
<213> ORGANISM: Pinus radiata

<400> SEQUENCE: 84

```
gttcggcact gagagatcca tttctttcaa tgttgagaca gtgagtagta t tagtttgat        60 atctctttca ggaatatatc gtgcttgcag gatctttagt ttctgcaaca a tgtcgttgc       120 aatcagtgcg tctatcttct gctctccttg ttttgctact agcatttgtt g cttacttag       180 ttgctgtaac aaacgcagat gtccacaatt ataccttcat tattagaaag a gacagttac       240 caggctatgc aataagcgta taatcgccac cgtcaatggc agctaccagg c ccaactatt       300 catgtacgtg atggagacgt tgttaattat caaagctt                                338
```

<210> SEQ ID NO 85
<211> LENGTH: 1229
<212> TYPE: DNA
<213> ORGANISM: pinus radiata

<400> SEQUENCE: 85

```
agagaaataa ttatatttgt aaatttaagt ctacgtttat taaaaaacta c aaccctaaa        60 tgcaggagaa aaacaagca tgctgtctac tgaagcttac aaatcaaatc c ctgcgatat       120 gtcttttctc gtgccgaatt cggcacgaga agatcttggt tcgagtctct c agctctctc      180 caaaggaatt ttgtgggtca tttgcaggtg aagacaccat ggtgaaggct t atcccaccg      240 taagcgagga gtacaaggct gccattgaca aatgcaagag gaagctccga g ctctcattg      300 cagagaagaa ctgtgcgccg atcatggttc gaatcgcatg gcacagcgct g ggacttacg      360 atgtcaagac caagaccgga gggcccttcg ggacgatgag atatgggccc g agcttgccc      420 acggtgctaa cagtggtctg gacatcgcag ttaggctcct ggagccaatc a ggaacagt      480 tccccataat cacctatgct gaccttatc agttggctgg tgtggtggct g ttgaagtga      540 ccggggacc tgacattccg ttccatcctg aagagaaga caagcctgag c tccagaag       600 aaggccgcct tcctgatgct acaaaaggac ctgatcatct gagggatgtt t ttggtcaca      660 tggggttgaa tgataaggaa attgtggcct tgtctggtgc ccacaccttg g ggagatgcc      720 acaaggagag atctggtttt gaaggaccat ggacctctaa ccccttatc t tgacaact      780 cttacttcac agagcttgtg actggagaga aggaaggcct gcttcagttg c catctgata      840 aggcactgct tgctgatcct agttttgcag tttatgttca gaagtatgca c aggacgaag      900 acgctttctt tgctgactat gcggaagctc acctgaagct ttctgaactt g ggtttgctg      960 atgcgtagat tcataccttc tgcagagaca attccttgct agatagcttc g ttttgtatt     1020 tcatctaatc ttttcgatta tatagtcaca tagaagttgg tgttatgcgc c atagtgata     1080 cttgaaccta catgtttttg aaaagtatcg atgttcttta aaatgaacat t gaatacaac     1140
```

| | |
|---|---|
| attttggaat ctggttgtgt tctatcaagc gcatatttta atcgaatgct t cgttcctgt | 1200 |
| taaaaaaaaa aataaaataa aaaaaaaaa | 1229 |

<210> SEQ ID NO 86
<211> LENGTH: 1410
<212> TYPE: DNA
<213> ORGANISM: Pinus radiata

<400> SEQUENCE: 86

| | |
|---|---|
| gaagatgggg ctgtgggtgg tgctggcttt ggcgctcagt gcgcactatt g cagtctcag | 60 |
| gcttacaatg tggtaagttc aagcaatgct actgggagtt acagtgagaa t ggattggtg | 120 |
| atgaattact atgggactc ttgccctcag gctgaagaga tcattgctga a caagtacgc | 180 |
| ctgttgtaca aaagacacaa gaacactgca ttctcatggc ttagaaatat t ttccatgac | 240 |
| tgtgctgtgg agtcatgtga tgcatcgctt ctgttggact caacaaggaa c agcatatca | 300 |
| gaaaaggaca ctgacaggag cttcggcctc cgcaactta ggtatttgga t accatcaag | 360 |
| gaagccgtgg agagggagtg ccccgggtc gtttcctgtg cagatatact c gttctctct | 420 |
| gccagagatg gcgttgtatc gttgggagga ccatacattc ccctgaagac g ggaagaaga | 480 |
| gatggacgga agagcagagc agatgtggtg gagaattacc tgcccgatca c aatgagagc | 540 |
| atctccactg ttctgtctcg cttcaaagcc atgggaatcg acacccgtgg g gttgttgca | 600 |
| ctgctggggg ctcacagcgt ggggaggact cactgcgtga agctggtgca c aggctgtac | 660 |
| ccggaagtag atccgacact ggaccctggg cacgtggagc acatgaagca c aagtgcccg | 720 |
| gacgcgatcc ccaacccgaa ggcagtgcag tatgtgcgga cgaccgggg a acgcctatg | 780 |
| aagctggaca caactacta cgtgaacctg atgaacaaca aggggctcct a atagtggac | 840 |
| cagcaactgt atgcagattc gaggaccagg ccgtatgtga agaagatggc a aaaagccag | 900 |
| gaatacttct tcaaatactt ctcccgggcg ctcaccatcc tctctgagaa c aatcctctc | 960 |
| accggcgctc gaggagaaat ccgtcggcag tgctcgctca aaaacaaatt g cacacaaaa | 1020 |
| agcaagcgtt gagcgatagc tcaatgccgc agtggtggga gtgatagcgt g atgccacag | 1080 |
| tggtgggcat ttcatatata aattgcagtt tgcgttttta ttagataatc a taatggtgt | 1140 |
| ggtgtgacta tgccctgcga atcacatcga tgaaccacaa ccgaaccgtg g aacagtagg | 1200 |
| cttattccct tatgtaagca gaaccttta ttataagcaa aaaagacaat c tgtctgtt | 1260 |
| attctagtat aattttgtca tcagttaaag ttgctcatct gataataact g gaaacggta | 1320 |
| aaatatgaca actacgtatc ttctttggtc atctgataat aaccggaaac g ataaaatat | 1380 |
| gacaactaca tatattcttt aaaaaaaaaa | 1410 |

<210> SEQ ID NO 87
<211> LENGTH: 687
<212> TYPE: DNA
<213> ORGANISM: Pinus radiata

<400> SEQUENCE: 87

| | |
|---|---|
| gtagtttcgt tttacaacaa tctcaggttt tgaatctcag aatagttgcg a aaggaagcg | 60 |
| atgacgaagt acgtgatcgt tagctccatt gtgtgtttct ttgtatttgt t tctgcgtgc | 120 |
| ataatttctg tcaatggatt agttgtccat gaagatgatc tgtcaaagcc t gtgcatggg | 180 |
| cttttcgtgga catttatata ggacagttgc cccgacttgg aggccatagt g aaatcggta | 240 |
| cttgagccgg cgttggacga agatatcact caggccgcag gcttgctgag a cttcatttc | 300 |
| catgactgtt ttgtgcaggg ttgcgatggg tccgtgttgc tgacaggaac t aaaagaaac | 360 |

```
cccagtgagc aacaggctca gccaaactta acactaagag cccgggcctt g cagctgatc      420 gacgaaatta aaaccgctgt agaagctagc tgcagtgggg ttgtaacttg t gcagacatt      480 ctggctttgg ctgctcgtga ctccgtccgc tcaggaggcc aaaatttcc a gtaccactt      540 ggccgcagag atagcctaaa gtttgccagt caatccgtag ttctcgccaa t ataccaact      600 ccaactttaa atttgacaca gctgatgaac atttttggct ccaaaggatt c agtttggcc      660 gaaatggttg ctcttcaggt ggcacac                                          687
```

<210> SEQ ID NO 88
<211> LENGTH: 688
<212> TYPE: DNA
<213> ORGANISM: Pinus radiata

<400> SEQUENCE: 88

```
gtagtttcgt tttacaacaa tctacaggtt ttgaatctca gaatagttgc g aaaggaagc      60 gatgacgaag tacgtgatcg ttagctccat tgtatgtttc tttgtatttg t ttctgcgtg     120 cataatttct gtcaatggat tagttgtcca tgaagatgat ctgtcaaagc c tgtgcatgg     180 gctttcgtgg acattttata aggacagttg ccccgacttg gaggccatag t gaaatcggt     240 acttgagccg gcgttggacg aagatatcac tcaggccgca ggttgctgag a cttcatttc     300 catgactgtt ttgtgcaggg ttgcgatggg tccgtgttgc tgacaggaac t aaaagaaac     360 ccccgagtga gcaacaggct cagccaaact taacactaag agcccgggcc t tgcagctga     420 tcgacgaaat taaaaccgct gtagaagcta gctgcagtgg ggttgtaact t gtgcagaca     480 ttctggcttt ggctgctcgt gactccgtcg ctcaggaggc ccaaaatttc c agtaccact     540 tggccgcaga gatagcctaa agtttgccag tcaatccgta gttctcgcca a tataccaac     600 tccaacttta aatttgacac agctgatgaa catttttggc tccaaaggat t cagtttggc     660 cgaaatggtt gctcttcagg tggcacac                                         688
```

<210> SEQ ID NO 89
<211> LENGTH: 278
<212> TYPE: DNA
<213> ORGANISM: Pinus radiata

<400> SEQUENCE: 89

```
tcttcgaatt ctctttcacg actgcttcgt taatggctgc gatggctcga t attgttaga      60 tgataactca acgttcaccg gagaaaagac tgcaggccca aatgttaatt c tgcgagagg     120 attcgacgta atagacacca tcaaaactca agttgaggca gcctgcagtg g tgtcgtgtc     180 atgtgccgac attctcgcca ttgctgcacg cgattcagtc gtccaactgg g gggcccaac     240 atggacggta cttctgggag aaaagacgga tccgatca                              278
```

<210> SEQ ID NO 90
<211> LENGTH: 1960
<212> TYPE: DNA
<213> ORGANISM: Pinus radiata

<400> SEQUENCE: 90

```
gtttccgcc attttcgcc tgtttctgcg gagaatttga tcaggttcgg a ttgggattg        60 aatcaattga aaggttttta ttttcagtat ttcgatcgcc atggccaacg g aatcaagaa     120 ggtcgagcat ctgtacagat cgaagcttcc cgatatcgag atctccgacc a tctgcctct     180 tcattcgtat tgctttgaga gagtagcgga attcgcagac agaccctgtc t gatcgatgg     240
```

-continued

| | |
|---|---|
| ggcgacagac agaacttatt gcttttcaga ggtggaactg atttctcgca a ggtcgctgc | 300 |
| cggtctggcg aagctcgggt tgcagcaggg gcaggttgtc atgcttctcc t tccgaattg | 360 |
| catcgaattt gcgtttgtgt tcatgggggc ctctgtccgg ggcgccattg t gaccacggc | 420 |
| caatcctttc tacaagccgg gcgagatcgc caaacaggcc aaggccgcgg g cgcgcgcat | 480 |
| catagttacc ctggcagctt atgtggagaa actggccgat ctgcagagcc a cgatgtgct | 540 |
| cgtcatcaca atcgatgatg ctcccaagga aggttgccaa catatttccg t tctgaccga | 600 |
| agccgacgaa acccaatgcc cggccgtgac aatccacccg gacgatgtcg t ggcgttgcc | 660 |
| ctattcttcc ggaaccacgg ggctccccaa gggcgtgatg ttaacgcaca a aggcctggt | 720 |
| gtccagcgtt gcccagcagg tcgatggtga aaatcccaat ctgtatttcc a ttccgatga | 780 |
| cgtgatactc tgtgtcttgc ctcttttcca catctattct ctcaattcgg t tctcctctg | 840 |
| cgcgctcaga gccggggctg cgaccctgat tatgcagaaa ttcaacctca c gacctgtct | 900 |
| ggagctgatt cagaaataca aggttaccgt tgccccaatt gtgcctccaa t tgtcctgga | 960 |
| catcacaaag agccccatcg tttcccagta cgatgtctcg gccgtccgga t aatcatgtc | 1020 |
| cggcgctgcg cctctcggga aggaactcga agatgccctc agagagcgtt t tcccaaggc | 1080 |
| cattttcggg cagggctacg gcatgacaga agcaggcccg gtgctggcaa t gaacctagc | 1140 |
| cttcgcaaag aatcctttcc ccgtcaaatc tggctcctgc ggaacagtcg t ccggaacgc | 1200 |
| tcaaataaag atcctcgata cagaaactgg cgagtctctc ccgcacaatc a agccggcga | 1260 |
| aatctgcatc cgcggacccg aaataatgaa aggatatatt aacgcccgg a tccacggc | 1320 |
| cgctacaatc gatgaagaag gctggctcca cacaggcgac gtcgggtaca t tgacgatga | 1380 |
| cgaagaaatc ttcatagtcg acagagtaaa ggagattatc aaatataagg g cttccaggt | 1440 |
| ggctcctgct gagctggaag ctttacttgt tgctcatccg tcaatcgctg a cgcagcagt | 1500 |
| cgttcctcaa aagcacgagg aggcgggcga ggttccggtg gcgttcgtgg t gaagtcgtc | 1560 |
| ggaaatcagc gagcaggaaa tcaaggaatt cgtggcaaag caggtgattt t ctacaagaa | 1620 |
| aatacacaga gtttactttg tggatgcgat tcctaagtcg ccgtccggca a gattctgag | 1680 |
| aaaggatttg agaagcagac tggcagcaaa atgaaaatga atttccatat g attctaaga | 1740 |
| ttcctttgcc gataattata ggattccttt ctgttcactt ctatttatat a ataaagtgg | 1800 |
| tgcagagtaa gcgccctata aggagagaga gagcttatca attgtatcat a tggattgtc | 1860 |
| aacgccctac actcttgcga tcgctttcaa tatgcatatt actataaacg a tatatgttt | 1920 |
| tttttataaa tttactgcac ttctcgttca aaaaaaaaa | 1960 |

<210> SEQ ID NO 91
<211> LENGTH: 701
<212> TYPE: DNA
<213> ORGANISM: Pinus radiata

<400> SEQUENCE: 91

| | |
|---|---|
| gtagtttcgt tttacaacaa tctcaggttt tgaatctcag aatagttgcg a aaggaagcg | 60 |
| atgacgaagt acgtgatcgt tagctccatt gtatgtttct ttgtatttgt t tctgcgtgc | 120 |
| ataatttctg tcaatggatt agttgtccat gaagatgatc tgtcaaagcc t tgcatggg | 180 |
| ctttcgtgga cattttataa ggacagttgc cccgacttgg aggccatagt g aaatcggta | 240 |
| cttgagccgg cgttggacga agatatcact caggccgcag gttgctgaga c ttcatttcc | 300 |
| atgactgttt tgtgcagggt tgcgatgggt ccgtgttgct gacaggaact a aaagaaacc | 360 |
| ccgagtgagc aacaggctca gccaaactta acactaagag cccgggcctt g cagctgatc | 420 |

```
gacgaaatta aaaccgctgt agaagctagc tgcagtgggg ttgtaacttg t gcagacatt      480 ctggctttgg ctgctcgtga ctccgtcgct caggaggccc aaaatttcca g taccacttg      540 gccgcagaga tagcctaaag tttgccagtc aatccgtagt tctcgccaat a taccaactc      600 caactttaaa tttgacacag ctgatgaaca tttttggctc caaggattc a gtttggccg       660 aaatggttgc tctttcaggt ggacacacaa tcggcattgg t                           701
```

<210> SEQ ID NO 92
<211> LENGTH: 626
<212> TYPE: DNA
<213> ORGANISM: Pinus radiata

<400> SEQUENCE: 92

```
gttgcaggtc ggggatgatt tgaatcacag aaacctcagc gattttgcca a gaaatatgg      60 caaaatcttt ctgctcaaga tgggccagag gaatcttgtg gtagtttcat c tcccgatct     120 cgccaaggag gtcctgcaca cccagggcgt cgagtttggg tctcgaaccc g gaacgtggt    180 gttcgatatc ttcacgggca aggggcagga catggtgttc accgtctatg g agatcactg    240 gagaaagatg cgcaggatca tgactgtgcc tttctttacg aataaagttg t ccagcacta    300 cagattcgcg tgggaagacg agatcagccg cgtggtcgcg gatgtgaaat c ccgcgccga    360 gtcttccacc tcgggcattg tcatccgtag cgcctccagc tcatgatgta t aatattatg    420 tataggatga tgttcgacag gagattcgaa tccgaggacc accgctttt c ctcaagctc     480 aaggccctca acgagagcg aagtcgattg gcccagagct ttgagtacaa t tatggggat     540 ttcattccca gtcttaggcc cttcctcaga ggttatcaca gaatctgcaa t gagattaaa    600 gagaaacggc tctctctttt caagga                                            626
```

<210> SEQ ID NO 93
<211> LENGTH: 660
<212> TYPE: DNA
<213> ORGANISM: Pinus radiata
<220> FEATURE:
<221> NAME/KEY: unsure
<222> LOCATION: (1)...(660)
<223> OTHER INFORMATION: n at all occurrences indicates unsure

<400> SEQUENCE: 93

```
acccagtgac cttcaggcct gagagatttc ttgaggaaga tgttgatatt a agggccatg      60 attacaggct actgccattg gtgcagggcg caggatctgc cctggtgcac a attgggtat    120 taatttagtt cagtctatgt tgggacacct gcttcatcat ttcgtatggg c acctcctga    180 gggaatgaag gcagaagaca tagatctcac agagaatcca gggcttgtta c tttcatggc    240 caagcctgtg caggccattg ctattcctcg attgcctgat catctctaca a gcgacagcc    300 actcaattga tcaattgatc tgatagtaag tttgaatttt gttttgatac a aaacgaaat    360 aacgtgcagt ttctccttt ccatagtcaa catgcagctt tctttctctg a agcgcatgc     420 agctttcttt ctctgaagcc caacttctag caagcaataa ctgtatattt t agaacaaat   480 acctattcct caaattgagw atttctctgt aggggnngnt aattgtgcaa t ttgcaagna   540 atagtaaagt ttantttagg gnattttaat agtcctangt aanangnggn a atgntagng   600 ggcattnaga aaaccctaat agntgttggn ggnngntagg nttttttnacc a aaaaaaaaa   660
```

<210> SEQ ID NO 94
<211> LENGTH: 1012
<212> TYPE: DNA

<213> ORGANISM: Pinus radiata

<400> SEQUENCE: 94

```
ctttgaggca acctacattc attgaatccc aggatttctt cttgtccaaa c aggtttaag      60
gaaatggcag gcacaagtgt tgctgcagca gaggtgaagg ctcagacaac c caagcagag     120
gagccggtta aggttgtccg ccatcaagaa gtgggacaca aaagtctttt g cagagcgat     180
gccctctatc agtatatatt ggaaacgagc gtgtaccctc gtgagcccga g ccaatgaag     240
gagctccgcg aagtgactgc caagcatccc tggaacctca tgactacttc t gccgatgag     300
ggtcaatttc tgggcctcct gctgaagctc attaacgcca agaacaccat g gagattggg     360
gtgtacactg gttactcgct tctcagcaca gcccttgcat tgcccgatga t ggaaagatt     420
ctagccatgg acatcaacag agagaactat gatatcggat tgcctattat t gagaaagca     480
ggagttgccc acaagattga cttcagagag ggccctgctc tgccagttct g gacgaactg     540
cttaagaatg aggacatgca tggatcgttc gattttgtgt tcgtggatgc g gacaaagac     600
aactatctaa actaccacaa gcgtctgatc gatctggtga aggttggagg t ctgattgca     660
tatgacaaca ccctgtggaa cggatctgtg gtggctccac ccgatgctcc c tgaggaaa      720
tatgtgagat attacagaga tttcgtgatg gagctaaaca aggcccttgc t gtcgatccc     780
cgcattgaga tcagccaaat cccagtcggt gacggcgtca ccctttgcag g cgtgtctat     840
tgaaaacaat ccttgtttct gctcgtctat tgcaagcata aaggctctct g attataagg     900
agaacgctat aatatatggg gttgaagcca tttgttttgt ttagtgtatt g ataataaag     960
tagtacagca tatgcaaagt ttgtatcaaa aaaaaaaaaa aaaaaaaaa a a              1012
```

<210> SEQ ID NO 95
<211> LENGTH: 1460
<212> TYPE: DNA
<213> ORGANISM: Pinus radiata

<400> SEQUENCE: 95

```
aaaacgtcca tagcttcctt gccaactgca agcaatacag tacaagagcc a gacgatcga      60
atcctgtgaa gtggttctga agtgatggga agcttggaat ctgaaaaaac t gttacagga     120
tatgcagctc gggactccag tggccacttg tccccttaca cttacaatct c agaaagaaa     180
ggacctgagg atgtaattgt aaaggtcatt tactgcggaa tctgccactc t gatttagtt     240
caaatgcgta atgaaatgga catgtctcat tacccaatgg tccctgggca t gaagtggtg     300
gggattgtaa cagagattgg cagcgaggtg aagaaattca aagtgggaga g catgtaggg     360
gttggttgca ttgttgggtc ctgtcgcagt tgcggtaatt gcaatcagag c atggaacaa     420
tactgcagca agaggatttg gacctacaat gatgtgaacc atgacggcac a cctactcag     480
ggcggatttg caagcagtat ggtggttgat cagatgtttg tggttcgaat c ccggagaat     540
cttcctctgg aacaagcggc ccctctgtta tgtgcagggg ttacagtttt c agcccaatg     600
aagcatttcg ccatgacaga gcccgggaag aaatgtggga ttttgggttt a ggaggcgtg     660
gggcacatgg gtgtcaagat tgccaaagcc tttggactcc acgtgacggt t atcagttcg     720
tctgataaaa agaagaaga agccatgaa gtcctcggcg ccgatgctta t cttgttagc     780
aaggatactg aaaagatgat ggaagcagca gagagcctag attacataat g gacaccatt     840
ccagttgctc atcctctgga accatatctt gcccttctga agacaaatgg a aagctagtg     900
atgctgggcg ttgttccaga gccgttgcac ttcgtgactc ctctcttaat a cttgggaga     960
aggagcatag ctggaagttt cattggcagc atggaggaaa cacaggaaac t ctagatttc    1020
```

```
tgtgcagaga agaaggtatc atcgatgatt gaggttgtgg gcctggacta c atcaacacg    1080 gccatggaaa ggttggagaa gaacgatgtc cgttacagat ttgtggtgga t gttgctaga   1140 agcaagttgg ataattagtc tgcaatcaat caatcagatc aatgcctgca t gcaagatga   1200 atagatctgg actagtagct taacatgaaa gggaaattaa attttattt a ggaactcga    1260 tactggtttt tgttacttta gtttagcttt tgtgaggttg aaacaattca g atgttttt    1320 taacttgtat atgtaaagat caatttctcg tgacagtaaa taataatcca a tgtcttctg   1380 ccaaattaat atatgtattc gtattttat atgaaaaaaa aaaaaaaaa a aaaaaaaa      1440 aaaaaaaaaa aaaaaaaaaa                                                 146 0
```

<210> SEQ ID NO 96
<211> LENGTH: 788
<212> TYPE: DNA
<213> ORGANISM: Pinus radiata

<400> SEQUENCE: 96

```
ataagactct cgagaaggtc tatgtccccg aggaggggt tctcaactta a tcgcagaga     60 caccatttcc agctaatatt ggcatagcaa ttggtcattc tatctttgtc a aaggagatc   120 aaacaaattt tgaaattgga cctaatggtg tggaggctag tcagctatac c cagatgtga   180 aatataccac tgtcgatgag tacctcagca aatttgtgtg aagtatgcga g attctcttc   240 cacatgcttc agagatacat aacagtttca atcaatgttt gtcctaggca t ttgccaaat   300 tgtgggttat aatccttcgt aggtgtttgg cagaacagaa cctcctgttt a gtatagtat   360 gacgagctag gcactgcaga tccttcacac ttttctcttc cataagaaac a aatactcac   420 ctgtggtttg ttttctttct ttctggaact ttggtatggc aataatgtct t tggaaaccg   480 cttagtgtgg aatgctaagt actagtgtcc agagttctaa gggagttcca a aatcatggc   540 tgatgtgaac tggttgttcc agagggtgtt tacaaccaac agttgttcag t gaataattt   600 tgttagagtg tttagatcca tctttacaag gctattgagt aaggttggtg t tagtgaacg   660 gaatgatgtc aaatcttgat gggctgactg actctcttgt gatgtcaaat c ttgatggat   720 tgtgtctttt tcaatggtaa aaaaaaaaa aaaaaaaa aaaaaaaaa a aaaaaaaa        780 aaaaaaaa                                                              788
```

<210> SEQ ID NO 97
<211> LENGTH: 577
<212> TYPE: DNA
<213> ORGANISM: Pinus radiata

<400> SEQUENCE: 97

```
gcccgacggc cacttgttgg acgccatgga agctctccgg aaagccggga t tctggaacc    60 gtttaaactg cagcccaagg aaggactggc tctcgtcaac ggcacagcgg t gggatccgc   120 cgtggccgcg tccgtctgtt ttgacgccaa cgtgctgggc gtgctggctg a gattctgtc   180 tgcgctcttc tgcgaggtga tgcaaggaa accggagttc gtagatccgt t aacccacca   240 gttgaagcac cacccagggc agatcgaagc gcggccgtc atggagttcc t cctcgacgg   300 tagcgactac gtgaaagaag cagcgcggct tcacgagaaa gacccgttga g caaaccgaa   360 acaagaccgc tacgctctgc gaacatcgcc acagtggttg gggcctccga t cgaagtcat   420 ccgcgctgct actcactcca tcgagcggga gatcaattcc gtcaacgaca a tccgttaat   480 cgatgtctcc agggacatgg ctctccacgg cggcaacttc cagggaacac c catcggagt   540
```

```
ttccatggac aacatgcgaa tctctttggc agccgtc                                577
```

<210> SEQ ID NO 98
<211> LENGTH: 492
<212> TYPE: DNA
<213> ORGANISM: Pinus radiata

<400> SEQUENCE: 98

```
tacctggcca accccgtcac gactcacgtc cagagcgccg aacaacacaa c caggatgtc       60
aattccctcg gcttgatctc cgccagaaag actgccgagg ccgttgagat t ttaaagctg      120
atgttcgcta catatctggt ggccttatgc caggcgatcg atctccggca c ctggaagaa      180
aacatgcgat ccgttgtgaa gcacgtagtc ttgcaggccg caagaaagac a ctgtgcact      240
gcagaagacg gaagcctcca cgacaccgga ttttgcgaga aggagctcct g caagtcatc      300
gatcatcagc ccgttttctc gtacatcgac gatcccacaa atccatcata c gcgcttatg      360
ctccaactca gagaagtgct cgtagatgag gctctcaaat catcttgccc a gacgggaat      420
gacgaatccg atcacaattt gcagcccgct gagagcgctg gagctgctgg a atattaccc      480
aattgggtgt tt                                                           492
```

<210> SEQ ID NO 99
<211> LENGTH: 391
<212> TYPE: DNA
<213> ORGANISM: Pinus radiata

<400> SEQUENCE: 99

```
cgttttccca aaggccattt tcgggcaggg ctacggcgca tgacagaagc a ggcccggtg       60
ctggcaatga acctagcctt cgcaaagaat cctttcccg ccaaatctgg c tcctgcgga      120
acagtcgtcc ggaacgctca aataaagatc ctcgattaca ggaactggcg a gtctctccc      180
gcacaatcaa gccggcgaaa tctgcatccg cggacccgaa ataatgaaag g atatattaa      240
cgacccggaa tccacggccg ctacaatcga tgaagaaggc tggctccaca c aggcgacgt      300
cgggtacatt gacgatgacg aagaaatctt catagtcgac agagtaaagg a gattatcaa      360
tataaaggct tccaggtgga tcctgctaat c                                      391
```

<210> SEQ ID NO 100
<211> LENGTH: 567
<212> TYPE: DNA
<213> ORGANISM: Eucalyptus grandis

<400> SEQUENCE: 100

```
ctgaattttc cctaactaga aataaagaga ttatatacat acacgagcaa a gcgctctcc       60
tccagttgtc ttccttcgtt cgctcatctc tcctcgtaca ttattagcat a cgacctctt      120
gtatcggacc cggatccgct atcgttaacg tacacacgtt ctagtgctga a tggagatgg      180
agagcaccac cggcaccggc aacggccttc acagcctctg cgccgccggg a gccaccatg      240
ccgacccact gaactggggg gcggcggcag cagccctcac agggagccac c tcgacgagg      300
tgaagcggat ggtcgaggag taccggaggc cggcggtgcg cctcggcggg g agtccctca      360
cgatagccca ggtggcggcg gtggcgagtc aggagggggt aggggtcgag c tctcggagg      420
cggcccgtcc cagggtcaag gccagcagcg actgggtcat ggagagcatg a acaagggaa      480
ctgacagcta cggggtcaca ccgggttcgg cggcaacttc tcaaccggag g ccgaagcaa      540
ggcggtcctt ttcagaagga acttata                                          567
```

<210> SEQ ID NO 101
<211> LENGTH: 612
<212> TYPE: DNA
<213> ORGANISM: Eucalyptus grandis

<400> SEQUENCE: 101

| | | | | | |
|---|---|---|---|---|---|
| aaagcaacac | attgaactct | ctctctctct | ctctctctct | ctctctctct c | cccacccc | 60 |
| cccttcccaa | ccccacccac | atacagacaa | gtagatacgc | gcacacagaa g | aagaaaaga | 120 |
| tggggtttc | aatgcagtca | atcgcactag | cgacggttct | ggccgtccta a | cgacatggg | 180 |
| cgtggagggc | ggtgaactgg | gtgtggctga | ggccgaagag | gctcgagagg c | ttctgagac | 240 |
| agcaaggtct | ctccggcaag | tcctacacct | tcctggtcgg | cgacctcaag g | agaacttgc | 300 |
| ggatgctcaa | ggaagccaag | tccaagccca | tcgccgtctc | cgatgacatc a | agcctcgtc | 360 |
| tcttgccttt | cttgcatcaa | tccttccaaa | cctatggcaa | agactcgttc a | catggatgg | 420 |
| gcccaacacc | aagagtgaac | attacgaacc | cggaacaaat | aaaggaggta t | tctctaaga | 480 |
| tatatgacta | tcccaagcca | gcctccaatc | ccctggtgaa | gttgctcgct g | atggactcg | 540 |
| cgaaccatga | gggcgagaaa | tgggctcggc | accgaaagat | tatcaatcca g | cattccaca | 600 |
| tggagaagtt | ga | | | | | 612 |

<210> SEQ ID NO 102
<211> LENGTH: 455
<212> TYPE: DNA
<213> ORGANISM: Eucalyptus grandis

<400> SEQUENCE: 102

| | | | | | |
|---|---|---|---|---|---|
| tgtctctctc | tctctctctc | tctgtaaacc | accatgctct | tcctcactca t | ctcctagca | 60 |
| gttctagggg | ttgtgttgct | cctgctaatt | ctatggaggg | caagatcttc t | ccgaacaaa | 120 |
| cccaaaggta | ctgccttacc | cccggagctg | ccgggcgcat | ggccgatcat a | ggccacatc | 180 |
| cacttgctgg | gcggcgagac | cccgctggcc | aggaccctgg | ccgccatggc g | acaagcag | 240 |
| ggcccgatgt | ttcggatccg | tctcggagtc | cacccggcga | ccatcataag c | agccgtgag | 300 |
| gcggtccggg | agtgcttcac | cacccacgac | aaggacctcg | cttctcgccc c | aaatccaag | 360 |
| gcgggaatcc | acttgggcta | cgggtatgcc | ggttttggct | tcgtagaata c | gggactttt | 420 |
| tggcgcgaga | tgaggaagat | caccatgctc | gagct | | | 455 |

<210> SEQ ID NO 103
<211> LENGTH: 1866
<212> TYPE: DNA
<213> ORGANISM: Eucalyptus grandis

<400> SEQUENCE: 103

| | | | | | |
|---|---|---|---|---|---|
| cgggctcgtg | gctcggctcc | ggcgcaagcc | gcccttccca | ccgggcccga g | gggcctccc | 60 |
| ggtcatcggg | aacatgctca | tgatgggcga | gctcacccac | cgcggcctcg c | gagtctggc | 120 |
| gaagaagtat | ggcgggatct | tccacctccg | catgggcttc | ctgcacatgg t | tgccgtgtc | 180 |
| gtccccgac | gtgcccgcc | aggtcctcca | ggtccacgac | gggatcttct c | gaaccggcc | 240 |
| tgccaccatc | gcgatcagct | acctcacgta | tgaccgggcc | gacatggcct t | cgcgcacta | 300 |
| cggcccgttc | tggcggcaga | tgcggaagct | gtgcgtgatg | aagctcttca g | ccggaagcg | 360 |
| ggctgagtcg | tgggagtcgg | tccgcgatga | ggtggacacg | atggtgcgca c | cgtcgcggg | 420 |
| cagcgagggg | accgccgtga | acatcggcga | gctcgtgttc | gagctcacgc g | ggacatcat | 480 |
| ctaccgcgcg | gccttcgcac | gagctcgacc | gagggccagg | acgagttcat c | agcatactg | 540 |

-continued

```
caggagttct cgaaattatt tggcgccttc aacatagccg attttatccc g tacctgagc        600 tggatcgatc cgcaagggct caccgccagg cttgtcaagg cgcgccagtc g ctggacggg        660 ttcatcgacc acattataga tgatcacatg gacaagaaga gaaacaagac g agttccggt        720 ggaggcgatc aagatgtcga taccgacatg gtcgacgatc tgctggcctt c tacagcgac        780 gaagcgaagg tgaacgagtc cgacgatttg cagaactcga tcaggctaac g agagacaac        840 atcaaggcca tcatcatgga cgtgatgttc ggcgggacgg agactgtggc g tcggctatc        900 gagtgggcca tggcggagct catgcgaagc cccgaggacc tgaagaaggt c cagcaagaa        960 ctcgcggatg tcgtgggcct agaccggaga gtcgaggaga gcgacttcga g aagctgacc       1020 tatctcaagt gctgcctcaa agagaccctc cgcctccacc cgccgatccc g ctgctcctc       1080 cacgagacgg cagaggacgc cgtgatctcc ggctaccgca tccccgcacg g tcccgggtc       1140 atgatcaatg catgggccat cgggcgtgac cccggctcgt ggaccgaacc t gacaagttc       1200 aaaccgtccc ggttcctgga gtcaggcatg cccgactaca aggggagcaa c ttcgagttc       1260 atcccttcg gtcgggccg gaggtcgtgc cagggatgc agctcgggct c tacgcgctc         1320 gacatggccg tggcccacct cctgcactgc ttcacgtggg aactgcccga c gggatgaag       1380 ccgagcgaga tggacatggg cgacgtcttc gggctcaccg cgccgaggtc c acccggctc       1440 gtggcggtgc cgactccgag gttggtgggg gctctatatt gagcaagcaa a tggagggtc       1500 gggttggggg gtgcgaggag gggaacgtat ttttcagctc ctggagggct g caagatttg       1560 gagtgcataa acccatccat acaagggcaa agagggtgg tgccaaaatg a tttgcatgg        1620 attttcgat ttttgttttg tattataaaa aaggtcaaat aaccgaagag g acaagaaag        1680 acaagaaaaa gaattgagac ggaacttgaa tcaatgttgt tctgttctct c tttctatt         1740 ctttgtggat attacaagac ttatctcatt tggtgggctt ttctttttctt g tgatttctt      1800 tgatcttgtc atacacaaat aaatatggaa tgaagaaacc tttccatcaa a aaaaaaaa         1860 aaaaaa                                                                    1866
```

<210> SEQ ID NO 104
<211> LENGTH: 519
<212> TYPE: DNA
<213> ORGANISM: Eucalyptus grandis

<400> SEQUENCE: 104

```
cacgagctcg tgagccttcc cggagacaag gccatcttac ttcgcaacaa a ttgcgtccg         60 cactcctttc tcaagaaacc tagtcatcca agaagcagag cattgcaact g caaacagcc        120 aaagcccaaa ctcgtacaga aggagagaga gagagagaat agaagcatga g tgcatgcac        180 gaaccaagca atcacgacgg ccagtgaaga tgaagagttc ttgttcgcca t ggaaatgaa        240 tgctctgata gcactcccct tggtcttgaa ggccaccatc gaactgggga t cctcgaaat        300 actggccgag tgcgggccta ggctccact ttcgcctgct cagattgcct c ccgtctctc         360 cgcaaagaac ccggaagccc ccgtaaccct tgaccggatc ctccggtttc t cgccagcta       420 ctccatcctc tcttgcactc tcgcccaaga cacagaaggc aacccctga g ctttacgg         480 tttgggaccc aaaagcaaac acttcgtcag agcccatgg                                519
```

<210> SEQ ID NO 105
<211> LENGTH: 594
<212> TYPE: DNA
<213> ORGANISM: Eucalyptus grandis

<400> SEQUENCE: 105

```
ccaaccctgg accaggtact tttggcaggc ggtccattgc ccttcaaacc g gtccaaacc      60 ggaccatcac tgtccttata tacgttgcat catgcctgct catagaactt a ggtcaactg     120 caacatttct tgatcacaac atattacaat attcctaagc agagagagag a gagagagag    180 agagagagag agagagagag tttgaatcaa tggccaccgc cggagaggag a gccagaccc    240 aagccgggag gcaccaggag gttggccaca agtctctcct tcagagtgat g ctctttacc    300 aatatatttt ggagaccagc gtgtacccaa gagagcctga gcccatgaag g agctcaggg    360 aaataacagc aaaacatcca tggaacataa tgacaacatc agcagacgaa g ggcagttct    420 tgaacatgct tctcaagctc atcaacgcca agaacaccat ggagattggt g tcttcactg    480 gctactctct cctcgccacc gctcttgctc ttcctgatga cggaaagatt t tggctatgg    540 acattaacag agagagctat gaacttggcc tgccggtcat ccaaaaagcc g gtg          594
```

<210> SEQ ID NO 106
<211> LENGTH: 407
<212> TYPE: DNA
<213> ORGANISM: Eucalyptus grandis

<400> SEQUENCE: 106

```
ccgttttatt tcctctgatt tcctttgctc gagtctcgcg gaagagagag a agagaggag    60 aggagagaat gggttcgacc ggatccgaga cccagatgac cccgacccaa g tctcggacg   120 aggaggcgaa cctcttcgcc atgcagctgg cgagcgcctc cgtgctcccc a tggtcctca   180 aggccgccat cgagctcgac ctcctcgaga tcatggccaa ggccgggccg g gcgcgttcc   240 tctccccggg ggaagtcgcg gcccagctcc gacccagaa ccccgaggca c ccgtaatgc    300 tcgaccggat cttccggctg ctggccagct actccgtgct cacgtgcacc c tccgcgacc   360 tccccgatgg caaggtcgag cggctctacg gcttagcgcc ggtgtgc              407
```

<210> SEQ ID NO 107
<211> LENGTH: 1630
<212> TYPE: DNA
<213> ORGANISM: Eucalyptus grandis

<400> SEQUENCE: 107

```
ccgttttatt tcctctgctt tcctttgctc gagtctcgcg gaagagagag a agagaggag    60 aggagagaat gggttcgacc ggatccgaga cccagatgac cccgacccaa g tctcggacg   120 aggaggcgaa cctcttcgcc atgcagctgg cgagcgcctc cgtgctcccc a tggtcctca   180 aggccgccat cgagctcgac ctcctcgaga tcatggccaa ggccgggccg g gcgcgttcc   240 tctccccggg ggaagtcgcg gcccagctcc gacccagaa ccccgaggca c ccgtcatgc    300 tcgaccggat cttccggctg ctggccagct actccgtgct cacgtgcacc c tccgcgacc   360 tccccgatgg caaggtcgag cggctctacg gcttagcgcc ggtgtgcaag t tcttggtca   420 agaacgagga cggggtctcc atcgccgcac tcaacttgat gaaccaggac a aaatcctca   480 tggaaagctg gtattacctg aaagatgcgg tccttgaagg cggaatccca t tcaacaagg   540 cgtacgggat gaccgcgttc gagtatcatg gcaccgaccc gcgattcaac a agatctta    600 accggggaat gtctgatcac tccaccatta ctatgaagaa gatactggaa a catacaagg   660 gcttcgaggg cctcgagacc gtggtcgatg tcggaggcgg cactggggcc g tgctcagca   720 tgatcgttgc caaataccca tcgatgaaag ggatcaactt cgacctgcct c acgtgattg   780 aagacgctcc accccttcct ggtgtcaagc acgtcggagg cgacatgttc g tcagcgttc   840
```

-continued

| | | |
|---|---|---|
| caaagggaga tgccattttc atgaagtgga tatgccatga ctggagtgac g accattgcg | 900 | |
| cgaagttcct caagaactgc tacgatgcgc ttcccaacaa tggaaaggtg a tcgttgcag | 960 | |
| agtgcgtact ccctgtgtac ccagacacga gcctagcgac caagaatgtg a tccacatcg | 1020 | |
| actgcatcat gttggcccac aacccaggcg ggaaagagag gacacagaag g agttcgagg | 1080 | |
| cattggccaa aggggccgga tttcagggct tccaagtcat gtgctgcgct t tcggcactc | 1140 | |
| acgtcatgga gttcctgaag accgcttgat ctgctcctct gtggtgatgt t catggttct | 1200 | |
| tggatttgaa aggtcgtgaa ggagcccttt tctcacagtt ggcttcggca t accaagttc | 1260 | |
| ttctcataaa aggaaacaat aagaagcgac tgtatgatgg cgcaagtgga a gttacaaga | 1320 | |
| tttgttgttt tatgtctata aagttttgag tcttctgcat actgatttca c agaatgtgt | 1380 | |
| aacgaaacgg cgtatatgga tgtgcctgaa tgatggaaat tgtgatattc t gtcttcttt | 1440 | |
| ttcagtaaat cacttcgaac aaaagttgtg ttgctcgtgg caaccaggaa a aaatctgtg | 1500 | |
| ggtgactttg agttaaagcc tgtcattcac aaaccccatg gcattgcctt t ggtcagggg | 1560 | |
| tcagccaagc cggaagcgtc aacgtgaaaa gatcctcaag ggtccattaa a atccccaca | 1620 | |
| aacccagagc | 1630 | |

<210> SEQ ID NO 108
<211> LENGTH: 1248
<212> TYPE: DNA
<213> ORGANISM: Eucalyptus grandis

<400> SEQUENCE: 108

| | | |
|---|---|---|
| atcactaacc atctgccttt cttcatcttc tttcttctgc ttctcctccg t ttcctcgtt | 60 | |
| tcgatatcgt gaaaggagtc cgtcgacgac aatggccgag aagagcaagg t cctgatcat | 120 | |
| cggagggacg ggctacatcg gcaagttcat cgtggaagcg agtgcaaaag c agggcatcc | 180 | |
| cacgttcgcg ctggttaggc agagcacggt ctccgacccc gtcaagggcc a gctcgtcga | 240 | |
| gagcttcaag aacttgggcg tcactctgct catcggtgat ctgtacgatc a tgagagctt | 300 | |
| ggtgaaggca atcaagcaag ccgacgtggt gatatcgaca gtggggcaca t gcaaatggc | 360 | |
| ggatcagacc aagatcgtcg acgccattaa ggaagctggc aacgttaaga g attctttcc | 420 | |
| ttccgaattc ggcaatgatg tggacagggt gcatgctgtg gagccagcga a gtctgctttt | 480 | |
| tgaattgaag gcccagatcc gccgtgccgt ggaggcggca ggcatcccctt a cacctacgt | 540 | |
| cccatgtggc tgcttcgccg gctacttcct cccaacactg cgcagcagg a ggtcactgc | 600 | |
| tcctccgaag gacaaagtca ccgtcatggg tgacggaaat gcaaaggcaa t tttcaacaa | 660 | |
| ggaagatgac attgcggcct tcaccatcaa ggctgtggat gatccgagat c gctgaacaa | 720 | |
| gatcctttac atcaggcctc ctaagaacgt ttactcattc aatgagcttg t tgccttgtg | 780 | |
| ggagaagaaa attggcaaga ccctcgagaa gatttaccctt cctgaagagc a aatcctgaa | 840 | |
| gcaaatccag gagtccccaa ttcccatcaa tgtcatatta gcagtgaacc a ttcaatcttt | 900 | |
| tgttaagggc gacggtgcca attttgagat cgaggagtct tttggtgtcg a ggcttctga | 960 | |
| gctgtaccca gatgtgaagt acactacagt ggaagaatac ctcgaaaatt t tgtctaaat | 1020 | |
| taaggccatg cgtctcctgt tcttcaagga gtgagttacc gtgactctgg t ggacagtcg | 1080 | |
| atatgtatta aaaggctgta cacctaaaga atatcaaagg tcacggtctt a tttagaatt | 1140 | |
| gtctctgatg tcatattctt cttggtcttc ttggacatgt atttgctttc c tttgccgtg | 1200 | |
| gtatccatga atttcccagg ttgttgaaat taaaaaaaaa aaaaaaaa | 1248 | |

<210> SEQ ID NO 109
<211> LENGTH: 481
<212> TYPE: DNA
<213> ORGANISM: Eucalyptus grandis

<400> SEQUENCE: 109

| | | | | | |
|---|---|---|---|---|---|
| gttaatggca | gtgcagcctc | aacaccaccc | accttcctcc | atctctctcc t | cccttcttc | 60 |
| tttctctgac | ttcaatggca | gccgactcca | tgcttgcgtt | cagtataaga g | gaaggtggg | 120 |
| gcagcctaaa | ggggcactgc | gggtcactgc | atcaagcaat | aagaagatcc t | catcatggg | 180 |
| aggcacccgt | ttcatcggtg | tgtttttgtc | gagactactt | gtcaaagaag g | tcatcaggt | 240 |
| cactttgttt | accagaggaa | aagcacccat | cactcaacaa | ttgcctggtg a | gtcggacaa | 300 |
| ggacttcgct | gatttttcat | ccaagatcct | gcatttgaaa | ggagacagaa a | ggattttga | 360 |
| ttttgttaaa | tctagtcttg | ctgcagaagg | ctttgacgtt | gtttatgaca t | taacggcga | 420 |
| gaggcggatg | aagtcgcacc | aattttggat | gcctgccaaa | ccttgaacca g | tcaactact | 480 |
| g | | | | | 481 |

<210> SEQ ID NO 110
<211> LENGTH: 458
<212> TYPE: DNA
<213> ORGANISM: Eucalyptus grandis

<400> SEQUENCE: 110

| | | | | | |
|---|---|---|---|---|---|
| cataagctct | cccgtaatcc | tcacatcaca | tggcgaagag | caaggtcctc g | tcgttggcg | 60 |
| gcactggcta | cctcgggcgg | aggttcgtga | gggcgagcct | ggaccagggc c | accccacgt | 120 |
| acgtcctcca | gcgtccggag | accggcctcg | acattgagaa | gctccagacg c | tactgcgct | 180 |
| tcaagaggcg | tggcgcccaa | ctcgtcgagg | cctcgttctc | agacctgagg a | gcctcgtcg | 240 |
| acgctgtgag | gcgggtcgat | gtcgtcgtct | gtgccatgtc | ggggtccac t | tccggagcc | 300 |
| acaacatcct | gatgcagctc | aagctcgtgg | aggctatcaa | agaagctgga a | atgtcaagc | 360 |
| ggtttttgcc | gtcagagttc | ggaatggacc | cggccctcat | gggtcatgca a | ttgagccgg | 420 |
| gaagggtcac | gttcgatgag | aaatggaggt | gagaaaag | | 458 |

<210> SEQ ID NO 111
<211> LENGTH: 448
<212> TYPE: DNA
<213> ORGANISM: Eucalyptus grandis

<400> SEQUENCE: 111

| | | | | | |
|---|---|---|---|---|---|
| aggaggcacc | tcctcgaaac | gaagaagaag | aaggacgaag | gacgaaggag a | cgaaggcga | 60 |
| gaatgagcgc | ggcgggcggt | gccgggaagg | tcgtgtgcgt | gaccggggcg t | ccggttaca | 120 |
| tcgcctcgtg | gctcgtcaag | ctcctcctcc | agcgcggcta | caccgtcaag g | ccaccgtcc | 180 |
| gcgatccgaa | tgatccaaaa | aagactgaac | atttgcttgg | acttgatgga g | cgaaagata | 240 |
| gacttcaact | gttcaaagca | aacctgctgg | aagagggttc | atttgatcct a | ttgttgagg | 300 |
| gttgtgcagg | cgttttttcac | actgcctctc | cctttttatca | tgatgtcaag g | atccgcagg | 360 |
| cagaattact | tgatccggct | gtgaagggaa | cactcaatgt | cctgaagtca t | gttccaaag | 420 |
| accttctctg | cagcgtgtgg | cttgacat | | | 448 |

<210> SEQ ID NO 112
<211> LENGTH: 578
<212> TYPE: DNA
<213> ORGANISM: Eucalyptus grandis

<400> SEQUENCE: 112

```
gttgaacctc ccgtcctcgg ctctgctcgg ctcgtcaccc tcttcgcgct c ccgcatact      60
ccaccaccgc gtacagaaga tgagctcgga gggtgggaag gaggattgcc t cggttgggc     120
tgcccgggac ccttctgggt tcctctcccc ctacaaattc acccgcaggg c cgtgggaag    180
cgaagacgtc tcgattaaga tcacgcactg tggagtgtgc tacgcagatg t ggcttggac    240
taggaatgtg cagggacact ccaagtatcc tctggtgcca gggcacgaga t agttggaat   300
tgtgaaacag gttggctcca gtgtccaacg cttcaaagtt ggcgatcatg t gggggtggg   360
aacttatgtc aattcatgca gagagtgcga gtattgcaat gacaggctag a agtccaatg   420
tgaaaagtcg gttatgactt ttgatggaat tgatgcagat ggtacagtga c aaagggagg    480
atattctagt cacattgtcg tccatgaaag gtattgcgtc aggattccag a aaactaccc    540
gatggatcta gcagcgcatt tgctctgtgc tggatcac                            578
```

<210> SEQ ID NO 113
<211> LENGTH: 454
<212> TYPE: DNA
<213> ORGANISM: Eucalyptus grandis

<400> SEQUENCE: 113

```
aactcatctt gaaatgtcat tggagtcatc atcctctagt gagaagaaac a aatgggttc      60
cgccggattc gaatcggcca caaagccgca cgccgtttgc attccctacc c tgcacaaag    120
ccacattggc gccatgctca agctagcaaa gctcctccat cacaagggct t ccacatctc    180
cttcgtcaac accgagttca accaccgcg gctcgccagg gctcgaggcc c cgagttcac   240
aaatggaatg ctgagcgact ttcagttcct gacaatcccc gatggtcttc c tccttcgga   300
cttggatgcg atccaagaca tcaagatgct ctgcgaatcg tccaggaact a tatggtcag   360
ccccatcaac gatcttgtat cgagcctggg ctcgaacccg agcgtccctc c ggtgacttg    420
catcaatctc ggatggtttc atgacactcg tgac                                454
```

<210> SEQ ID NO 114
<211> LENGTH: 479
<212> TYPE: DNA
<213> ORGANISM: Eucalyptus grandis

<400> SEQUENCE: 114

```
catgattgag ggaatcaagg actcttcagg actcatcctg aacacatttg a agatctcga      60
gcagcccgct ctttctttac tccgccaaga agatccaatc gcagttttcg c aattggccc    120
attacacaaa tgcggtccat cttcatcggg aagtctcttg gcagaagacc g gagttgcat    180
ttcctggctg gacaagcaag cccctaactc agtggtctat gtgagttttg g gagcatcgc    240
ctctgtgaac gagtcggaat tttccgaaat gctttaggt ttagccgata g ccagcagcc    300
attcttgtgg gtggttcgac ccgggtcagt gagcggctcg gaactcttag a gaatttgcc   360
cggttgcttt ctgagggcat tacaggagag ggggaagatt gtgaaatggg c gcctcaaca   420
tgaagtgctg gctcatcggg gtgtcggagc gttttggact cacaatggat g gaactcca   479
```

<210> SEQ ID NO 115
<211> LENGTH: 420
<212> TYPE: DNA
<213> ORGANISM: Eucalyptus grandis

<400> SEQUENCE: 115

```
caacattgtg tttagagaga ggagagagaa ggcaaacacg cccgttttcg t tttactaag    60 agaagatggt gagcgttgtg gctggtagag tcgagagctt gtcgagcagt g gcattcagt   120 cgatcccgca ggagtatgtg aggccgaagg aggagctcac aagcattggc g acatcttcg   180 aggaggagaa gaagcatgag ggccctcagg tcccgaccat cgacctcgag g acatagcgt   240 ctaaagaccc cgtggtgagg gagaggtgcc acgaggagct caggaaggct g ccaccgact   300 ggggcgtcat gcacctcgtc aaccatggga tccccaacga cctgattgag c gtgtcaaga   360 aggctggcga ggtgttcttc aacctcccga tcgaggagaa ggagaagcat g ccaacgacc   420
```

<210> SEQ ID NO 116
<211> LENGTH: 679
<212> TYPE: DNA
<213> ORGANISM: Eucalyptus grandis

<400> SEQUENCE: 116

```
ctaagagagg agaggagagg agcaagatgg cactagcagg agctgcactg t caggaaccg    60 tggtgagctc ccccttttgtg aggatgcagc ctgtgaacag actcagggca t tccccaatg   120 tgggtcaggc cctgtttggt gtcaactctg gccgtggcag agtgactgcc a tggccgctt   180 acaaggtcac cctgctcacc cctgaaggca agtcgaact cgacgtcccc g acgatgttt   240 acatcttgga ctacgccgag gagcaaggca tcgacttgcc ctactcctgc c gtgccggct   300 cttgctcctc ctgcgcgggc aaggtcgtgg cggggagcgt cgaccagagc g acggcagct   360 tcctggatga tgatcagatt gaggaaggtt gggtcctcac ttgtgtcgcc t accctaagt   420 ctgaggtcac cattgagacc cacaaggaag aggagctcac tgcttgaagc t ctcctatat   480 ttgcttttgc ataaatcagt ctcactctac gcaactttct ccactctctc c cccttcac    540 tacatgtttg ttagttcctt tagtctcttc ctttttact gtacgaggga t gatttgatg    600 ttattctgag tctaatgtaa tggcttttct ttttcctatt tctgtatgag g aaataaaac   660 tcatgctcta aaaaaaaaa                                                 679
```

<210> SEQ ID NO 117
<211> LENGTH: 763
<212> TYPE: DNA
<213> ORGANISM: Eucalyptus grandis

<400> SEQUENCE: 117

```
catacaacta cactgcgacg ccgccgcaga acgcgagcgt gccgaccatg a acggcacca    60 aggtctaccg gttgccgtat aacgctacgg tccagctcgt tttacaggac a ccgggataa   120 tcgcgccgga gacccacccc atccatctgc acggattcaa cttcttcggt g tgggcaaag   180 gagtgggga ttatgaccca aagaaggatc ccaagaagtt caatctggtt g acccagtgg   240 agaggaacac cattggaatc ccatctggtg gatggatagc catcagattc a cagcagaca   300 atccaggagt ttggttcctg cactgccatc tggaagtgca cacaacttgg g gactgaaga   360 tggcattctt ggtggacaat gggaaggggc ctaaagagac cctgcttcca c ctccaagtg   420 atcttccaaa atgttgatca tttgatcatg aggacgacaa gcgattacta t gacaccaa    480 gttagtggaa tcttctcttt gaaaagaag aagaagagca agaagaataa g aaagatgag   540 gagagaagcc atagaagatt tgaccaagaa gagagagggc aataaaccaa a gagaccctt   600 gagatcacga catcccgcaa ttgtttctag agtaatagaa ggatttactc c gacactgct   660 acaataaatt aaggaagaca aggaatttgg ttttttcat tggaggagtg t aatttgttt   720 tttggcaagc tcatcacatg aatcacatgg aaaaaaaaa aaa                       763
```

<210> SEQ ID NO 118
<211> LENGTH: 538
<212> TYPE: DNA
<213> ORGANISM: Eucalyptus grandis

<400> SEQUENCE: 118

| | | | | | |
|---|---|---|---|---|---|
| atcaagagtt | tgagtctaaa | ccttgtctaa | tcctctctcg | catagtcatt t | ggagacgaa | 60 |
| gtgctgatcg | gccgcagctg | cattctcttc | gtaaaacatg | acggctgtcg g | caaaacctc | 120 |
| tttcctcttg | ggagctctcc | tcctcttctc | tgtggcggtg | acattggcag a | tgcaaaagt | 180 |
| ttactaccat | gattttgtcg | ttcaagcgac | caaggtgaag | aggctgtgca c | gacccacaa | 240 |
| caccatcacg | gtgaacgggc | aattcccggg | tccgactttg | gaagttaacg a | cggcgacac | 300 |
| cctcgttgtc | aatgtcgtca | acaaagctcg | ctacaacgtc | accattcact g | gcacggcgt | 360 |
| ccggcaggtg | agatctggtt | gggccgatgg | gccggaattt | gtgactcaat g | cccgattag | 420 |
| acccggcgga | agttacacgt | accgtttcac | catccaagga | caggtaggaa c | gctgtggtg | 480 |
| gcatgcacat | agctcttggc | taagagcgac | tgtgtatggt | gctctggcat t | cgtccaa | 538 |

<210> SEQ ID NO 119
<211> LENGTH: 515
<212> TYPE: DNA
<213> ORGANISM: Eucalyptus grandis

<400> SEQUENCE: 119

| | | | | | |
|---|---|---|---|---|---|
| ctctctctct | ctctctctct | gtgtgttcat | tctcgttgag | ctcgtggtcg c | ctcccgcca | 60 |
| tggatccgca | caagtaccgt | ccatccagtg | ctttcaacac | ttctttctgg a | ctacgaact | 120 |
| ctggtgctcc | tgtctggaac | aataactctt | cgttgactgt | tggaagcaga g | gtccaattc | 180 |
| ttcttgagga | ttatcacctc | gtggagaaac | ttgccaactt | tgataggag a | ggattccag | 240 |
| agcgtgtggt | gcatgccaga | ggagccagtg | caaagggatt | ctttgaggtc a | ctcatgaca | 300 |
| tttcccagct | tacctgtgct | gatttccttc | gggcaccagg | agttcaaaca c | ccgtgattg | 360 |
| tccgtttctc | cactgtcatc | cacgaaaggg | gcagccctga | aaccctgagg g | accctcgag | 420 |
| gttttgctgt | gaagttctac | acaagagagg | gtaactttga | tctggtggga a | acaatttcc | 480 |
| ctgtcttctt | tgtccgtaat | gggataaatt | ccccg | | | 515 |

<210> SEQ ID NO 120
<211> LENGTH: 458
<212> TYPE: DNA
<213> ORGANISM: Eucalyptus grandis

<400> SEQUENCE: 120

| | | | | | |
|---|---|---|---|---|---|
| gctccctctc | gtactgccat | actcctgggc | cgggattcgg | ataggttttt g | cggcgatcc | 60 |
| atttctcgat | tcaagggggaa | gaatcatggg | gaagtcctac | ccgaccgtga g | cgaggagta | 120 |
| caagaaggct | gtcgagaaat | gcaagaagaa | gttgagaggc | ctcatcgctg a | gaagagctg | 180 |
| cgctccgctc | atgctccgca | tcgcgtggca | ctccgccggt | accttcgatg t | gaagacgaa | 240 |
| gaccggaggc | ccgttcggga | ccatgaagca | cgccgcggag | ctcagccacg g | gccaacag | 300 |
| cgggctcgac | gttgccgatc | aggtcttgca | gccgatcaag | gatcagttcc c | cgtcatcac | 360 |
| ttatgctgat | ttctaccagc | tggctggcgt | cgttgctgtg | gaagttactg g | tggacctga | 420 |
| agttgctttt | cacccaggaa | gagaggcaaa | ccacaacc | | | 458 |

<210> SEQ ID NO 121

<211> LENGTH: 1243
<212> TYPE: DNA
<213> ORGANISM: Eucalyptus grandis

<400> SEQUENCE: 121

| | | | | | |
|---|---|---|---|---|---|
| ctcccacttc | tgtctcgcca | ccattactag | cttcaaagcc | cagatctcag t | ttcgtgctc | 60 |
| tcttcgtcat | ctctgcctct | tgccatggat | ccgtacaagt | atcgcccgtc c | agcgcttac | 120 |
| gattccagct | tttggacaac | caactacggt | gctcccgtct | ggaacaatga c | tcatcgctg | 180 |
| actgttggaa | ctagaggtcc | gattctcctg | gaggactacc | atctgattga g | aaacttgcc | 240 |
| aacttcgaga | gagagaggat | tcctgagcgg | gtggtccatg | cacggggagc c | agcgcgaaa | 300 |
| gggttcttcg | aggtcaccca | cgacatctct | cacttgacct | gtgctgattt c | ctccgggct | 360 |
| cctggagtcc | agacgcccgt | catcgtccgt | ttctccaccg | tcatccacga g | cgcggcagc | 420 |
| cccgaaaccc | tcagggaccc | tcgtggtttt | gcagtgaagt | tctacaccag a | gagggaaac | 480 |
| tttgatctgg | tggggaacaa | tttcccagtc | ttcttcgttc | gcgatgcaat g | aaattcccg | 540 |
| gacgcgatcc | atgcgttcaa | gccgaacccg | aagtctaaca | tccaggagat g | tggagaatc | 600 |
| atcgatttct | tctcccacca | gcccgagagt | ctgtccacgt | tcgcgtggtt c | ttcgatgat | 660 |
| gtgggcattc | tcaggactac | caggcacatg | gagggattcg | gtgtgcacgc t | ttcaccttc | 720 |
| atcaacaaga | ccggaaagac | gaattacgtt | aaattccact | ggaagccaac t | gcggggtg | 780 |
| aagtgcttgc | tggaggagga | ggcgatcctc | attggaggat | cgaaccacag c | catgcgacc | 840 |
| aaggatcttt | atgactcgat | cgctgctggc | aactaccgg | agtggaagct c | tacatccaa | 900 |
| gtgatggatc | cwgctcttga | agacagcttc | gacttcgatc | cgctggatat g | acgaaggaa | 960 |
| tggcctgagg | acatcttgcc | tctgcaacca | gtaggccgct | tggtgctgaa c | aaaaacgtc | 1020 |
| gataacttct | tcgctgagaa | tgagcagcta | gcgtttaacc | cagcatttgt g | gtccctggc | 1080 |
| atctattact | ccaatgataa | gcttctccaa | gctaggattt | tcgcctattc t | gatactcac | 1140 |
| cgatatcgcc | ttggaccaaa | ctaccttcaa | ctccccgtta | atgtcccaag t | gcgtcatca | 1200 |
| caacaaccac | catgatggtt | tcatgaatat | catgcacagg | gat | | 1243 |

<210> SEQ ID NO 122
<211> LENGTH: 404
<212> TYPE: DNA
<213> ORGANISM: Pinus radiata

<400> SEQUENCE: 122

| | | | | | |
|---|---|---|---|---|---|
| gacaaggtca | taggccctct | cttcaaatgc | ttggatgggt | ggaaaggaac t | cctggccca | 60 |
| ttctgaaata | aataatcttc | caagatcgcc | tttatacaac | gactgctatg a | tttgagtcc | 120 |
| tcggatcttt | tgttgatgc | agttgtttac | cgatctggaa | tttgattggt c | ataaagctt | 180 |
| gattttgttt | ttctttcttt | tgttttatac | tgctggattt | gcatcccatt g | gatttgcca | 240 |
| gaaatatgta | agggtggcag | atcatttggg | tgatctgaaa | catgtaaaag t | ggcggatca | 300 |
| tttgggtagc | atgcagatca | gttgggtgat | cgtgtactgc | tttcactatt a | cttacatat | 360 |
| ttaaagatcg | ggaataaaaa | catgatttta | attgaaaaaa | aaaa | | 404 |

<210> SEQ ID NO 123
<211> LENGTH: 415
<212> TYPE: DNA
<213> ORGANISM: Pinus radiata

<400> SEQUENCE: 123

| | | | | | |
|---|---|---|---|---|---|
| caaggaagaa | aatatggttg | cagcagcaga | aattacgcag | gccaatgaag t | tcaagttaa | 60 |

```
aagcactggg ctgtgcacgg acttcggctc gtctggcagc gatccactga a ctgggttcg      120 agcagccaag gccatggaag gaagtcactt tgaagaagtg aaagcgatgg t ggattcgta      180 tttgggagcc aaggagattt ccattgaagg gaaatctctg acaatctcag a cgttgctgc      240 cgttgctcga agatcgcaag tgaaagtgaa attggatgct gcggctgcca a atctagggt      300 cgaggagagt tcaaactggg ttctcaccca gatgaccaag gggacggata c ctatggtgt      360 cactactggt ttcggagcca cttctcacag gagaacgaac cagggagccg a gctt          415
```

<210> SEQ ID NO 124
<211> LENGTH: 1659
<212> TYPE: DNA
<213> ORGANISM: Pinus radiata

<400> SEQUENCE: 124

```
gttgcaggtc ggggatgatt tgaatcacag aaacctcagc gattttgcca a gaaatatgg      60 caaaatcttt ctgctcaaga tgggccagag gaatcttgtg gtagtttcat c tcccgatct     120 cgccaaggag gtcctgcaca cccagggcgt cgagtttggg tctcgaaccc g gaacgtggt     180 gttcgatatc ttcacgggca aggggcagga catggtgttc accgtctatg g agatcactg     240 gagaaagatg cgcaggatca tgactgtgcc tttctttacg aataaagttg t ccagcacta     300 cagattcgcg tgggaagacg agatcagccg cgtggtcgcg gatgtgaaat c ccgcgccga     360 gtcttccacc tcgggcattg tcatccgtag gcgcctccag ctcatgatgt a taatattat     420 gtataggatg atgttcgaca ggagattcga atccgaggac gacccgcttt t cctcaagct     480 caaggccctc aacggagagc gaagtcgatt ggcccgagc tttgagtaca a ttatgggga     540 tttcattccc attcttaggc ccttcctcag aggttatctc agaatctgca a tgagattaa     600 agagaaacgg ctctctcttt tcaaggacta cttcgtggaa gagcgcaaga a gctcaacag     660 taccaagact agtaccaaca ccggggagct caagtgtgca atggaccata t tttagatgc     720 tcaggacaag ggagagatca atgaggataa tgttttgtac atcgttgaga a catcaacgt     780 tgcagcaatt gagacaacgc tgtggtcgat ggaatgggga atagcggagc t ggtgaacca     840 ccaggacatt cagagcaagg tgcgcgcaga gctggacgct gttcttggac c aggcgtgca     900 gataacggaa ccagacacga caaggttgcc ctaccttcag gcggttgtga a ggaaaccct     960 tcgtctccgc atggcgatcc cgttgctcgt cccccacatg aatctccacg a cgccaagct    1020 cggggggctac gatattccgg cagagagcaa gatcctggtg aacgcctggt g gttggccaa    1080 caaccccgcc aactggaaga accccgagga gttccgcccc gagcggttct t cgaggagga    1140 gaagcacacc gaagccaatg caacgacttt caaattcctg ccttgcggtg t ggggaggag    1200 gagctgcccg ggaatcattc tggcgctgcc tctcctcgca ctctccatcg g aagacttgt    1260 tcagaacttc caccttctgc cgccgcccgg gcagagcaaa gtggatgtca c tgagaaggg    1320 cgggcagttc agccttcaca ttctcaacca ttctctcatc gtcgccaagc c catagcttc    1380 tgcttaatcc caacttgtca gtgactggta tataaatgcg cgcacctgaa c aaaaaacac    1440 tccatctatc atgactgtgt gtgcgtgtcc actgtcgagt ctactaagag c tcatagcac    1500 ttcaaaagtt tgctaggatt tcaataacag acaccgtcaa ttatgtcatg t ttcaataaa    1560 agtttgcata aattaaatga tatttcaata tactattttg actctccacc a attggggaa    1620 ttttactgct aaaaaaaaaa aaaaaaaaaa aaaaaaaa                             1659
```

<210> SEQ ID NO 125

<211> LENGTH: 461
<212> TYPE: DNA
<213> ORGANISM: Pinus radiata

<400> SEQUENCE: 125

| | | | | | |
|---|---|---|---|---|---|
| atttccatgg | cgattccgtt | tggcttcaat | tcgtttcctc | tggctgtcct c | gtcctcgtt | 60 |
| ttccttgttc | ttcctccgac | tttttctctg | gaagatatgg | cgtaatagga a | cctgccgcc | 120 |
| aggaccccg | gcatggccga | tcgtagggaa | cgtccttcag | attggatttt c | cagcggcgc | 180 |
| gttcgagacc | tcagtgaaga | aattccatga | gagatacggt | ccaatattca c | tgtgtggct | 240 |
| cggttcccgc | cctctgctga | tgatcaccga | ccgcgagctt | gcccacgagg c | gctcgtaca | 300 |
| gaagggctcc | gtcttcgctt | gaccgcccgc | ccgccctcgg | gatgcagaaa a | tcttcagta | 360 |
| gcaaccagca | caacatcact | tcggctgaat | acggcccgct | gtggcggagc t | tcgcaggaa | 420 |
| tctggttaaa | gaagccctga | gacttcggcg | atgaaggctt | t | | 461 |

<210> SEQ ID NO 126
<211> LENGTH: 569
<212> TYPE: DNA
<213> ORGANISM: Pinus radiata

<400> SEQUENCE: 126

| | | | | | |
|---|---|---|---|---|---|
| acccagtgac | cttcaggcct | gagagatttc | ttgaggaaga | tgttgatatt a | agggccatg | 60 |
| attacaggct | actgccattc | ggtgcagggc | gcaggatctg | ccctggtgca c | aattgggta | 120 |
| ttaatttagt | tcagtctatg | ttgggacacc | tgcttcatca | tttcgtatgg g | cacctcctg | 180 |
| agggaatgaa | ggcagaagac | atagatctca | cagagaatcc | agggcttgtt a | ctttcatgg | 240 |
| ccaagcctgt | gcaggccatt | gctattcctc | gattgcctga | tcatctctac a | gcgacagc | 300 |
| cactcaattg | atcaattgat | ctgatagtaa | gtttgaattt | tgttttgata c | aaaacgaaa | 360 |
| taacgtgcag | tttctccttt | tccatagtca | acatgcagct | ttcttctct g | aagcgcatg | 420 |
| cagcttctt | tctctgaagc | ccaacttcta | gcaagcaata | actgtatatt t | agaacaaa | 480 |
| tacctattcc | tcaaattgag | tatttctctg | taggcgatgt | tcacttgtgc a | atttgcaag | 540 |
| atatagtaaa | gtttactcta | aaaaaaaaa | | | | 569 |

<210> SEQ ID NO 127
<211> LENGTH: 661
<212> TYPE: DNA
<213> ORGANISM: Pinus radiata

<400> SEQUENCE: 127

| | | | | | |
|---|---|---|---|---|---|
| gttttatctg | aaggacgctg | tgcttgaagg | ctcccagcca | ttcaccaaag c | ccatggaat | 60 |
| gaatgcgttc | gagtacccgg | ccatcgatca | gagattcaac | aagattttca a | cagggctat | 120 |
| gtctgagaat | tctaccatgt | tgatgaacaa | gattttggat | acttacgagg g | ttttaagga | 180 |
| ggttcaggag | ttggtggatg | tgggaggagg | tattgggtcg | actctcaatc t | catagtgtc | 240 |
| taggtatccc | cacatttcag | gaatcaactt | cgacttgtcc | catgtgctgg c | cgatgctcc | 300 |
| tcactaccca | gctgtgaaac | atgtgggtgg | agacatgttt | gatagtgtac c | aagtggcca | 360 |
| agctattttt | atgaagtgga | ttctgcatga | ttggagcgat | gatcattgca g | gaagctttt | 420 |
| gaagaattgt | cacaaggcgt | tgccagagaa | ggggaaggtg | attgcggtgg a | ccaccattct | 480 |
| cccagtggct | gcagagacat | ctccttatgc | tcgtcaggga | tttcatacag a | tttactgat | 540 |
| gttggcatac | aacccagggg | gcaaggaacg | cacagagcaa | gaatttcaag a | tttagctaa | 600 |
| ggagacggga | tttgcaggtg | gtgttgaacc | tgtatgttgt | gtcaatggaa t | gtgggtaat | 660 |

| | |
|---|---:|
| g | 661 |

<210> SEQ ID NO 128
<211> LENGTH: 427
<212> TYPE: DNA
<213> ORGANISM: Pinus radiata

<400> SEQUENCE: 128

| | | | | | |
|---|---|---|---|---|---:|
| aattttctg | tggtaagcat | atctatggct | caaaccagag | agaaggacga | 60 |
| acaaactcca | aaggattggt | atgcgtgaca | ggagcggctg | gttacttggc a | 120 |
| atcaagcgtc | tcctccagtg | tggttaccaa | gtgagaggaa | ctgtgcggga t | 180 |
| gagaaaaga | tggctcattt | atggaagtta | gatggggcga | agagagact g | 240 |
| aaagctgatt | taatggacga | gggcagcttc | gatgaggtca | tcagaggctg c | 300 |
| tttcacacag | cgtctccagt | cgtgggtgtc | aaatcagatc | ccaagatatg g | 360 |
| gccaagactt | tagcagaaaa | agcagcatgg | gattttgccc | aagaaaacca t | 420 |
| gttgcag | | | | | 427 |

<210> SEQ ID NO 129
<211> LENGTH: 1412
<212> TYPE: DNA
<213> ORGANISM: Pinus radiata

<400> SEQUENCE: 129

| | | | | | |
|---|---|---|---|---|---:|
| gaaaacatca | tccaggcatt | ttggaaattt | agctcgccgg | ttgattcagg a | 60 |
| ggcttttggc | gaagagcaga | ctgccttgcc | acaagaaacg | cctttgaatc c | 120 |
| tcgaggaaca | gtgtgcgtta | caggagctgc | tgggttcata | gggtcatggc t | 180 |
| attgcttgag | cgaggatata | gtgttagagc | aactgtgcga | gacactggta a | 240 |
| gacaaagcat | ctgttggatc | tgccgggggc | aaatgagaga | ttgactctct g | 300 |
| tttggatgat | gaaggaagct | ttgatgctgc | cattgatggg | tgtgagggtg t | 360 |
| tgccactccc | atggatttcg | agtccgagga | tcccgagaat | gagataatta a | 420 |
| caacggggtc | ttgaatgtta | tgagatcgtg | tgcaaaagcc | aagtccgtga a | 480 |
| tttcacgtca | tctgctggga | ctgtgaattt | tacagatgat | ttccaaacac c | 540 |
| ttttgacgaa | tcatgctgga | ccaacgtgga | tctttgcaga | aaagttaaaa t | 600 |
| gatgtacttt | gtatcgaaga | cattagcaga | gaaagctgct | tgggattttg c | 660 |
| caagatcgat | ctcattactg | ttatccccac | attggtcgtt | ggaccattca t | 720 |
| catgccaccg | agcatgatca | cagccttggc | actgttaacg | cggaatgaac c | 780 |
| gatactgaga | caggtacagc | tggttcactt | ggatgatctc | tgtatgtcac a | 840 |
| atatgaacat | cctgaagcaa | aggcagata | catctcttcc | acatgtgatg c | 900 |
| ccaagtggcc | aagatgctgg | ctcagaaata | cccagagtac | aatgtaccaa c | 960 |
| ggatgcggat | gagtccctgc | cggccgtgcc | attttcgtca | agaagctcc t | 1020 |
| cttcaagttc | aactacacca | tggaagagat | gtttgatggg | gccattaagt g | 1080 |
| gaaaggattg | ctgcctgaga | aagcatcttt | ctgataagta | tctactgatg c | 1040 |
| acaccgttgg | catgtgtggt | ttgtgtaaga | catggtggca | gtggagaaat a | 1200 |
| atttggttta | tagaaaacag | caggaattac | tacttgcaag | agtgacttat g | 1260 |
| atagaaataa | gaagaatacc | ggctgatcgc | tgttgtttat | taatgcgaat t | 1320 |

```
ttgacaaggt cataccaggg ctcctggaat gctacatatg tacggctgat t ctagctcca    1380 gtaatataat ttttcaaatt ctaaaaaaaa aa                                    1412
```

<210> SEQ ID NO 130
<211> LENGTH: 666
<212> TYPE: DNA
<213> ORGANISM: Pinus radiata

<400> SEQUENCE: 130

```
atcaattttt gcatattatt aaaaagtaag tgtattcgtt ctctatattg a tcagtcaca      60 gagtcatggc cagttgtggt tccgagaaag taagagggtt gaatggagat g aagcatgcg    120 aagagaacaa gagagtggtt tgtgtaactg gggcaaatgg gtacatcggc t cttggctgg    180 tcatgagatt actggaacat ggctattatg ttcatggaac tgttagggac c cagaagaca    240 cagggaaggt tggcatttg ctgcggctcc caggggcaag tgagaagcta a agctgttca     300 aggcagagct taacgacgaa atggcctttg atgatgctgt gagcggttgt c aaggggttt    360 tccacgttgc caagcctgtt aatctggact caaacgctct tcaggggag g ttgttggtc    420 ctgcggtgag gggaacagta atctgcttc gagcctgcga acgatcgggc a ctgtgaaac    480 gagtgataca tacctcgtcc gtttcagcag tgagattcac tgggaaacct g accccctg    540 atactgtgct ggatgaatct cattggactt cggtcgagta ttgcagaaag a caaagatgg    600 tcggatggat gtactacatc gccaacactt atgcagaaga gggagcccat a agttcggat    660 cagaga                                                                666
```

<210> SEQ ID NO 131
<211> LENGTH: 478
<212> TYPE: DNA
<213> ORGANISM: Pinus radiata

<400> SEQUENCE: 131

```
gctggttcaa gtgtcagccc aatggcctcc cctacagaga atccccagat t cagaagag      60 ctgctaaatc atgagatcca tcaaggaagt acagtatgtg tgacaggagc t gctggcttc    120 ataggatcat ggctcgtcat gcgtttgctt gagcgaggat atactgttag a ggaactgtg    180 cgagacactg gtaatccggt gaagacgaag catctattgg atctgcctgg g gcgaatgag    240 aggttaactc tctggaaagc agatttggat gatgaaggaa gctttgacgc c gccattgat    300 ggttgtgagg gagttttcca tgttgccact cccatggatt tgaatccga g gaccccgag    360 aacgagataa ttaaacccgc tgtcaatggg atgttgaatg ttttgagatc g tgtgggaaa    420 accaagtcta tgaagcgagt tgttttcacg tcgtctgctg ggactctgct t tttacgg      478
```

<210> SEQ ID NO 132
<211> LENGTH: 510
<212> TYPE: DNA
<213> ORGANISM: Pinus radiata

<400> SEQUENCE: 132

```
cttgttcaaa gtcacatatc ttatttctt tgtgatatct gcaatttcca a gcttttcgt      60 ctacctccct gaaaagatga gcgaggtatg cgtgacagga ggcacaggct t catagctgc    120 ttatctcatt cgtagtcttc tccagaaagg ttacagagtt cgcactacag t tcgcaaccc    180 agataatgtg gagaagttta gttatctgtg ggatctgcct ggtgcaaacg a aagactcaa    240 catcgtgaga gcagatttgc tagaggaagg cagttttgat gcagcagtag a tggtgtaga    300 tggagtattc catactgcat cacctgtctt agtcccatat aacgagcgct t gaaggaaac    360
```
cctaatagat ccttgtgtga agggcactat caatgtcctc aggtcctgtt c aagatcacc        420 ttcagtaaag cgggtggtgc ttacatcctc ctgctcatca ataccgatac g actataata        480 gcttagagcg ttccctgctg gactgagtca                                          510

<210> SEQ ID NO 133
<211> LENGTH: 890
<212> TYPE: DNA
<213> ORGANISM: Pinus radiata

<400> SEQUENCE: 133
tcctaattgt tcgatcctcc cttttaaagc ccttccctgg ccttcattcc a ggtcacaga        60 gttgttcatg cagtgctagc aggaggagca gcgttgcaat tggggaaaat t ccaaaatca       120 ataacgagag gacagaagta agtttgtgga aatagcaacc atgccggtgt t tccttctgg       180 tctggacccc tctgaggaca atggcaagct cgtttgtgtc atggatgcgt c cagttatgt       240 aggtttgtgg attgttcagg gccttcttca acgaggctat tcagtgcatg c cacggtgca       300 gagagacgct ggcgaggttg agtctctcag aaaattgcat ggggatcgat t gcagatctt       360 ctatgcagat gtcttggatt atcacagcat tactgatgcg ctcaagggct g ttctggtct       420 gtctatacct tgagcaccc tcagagtgct gcaggctatg atgaagtgat g gcagaaatt       480 gaagtacaag cagcccacaa tgcactggaa gcgtgtgctc agactgagac c attgagaaa       540 gttgtgttca cttcttctgt ggctgcagca atttggagag aagatggaga c tacaaggtt       600 aatgcccttg acgagaggca ttggagtgat gcaaatcttt gcaggaaatt g aagttgtgg       660 tacgcattag ccaagacact gtcagagaag gctgcatggg cgctggcaat g gacagaggg       720 ttgaatatgg tgacaatcaa cgcatctctg attgtaggac ctggcatcac a tacaaaagc       780 tcaggatcta ccattgcata tcttaaaggg gctgcacaaa tgtatgagaa g ggcactta       840 gctagtgtgg acataaggtt tctagcggat gcacatatat gcgcttatga                   890

<210> SEQ ID NO 134
<211> LENGTH: 955
<212> TYPE: DNA
<213> ORGANISM: Pinus radiata

<400> SEQUENCE: 134
aatcactgac cttcacatat ttattccaat tctaatatct ctactcgctg t ctacctgat        60 ttttcagtgg cgaaccaact tgacagggtt ggacatggcc aacagcagca a gattctgat       120 tattggagga acaggctaca ttggtcgtca tataaccaaa gccagccttg c tcttggtca       180 tcccacattc cttcttgtca gagagaccct cgcttctaat cctgagaagg c taagcttct       240 ggaatccttc aaggcctcag gtgctattat actccatgga tctttggagg a ccatgcaag       300 tcttgtggag gcaatcaaga aagttgatgt agttatctcg gctgtcaagg g accacagct       360 gacggatcaa cagaatatta tcaaggctat taaggaggtt ggaaccatca a gaggttttt       420 gccatctgag ttcggaatg acgttgatag aacccatgca gtggagcctg c aaagaccat       480 gtttgctacc aaagcgaaaa ttcgcagggc cattgaggca gaaggcatcc c ttacacatt       540 tgtctctagc aactgttttg ctgggttgtt cttgccaagt ttggggcagc c aggccttac       600 cgccccgcca agggataaag ttgtgatatc tggagatgga aatgccaaag t gttttttgt       660 gaaggaggag gatatagga cattcaccat caaggcagtg gatgaccta g aactctaaa       720 caagatcctg tatttgaggc ttcctgccaa cacatattct cttaacgagc t tgtagctgt       780

```
gtgggagaag aagattggca agtctctgga gaagacctat ataccagagg a agaggtcct    840 gaaaaaatt gcagagtcgc cattcccact caatgctata atgtcaaccg g ccactctat    900 ttttgtgaaa ggggatcaaa caaattttga atcggacct gatggtgtgg a ggct         955
```

<210> SEQ ID NO 135
<211> LENGTH: 1024
<212> TYPE: DNA
<213> ORGANISM: Pinus radiata

<400> SEQUENCE: 135

```
agagggttat atatcttgat tctgacctga ttgtcgtcga cgacattgcc a agctctggg    60 ccacggattt ggaatctcgt gtcctcgggg caccagagta ctgcaaggcg a atttcacaa   120 agtatttcac cgataatttc tggtgggatc ccgcattatc caagaccttt g agggaaaaa   180 aaccctgcta cttcaacaca ggcgtaatgg tgatcgatct tgaaaatgg c gggcagggg    240 aattcacaag aaagatcgaa atctggatgg acatacagaa ggaacgccgt a tctatgagc   300 tcggatcatt accgccattt ttactggtat ttgctggttt ggttaagcaa g tcgatcatc   360 gttggaatca gcacggttta ggcggagata atttgcaagg cctttgccga g atcttcacc   420 ctggacctgt cagtttgttg cattggagtg gtaagggcaa accttggcta c gcctggaat   480 gccaagcgga cttgccctct ggatacttta tgggctcctt atgatcttta t cgatcaacg   540 tattacctaa atgggtgaga gagcctctct cctcggggtg ctttttatcg a attaaacct   600 gatttgataa aatgccaaat agaacttac gcctatgcat ctttcagttt t gaatttcaa    660 ttctggtaac gaatagaaga aaacaatagc acagccacag gcaggacaaa t ccatcatga   720 gggaccaatc gtttgaattt agtattaata aggttgttcc atataacgcc t gtgaagaat   780 gatattgtgg actgatctat ttatatttgt actgccatgc catcctcagc c agcagagag   840 gcaagcaatg ccgctgcaag tcatgtaggg aaggcgttgt gaactcaatt t tcggcgact   900 gtacaggatg taaattttg gaacattaat atcattatga taagttcctg a accaacaac   960 tgtataatac cttataaatg tatctgcaac tccattttttg cataaaaaaa a aaaaaaaa   1020 aaaa                                                                1024
```

<210> SEQ ID NO 136
<211> LENGTH: 497
<212> TYPE: DNA
<213> ORGANISM: Pinus radiata

<400> SEQUENCE: 136

```
agaacataaa tccgaacaat gaacttgcaa atttcctgca ttgccatcgc c agcccaaga   60 aacttttggc cgcaaagcaa tctgtacact ttctctctca ttccttgcta c aagcatgga   120 tataggttct aggggtcttg ggggctcctg atgcccaatt gttgctgtgc t tggcatgac   180 ccaaacatgc aagagatctg tagtcagtag tcttgttgga tctatagctt t tagaaaaga   240 gtcacgtcct tttagggtaa catcattcca accatatcca gttccaccac c ggctacacc   300 ttcaacggga ggaggagcaa gatattcagc attgctttgg gcaccagatg g ataggcatt   360 attttccatc ggaattcagc cgagctcgcc ccctcagtcc aatcgtcgtg a aaatccctc   420 aaaattgggc aattctggct cgaaatcgcc aaattatggg ctacaacagg a ttaaaattg   480 cacagaaatc tgccagt                                                   497
```

<210> SEQ ID NO 137
<211> LENGTH: 528

<212> TYPE: DNA
<213> ORGANISM: Pinus radiata

<400> SEQUENCE: 137

| | | | | | |
|---|---|---|---|---|---|
| ggcaatccga | gcctagccaa | ccaacttggc | agcaaggagc | acagggagtt g | gcgagagaa 60 |
| gctgttagga | aatctttggt | attgttgaaa | aatgggaagt | cagccaacaa g | cctttgctc 120 |
| cctttggaga | agaatgcttc | caaggttctt | gttgcaggaa | cccatcctga t | aatctgggt 180 |
| tatcagtgtg | gtggatggac | gatggaatgg | caaggattaa | gtggaaacat a | accgtagga 240 |
| actacaattc | tggaagctat | caaactagct | gtcagcccct | ctactgaagt g | gtttatgag 300 |
| caaaatccag | atgctaacta | tgtcaaagga | caagggtttt | catatgccat t | gtggttgtg 360 |
| ggtgaggcac | catacgcaga | aacgtttgga | gacaatctta | atttgaccat t | ccctaggc 420 |
| ggagggaca | cgattaagac | ggtctgtggc | tccttgaaat | gccttgtaat c | ttgatatct 480 |
| ggaaggccac | ttgttattga | accttatctt | ccattggtgg | atcgtttt | 428 |

<210> SEQ ID NO 138
<211> LENGTH: 424
<212> TYPE: DNA
<213> ORGANISM: Pinus radiata

<400> SEQUENCE: 138

| | | | | | |
|---|---|---|---|---|---|
| aaaaaacaaa | tgttagctag | cctagtgatg | agctttacgt | atacctggcc t | tttatacat 60 |
| ggatctgagt | ttttatgcag | gtgtagagcc | ttttgttact | ctgtatcact g | ggacttgcc 120 |
| acaagctctg | gaggacgaat | acggtggatt | tcgtagcaaa | aaagttgtgg a | tgactttgg 180 |
| catattctca | gaagaatgct | ttcgtgcttt | tggagaccgt | gtgaagtact g | ggtaactgt 240 |
| taacgaaccg | ttgatcttct | catattttc | ttacgatgtg | gggcttcacg c | accgggccg 300 |
| ctgttcgcct | ggatttggaa | actgcactgc | gggaaattca | gcgacagagc c | ttatattgt 360 |
| agcccataac | atgcttcttg | cacatagtac | cgctgttaaa | aatatatagc a | taaataccc 420 |
| aggg | | | | | 424 |

<210> SEQ ID NO 139
<211> LENGTH: 404
<212> TYPE: DNA
<213> ORGANISM: Pinus radiata

<400> SEQUENCE: 139

| | | | | | |
|---|---|---|---|---|---|
| gctaccatct | tccctcataa | tattgggctt | ggagctacca | gggatcctga t | ctggctaga 60 |
| agaatagggg | ctgctacggc | tttggaagtt | cgagctactg | gcattcaata c | acatttgct 120 |
| ccatgtgttg | ctgtttgcag | agatcctcga | tggggccgct | gctatgagag c | tacagtgag 180 |
| gatccaaaaa | ttgtcaaggc | catgactgag | attatcgttg | gcctgcaagg g | aatcctcct 240 |
| gctaattcta | caaaaggggg | gccttttata | gctggacagt | caaatgttgc a | gcttgtgct 300 |
| aagcattttg | tgggttatgg | tggaacaacc | aaaggtatcg | atgagaataa t | actgttatc 360 |
| aactatcaag | ggttatttca | acattccaaa | ttacccccaa | tttt | 404 |

<210> SEQ ID NO 140
<211> LENGTH: 437
<212> TYPE: DNA
<213> ORGANISM: Pinus radiata

<400> SEQUENCE: 140

| | | | | | |
|---|---|---|---|---|---|
| cctagaattc | tatggtgaaa | attgttggga | caaggctgcc | caagtttaca a | aggaacagt 60 |

-continued

```
cccaaatggt taaaggttca atagactatc taggcgttaa ccaatacact g cttattaca    120 tgtatgatcc taaacaacct aaacaaaatg taacagatta ccagactgga c tggaataca    180 ggctttgcat atgctcgcaa tggagtgcct attggaccaa gggcgaactc c aattggctt    240 tacattgtgc cttggggtct atacaaggcc gtcacatacg taaaagaaca c tatggaaat    300 ccaactatga ttctctctga aaatggaatg gacgacctgg aaacgtgaca c ttccagcag    360 gactgcatga taccatcagg ggtaactact ataaaagcta tttgcaaaat t tgattaatg    420 cacgtgaatg accgggg                                                    437
```

<210> SEQ ID NO 141
<211> LENGTH: 470
<212> TYPE: DNA
<213> ORGANISM: Pinus radiata

<400> SEQUENCE: 141

```
gatacatcca agctgagaat ggaagagatt aatggtgata acgcagtaag g aggagctgc     60 tttcctccag gtttcatgtt tgggatagca acttctgctt atcagtgtga a ggagctgcc    120 aacgaaggtg gaaaaggccc aagcatctgg gactcatttt cacgaacacc a ggcaaaatt    180 cttgatggaa gcaacggtga tgtagcagtg gatcagtatc atcgttataa g gcagatgta    240 aaactgatga agatatgggg cgtggctacc tacagattct cgatttcatg g cctcgtata    300 tttccaaagg gaaaggagag gatcaatgag gaaggagtag cctattacaa t aacctcatc    360 aatgaactcc tccagaatgg aatccaagcg tctgtcaact ttgtttcact g ggatactcc    420 ccagtctctg gaggatgaat atggcggatt tctgaggcca accattgtga               470
```

<210> SEQ ID NO 142
<211> LENGTH: 413
<212> TYPE: DNA
<213> ORGANISM: Pinus radiata

<400> SEQUENCE: 142

```
ataagactaa ttttccagac aatcctccat tcccattcaa ttacactggt a ctccaccca     60 ataatacaca ggctgtgaat gggactagag taaaagtcct tccctttaac a caactgttc    120 aattgattct tcaagacacc agcatcttca gcacagacag ccaccctgtc c atctccatg    180 gtttcaattt ctttgtggtg ggccaaggtg ttggaaacta caatgaatca a cagatgcac    240 caaatttta cctcattgac cctgtcgaga gaaacactgt gggagttccc a aaggaggtt    300 gggctgctat aagatttcgt gcagacaatc caggggtttg gttcatgcac t gtcatttgg    360 aggttcacac atcgtgggga ctgaaaatgg cgtgggtagt aaagaacgga a aa          413
```

<210> SEQ ID NO 143
<211> LENGTH: 457
<212> TYPE: DNA
<213> ORGANISM: Pinus radiata

<400> SEQUENCE: 143

```
aaaaccttt cagacgaatg ttctgatgct cggccccggc cagacaacag a catacttct     60 cactgccaat caggctacag gtagatacta catggctgct cgagcatatt c caacgggca    20 aggagttccc ttcgataaca ccactaccac tgccatttta gaatacgagg g aagctctaa    80 gacttcaact ccagtcatgc ctaatcttcc attctataac gacaccaaca g tgctactag    40 cttcgctaat ggtcttagaa gcttgggctc acacgaccac ccagtcttcg t tcctcagag    00 tgtggaggag aatctgttct acaccatcgg tttggggttg atcaaatgtc c ggggcagtc    60
```

```
ttgtggaggt ccaacggatc aagatttgca gcaagtatga atacatatca t tgtcccgc      20
aaccacttct tccaatcctt caagctcagc attttgg                               57

<210> SEQ ID NO 144
<211> LENGTH: 598
<212> TYPE: DNA
<213> ORGANISM: Pinus radiata

<400> SEQUENCE: 144
gttcggcact gagagatcca tttctttcaa tgttgagaca gtgagtagta t tagtttgat      60
atctctttca ggaatatatc gtgcttgcag gatctttagt ttctgcaaca a tgtcgttgc      20
aatcagtgcg tctatcttct gttctccttg ttttgctact agcatttgtt g cttacttag      80
ttgctgtaac aaacgcagat gtccacaatt ataccttcat tattagaaag a agacagtta      40
ccaggctatg caataagcgt ataatcgcca ccgtcaatgg acagctacca g cccaacta       00
ttcatgtacg tgatggagac gttgttaata tcaaagctta taacaaagct g gtacaatg      60
ccactcttca ctggcatgga gtcgagcagt tgcgtacagg atgggccgat g gacctgcat     20
atgttacaca gtgccccatt ccaccaggtg gtcgttatac atacagattc a ccatttctg     80
aacaggaagg caccgtgtgg tggcacgctc atgtgtcatg gctccgagct a cggtgcatg     40
gagctttcgt aatccttcct aagagaggca aaccatatcc ctttcctaaa c cccgtgc      98

<210> SEQ ID NO 145
<211> LENGTH: 1080
<212> TYPE: DNA
<213> ORGANISM: Pinus radiata

<400> SEQUENCE: 145
aagatcttgg ttcgagtctc tcagctctct ccaaaggaat tttgtgggtc a tttgcaggt     60
gaagacacca tggtgaaggc ttatcccacc gtaagcgagg agtacaaggc t gccattgac    20
aaatgcaaga ggaagctccg agctctcatt gcagagaaga actgtgcgcc g atcatggtt    80
cgaatcgcat ggcacagcgc tgggacttac gatgtcaaga ccaagaccgg a gggcccttc    40
gggacgatga gatatgggc cgagcttgcc cacggtgcta acagtggtct g gacatcgca    00
gttaggctcc tggagccaat caaggaacag ttccccataa tcacctatgc t gacctttat     60
cagttggctg gtgtggtggc tgttgaagtg accgggggac ctgacattcc g ttccatcct    20
ggaagagaag acaagcctga gcctccagaa gaaggccgcc ttcctgatgc t acaaaagga    80
cctgatcatc tgagggatgt ttttggtcac atgggttga atgataagga a attgtggcc    40
ttgtctggtg cccacacctt ggggagatgc cacaaggaga gatctggttt t gaaggacca    00
tggacctcta accccttat ctttgacaac tcttacttca cagagcttgt g actggagag     60
aaggaaggcc tgcttcagtt gccatctgat aaggcactgc ttgctgatcc t agttttgca    20
gtttatgttc agaagtatgc acaggacgaa gacgctttct tgctgactat g cggaagct    80
cacctgaagc tttctgaact tgggtttgct gatgcgtaga ttcataccct c tgcagagac    40
aattccttgc tagatagctt cgttttgtat ttcatctaat cttttcgatt a tatagtcac    00
atagaagttg tgttatgcg ccatagtgat acttgaacct acatgttttt g aaaagtatc    60
gatgttcttt aaaatgaaca ttgaatacaa cattttggaa tctggttgtg t tctatcaag   120
cgcatatttt aatcgaatgc ttcgttcctg ttaaaaaaaa aataaaata a aaaaaaaa    180

<210> SEQ ID NO 146
```

<211> LENGTH: 701
<212> TYPE: DNA
<213> ORGANISM: Pinus radiata

<400> SEQUENCE: 146

| gtagtttcgt | tttacaacaa | tctcaggttt | tgaatctcag | aatagttgcg | a aaggaagcg | 60 |
| atgacgaagt | acgtgatcgt | tagctccatt | gtatgtttct | ttgtatttgt | t tctgcgtgc | 120 |
| ataatttctg | tcaatggatt | agttgtccat | gaagatgatc | tgtcaaagcc | t gtgcatggg | 180 |
| ctttcgtgga | cattttataa | ggacagttgc | cccgacttgg | aggccatagt | g aaatcggta | 240 |
| cttgagccgg | cgttggacga | agatatcact | caggccgcag | gttgctgaga | c ttcatttcc | 300 |
| atgactgttt | tgtgcagggt | tgcgatgggt | ccgtgttgct | gacaggaact | a aaagaaacc | 360 |
| ccgagtgagc | aacaggctca | gccaaactta | acactaagag | cccgggcctt | g cagctgatc | 420 |
| gacgaaatta | aaaccgctgt | agaagctagc | tgcagtgggg | ttgtaacttg | t gcagacatt | 480 |
| ctggctttgg | ctgctcgtga | ctccgtcgct | caggaggccc | aaaatttcca | g taccacttg | 540 |
| gccgcagaga | tagcctaaag | tttgccagtc | aatccgtagt | tctcgccaat | a taccaactc | 600 |
| caactttaaa | tttgacacag | ctgatgaaca | tttttggctc | caaaggattc | a gtttggccg | 660 |
| aaatggttgc | tctttcaggt | ggacacacaa | tcggcattgg | t |  | 701 |

<210> SEQ ID NO 147
<211> LENGTH: 338
<212> TYPE: DNA
<213> ORGANISM: Pinus radiata

<400> SEQUENCE: 147

| ctcaattctg | tgctgctctg | ctcgctcagg | gccgggtctg | ctattctgct | c atgcacaag | 60 |
| tttgagatcg | ggagcctgct | ggatctggtg | cagaggttca | aggtcacggt | a gcgcctgtc | 120 |
| gtgcctccca | ttgttctcgc | ctttgccaag | aacgcgctcg | tggaaagcta | t gatctgtcg | 180 |
| tccattaggg | ttgtgctgtc | cggtgccgcg | cctctcggaa | aggagctgga | g gatgcatta | 240 |
| aggctacgac | ttcccaaagc | cacttttggt | caggatacg | gtatgacaga | g gcaggaccg | 300 |
| gtgctatcaa | tgtgtctggc | cttcgctaag | gagcccctt |  |  | 338 |

<210> SEQ ID NO 148
<211> LENGTH: 357
<212> TYPE: DNA
<213> ORGANISM: Pinus radiata

<400> SEQUENCE: 148

| ctcaattctg | tgctgctctg | ctcgctcagg | gccgggtctg | ctattctgct | c atgcacaag | 60 |
| tttgagatcg | ggagcctgct | ggatctggtg | cagaggttca | aggtcacggt | a gcgcctgtc | 120 |
| gtgcctccca | ttgttctcgc | ctttgccaag | aacgcgctcg | tggaaagcta | t gatctgtcg | 180 |
| tccattaggg | ttgtgctgtc | cggtgccgcg | cctctcggaa | aggagctgga | g gatgcatta | 240 |
| aggctacgac | ttcccaaagc | cacttttggt | caggatacg | gtatgacaga | g gcaggaccg | 300 |
| gtgctatcaa | tgtgtctggc | cttcgctaag | gagcccttc | cgatgaagtc | c gggtcg | 357 |

<210> SEQ ID NO 149
<211> LENGTH: 470
<212> TYPE: DNA
<213> ORGANISM: Eucalyptus grandis
<220> FEATURE:
<221> NAME/KEY: unsure
<222> LOCATION: (437)...(437)

<400> SEQUENCE: 149

```
gagaaattca caagcttcac agcacgagag ttaaagagcg agacacggtt t gatccagtg        60
aagggccggc ccccggagat ggcgaagacg ctcaccgcgc tggctggggg a gaagaccct       120
ccagtccaaa gttcgtccgc gataaggatg agcgcccac ggtggcctac a accagttca       180
gcaacgtgat ccccgtgata tccctggcgg ggattgacga ggccggcggc c ggaagggcc       240
gagatctgca agaagatcgt ggaggcgtgc gaggactggg gcgtcttcca g gtggttgac       300
cacggggttg atacggggct catcactgac atgacccggc tcgcgcgtaa g tncttcgct       360
ctgccctcgg aggaaaagct ccggttcgac atgactggcg gaaaaagggg g ggttatcgt       420
ctccagcatc tcaaggngaa caagttcagg actggtgcaa agtacgaac              470
```

<210> SEQ ID NO 150
<211> LENGTH: 380
<212> TYPE: DNA
<213> ORGANISM: Eucalyptus grandis

<400> SEQUENCE: 150

```
ggaggtcggt gacagagcag tacagcgaga agctcatggc cctcgcttgc a agctcttgg        60
aggtcctctc ggaggcaatg ggactggaga aggaggcact gaccaaggca t gcgtggaca       120
tggaccagaa ggtggtggtc aactactacc ccaaatgccc gcagcccgac c tcacgctcg       180
ggctgaagcg ccacactgac ccgggaacca tcactcttct gctccaggac c aggtggggg       240
gcctccaggc caccagagat ggcggcaaga gctggatcac cgtccagcct g tggaagggg       300
cttttgtggt caacctaggc gatcatggtc atttcctgag caacgggagg t caagaacg       360
cggaccacca ggcggtggtg                                               380
```

<210> SEQ ID NO 151
<211> LENGTH: 349
<212> TYPE: DNA
<213> ORGANISM: Pinus radiata
<220> FEATURE:
<221> NAME/KEY: unsure
<222> LOCATION: (212)...(212)

<400> SEQUENCE: 151

```
ttggactcca tacctctcgt ggacctccaa ggtcttttac gcgattctgc t agagcccac        60
gttattcaac aaattggccg ggcctgcgct gaatatggct tcttccagat a atcaatcat       120
ggcatcccag atgcagttat caacaggatg ctggaagtag cgaaggagtt t ttcagaatg       180
cctgtggagg accgaatgga atactattcc gncgatccgt ccagaaaaac a cgtttgtcg       240
acgagcttca acatccataa agaacaagtc ttcaactggg gggctatctc a gacatcatt       300
gttatccgtt agaagatcat gttcacactt ggccttcaaa acctgcggg               349
```

<210> SEQ ID NO 152
<211> LENGTH: 427
<212> TYPE: DNA
<213> ORGANISM: Pinus radiata
<220> FEATURE:
<221> NAME/KEY: unsure
<222> LOCATION: (234)...(234)
<221> NAME/KEY: unsure
<222> LOCATION: (240)...(240)

<400> SEQUENCE: 152

```
atggtctggg cagcatacgg aggacgatgg aagatggaac gcaaggtgtg c aacatgcac        60
atgttgggag ggaaggcgtt ggaagattgg cagccggtga gggacgccga a atgggcttc       120
```

```
atgctccgga atattctcag tcactcgcag cgcggcgaga cggtgaatgt g ccggacctc      180 ctgaacatct gcgccgccaa catgatcggg cagatcattc taagcaagcg g gtnttcgan      240 acagaagggg acgaggccaa cgagttcaag gacatggtgg tggaactcat g acctgcgct      300 ggatacttca atatcggaga cttcattcca tcgctagcgt ggatggactt g cagggcatt      360 cagcggggta tgaagaagct ccacaagaaa tgggacgcac tcatacagag g attattgat      420 taacacc                                                                 427
```

<210> SEQ ID NO 153
<211> LENGTH: 298
<212> TYPE: DNA
<213> ORGANISM: Eucalyptus grandis
<220> FEATURE:
<221> NAME/KEY: unsure
<222> LOCATION: (214)...(214)

<400> SEQUENCE: 153

```
gttaccaaag ggcagcaacg tattcttaaa catgggttct atccacaggg a tcccaagat      60 ttgggacaaa ccgttggagt ttagacccga gaggttcttg gaaggtccta g caagtatga     120 tttctcaggt aacaacttcg catacatgcc attcggttct ggtcgaaggg t gtgtgcagg     180 gcttgcgctg gcagagagga tgctaccata tgtnttggcc tctcttttgc a ctcattcaa     240 gtgggaaata ccaccagggt ctgagctgga tttacctgga caagttcggc c ttgtggt      298
```

<210> SEQ ID NO 154
<211> LENGTH: 251
<212> TYPE: DNA
<213> ORGANISM: Eucalyptus grandis

<400> SEQUENCE: 154

```
gacttcaaag ggcaggattt tgagctgata cccttcggtg caggtagaag g agctgcccg      60 gctattgcat ttggaaatgc cagtgttgag cttgctttag ctcaacttct t cacagtttc     120 gattgggagc ttcctgatgg gatccagcct agggacttgg atatgaccga a gttttggc      180 atcacaatgc acagaattgc caacctcatg gttgtagcca accccgctt c tcctagacg      240 atactcgtgc c                                                            251
```

<210> SEQ ID NO 155
<211> LENGTH: 411
<212> TYPE: DNA
<213> ORGANISM: Pinus radiata
<220> FEATURE:
<221> NAME/KEY: unsure
<222> LOCATION: (198)...(198)

<400> SEQUENCE: 155

```
acggggctcc ggtgacgaga tactggcagg tcgttgaagc tggttggagg t tcgaatatc      60 cgagagggat cctgttttctt gtccccttac cttggttttc ctcatccttc c gaatgcagt     120 ctaattcgaa gaccgtggaa gagcggcgcc cggggcctgg taagagcttg c tggagata     180 tctcggcttg actatgtntt ggctcttttc gtgaatggca agggggatct a gggcgatg     240 atgggtcgg ctgtcgtttt gagggaaaat tcgcaactgt tgatggtctt g actacatct     300 ctggccgtct tgattggttg cgttttgttc tttgtttggc ggagagggg a tcggctccc     360 tcgaagcagc cggagaagcc aactcccctg gtgaaagaag aggaagagga g             411
```

<210> SEQ ID NO 156

<211> LENGTH: 404
<212> TYPE: DNA
<213> ORGANISM: Pinus radiata

<400> SEQUENCE: 156

| | | | | | |
|---|---|---|---|---|---|
| gctgaagtta | ataaaactaa | gtacattgag | gttgacatgg | aggcagaatt t | tcaaatcta | 60 |
| gctttggaca | ttattggatt | gtgtgtattt | aactatgatt | ttggatccgt t | actcgagaa | 120 |
| tcaccagtaa | tcaaggcagt | ctatggtaca | ttgtttgaag | ctgagcatag a | tcaaccttt | 180 |
| tacataccat | actggaaatt | ccgctggca | agatggttag | ttcctcgcca a | cgaaagttc | 240 |
| catgaagacc | taaaggtcat | taatgaatgt | cttgataatc | tgatagcagg g | gccaaggaa | 300 |
| acaagacagg | aagacgatat | cgaggctctt | caaggaagag | attactctaa a | gtgaaatat | 360 |
| gcaagtttgc | tcagatttct | agttgatatg | agggagaaga | tgtt | | 404 |

<210> SEQ ID NO 157
<211> LENGTH: 259
<212> TYPE: DNA
<213> ORGANISM: Pinus radiata
<220> FEATURE:
<221> NAME/KEY: unsure
<222> LOCATION: (116)...(116)
<221> NAME/KEY: unsure
<222> LOCATION: (246)...(246)

<400> SEQUENCE: 157

| | | | | | |
|---|---|---|---|---|---|
| ccaatcatcg | gcaatttcca | ccaagtgaga | cttcctcttc | accgtgctct c | aaaaatcttt | 60 |
| gctgagaaat | atggtcccat | tttgtttctg | cgctttggct | ctgtacccac t | gtggntgtt | 120 |
| tcttcatctg | agatggccaa | acactttctt | aaaactcatg | atttgatatt t | gccagccga | 180 |
| cctccaacat | cggtaggaaa | atatttcttc | tataacttca | aagatattgc c | ttcagtcct | 240 |
| tatggngatc | actggagga | | | | 259 |

<210> SEQ ID NO 158
<211> LENGTH: 338
<212> TYPE: DNA
<213> ORGANISM: Pinus radiata

<400> SEQUENCE: 158

| | | | | | |
|---|---|---|---|---|---|
| aatggcagtt | gggggtcaag | gaaatgtggt | ctcagcttgc | aggcagccat g | gaagctaca | 60 |
| atcgtctggt | gggtgttttg | gtagtaatag | tttctctggc | agttttttat t | tgaagagta | 120 |
| gaggttcgaa | gaagcgtctg | cctccagggc | cgaagggtgg | cctctggttg g | aaatttgtt | 180 |
| tcaggttgca | ttctccggga | agcccttcat | gtatgtggtg | cgagatctga g | ggagcagtt | 240 |
| tggctcgatt | ttcacgctcc | aaatgggca | aaaaacgccc | caaattacca c | ctccccgaa | 300 |
| atttccaaca | cggggcctct | taaaaagag | gggccccc | | | 338 |

<210> SEQ ID NO 159
<211> LENGTH: 539
<212> TYPE: DNA
<213> ORGANISM: Pinus radiata
<220> FEATURE:
<221> NAME/KEY: unsure
<222> LOCATION: (1)...(539)
<223> OTHER INFORMATION: n at all occurrences indicates unsure

<400> SEQUENCE: 159

| | | | | | |
|---|---|---|---|---|---|
| aatgtggccg | aggagttcct | gnaagactca | tggatctggc | tttcgccagc a | gacctccaa | 60 |
| ccatcggtaa | cgaatatttt | ggtataattc | ctccgacgtc | gcattttccc c | ctatggtcc | 120 |

-continued

| | |
|---|---|
| ttactggagg cagatgcgta aaatctgtgt gttaaagttg ctgagctcaa g acgcataga | 180 |
| ttccttccgc cacataagag aagaggaagt ctcttctatg gttcgctcta t tgctaattc | 240 |
| ggatctgcat cctgtgaaca ttagcagggc cgtgtcagcc cttgggattg a tataatctg | 300 |
| caggatggcc ttcggtaaaa agtactgtga ccaagaccta attggtggca t tgggatnaa | 360 |
| gtcaatgata aaggaaacgt tgtgtnagc agggtcnttg aacatgggag a ttttatacc | 420 |
| atacttggca tggattgatc ttcaaggtct caaccgtcga ttgaagaaca t acacaagat | 480 |
| ccaagacgac ttgttagggg aagatactag aggcacacgc ttcgccaacc g cagaataa | 539 |

<210> SEQ ID NO 160
<211> LENGTH: 310
<212> TYPE: DNA
<213> ORGANISM: Pinus radiata
<220> FEATURE:
<221> NAME/KEY: unsure
<222> LOCATION: (16)...(16)

<400> SEQUENCE: 160

| | |
|---|---|
| cgaatgggtg gtcggnaaag accgcacagt aaaggagtct gatttggtaa g tctgaaata | 60 |
| ccttcagtgt gtggtgaaag agacgctacg attataccg ggaggacctc t agcacttcc | 120 |
| ccatgagtct gtggaggctg tgacagtaga agggtactat atacctaaga a gacgatgct | 180 |
| gttggtgaat gtgtgggcta taggaaggga ccccaaagtg tggggattg a tgcttcaga | 240 |
| attcaagcca gagagattta tggaggaatt aggtgggcat ctgcatgata a tgtcatgga | 300 |
| tttagcaggc | 310 |

<210> SEQ ID NO 161
<211> LENGTH: 412
<212> TYPE: DNA
<213> ORGANISM: Eucalyptus grandis

<400> SEQUENCE: 161

| | |
|---|---|
| cgccacctcc ctcctcctct tcccctcct cctgctcctc ctggtcgccc c gcaaaagcc | 60 |
| ctccgcctct gtccgcagtc accgccagcc atggatctcc tcctcctgga g aagaccctc | 120 |
| ctgggcctct tcgccgccgc catcgtggcc atcgcggtct ccaagctccg g ggcaagcgg | 180 |
| ttccgcctcc ccccgggccc cctccccgtg cccatcttcg gcaactggct c caggtcggc | 240 |
| gacgacctca accaccgcaa cctcaccgac ctcgccaaga ggttcggcga c atcctcctc | 300 |
| ctccgcatgg ggcagcgcaa cctcgtggtc gtctcgtccc cggacctctc c aaggaggtg | 360 |
| ctccacacgc agggcgtcga gttcgggtcc cgcacccgga acgtcgtctt c t | 412 |

<210> SEQ ID NO 162
<211> LENGTH: 329
<212> TYPE: DNA
<213> ORGANISM: Pinus radiata

<400> SEQUENCE: 162

| | |
|---|---|
| acttttacaa tgagtgatca caaacaattt tttccaaaat tcataacaaa a ttttggata | 60 |
| cagtgcatat tcgggcaaac aatctgacgg acttcaaaac tactgacaac a aaacaaacc | 120 |
| atctggggat gaattacaat ggaaatccac acttcatttg gctgcaactg t atatataaa | 180 |
| gtgtttattg cttccagctc ctccagactt tggaagaaat tctatatttt t ttttcagga | 240 |
| tctgagcttc aggctattgg tttggccaca acaacggagt ggttgagaat g tgcaggctg | 300 |

-continued

| aattgccctc ctttctctgt cacatccac | 329 |

<210> SEQ ID NO 163
<211> LENGTH: 475
<212> TYPE: DNA
<213> ORGANISM: Pinus radiata

<400> SEQUENCE: 163

| atttgcgtca gtctctacct tgcctgcaa cattcacagt cgctgatgga g ggcctcccg | 60 |
| cagcaactgt cctgtgctta ctctgggctt tcttcatgat atggtttttg g gcaagagaa | 120 |
| gaactagtgc cacgctgcca ccaggaccct atgcatggcc catcatagga a acctctacc | 180 |
| aattaatact gcccgctcac cgttctctta gaggccttgc tgacaaatat g gtcccatta | 240 |
| tgtttctgcg cttaggctct gtccctaccg tcgtcgtttc ttcttctgag a cggccaaag | 300 |
| agtttctcaa aactcatgac ttgatttttg ccagccgacc cccaacagcc g ctgggagat | 360 |
| tgatgttttc caactctaaa gacgtggtgt tcgctccgta tggagatcac t ggaggcaaa | 420 |
| tgagaaaaat atgcgtgtta gaactactga ctgccaaaag aatcgagctc g tgcc | 475 |

<210> SEQ ID NO 164
<211> LENGTH: 372
<212> TYPE: DNA
<213> ORGANISM: Pinus radiata
<220> FEATURE:
<221> NAME/KEY: unsure
<222> LOCATION: (22)...(22)

<400> SEQUENCE: 164

| tggaaataca gttcgactct gngatttcat aaaatatgat gaggaaagga g aatcaggtg | 60 |
| gatttgaggt taagggatgg gctgccatgg atgactccgg cgtcctctcg c ctttcaact | 120 |
| ttactcgcag gaaaacggga tcccacgatg tactttcaag gtagcatact g tggaatctg | 180 |
| tcactccgat ctgcatcaaa ttcggaatga atggaaaaat tccctatacc c aaatgggtt | 240 |
| ccaggccacg aaatcgtagg aactgttgct tgaagttcgg tcagaagtga a gaattttgg | 300 |
| ctggctggag aatcggcggt gggtgtaagg gttgcatggg tttggaggtg c cagccaatt | 360 |
| ggtgaattct tg | 372 |

<210> SEQ ID NO 165
<211> LENGTH: 307
<212> TYPE: DNA
<213> ORGANISM: Eucalyptus grandis

<400> SEQUENCE: 165

| tctctctctc tctccctctt gagagtgttg aagtgttagg atgaggattc g agtgccgtc | 60 |
| gatgctgttg ttgtggtcac tgttgggcct cgtggcgagg tcgacaatgg c cgaagagac | 120 |
| ggtgatcccc gagacaacgc gtttcgacac cggtgggctg agcagatcgg c cttcccgaa | 180 |
| gggcttcgtc tggggacgg cgacctcggc ttatcaagtc gaaggcatgg c cgacaaaga | 240 |
| gggacgcggg cctagcatct gggacgtctt cgtcaagatt ccaggaattg t ggccggtaa | 300 |
| tgcaact | 307 |

<210> SEQ ID NO 166
<211> LENGTH: 454
<212> TYPE: DNA
<213> ORGANISM: Eucalyptus grandis

<400> SEQUENCE: 166

```
gaagaaatta ggtttcttgt tgcggctttt ggtagtgggc ctggtgatag c agagacggt      60 ccatggtgct tatgagttca gcagatacga ctttcctcct ggctttgtgt t tggtgctgg     120 cacttcagct tatcaggtcg aaggagcagc aaatgaggat gggaagactc c aagtataat     180 ggacacctgg gcccactctg actcagggat tacaagcgga gcaaatggag a tattgcctg     240 tgatcaatat cacaaataca aggtagatgt ccaactcatg gcagaaatgg g attagacgc     300 ataccggttt tccatctcat ggtcaaggct catcccaaat gggagaggct c tgtgaatcc     360 gaagggattg cagtactaca caacctcat caatgaactg atcagccatg g gattgaacc      420 cgcacgtgac cctgcaccat tttgatctgc caca                                  454
```

<210> SEQ ID NO 167
<211> LENGTH: 433
<212> TYPE: DNA
<213> ORGANISM: Pinus radiata

<400> SEQUENCE: 167

```
gagaagcaat aggaaaatat ggccctggag aatggtgaaa gaagcagagt a ctgatcatt      60 ggaggaaccg gttattttgg cagaaggtta gtgaaggcca gccttgcctt c ggacatgag     120 acttatgtcc agtatcgtgc ccaggcagcc tctgatatca caaagtggga g acgcttatt     180 tccttcaaat ctcaaggagc acacctggtg gatgcttcca ttgacaatca c acaagcctc    240 gtaaatgccg tgaaacgagt ggaagttgta atatcggcga tgggtgccga g ggtctgaga    300 gaggggcagc tgaaagtgat cgaggccatt aaagaggcag gaaccgtcaa g cgctttctt    360 ccttctgagt tcgggatggc ccagacagaa tggtgcacgc catctatccg g gcaacgagg    420 ttttctctga taa                                                        433
```

<210> SEQ ID NO 168
<211> LENGTH: 330
<212> TYPE: DNA
<213> ORGANISM: Pinus radiata

<400> SEQUENCE: 168

```
cggggagctt gacttgggac tggaaagcag cgggcatcgt ttcctgtggg t tctccgcgg     60 tcatccttcc aatccaaact tatctgcgct gctgcccccg ggtttcgaac a gcggaccaa   120 agatcgtggt ctcgtggtta cctcatgggc tccgcaggtt tctatccttg c acacccgtc   180 aacaggaggt tttgtgagtc actgcggttg gaactcgatg ctggagagca t ttggtttgg   240 agttcccatt atcgcttggc ccctccaagc tgaccaaagg ccgatcgggt t actttctgg   300 tgaatgatag tagaatagac ggtaggcttg                                       330
```

<210> SEQ ID NO 169
<211> LENGTH: 398
<212> TYPE: DNA
<213> ORGANISM: Eucalyptus grandis

<400> SEQUENCE: 169

```
ggaaaatttg gtatcggtag agagatcctg tgagatcgac gcgtgggtcg a ccttcaaaa     60 tttgacccgt gaggtgatct ctcgaacagc gtttggcagt agcttcgaag a aggcaaaag   120 gatctccgaa cttcaggggg aacaagccca gctcacgata atagcccttc a tcggtcta   180 catccctggt tggaggtttg tgccaactaa gatgaacagg aggatgaaga g catagataa   240 ggaagtgcgg gctctgctca tggacatcat ccgcagaaga gagaaagcaa t aagggaagg   300 ggaagctgct ggcgatgatc tgctggggct gttgctggag tcaaacatga a ggagaatgt   360
```

```
cgggatgagc cttcacgatg tgatggacgg agttgcag                            398
```

<210> SEQ ID NO 170
<211> LENGTH: 432
<212> TYPE: DNA
<213> ORGANISM: Eucalyptus grandis
<220> FEATURE:
<221> NAME/KEY: unsure
<222> LOCATION: (214)...(214)

<400> SEQUENCE: 170

```
gttaccaaag ggcagcaacg tattcttaaa catgggttct atccacaggg a tcccaagat    60
ttgggacaaa ccgttggagt ttagacccga gaggttcttg gaaggtccta g caagtatga  120
tttctcaggt aacaacttcg catacatgcc attcggttct ggtcgaaggg t gtgtgcagg  180
gcttgcgctg gcagagagga tgcaaccata tgtnttggcc tctcttttgc a ctcattcaa  240
gtgggaaata ccaccagggt ctgagctgga tttactggac aagttcggcc t tgtggtcaa  300
gaaaatgaag ccccttgtcg ccattccaag accaagattg tccactctgg a gctctacat  360
gtcgagatag atatttcatt agagtcccaa agctcttcat ttcaattcta a gaaataaac  420
gtatcctgcc ag                                                       432
```

<210> SEQ ID NO 171
<211> LENGTH: 303
<212> TYPE: DNA
<213> ORGANISM: Eucalyptus grandis
<220> FEATURE:
<221> NAME/KEY: unsure
<222> LOCATION: (105)...(105)

<400> SEQUENCE: 171

```
ccatcgcggc cctggcccgg acctacgggc cgctcatgca cctgcggctc g ggttcgtac    60
gacgtggtgg tggccgcgtc ggcctccgtg gccgccgagt cctnaagac c cacgacgcc  120
aacttctcga gccggccgcc caactccggg gcgaacacat cgcgtacaac t accaggacc  180
tgatgttcgc gccctacggc ccgcggtggc ggatgctaag gaagataagc t ccgtccacc  240
tcttctccgg caaggctctt aagcattaca gacacgttcg ccagaaaaag g tcgcaatcc  300
tca                                                                 303
```

<210> SEQ ID NO 172
<211> LENGTH: 518
<212> TYPE: DNA
<213> ORGANISM: Pinus radiata

<400> SEQUENCE: 172

```
cattagatat atatatatag acacgcattt acgatatcat tgcaacaatg t cattggtag    60
gctgggttgt ttttctaatc gctttgattt cgtatttggc tgccatcaca a atgcagcaa  120
tcgtcaatta taccttcatc attgaagcga agacagttac caggctatgc a aggagaata  180
caataatcac cgtcaatggg cagctaccag gtccgaccat ctatgtccat g acggagaca  240
ctgttattgt tgaaacttat aacaaggccg agtacaatgc cactcttcac t ggcatggag  300
tggagcagtt gcgtacacca tggctgatgg acctgcata tgttactcaa t gtcccattc  360
caccaggtgg tcgttataca tacagattca acatctctgg acaagaagga a ccgtgtggt  420
ggcatgccca ttactcatgg ctccgagcta cggtccatgg agcttttgta a tccttccta  480
aggaaggaag ctcatatccc tttctaaac ccaatgcc                            518
```

<210> SEQ ID NO 173
<211> LENGTH: 309
<212> TYPE: DNA
<213> ORGANISM: Eucalyptus grandis
<220> FEATURE:
<221> NAME/KEY: unsure
<222> LOCATION: (284)...(284)
<221> NAME/KEY: unsure
<222> LOCATION: (294)...(294)

<400> SEQUENCE: 173

```
gccgctgatc ctaggattga gatctgcatg ctccccgtgg gtgatggcat c actctctgc      60
cgtcggatca gctgagcatc taatctcaag tccttatgat cagggttcat t cttaatgta     120
gaacccacga aaagagagg gatttatgta tatcttgttg ctgtttcttt t ccatgaacc     180
tagaaacggg attcgcaatt aaatgccaaa ttatgttgct gtttctcttt a gtgctctcg     240
atttcttttt attttttaat tttttgatc agtttcttcg aatnatctca a gtncttcca     300
aaaaaaaaa                                                              309
```

<210> SEQ ID NO 174
<211> LENGTH: 381
<212> TYPE: DNA
<213> ORGANISM: Eucalyptus grandis

<400> SEQUENCE: 174

```
taagacgaag aaatggaaac aacggccaag ccatcgcgaa acgcctttcc g catatggaa      60
tgcactatat ttgatcttcc gcatgtggtg gccaatttag aagttagcga g aacgtgaga    120
tgtgttcctg gggacatgtt tgagtccata ccaccagcag atgcaataat a ttgaagtgg    180
atactccatg attggagcga tgaagacgct gtgaagatac tgaagcgatg c aaggaggcc    240
ttaggcaagg gcaagggcaa gaaacagaag gtaattataa ttgacatggt g atggacaac    300
acgaagagcg ccaaagagac ggtcgaaacc cagctcttct atgacatgtt g attgatgaa    360
ccctcgccgt cgggaaaggg g                                                381
```

<210> SEQ ID NO 175
<211> LENGTH: 236
<212> TYPE: DNA
<213> ORGANISM: Pinus radiata
<220> FEATURE:
<221> NAME/KEY: unsure
<222> LOCATION: (37)...(37)

<400> SEQUENCE: 175

```
tgaattacca catgcggctg atagatctgg tgaaggncgg aggattgatt g cgtatgaca      60
atactctgtg gcaaggatcc gttgcgcttc ccccagaagt cgccatgagc g aaggcatga    120
gttatgggga agacagagag catatgttgg aactaaacag ggcccttgct g cagaccctc    180
gcatcgagat tgctcagatc ccaattgccg atggagtgac gctgtgcagg c gcctt        236
```

<210> SEQ ID NO 176
<211> LENGTH: 404
<212> TYPE: DNA
<213> ORGANISM: Pinus radiata
<220> FEATURE:
<221> NAME/KEY: unsure
<222> LOCATION: (1)...(404)
<223> OTHER INFORMATION: n at all occurrences indicates unsure

<400> SEQUENCE: 176

```
gtcgggaatt ccacttacca gaccattaat tcacgattca tcccacctca g cctggaaat     60
```

```
ttggtctgaa tctggagccc aatactgtac aagtagcctt ggtctcttcg g gaatccgtg        120 tntggaaaga agaaattgag atccggccaa agatggttgc agggtcagac c tgggcgctg        180 tgcaggccaa tggaaatcaa aatggaaatg gatttcatca tgtgcattct g ttgatctct        240 gcattcagaa tggnccagac cctctgaact ggggcaggc tgccaaggcc c tgcagggct         300 cccactttga agaagtgaag ctcatggtgg ngtcctattt cggatccgng g aagtttcca        360 ttgaaggcaa atcngtcaca atcgcggatg tgaccgcagt tgcc                         404
```

<210> SEQ ID NO 177
<211> LENGTH: 415
<212> TYPE: DNA
<213> ORGANISM: Pinus radiata
<220> FEATURE:
<221> NAME/KEY: unsure
<222> LOCATION: (20)...(20)

<400> SEQUENCE: 177

```
cccaacgcta tgcgtctgan caggcaactt tcttcagtgc atttgtggcg g ccatggata        60 aattgggcag tgtgggtgta aaaactggca cacaggggga ggtcaggagg a gatgtgatg       120 cgttcaattg agaagagtaa agttcaaatt ctctccatta ttaaggtggg a ttgtatgca       180 tggttgagat taatgaacgg aacaaagaaa atttaatgtt ttgtaactag t gagattgat       240 gaattgaata aagaatttt cctgtcctct gattcaacct gttttgcact c tgtgaagca        300 ctttacagtc tggactctgg aaggaatcca tcaaatcgtg actaagaaaa g ggtaatgat      360 tttaaagaga ttccgttgcg ctcattccat tgggggattc ctgaaaatat c tgcc           415
```

<210> SEQ ID NO 178
<211> LENGTH: 409
<212> TYPE: DNA
<213> ORGANISM: Pinus radiata

<400> SEQUENCE: 178

```
gatgggcgcg caattctttt cagccggctg gtgtagttgc tgttgaggtt a cgggaggtc       60 ccacaattga gtttgtccct ggtcgtaagg attcactggc atcaccacga g aagggcggc      120 ttcctgatgc gaagaaaggt tcacaacacc taagggatat cttttatagg a tgggcctat      180 ctgacaagga tatagttgct ctttctggag cgcacaccat tgggaaaagc a catccagaa     240 aggtcaggct ttgatggagc atggaccgag cagcctctga agtttgataa t tcatatttt       300 gtagagcttc tcaaaggcga gtctgaagga ttactccaat tgcctacgga c aaatgcttg     360 gtagaggatc ccagtttccg cccttatgtg gatctttatg ccaaggatg                    409
```

<210> SEQ ID NO 179
<211> LENGTH: 411
<212> TYPE: DNA
<213> ORGANISM: Eucalyptus grandis
<220> FEATURE:
<221> NAME/KEY: unsure
<222> LOCATION: (393)...(393)

<400> SEQUENCE: 179

```
agagcttctc ccagagaggc ctctctatgg aagatctcgt cgctctttcg g gaggccaca      60 cactaggatt ttcccactgc tcctccttcg caggcaggat ccgcaacttc a acaccacgc     120 acgacatcga cccatcgatg cacccatccc tggcagcgag cctaagaggc g tgtgcccga     180 gcaagaacag gccaaaaaac gcagggacca ccatggaccc ttcctcgacc a ccttcgaca     240
```

```
acacgtacta cgggctgatc ctccagggga agggcctgtt ctcttcggac c aggccctcc      300 tggcagtgcc caagacgaag gatctggtcg agaagttcgc aggctcgcac a aggaattca      360 cggatgcatt cgtcaagtcc atgatcaaga ttnagcagca tcacaggcgg a                411
```

<210> SEQ ID NO 180
<211> LENGTH: 334
<212> TYPE: DNA
<213> ORGANISM: Pinus radiata

<400> SEQUENCE: 180

```
gcatcatggg aagtacaact gggaagaaga gacagcctaa cagcaagcaa a acagcagca      60 aataacaaca ttccagcccc cacatcaaat gttgcaacac ttaactccaa g tttcagaat      120 gtaggcctca ctgaacaaga catggtcaca ctctcaggag cccatacaat a ggaaaggcg      180 cgttgtgcaa cattcaactc taggctcacg ggacaaccgg atcccactct t cagaaagag      240 ttttttgacat cgctccaaca aatctgcttt caagggctag ccagtaataa c aacaccgta      300 acttcactgg atgtggagac tcccgtcatt tttg                                   334
```

<210> SEQ ID NO 181
<211> LENGTH: 343
<212> TYPE: DNA
<213> ORGANISM: Pinus radiata

<400> SEQUENCE: 181

```
atttcgctga actggatctg gatcgaagaa ggtattgcat atcaaagaaa g aggcaaata      60 tgactccggc cactgttttg ctttctatat ttgtgattgt atatggtagt g ctgtgaacg      120 ctctgccaac tcccgtggcg ggtctttcgt ggacgttcta caacacaagt t gcccgtcat      180 tggagtcgat agtgcggaag cgcatggaag cctatttgag tgcagacatc a cacaagctg      240 caggattgct gaggctccac ttccacgact gttttgtcca gggatgcgac g ggtctgtgt      300 tgctgaactc aacatcgggg gagcaaacag ttgcgcccaa ctt                        343
```

<210> SEQ ID NO 182
<211> LENGTH: 443
<212> TYPE: DNA
<213> ORGANISM: Pinus radiata
<220> FEATURE:
<221> NAME/KEY: unsure
<222> LOCATION: (164)...(164)

<400> SEQUENCE: 182

```
atttcgctga actggatctg gatcgaagaa ggtattgcat atcaaagaaa g acgcaaata      60 tgactccggc cactgttttg ctttctatat ttgtgattgt atatggtagt g ctgtgaacg      120 ctctgccaat tcccgtggcg ggtctttcgt ggaccgtttt acancacaag t tgcccgtca      180 ttggagtcga tagtgcggaa gcgcatggaa gcctatttga gtgcagacat c acacaagct      240 gcaggattgc tgaggctcca cttccacgac tgttttgtcc agggatgcga c gggtctgtg      300 ttgctgaact caacatcggg ggagcaaaca gttgcgccca acttatcact c agagcggag      360 gctctgaaaa tcatcaatga catcaaagag aacgtagaag cggcgtgcag c ggaactgtg      420 tcgtgtgcag acattcttgc ctt                                               443
```

<210> SEQ ID NO 183
<211> LENGTH: 243
<212> TYPE: DNA
<213> ORGANISM: Pinus radiata -continued

<400> SEQUENCE: 183

| acattgatga ttgtgctacg cgtatttttt tcaatctcta gcacttggga a ggtctggag | 60 |
| gaggcggctc caaggttgcc tgagggccgt gaccgttctt cactataaac a ccatattca | 120 |
| gtccccatac taaatggtcg tctaaatggc agtggagaaa ccacactcct g gattgtcag | 180 |
| cttttgaatct tatcgcaacc caaccgctca caggagctat tactgtgttg c gtagtgggg | 240 |
| atc | 243 |

<210> SEQ ID NO 184
<211> LENGTH: 473
<212> TYPE: DNA
<213> ORGANISM: Pinus radiata

<400> SEQUENCE: 184

| ggtggcccct agaagaaaca cactcagaga gtttgatcta taagaggaga g attcactcc | 60 |
| aaaatgcaca gggagattca ctccaccatc aaatttaat cattggcctt t ttcctctca | 120 |
| acggccgatg gcgtaaacac gcgtaagcaa acaccaagat cctgaaacag t cgactgatc | 180 |
| gattcagaat aatttgaaag gaaactggac tactcaatca atttgttgac a tttatcaag | 240 |
| aaatggatga ttcagtacag gaggtatcca aggaaggcaa tcaatgggca g gattcattg | 300 |
| agggtgagaa tgtaatccga agaggaaggg agattcttct acagcatgat a accgggagg | 360 |
| cacataactg ggagtcacat aaacataagt ggtggccaca tttggaagaa a aatcccgc | 420 |
| acattgccaa agcaggattt acatctatat ggctgccgcc tgcttttgat t cg | 473 |

<210> SEQ ID NO 185
<211> LENGTH: 641
<212> TYPE: DNA
<213> ORGANISM: Pinus radiata

<400> SEQUENCE: 185

| ggcaccgagc tgggataccc ctgctgcgac ttgatccctt ttgaacagga a ttatttaat | 60 |
| tttcctaatt attttagttt gcaaggaaac ttgactactc catcaatttg t ttacagttt | 120 |
| tcgaaaaatg ggctatccag ttcaggaggt atccaaggaa cacgatcaat g ggcaggatt | 180 |
| tgttgaaggt gaaagtgtgc ttcaaagagg aagggagatt cttctccagg g ttttaactg | 240 |
| ggagtcacat aaatacaagt ggtggccaaa tttggaagaa aagatcccgc a cattgctaa | 300 |
| agcaggattt acatctgtat ggctgccacc tgcttttgat tctgctgcac c ccaaggtta | 360 |
| cttgccccga acatttatt ctctgaactc tgcatatggt tcagaatatc a gctgaaaag | 420 |
| cttacttatg acaatgcgaa agaaaatgt gagagccatg gctgacatag t tatcaatca | 480 |
| tcgcatggga agctctcagg ggtttggagg cttgtataat cgctattatg g ttgcctgcc | 540 |
| ttgggatgaa cgtgctgtta cacgttgttc tggtggactt ggaaactgga g cacagggga | 600 |
| taattttcat ggagtaccaa acgttgatca cacccaagat t | 641 |

<210> SEQ ID NO 186
<211> LENGTH: 655
<212> TYPE: DNA
<213> ORGANISM: Pinus radiata

<400> SEQUENCE: 186

| agaatggcca agtttcgatc tctgtctta ttgttatggt tctcctgcat c atagtcaat | 60 |
| gcagcctctc ctgcacaagc agaagctaca acgcctcctc tgaataccct c ttacttcag | 120 |

-continued

```
ggcttcaatt gggattcagc ccagagttct actccttggt ataatgtatt g aagggaatt      180 gtagacgatg cagcggacgc cggcattacg tacgtctggt ttccgccgcc c tcacaatcc      240 ggcgcccctc aaggttattt gccagcgaag ctctatgatt tagactcgtc c tacgggagc      300 gagcaacaac taaaggatgc cgtgaatgcg ttccaccaaa agggaattgc g attatgggc      360 gacatcgtga taaaccatcg gaacgggacg aagcaggacg ataaaggata t tggtgcgtg      420 tttgagggcg ggaaggggga cggtactctg gactggggac cctgggcggt c accgtgaag      480 gaccaaccat atccgttgtg cggctccggc caggcggaca ccgaggggga c ttcaagtac      540 gccccggacg tggaccacac caatcccaag atacagcaag atttgtcgga g tggatgaat      600 tggctcaagt ccatgtcgga tttgatggct ggaggttcga ctacgtcaag g ctac          655
```

<210> SEQ ID NO 187
<211> LENGTH: 438
<212> TYPE: DNA
<213> ORGANISM: Eucalyptus grandis

<400> SEQUENCE: 187

```
ctggggtggg gaggctggtc gacgtgggcg ggagcgcggg ggactgcctc c ggatgatca      60 tggggaagca cacgcacgtc cgggaaggga tcaacttcga cttgcccgag g tcgtggcca    120 aagcgcctcc cattcctggg gtgacccatg ttggtggcga catgttcaag t ccatccctg    180 ctggtgatgc cattttcatg aggtggatac tgacgacatg gacggacgac g agtgcaagc    240 agatactgga aaactgcttc aaggcactcc ctgcgggagg gaagctgatt g cctgcgagc    300 cggtgctacc gcagcactca gatgataggcc acaggactcg agcacttctt g agggcgaca    360 tcttcgtgat gaccatctac agggccaagg gcaagcatag gactgagcag g aattccagc    420 agctcgggct ctctaccg                                                    438
```

<210> SEQ ID NO 188
<211> LENGTH: 597
<212> TYPE: DNA
<213> ORGANISM: Eucalyptus grandis

<400> SEQUENCE: 188

```
acccaacaat ggccgacaac caagaacgcg aagggcgcga tcaagaagag g aagtcggga    60 agctggcggt ccagctggcc agcgcggtgg tgctcccgat gaccctcaag t cggccctcg   120 agctcggcat catcgacgcc ctcgtctccg ccggtgggtt cctctcggct g ccgagatag   180 cgagccgggt tggcgccaag aacccggggg ccccagtcct ggtggaccgg a tgatgcgcc   240 tcctggcgag ccacggcgtg atcgagtggc ggttgaggag gggcgacggc a acggagatg   300 gagggagag agagtacggt ccaggaccca tgtgcaggtt ctttgccaag g accaagaag   360 gtggagatgt tggtcctctg tttctgctaa ttcacgacaa ggtcttcatg g agagttggt   420 accacttgaa cgatgtcatc atggaaggag gggttccgtt cgagagggca t acgggatga   480 cggcgttcga gtatcctgcc gttgacgata ggttcaatca agttttcaac c gggccatgg   540 cgagtcatac ttccctcatc atgaagaaaa tactcgatgt ctacagaggg t ttgaag       597
```

<210> SEQ ID NO 189
<211> LENGTH: 470
<212> TYPE: DNA
<213> ORGANISM: Eucalyptus grandis

<400> SEQUENCE: 189

```
cccgaccccg ctttacatga acaagatcct cgagtcgtac cgtgggtttg a gggcgcaaa      60 gacgattgcc gacctaggtg gcggcgtcgg ccagaacctt cggctcatat t ggacaagtt     120 cccaaatctc aggggcatac tctatgatct gcctcatgtg atcaaagatg c acctgccca    180 tcctcgtatg gagcgtgtcg gaggagacct gttaaagtct gttccgaaag c agatatact    240 cttcatgaag tggcttttcc atggtctacg agacgatttc tgcaaaatgc t actccagaa    300 ctgttacgag gcgctgccac caaatggcaa ggtggtcatc gtggacccga t ccttcccga    360 atacccgag acagacatag tgtcgaggaa ctcgttcacc tccgacatga t catgctata     420 cacgagccct ggagaagacc ggacgaggaa agagctggag gtgctcgcac               470
```

<210> SEQ ID NO 190
<211> LENGTH: 499
<212> TYPE: DNA
<213> ORGANISM: Eucalyptus grandis

<400> SEQUENCE: 190

```
gtccagtttt cagccgtgct atgaagaagc caacagttta gaccgttgga t tcagcctcc      60 gtcggatctg cttcataata tgtccgataa agaactattt tggagagcga c ccttgttcc    120 taaaatcaag aagtatccat tcagaagagt tccaaaaatt gctttcatgt t cttgaccaa    180 gggtccattg ccgctggctc ctctttggga gaggttcttc aagggccatg a gggcttta     240 ttcgatctat attcattccc atccatcatt ccatgcccac tttcatcctt g gtcggtatt    300 taacaggaga caaatcccaa gtcaggtgtc tgagtggggc aggatgagca t gtgtgatgc    360 agagaaaaga ctcctagcca acgcattgct agacatatcc aatgagcggt t cattcttct    420 ttctgaatca tgcattccgc tgtataactt cagcctcatc tatcactaca t tatgaagtc    480 cggatatagc ttcatgggt                                                 499
```

<210> SEQ ID NO 191
<211> LENGTH: 1036
<212> TYPE: DNA
<213> ORGANISM: Eucalyptus grandis

<400> SEQUENCE: 191

```
ggcaagtggt ggctggaatt cacacccatt gcgctctctc tctctctcta g atcctatct      60 cgaaagccaa aagaaaagac agtcggaaga aaaatataa aaaaaaacat g agttcgaag     120 gaagccccag tcattacaac ttcccatgaa gatgaagaaa ttttgaatgc c tttgaggtc    180 ccctcaatgg cttttgttcc catggtcttg aaaggcgtcc atgagctggg g attcttgaa    240 ttgctggcca agggtgacca gctctctccg ttggacatcg tgcccgcct c tctatcgac     300 aacccggccg caccggacac gatcgaccgg atgctgcggc tccttgcgag t tactccatc    360 ttatcgtgca ctcgtgtgga ggataaagaa ggccgcccc agaggctcta c ggcctcggg     420 cctcggagca agttcttttt ggaccagaat ggagcttcta ctttaccaac t catatgcta    480 ctccaagaaa agactctcct ggaatgctgg aactgcctta agatgcagt t aaggaagga    540 ggggcagatc ctttcacccg caggcacggc atgaacgtgt tcgactacat g gccaggac    600 ccgagattca cgacctgta caacaagtcg atgaggaccg gtcggcgat t acatgccc     660 aagatcgctc agcattatcg tgggttttca aaggcgaaga cggtcgtcaa t gtgggcggt    720 ggcatcggcg agaccctgaa aaccatactc tccaagaatc cccacatccg c gccatcaac    780 tacgacttgc tcatgtgat cgcaactgct cctcccattc tggtattac g catgttgga    840 ggagacattc taaagtccgt ccctaaagcg gatgtccatt tcctgaagtc g gttctccat    900
```

| | |
|---|---|
| cgcggggatg atgagttctg cgtgaaggtg ctcaagaatt gctggaggc a ttgccgccg | 960 |
| acggggaaag tggtgatcgt ggaggaagtg accccggagt atcctgggac c gacgatgtc | 020 |
| tcacagacca cgctct | 036 |

<210> SEQ ID NO 192
<211> LENGTH: 682
<212> TYPE: DNA
<213> ORGANISM: Pinus radiata

<400> SEQUENCE: 192

| | |
|---|---|
| agacgttgga ggaggtatag gctctgcctt gtccatcatt gtgaaggaac a tccacacat | 60 |
| tcgtggcatt aatctcgatc tgcctcatgt cattgccact gcgcctctca t aactgggt | 120 |
| ggagcacatg gagggaaata tgttcgagca catacctctt gccgatgcag t catgatgaa | 180 |
| gtggatcctc catgactggg cggacgagga gtgtgtgaaa ttgctgagaa g aagctacga | 240 |
| cgcaacgcca gcgaagggaa aggtgttaat tgtggaagca gttgttgagg g agacaaaga | 300 |
| aggtgaaagc atgtcgaggc gattgggatt gttatatgat atatcgatga t ggcttacac | 360 |
| aactggtggg aaggagagaa cagaggaaga attcaagggg ttgttccagc g cgcagggtt | 420 |
| caagagccac accatcatca agttgccttt ccttcagtcg ctcatagtgc t gtccaaagc | 480 |
| ctaataagct attgcgcttc cgattatcgt tacaataacg ttggttttgc t ggggttgtt | 540 |
| atcatgcagt atatgaccta tgtttttatgt tatctggcag tataagattt c tgaagacat | 600 |
| ggttgaaatt attgtgagat tttaaagata tttatccatc ataaaaataa t ggaatatga | 660 |
| taatattttt acaaaaaaaa aa | 682 |

<210> SEQ ID NO 193
<211> LENGTH: 399
<212> TYPE: DNA
<213> ORGANISM: Eucalyptus grandis

<400> SEQUENCE: 193

| | |
|---|---|
| agcgtctaat ggttcctatt tagaagttca gaaagtctct gtctttccta c cttgcgggg | 60 |
| tagtctcttc ggacgtactc aaacatggag caaggctggg acaagggcga g atcctggca | 120 |
| agcaaagctc tctcgaagta catattggag accaatgcat atccgagaga g cacgagcag | 180 |
| ctgaaagaac tcagggaggc cacggtccag aagtaccaaa tccggagtat a atgaacgtg | 240 |
| ccggttgatg agggcagct gatctccatg atgttgaagc tcatgaatgc g aagaagaca | 300 |
| atcgagatcg gagtcttcac cggctactct cttctgacca ccgcacttgc a cttccggcc | 360 |
| gacggcaaga taatagcgat agaccaggat aaggaggcc | 399 |

<210> SEQ ID NO 194
<211> LENGTH: 399
<212> TYPE: DNA
<213> ORGANISM: Eucalyptus grandis

<400> SEQUENCE: 194

| | |
|---|---|
| cggacgtact cagacatgga gcgaggcggg gacaagggcg agatcctggc a agcaaagct | 60 |
| ctctcgaagt acatattgga gacgaatgca tatccgagag agcacgagca g ctaaaagaa | 120 |
| ctcagggagg ccacggtcca aaagtaccaa atgcggagta atgagcgtg g ccggctgat | 180 |
| gaggggcagc taatctccat gatgttgaag ctcatgaatg cgaagaaaac a atcgagatc | 240 |
| ggagtcttca cggctattc tcttctcacc accgcacttg cacttccggc c gacggcaag | 300 |

```
ataatagcaa tagacccgga taaggaggcc tatgaaattg gcctgccata t atcaaaaaa      360 gccggagtcg atcataagat caacttcatc cagtcggat                             399
```

<210> SEQ ID NO 195
<211> LENGTH: 296
<212> TYPE: DNA
<213> ORGANISM: Eucalyptus grandis

<400> SEQUENCE: 195

```
ttgcagtaca tattggagac gaatgcatat ccgagagagc acgagcagct g aaagaactc      60 agggaggcca cagtccagaa gtaccaaatc cggagtataa tgaacgtgcc g gctgacgag     120 gggcagctaa tctccatgat gttgaagctc atgaatgcga agaagacgat c gagatcgga     180 gtcttcaccg gctgttctct tctcaccacc gcacttgcac ttccggccga t ggcaagata     240 atagcgatag acccggataa ggaggcctat gaaattggcc taccatatat c cgaaa        296
```

<210> SEQ ID NO 196
<211> LENGTH: 474
<212> TYPE: DNA
<213> ORGANISM: Eucalyptus grandis

<400> SEQUENCE: 196

```
gcgccaccac caaacgctca ccttctcatc atcagccctc tgtctctgtc t ctgtctctc      60 gattctccgc cccgccacga caatggaggc gaagccgtcg agcagcccc g cgagttcat     120 cttccggtcg aagctccccg acatctacat tcccgacaac ctctccctcc a cgcctactg     180 cttcgagaac atctccgagt cgccgaccg ccctgcgtc atcaacgggg c caccggccg     240 gacctacacc tatgccgagg tcgagctgat ctcccgccgg gtctcagccg g cctcaacgg     300 gctcggcgtc ggacagggcg acgtgatcat gctgctcctc cagaactgcc c tgagttcgt     360 gttcgcgttc ctcggcgcgt cctacggggg cgccatcagc acgaccgcga a cccgttcta     420 caccccgggc gagatcgcca agcaggcctc agctgcccgg gccaagatcg t gat         474
```

<210> SEQ ID NO 197
<211> LENGTH: 543
<212> TYPE: DNA
<213> ORGANISM: Eucalyptus grandis

<400> SEQUENCE: 197

```
gttcgccgac aaggtgaggc cgttcgcgga ggagaacggg gtgaaggtcg t gtgcatcga      60 taccgcgccg gagggctgcc tgcacttctc ggaattgatg caggcggacg a gaacgccgc     120 ccccgcggcg gacgtcaagc cggacgacgt cttggcgctc ccctattcgt c gggcacgac     180 ggggcttccc aagggagtga tgcttacgca caggggtcaa gtgaccagcg t ggcgcagca     240 ggtcgacgga gacaacccca acttgtactt ccacaaggag gacgtgatcc t gtgcacgct     300 cccgttgttc cacatatact ccctcaactc ggtgatgttc tgcgcgctcc g tgtcggcgc     360 cgccatcctg atcatgcaga agttcgagat cgtggcgctg atggagctcg t gcagcggta     420 ccgggtgacg atcctgccca ttgtcccgcc gatcgtgctg gagatcgcaa a gagcgccga     480 ggtggaccgg tacgacctgt cgtcgatccg gaccatcatg tcgggtgcgg c ccgatgggg     540 aag                                                                    543
```

<210> SEQ ID NO 198
<211> LENGTH: 564
<212> TYPE: DNA
<213> ORGANISM: Eucalyptus grandis

<400> SEQUENCE: 198

```
ctggacaact agttgcagga gttgaagctc aagttatcag cgtggataca c taaaatctc      60
ttcccctaa tcagttaggg gaaatatggg ttcgtggacc taacatgatg a aaggatatt     120
ataacaatcc acaagcaact aaattgacaa ttgataacaa gggttgggtg c acactggag   180
accttggata ttttgatgag gaagggcaac tatatgttgt tgatcgaatc a aagagctca   240
tcaagtacaa aggttttcag attgctccag ctgagcttga aggactcctt c tttcacatc   300
ctgaaatttt agatgctgtt gtcattccat ttcctgatgc tgaagctggt g aagttccta   360
ttgcatatgt cgttcgctca cctaccagct ctctaactga agaggaagtc c agaaattca   420
ttgccaatca ggttgcacca ttcaaaagac taaggagggt gacattcgtc a acagcgtcc   480
caaagtctgc ttccggcaaa attttgagac gtgagctgat gcaaaagta c gagcaaaga    540
tataactgtg catgctcgat gcgt                                           564
```

<210> SEQ ID NO 199
<211> LENGTH: 455
<212> TYPE: DNA
<213> ORGANISM: Pinus radiata

<400> SEQUENCE: 199

```
ggctactttg atgaggaagg aggattattt attgtggatc gtattaaaga a ctaatcaaa     60
tacaaaggtt tccaggttgc ccctgctgag ttggagggca tattgttgac a catccccaa   120
attgcagatg ctggagttat tcccttcct gatctaaaag ctggagaggt t ccaatagca   180
tatgttgtac gtaccctgg aagctctttg acggaaaagg atgccatgga t tatgttgcc   240
aagcaggtcg caccatttaa aaggttgcat agagtcaatt ttgtagactc t atacccaag   300
tctgcctcag ggaagattct tcgacgagag cttattgcta aggccaaatc a aaattgtaa   360
gcaaagaaat atatcatttt ttctggtatc atgatacaaa gttgcacaaa c ttatttgta   420
agtgtcaccc cagatgaaca aggaatttgt tccgc                               455
```

<210> SEQ ID NO 200
<211> LENGTH: 569
<212> TYPE: DNA
<213> ORGANISM: Pinus radiata

<400> SEQUENCE: 200

```
gtcgtctgta aattactctg tgagtgttta gtgttttctt ctcttattga t ttcagggga     60
caagtaggtg ggggtggggg agcttaagtc aaatctagtg cttctctgt a agattttcc    120
cttttttttc ttgctaagag tagccatgat tgaggtacga tcagctcccc c catggcacg   180
gtccactgag aacgagaata accagcatga tgccgaagaa ggggcggtat t gaatgaggg   240
cggcatggat tttctgtatc ggtcaaagct tccagacata gatattccat a ccatcttcc   300
attgcactcg tattgcttcg agaaactgga cgagctcaga gagaagccat g tctgataca   360
ggggtcgaac gggaagattt acagctatgg cgaagtggaa ttgatatctc g caaggtggc   420
ctcgggtttg gccaaattgg gattcaaaaa ggggacgtg tcatgctgc t gctgcccaa    480
ttgccccgaa tttgtctttg ttttcctagg gcgtccatg gctggtgcca t tgccaccac   540
ggcgaaccct ttttacactc cctccgata                                      569
```

<210> SEQ ID NO 201
<211> LENGTH: 993
<212> TYPE: DNA

<213> ORGANISM: Eucalyptus grandis

<400> SEQUENCE: 201

| | | | | |
|---|---|---|---|---|
| tgaccatcct | ccggcaatgg | ctcttcacat | cctcttcaca tggcttgctc t | ttcccttcc 60 |
| tctcctcctc | ctcctcctcc | tctcagtgaa | aacttcaat aacaaaaga a | gaacctccc 120 |
| tccagggcct | ccatcacttc | ccatcatagg | caacttccac cagctcggcc c | cctgcctca 180 |
| tcagtctctg | tggaaactct | ccagacgata | tggccccgtc atgctcatcc g | cctcggtgg 240 |
| cacccctacc | atcgtaatct | cctcccctga | tgctgccagg gaggtcctca a | gacccacga 300 |
| ccttgatagt | tgcagtcgcc | cgcagatggt | cggcccggga cgcctctcct a | tgactccct 360 |
| cgacatggcc | ttcgtggagt | acggcgatta | ctggagggga ttaaggacgc t | gtgtgtgct 420 |
| cgagctgttt | agcatgaagc | gagtccagtc | cttccgatac atcagggaag a | ggaggtggg 480 |
| atctatgatc | gaatcgatcg | caaaatcagc | agagagcgga actccggtta a | tatgagcga 540 |
| gaagttcatg | gctctgacgg | ctaacttcac | ttgcagggtc gcatttggga a | gccatttca 600 |
| ggggacggag | ttggaagacg | aagggttcat | ggatatggtt cacgagggaa t | ggcgatgtt 660 |
| gggaagcttc | tcggcatctg | attatttccc | tcgactcggc tggattgtgg a | caggttcac 720 |
| ggggctccat | tcgaggttgg | agaagagctt | tcgcaatttg gacgatctct a | tcagaaggt 780 |
| gatcgaagag | catcggaatg | cgaataagag | caacgaggga aaggaggaca t | tgtcgatgt 840 |
| gctgctgaag | atggagaaag | atcagactga | gctcgcgggg gtccggctca a | ggaagataa 900 |
| catcaaggcc | atcttgatga | atatatttct | cggaggagtg gacaccggtg c | agtgtcatg 960 |
| gactggacaa | tggctgagct | cgctaggaac | ccg | 993 |

<210> SEQ ID NO 202
<211> LENGTH: 349
<212> TYPE: DNA
<213> ORGANISM: Eucalyptus grandis

<400> SEQUENCE: 202

| | | | | |
|---|---|---|---|---|
| ggacggagtt | ggaagacgaa | gggttcatgg | atatggttca cgagggaatg g | cgatgttgg 60 |
| gaagcttctc | ggcatctgat | atttccctc | gactcggctg gattgtggac a | ggttcacgg 120 |
| ggctccattc | gaggttggag | aagagctttc | gcaatttgga cgatctctat c | agaaggtga 180 |
| tcgaagagca | tcggaatgcg | aataagagca | acgagggaaa ggaggacatt g | tcgatgtgc 240 |
| tgctgaagat | ggagaaagat | cagactgagc | tcgcgggtgt ccggctcaag g | aagataaca 300 |
| tcaaggccat | cttgatggta | tatcatacaa | tctctacgta ttacttaat | 349 |

<210> SEQ ID NO 203
<211> LENGTH: 432
<212> TYPE: DNA
<213> ORGANISM: Eucalyptus grandis

<400> SEQUENCE: 203

| | | | | |
|---|---|---|---|---|
| cttggtcgta | gcagctttgc | tgattgttct | cttgaggagc aagtctagga a | aagaaagag 60 |
| caacctccca | ccgagccctc | ctaagttgcc | gatcatcggc aatcttcacc a | gcttggcaa 120 |
| atcgccacac | atatctctcc | atcgccttgc | gagaaactac gggccaatca t | gtccttgca 180 |
| gctcggcgaa | gtcccaacca | tagtcgtttc | ctcagccgca atggccaagg a | ggtgatgaa 240 |
| aacccatgac | ctagtgctcg | caaaccgccc | tcagatcttc tctgccaagc a | cttgtttta 300 |
| tgactgcaca | gacatggcct | tctctcccta | tggcgcttat tggaggcaca t | aaggaaaat 360 |
| ctgcatactt | gaagtgctta | gcgcaaaacg | ggttcagtca tttagtcatg t | cagggagga 420 |

-continued

<210> SEQ ID NO 204
<211> LENGTH: 407
<212> TYPE: DNA
<213> ORGANISM: Eucalyptus grandis

<400> SEQUENCE: 204

```
ctcaccttca aatgcctccg cttcctcttc tcctctgccg ccgctactaa c cttcacctt    60
ccgccatcac cgccgaagct ccctatcatc gggaacctcc accagctcag t gatcaccct   120
caccgctcgc tccaagccct gtcgagacgc tatgcccct tgatgatgct c cacttcgga   180
agcgtgcccg tcctcgtcgt atcttccgcc gactgtgcac gggacatctt g aagacccac   240
gacctcattt tctccgaccg acccaggtca accctgtcgg agaggctttt g taccaccgc   300
aaggacgtgg ctctggcgcc gtttggcgag tactggaggg aaatgaggag c atctgtgtc   360
ctccagctgc tgagcaacaa gagggtccac tcgtttcgga cggtcca             407
```

<210> SEQ ID NO 205
<211> LENGTH: 384
<212> TYPE: DNA
<213> ORGANISM: Eucalyptus grandis

<400> SEQUENCE: 205

```
gggaaattac cccacaggtc gctggatcga ctctccaaaa catatggccc c ctcatgtat    60
atgagactcg gatccatgcc atgcgtggtc ggctcatccg ctgagatggc c cgagagttt   120
ctcaagaccc acgatctcac attctcgtcc gaccccgtg tggcggccgg g aaatacact   180
gtttacaact actccgacat cacctggtct ccctacgag agcactggcg t ctcgccaga   240
aaaatctgcc tcatggagct cttcagtgcc aaacgcctcg aatctttcga g tacatcaga   300
gtagaagagg tcgcccggat gctgagttcc gtcttcgaaa ccagccggca g ggccttcct   360
gtagaaatca gggaagagac gact                                          384
```

<210> SEQ ID NO 206
<211> LENGTH: 543
<212> TYPE: DNA
<213> ORGANISM: Eucalyptus grandis

<400> SEQUENCE: 206

```
ataaataaga atggtgaacg agttagggtc ggaaaagccc ttctggtat g cctagagtt    60
ttatatgaaa ctcgctattg ctctagttgc gttggtggtg gcatggagct t cttcgtcaa   120
gggaagaaat aggaagctgc ccccgggacc gttctctttg cccatcatcg g aaatctcca   180
tttgctggga cagcttccac accgagcact gaccgctctt tctctcaaat t cgggcctct   240
tatgtcgctt cgcctcggct ctgctcttac attagtagtc tcttcacctg a tatggccaa   300
ggagtttctg aagacacatg atctgctttt tgctagcaga cctccatccg c ggctactaa   360
ttatttttgg tataattgca ctgacatcgg ttttgctccg tatggcgctt a ctggaggca   420
agtgcgtaag gtgtgcgttt tacagttgct gagctccaga cgcttggatt a tttccgctt   480
tataagagaa gaggaggtct ctgctatgat tcattctatt gctcattccg a tcatcctgt   540
aaa                                                                 543
```

<210> SEQ ID NO 207
<211> LENGTH: 1320
<212> TYPE: DNA

<213> ORGANISM: Eucalyptus grandis

<400> SEQUENCE: 207

| | | | | | |
|---|---|---|---|---|---|
| tcatcacttg | catttggcca | gcacatcata | gctacctctt | atagctgtaa t | cttcaccaa 60 |
| attggagaga | tgagcttcca | gaaccagctc | ttcatcttct | gcacgttgct a | ctagggttt 120 |
| ctgaagttgg | cagaaggcaa | aacgaggcac | tacaccttcc | atatcgattc c | cataacatg 180 |
| acgaggctgt | gccacacgag | gagtgtgctg | agtgtaaaca | agcagtatcc a | gggccgccg 240 |
| cttgtggcga | gggaaggcga | caacatcctc | gtcaaggtgg | tgaatcatgt t | gccgccaac 300 |
| gtcacgattc | actggcatgg | ggttcggcaa | ctgaggacgg | gatgggcgga t | ggaccggct 360 |
| tacgtaaccc | agtgtcccat | acagaccaac | cagagctaca | cctacaactt c | accctcacc 420 |
| ggccagagag | gaacgctgct | gtggcacgcg | cacgtctcgt | ggctaagatc g | agcatccac 480 |
| ggccccatca | tcatcctccc | caagcggaac | gagtcctacc | cgttcgagaa a | ccctccaag 540 |
| gaagtcccca | taatatttgg | agagtggttt | aatgtagacc | ccgaagcggt c | atcgcccaa 600 |
| gctcttcaga | gtggaggagg | tcccaatgtc | tccgatgcct | ataccatcaa t | ggccttcca 660 |
| ggacccttgt | acaattgctc | ctctaaagac | accttcaagt | tgaaggtgaa a | cctgggaag 720 |
| acatacctcc | tccggctgat | caacgctgca | ctcaacgacg | agctcttctt c | agcatagcc 780 |
| aaccacgcag | tcaccgtcgt | cgaggttgat | gccgtgtaca | ctaagcccct t | tctgcgggc 840 |
| tgcctccacc | taaccccggg | ccaaaccatg | aatgtcctcc | tcaagacaaa a | accgactttt 900 |
| cccaactcca | ccttcctcat | ggcagcgtgg | ccctatttca | ccggcatggg c | actttcgac 960 |
| aattccaccg | tcgccggaat | ccttgagtac | gaacatccaa | agagctcaaa t | tacccgccg 020 |
| ctcaagaagc | tcccccaata | taaaccaact | ctccctccca | tgaacagcac c | ggttttgtc 080 |
| gccaaattta | cagggcaatt | gcgtagtttg | gccagcgcta | agtttcctgc c | aacgtgcca 140 |
| caaaaggttg | acagaaaatt | cttcttcacc | gtcggccttg | ggaccagtcc g | tgccccaaa 200 |
| aacaccacgt | gtcaaggacc | aaatggcacg | aaattcgccg | catcagtcaa c | aacatatcg 260 |
| tttgtgctgc | cgtccgtcgc | tctcctgcag | gctcacttct | tcggccagtc c | aacggagtg 320 |

<210> SEQ ID NO 208
<211> LENGTH: 980
<212> TYPE: DNA
<213> ORGANISM: Eucalyptus grandis

<400> SEQUENCE: 208

| | | | | | |
|---|---|---|---|---|---|
| ctccggccgt | ggttgagggc | agagtccgta | actacacatt | caatgtggta a | tgaagaata 60 |
| ccacgagact | gtgttcgagc | aagcccatcg | tgaccgtgaa | cgggatgttc c | cgggaccca 120 |
| ctctctatgc | tagggaagat | gacaccgtgc | tcgtgagggt | ctctaaccgt g | tcaaataca 180 |
| atgtcaccat | ccattggcat | ggtatccggc | agttgaggac | ggggtgggcc g | acgggccag 240 |
| catacattac | ccaatgcccg | atccagccgg | gccaaagcta | tgtgtacaat t | tcaccatca 300 |
| cgggccaacg | gggcaccctc | ctgtggcatg | cacacatact | ctggctcagg g | caaccctgc 360 |
| acggagccat | tgtcatcttg | cccaagcgtg | gtgttccata | cccttttccct a | aaccccaca 420 |
| aggaagttgt | tgtcgtattg | ggcgaatggt | ggaaatctga | tacagaaggt g | tgatcagtc 480 |
| aagccatcaa | gtccggatta | gcaccgaatg | tctccgatgc | tcacacgatc a | atggccatc 540 |
| cagggccaag | ttccaattgc | ccttcccagg | gtggatttac | gttgcctgtt g | agagtggca 600 |
| agaagtacat | gctgcgaatc | atcaacgctg | cgctcaatga | ggagctcttc t | tcaagattg 660 |
| ccgggcacca | gctgaccatc | gtggaggtcg | acgccaccta | cgtcaagcct t | tcaagaccg 720 |

```
acacgatcgt gattgcacct ggccaaacca ccaatgccct catctccacc g accagagct      780 ctggcaagta catggtcgcc gcctcccctt ttatggactc cccgatcgcc g tcgacaaca      840 tgaccgcgac cgccacatta cactactctg gcacgcttgc tgcgacctcc a cgaccctca      900 ccaagactcc cccacaaaac gcgaccgctg tggccaacaa tttcgttaac t cgctccgga      960 gcctcaactc gaagaggtac                                                  980

<210> SEQ ID NO 209
<211> LENGTH: 305
<212> TYPE: DNA
<213> ORGANISM: Eucalyptus grandis

<400> SEQUENCE: 209
gaggctgtgt tcgagcaagc ccatcgtgac cgtgaatggg atgttcccgg g acccactct       60 ctacgctagg gaagacgaca ccgtgctcgt gagggtctcc aaccgtgtca a atacaatgt      120 caccatccat tggcatggta ttcggcagct gaggtcgggg tgggccgacg g gccggcata      180 catcacccaa tgcccaattc agccaggcca aagctatgtg tacaatttca c catcacggg      240 ccaacggggc accctccttt ggcatgcgca catactctgg ctcagggcaa c cctgcacgg      300 agcca                                                                  305

<210> SEQ ID NO 210
<211> LENGTH: 411
<212> TYPE: DNA
<213> ORGANISM: Eucalyptus grandis

<400> SEQUENCE: 210
ttaccgtcga tcacagcctc cttttcacag ttggactagg aatcaaccct t gcccttcct       60 gcaaagctgg caacggaagc agagtcgtgg caagcatgaa caacgtgaca t tcgtgatgc      120 cgacgacagc cattctccaa gcacatttct tcaacaaaag cggcgtcttc a cgagcgatt      180 tccccggtaa cccgccaacc attttcaact acacggggtc accgccatca a atttgcgga      240 ccacaagcgg gacaaaggtg taccggttgc gttataactc gacggtccag c tggtgtttc      300 aagacaccgg gattatcgcc ccagagaacc acccaattca tcttcacggg t tcaatttct      360 tcgccattgg gaagggatta ggaaattata atccgaaagt ggatcagaag a               411

<210> SEQ ID NO 211
<211> LENGTH: 311
<212> TYPE: DNA
<213> ORGANISM: Eucalyptus grandis

<400> SEQUENCE: 211
cacaaggaag ttgttgtcgt attgggcgaa tggtggaagt ctgatacaga a gctgtgatc       60 aatcaagcca tcaagtccgg attggcaccg aatgtctcgg atgctcacac g atcaatggc      120 catccagggc caagttccaa ttgcccttcc cagggtggat ttacattgcc t gttgagagt      180 ggcaagaagt acatgctccg aatcatcaat gctgcgctca atgaggagct c ttcttcaag      240 attgctgggc accagctgac catcgtggag gtcgacgcca cctacgtcaa g cctttcaag      300 accaacacgg g                                                           311

<210> SEQ ID NO 212
<211> LENGTH: 334
<212> TYPE: DNA
<213> ORGANISM: Eucalyptus grandis
```

<400> SEQUENCE: 212

```
agcgtggcgt tccatatcct ttccctaaac cccacaagga agttgttgtc g tattgggcg    60
aatggtggaa gtctgataca gaagctgtga tcaatcaagc catcaagtcc g gattggcac   120
cgaatgtctc ggatgctcac acgatcaatg ccatccagg  gccaagttcc a attgccctt   180
cccagggtgg atttacattg cctgttgaga gtggcaagaa gtacatgctc c gaatcatca   240
atgctgcgct caatgaggag ctcttcttca agattgctgg gcaccagctg a ccatcgtgg   300
aggtcgacgc cacctacgtc aagcctttca agac                                334
```

<210> SEQ ID NO 213
<211> LENGTH: 1374
<212> TYPE: DNA
<213> ORGANISM: Eucalyptus grandis

<400> SEQUENCE: 213

```
accgaacgtg tccgacgctt ataccatcaa cggtcaacct ggagatctct a caactgctc    60
aagcaaagac accgtcatag ttccgatcga ttccggggag acccacctcc t ccgagtcat   120
caacgctgcg ctcaatcagg aactcttctt caccgtagcg aaccataggt t cactgtggt   180
cggtgccgac gcctcctacc tgaaaccctt caccacctcg gtgatcatgc t tgggccagg   240
ccaaacgacg gatgtattga tctctggaga ccagcccccg gctcggtact a catggcggc   300
cgaaccctac cagagtgctc agggagcgcc ttttgacaac accacgacca c ggccatact   360
ggagtacaag tccgccccgt gccccgccaa gggcatatcg agcaagccag t catgccaac   420
cctaccggct ttcaacgaca cggctaccgt cacagccttc attcagagct t caggagccc   480
aaataaggtt gacgtcccga ccgacatcga cgaaaacctc tttatcacgg t cggcctagg   540
actcttcaac tgcccaaaga atttcggtag cagtaggtgc caggggccga a tgggacccg   600
tttcacggcc agcatgaaca acgtgtcctt cgtgctgccg tctaatgtct c gatcctgca   660
agcctacaag cagggcgtgc ctggagtttt taccaccgat ttccctgcta a ccccctgt    720
ccagttcgat tacacgggga acgtgagccg ctcgctgtgg cagcccgttc c ggggaccaa   780
ggtgtacaag ttgaagtacg ggtctagagt acagattgtc ttgcaaggaa c caacataca   840
aacggccgag aaccacccga tccacattca cgggtacgat ttctacatcc t cgccacagg   900
cttcgggaac ttcaaccccc agaaagatac agcgaagttc aaccttgtcg a cccgccaat   960
gaggaacaca gttggcgtct ctgtgaacgg gtgggctgtc attagatttg t cgccgacaa  1020
tccaggtgct tggttgatgc actgtcactt ggatgttcac atcacctggg g attggccgt  1080
ggttttcctt gtcgagaatg gagttggcga attgcaatct ctacagcctc c tcctgcaga  1140
tttgcctcca tgttaaaaga tctgcggctg acagatagtc ctccacgaga a attcataac  1200
gcccacaaca cgggcctatt ctaattttct tcttcttctt tcacctttcc g ttttcgttt  1260
cgcggagttt cagttcagtg attgtttccc ctgaattcag ggagccacca g ttgtttgct  1320
tgtctcatac tttttttttat agataaaatt gtcttgcata aaaaaaaaaa a aaa        1374
```

<210> SEQ ID NO 214
<211> LENGTH: 418
<212> TYPE: DNA
<213> ORGANISM: Eucalyptus grandis

<400> SEQUENCE: 214

```
atcctgtctc agtctccatc atcacttgcg ccaagtaaca tctgatttcg a ggaagacga    60
ggagcgcaaa atgggctccg ctactgctgc tggtgcctcg gtttcgtcgc g aatgattct   120
```

```
gatgagagcc gccttcttca cactgtgcgc tctcgtgttc ttgccggctc t tgctcaggc    180 gaagcacgga ggtgtcacca ggcattacaa gtttgatatc aagatgcaga a tgtgacgag    240 gttgtgccag acgaagagca ttgtcacggt caatggccag ctcccggggc c tcgaatcat   300 cgctagagaa ggcgaccggc tcctaatcaa agtcgttaac aatgtccagt a caatgtcac    360 aatccactgg catggagtcc gacaactcag aagcgggtgg gctgacggac c ggcatac     418

<210> SEQ ID NO 215
<211> LENGTH: 466
<212> TYPE: DNA
<213> ORGANISM: Eucalyptus grandis

<400> SEQUENCE: 215
ccggatcgag tgattagtac aagttcaatt ttgtatcagg gagagagagg g acgatggga    60 acatttctag ggttcgcagt cactgcgacc ctgctcttct gcgtggctca a ggcgaagtc   120 ctcttttatg attttgtggt aaatgagaca cctattgaga tgctatgtga g acaaatcgg   180 agcgtactaa ctgtgaacgg tctatttcct gggccggaga tccatgctca c aagggtgac   240 actatttacg ttaatgtcac caacttagga ccttatggag tcactattca c tggcatgga   300 gtgagacaaa tacggtatcc ttggtctgat ggcccagaat atgtcacgca a tgccccatc   360 cctacaaact cgagctttct tcaaaaaatc aaactcaccg aggaagaggg c acggtgtgg   420 tggcacgccc acagcgactg gtcacgtgcc acaatacatg gcctat                   466

<210> SEQ ID NO 216
<211> LENGTH: 757
<212> TYPE: DNA
<213> ORGANISM: Eucalyptus grandis

<400> SEQUENCE: 216
tcgggttctt tgtacaactt aatcggttgt atgtggatac agtgcagaaa c tgcccacga    60 attcagaatc aaatattatg agatgctcca cagttccccg gtttaagtac c ttcccatca   120 gtgtacctgc attgtcttca aggaggacat ctaaagcaac tactgtaaga c tttggaccg   180 gcacgagcac aagtctcctt ctttgttctg gatcaagtga ttgttacaag t tcattttc    240 tcttgttgag agagagagag agatgggaac atttctaggg tttgtggtca c catgaccct   300 gctcttttgc atggctcaag gcgaagtcat ctactatgat ttcgtggtga a ggagacacc   360 tattcagatg ttatgtggga cgaatcagac cgtattgact gtgaatggtc t gtttcctgg   420 gccagagatt catgctcaca aaggcgacac catctacgtt aatgtcacca a cacaggacc   480 ttatggagtc actattcatt ggcatggagt gagacaaata agatatccct g gtccgacgg   540 cccggagtac atcacacaat gcccaatccc tacaaactca gtttccttc a aaaaatcat   600 actcactgaa gaagaggca cactatggtg gcacgctcat agtgactgga c acgtgccac   660 tatacacggc cctataatca ttttgcctgt caacggcacc aactacccct a caagtttga   720 cgaacaacac acaatcgtga tatctgaatg gtatgca                             757

<210> SEQ ID NO 217
<211> LENGTH: 251
<212> TYPE: DNA
<213> ORGANISM: Eucalyptus grandis

<400> SEQUENCE: 217
acacaagtct ccttctttgt tctggatcaa gtgattgtta caagttcatt t ttctcttgt    60
```

-continued

| | |
|---|---|
| tgagagagag agatgggaac atttctaggg tttgtggtca ccatgaccct g ctcttttgc | 120 |
| atggctcaag gcgaagtcct ctactatgat ttcgtggtga aggagacacc t attcagatg | 180 |
| ttatgtggga cgaatcagac cgtattgact gtgaatggtc tgtttcctgg g ccagagatt | 240 |
| catgctcaca a | 251 |

<210> SEQ ID NO 218
<211> LENGTH: 762
<212> TYPE: DNA
<213> ORGANISM: Pinus radiata

<400> SEQUENCE: 218

| | |
|---|---|
| gcctggcagt aatgtctaat gaacaactcc tggaatttgc ttggggattg g cttccagta | 60 |
| accaatcctt cttgtgggtt gtgaggtcag atatcgtgca tggtgaatct g ccatattac | 120 |
| ccaaagagtt cattgaggaa accaaggata gaggtatgct ggtgggttgg g cgcctcaga | 180 |
| taaaggtact gtcgcaccca tctgtgggag gatttctaac tcacagcggt t ggaactcta | 240 |
| cattggaaag cattagtgcg ggtgtgccaa tgatgtgctg gcccttcttt g ccgagcaag | 300 |
| aaacaaatgc taaatttgtg tgtgaagagt ggggaatagg aatgcaggtg a agaaaatgg | 360 |
| tgaagagaga agagttggcg atactggtga ggaattcgat caaaggtgaa g aaggagatg | 420 |
| aaatgaggaa aagaattgga aaactgaagg aaactgccaa gcgagcagtt a gtgaaggag | 480 |
| gctcttctaa gaacaactta gacaagttac tccatcatat attcctcaag g gaatgcatc | 540 |
| aaatgatagt ccagaatgtt gaagcaaaca attagttaga agaacgtg t aggacgaac | 600 |
| gaaaacatcc cagtacccca agcgttcata tttctgcatt tcgcattaaa t ttactttgt | 660 |
| attgttccgc acatatgtat tttcaggttg tcaggtttcc ccagagttga a cctcattt | 720 |
| caattagatt gtttcacgtc tttacggcgc agggggttgt ga | 762 |

<210> SEQ ID NO 219
<211> LENGTH: 1144
<212> TYPE: DNA
<213> ORGANISM: Eucalyptus grandis

<400> SEQUENCE: 219

| | |
|---|---|
| aaatagctca aaggttagtg tcgcgaccta aattggtgtc aacagctagc c aatggagtc | 60 |
| ctgctctatt tcgctatttt ggctgggcct cctcctcccg gcacttctag t tttccttct | 120 |
| caaccgtcgg aagcgcacca agcttccccc tcagccccca gcatgcccg t gatcggcaa | 180 |
| cattttcgac ctcgggacca tgccgcacca gaacctccac aacctccgag c caagcatgg | 240 |
| gcctgtcttg tggttgaagc tcggttccgt gaacaccatg gtgatccaat c agctcgagc | 300 |
| ggccatggag ttattcaagg gccatgactt cgtgttcgca gaccgcaagt g ttcccaagc | 360 |
| gtttactgct ctcggctatg accaaggctc gctcgtctt ggtcgtcatg g tgactactg | 420 |
| gcgcgctctc cggcgtctct gctccgcgga gctcctcgtg aacaagcgcg t caacgatac | 480 |
| ggcccacctc aggcaaaagt gtgtcgacag catgatcatg tatatagaag a gaaatggc | 540 |
| agtcaaacaa gcaacaaaag ggcaaggaat cgacttatct cacttcctct t tctcctggc | 600 |
| atttaatgtg gtgggcaaca tggtgctctc acgggatcta ttggacccaa a atcgaagga | 660 |
| tgggcccgag ttctacgacg ccatgaaccg gttcatggag tgggctggca a gcccaacgt | 720 |
| agccgacttc atgccatggt tgaaatggtt ggatccgcag gggatcaagg c aggcatggc | 780 |
| gaaggacatg ggtcgagcca tgaggattgc cgaaggcttt gtgaaagaga g gttggagga | 840 |
| gcgaaagcta aggggagaga tgagaacaac gaatgatttc ttggacgcag t attggatta | 900 |

```
tgagggcgat ggaaaagaag gccctcacaa tatctcttcc cagaacataa a tataatcat    960 tctggaaatg tttttcgccg gatcggagag tacaagtagc accatcgagt g ggcgatggc   1020 ggagctactc cgccaacccg agtcaatgaa aaaggccaaa gatgagattg a ccaggttgt   1080 ggggttgaac agaaagctcg aggaaaatga cacggaaaag atgccatttt t gcaagccgt   1140 ggtg                                                                 1144

<210> SEQ ID NO 220
<211> LENGTH: 563
<212> TYPE: DNA
<213> ORGANISM: Eucalyptus grandis

<400> SEQUENCE: 220
agctcaaagc ttagccaatg gagtcctgct ctatttcgct attttggctg g gcctcctcc     60 tcccggcact tctagttttc cttctcaacc gtcggaagcg caccaagctt c cccctcagc    120 ccccagcatg gcccgtgatc ggcaacattt tcgacctcgg gaccatgccg c accagaacc    180 tccacaacct ccgagccaag catgggcctg tcttgtggtt gaagctcggt t ccgtgaaca    240 ccatggtgat ccaatcagct caagcggcca tggagttatt caagggccat g acttcgtgt    300 tcgcggaccg caagtgttcc caagcgttta ctgctcttgg ctatgaccaa g gctcgctcg    360 ctcttggtcg tcatggtgac tactggcgcg ctctccggcg tctctgctcc g cggagctcc    420 tcgtgaacaa gcgcgtcaac gagacggccc acctcaggca aaagtgtgtc g acagcatga    480 tcatgtacat agaggaagaa atggcagtca acaagcaac aaaagggcaa g gaatcgact    540 tatctcactt cctctttctc ctg                                            563

<210> SEQ ID NO 221
<211> LENGTH: 447
<212> TYPE: DNA
<213> ORGANISM: Eucalyptus grandis

<400> SEQUENCE: 221
taatgaaggc ccaagatgag attgattcta tgattggcca tgatagtttg t tagaagaat     60 cggatgtttc aaaactacct taccttcagt gcattatctt ggagacccct c gactaaaca    120 cgacggcacc acttctcctc ccacacgcgt catcggctga ttgcactata g gaggatact    180 tcgtcccacg cgacactatt gtgatggtga atgcatgggc cattcacaaa g accctcagt    240 tgtgggagga tccattgagc ttcaagcctg aaaggttcga gggcaatggc a cgaaaagc    300 aacaaaagct actattgcct tttggactgg gacggagggc atgccctggt g ccccttgg    360 ctcatcgggt catggggtgg acgttgggct tgttgattca gtgttttgat t ggaaaagag    420 taagcgaaga agagattgac atgacgg                                        447

<210> SEQ ID NO 222
<211> LENGTH: 494
<212> TYPE: DNA
<213> ORGANISM: Eucalyptus grandis

<400> SEQUENCE: 222
ttaccttggc gatttcctgc ccatactaaa gttggtcgat acaatggag t caagaagag     60 ggtggttgag ctgaaagaga aattcgatgc gttcattcag ggcttgatca a cgagcaccg    120 gaggaagaag ggcgacccag agctcgcaga cagcatgatc agtcatcttc t gcatctaca    180 agaatctcag ccggaagact actcggactc catgatcaaa gggcttgtcc t tgttttgtt    240
```

```
agttgcggga acagacacgt catcgcttac attagaatgg ataatgacaa a cttactaaa       300 caatcctgaa aagttagaga aggcccgaaa tgagattgat tctgttattg g ccacgatcg       360 tctggtagaa gaatcggatg tttcgaatct accttacctt cagtgcatca t cttagagac      420 ccttcgacta aacaccacgg tgccacttct cgtcccgcac gcatcatcag c tgattgcac      480 cattggtgga tact                                                         494

<210> SEQ ID NO 223
<211> LENGTH: 492
<212> TYPE: DNA
<213> ORGANISM: Eucalyptus grandis

<400> SEQUENCE: 223
gttgtcagat gcgatcccgg ctcttggctg gttggactca ggtggctata g acgatcgat       60 ggacgagaca gcgaaagagt tggatgtttt ggctcagggg tggctagagg a gcatagaag      120 gaagagattg tcctgcccca agacgacag agagcaagat ttcatggatt g gatgatcaa      180 cgccctcgaa ggtcggaatt ttccagattt tgacgcggat acagttatta a ggcgacttg     240 tttgaacatg ataatagcgg ggactgatac ttcgacggtg gcgatcacct g ggcgctatc     300 gctgctaatg aacaaccgtc gtgcattgaa gaaggcgcaa caagagctgg a cacccatgt     360 tggcaggagt aggcccgtgg aagagtccga tgtgaaaaac ttgacctacc t ccaagccat     420 cgtcaaggaa gcactgcgtt tatatcctcc agtaccggtg aacggcctta g aagctccat     480 ggaagagtgc ac                                                          492

<210> SEQ ID NO 224
<211> LENGTH: 391
<212> TYPE: DNA
<213> ORGANISM: Pinus radiata

<400> SEQUENCE: 224
gcaggcttcc tccgggacct ccagggtggc cgattgtggg aaacctgttc c agttgggta      60 acaaacccca cgaagctctc ttccacctcg ctcagaagta cggccctctc a tgtgtgtct     120 ctctcggaat gaaaactaca gtggtagtct cctctccggc catggcaaag c aagttctca    180 agacccatga ccatgttttt gcgggccgaa cggtcataca gtcagttcag t gcctttctt    240 acgacaagtc ctcagtaatt tgggcccaat atggatccca ctggcgtttg c tcagacgca    300 tatccaaatac aaagctcttc agcgtcaaga ggttagaagc cctggaacat t tgagaagag  360 atgaagtatt ccgaacaatc aagcagattc t                                    391

<210> SEQ ID NO 225
<211> LENGTH: 536
<212> TYPE: DNA
<213> ORGANISM: Pinus radiata

<400> SEQUENCE: 225
ctcgtttatt tacaagctgc ggtgaaagaa actcttcgac tccatccatc c gggccttta    60 ttggtgcgcc atttatttgg taccgcgtcc tgcaatgtat tggggtatga a atcccgcag   120 aatactctcg ttctcgtgaa tgtttgggcg attgggagga accctaagtc a tgggaggac   180 gccgaagttt tcaagccaga gagattcatg gaaaaagttg ggtctgaagt a gatgcaaat   240 ggagatcaaa actttgggtg ccttctcttc ggagcagggc ggagaagatg c ccaggacag   300 caattgggaa cgcttcttgt agagtttggg ttggcacagc tgttgcactg c ttcaactgg   360 aggcttccct tggatgacat aaatggcgaa aatcaagaag tggatatgaa t gaaatgttt   420
```

```
aatggagtca cgctgcgcaa agctcgtgag ctctcggcta ttccgacacc a cgccttgaa      480 tgcattgctc acctgaaata ggtcatcagg tttcgagtga aacctgtgga g ataga          536

<210> SEQ ID NO 226
<211> LENGTH: 463
<212> TYPE: DNA
<213> ORGANISM: Pinus radiata

<400> SEQUENCE: 226
gaaaggtacc gtcccgcttg aaaaatatct acagctttta gattggacgc a attataaac      60 attttattcc agtttgtatg tgttatctct gatcgtgttg gagatgtgtg g ctgagccta     120 atcatgcatg gagcaacttg tccaggaaaa gaaaggcag  actgccccg g ggcctttct      180 cgttgcccat tatcggcaat cttcacatgc taggaaagat tcctcaccga t cactggcag    240 agctgtctat gaaatacggg cctctcctgt ctctccgcct cggctctact c cgccttag    300 tcgtctcttc tccagaaata gccagtgaat ttctcaaaac ccatgatcag c tttttgcca    360 gcagaattcc ctctgctgct attaaggtat tgacctacaa tttgtccggc c tcatatttt    420 ccccgtatgg cccttgctgg aggcaagtgc gtaaactttg cgt                        463

<210> SEQ ID NO 227
<211> LENGTH: 463
<212> TYPE: DNA
<213> ORGANISM: Pinus radiata

<400> SEQUENCE: 227
ggctgagcct aatcatggtt attacatatc ttgaaccttt gtagtagatg t tgtttgtgg     60 atatagctaa tatcaaattg tttgagatag atgtttgctg gtagatatag c tagattagt   120 acagtgaacc atctaaaaaa ctggcgatgg agtttgtaga gttttgtata a cactcgtca   180 ctgctcttct ttttgttgta ttggtagcag catggagcaa cttgttcagg a aagaaaag    240 gcagactgcc cccggggcct ttctcgttgc ccattatcgg caatcttcac a tgctaggaa   300 agattcctca ccgatcactg gcagagctgt ctatgaaata cgggcctctc c tgtctctcc   360 gcctcggctc tactcccgcc ttagtcgtct cttctccaga aatagccagt g aatttctca   420 aaacccatga tcagcttttt gccagcagaa ttccctctgc tgc                        463

<210> SEQ ID NO 228
<211> LENGTH: 463
<212> TYPE: DNA
<213> ORGANISM: Pinus radiata

<400> SEQUENCE: 228
gaattgcttt ctgcgtgtcc agttcatgaa tgcccatact tttattttaa t ctcgctact     60 gttattcttc tgggcgtggt gacgggatgg ggtttccttat tccggggaag a aaacagaag  120 cttcctccgg ggccttttca gtggccgatt gttggaaacc ttcacatgat g ggagagctt   180 ccacaccaag caattacagc tctctctatg aaatatgggc ctctcatgtc t ctccgcctc   240 ggctcctatc tcactttggt cgtttcttct ccagatgtgg ccgaggagtt c ctgaagact   300 catgatctgg ctttcgccag cagacctcca accatcggta cgaagtactt t tggtataat   360 tcctccgacg tcgcattttc cccctatggt ccttactgga ggcagatgcg t aaaatctgt   420 gtgttacagt tgctgagctc aagacgcata gattccttcc gcc                        463

<210> SEQ ID NO 229
```

<211> LENGTH: 463
<212> TYPE: DNA
<213> ORGANISM: Pinus radiata

<400> SEQUENCE: 229

| | | | | | |
|---|---|---|---|---|---|
| actgtgacca | agacctaatt | ggtggcattg | ggatcaagtc | aatgataaag g | aaacgtttg | 60 |
| tgttagcagg | gtcttttgaac | atgggagatt | ttataccata | cttggcatgg a | ttgatcttc | 120 |
| aaggtctcaa | ccgtcgattg | aagaacatac | acaagatcca | agacgacttg t | tagggaaga | 180 |
| tactagagga | acacgcttcg | ccaccgcaga | ataaccccaa | ctacatgcca g | atctcgtgg | 240 |
| atgttttgct | cgcggcctct | gcggatgaag | atctggagtt | cgaaattact c | gagacaata | 300 |
| taaaatctgt | catctatgta | tatattgtcc | atgcaattat | tagatttcaa t | gacttaaat | 360 |
| aaaacatgac | acggtgatta | tatcttgaca | tttgttttgg | atttgttttg t | tggtaggat | 420 |
| atcttgtccg | ctggttcgga | ctcgtcgtct | gcaagcatag | agt | | 463 |

<210> SEQ ID NO 230
<211> LENGTH: 543
<212> TYPE: DNA
<213> ORGANISM: Pinus radiata

<400> SEQUENCE: 230

| | | | | | |
|---|---|---|---|---|---|
| ggcaccagac | gagctggaac | gtgtcgttgg | attgggtcgt | atggtaaggg a | atctgatct | 60 |
| gcctcgtctc | gtttatttac | aagctgtggt | gaaagaaact | ctgaggctat a | cccacaggg | 120 |
| gccgatttta | ttccgccact | tgtcttcgga | gccctgcaat | gtcctgggct a | tgaaatctc | 180 |
| tcaaaacact | caagttctgg | ttaatatttg | ggcgattgga | aggaactctg a | gtcatggga | 240 |
| agatgccgga | agcttcaaac | ctgagagatt | catgaaaga | gttgggtctg a | ggtagatac | 300 |
| aaatggagat | caaaattctg | cgtggcttcc | cttcggagca | gggaggagaa g | atgcccagg | 360 |
| acagcaattg | ggaacgcttg | ttgcagaaat | tgggctggca | cagctcttgc a | ctgtttcaa | 420 |
| atggaggctt | cccgaagctg | atatggatgg | cccaaatcaa | gaacttgaca t | gatggaaag | 480 |
| gtttaatgga | atcacatcgc | cgagggctaa | ggaactgttt | gcgattccga c | accccgcct | 540 |
| tga | | | | | 543 |

<210> SEQ ID NO 231
<211> LENGTH: 381
<212> TYPE: DNA
<213> ORGANISM: Pinus radiata

<400> SEQUENCE: 231

| | | | | | |
|---|---|---|---|---|---|
| ggaatcctct | ttgatatgtt | gctcggtggg | tcagacacag | cgcctacaat a | atagagtgg | 60 |
| gcaatatcgg | aggcgctgat | aaaccctcca | gtgatgaaga | aacttcagga c | gagctggaa | 120 |
| cgcgtcgttg | gattggatcg | catggcatgc | gaatctgatc | tgcctcagct c | gtttatta | 180 |
| caagctatgg | taaaagaaac | gcttcgactt | cacccagcgg | ggcctctttt g | aaccgtcgc | 240 |
| ttatccgctg | agtcctgcaa | tgtgttgggg | tacgaattcc | ctaaaaacac t | cgtgttctc | 300 |
| gttaatgctt | gggcgattgg | gaggaaccca | aagttatggg | aggacgctga a | actttcaag | 360 |
| ccagaaagat | tcacgggaag a | | | | 381 |

<210> SEQ ID NO 232
<211> LENGTH: 384
<212> TYPE: DNA
<213> ORGANISM: Pinus radiata

<400> SEQUENCE: 232

```
ccacttcggc aacagttgaa tgggcaatgg ctgagcttat cagaaaacca a cgctactga      60 aaaaggccca ggcagagctg gatgaggttg ttggtcgaga gaagagaatg g aggaatcag     120 acatagcaaa attgccctat ctacaagcag tagtgaagga ggtactcaga t tgcacccag    180 cagctccact gataattcct cgaagagcag acaactctgc cgagattggt g gatatgttg    240 tcccagagaa cacgcaggtg tttgtgaata tctggggcat cggaagagat c ccaacgttt    300 ggaaggaacc tctgaaattc aaaccggaaa ggttttttaga ctgtaatact g actacagag  360 gccaggattt tgaactgata ccat                                             384

<210> SEQ ID NO 233
<211> LENGTH: 405
<212> TYPE: DNA
<213> ORGANISM: Pinus radiata

<400> SEQUENCE: 233
gagaagatga agtttccgct atgattcgct ctattgttaa ttcagatgcc c acaaggact    60 ctcgtcctgt caacatcaag caacttgcgt catcccttgt gacagctata g tcttgagga   120 tgaccttcgg taaaaagtat tcggaccggg attcaggagc attcagttca a tgatcaaag   180 aaagtttact gttactcggc tcctttaata ttggagaata cataccttac t gaactgga    240 tggatttgca aggtctcaac cgccggctga agaagctacg tacaacacaa g accagttgc  300 tagagaaagt aatagaggaa catgctgccc agaatcggag caacatgacg c atgatcttg  360 tggatgcctt acttgcagcc tctgcggata agatagaga gctcc                     405

<210> SEQ ID NO 234
<211> LENGTH: 348
<212> TYPE: DNA
<213> ORGANISM: Eucalyptus grandis

<400> SEQUENCE: 234
catatacgat caagagagtt tgctgaatgc aattaagcag gttgatgtgg t aatctctgc    60 tgtggggcaa gcacaaacgg aggaccaaga ccggattgtt gctgccatca a agcagccgg  120 gaatatcaag agattcttgc cttcagagtt tggaaatgat gtggatcgtg t ccatgctgt  180 ggagccagta aaaactggat tgctctcaa ggccaagatc cgccgccttg t tgaggccga   240 gggaatccct tatacctatg tgtcttctaa ctcttttgca ggttactacc t tcaaacatt   300 gtcacagccc ggggctacag ctcccctag agataacgtt gttatctt                348

<210> SEQ ID NO 235
<211> LENGTH: 640
<212> TYPE: DNA
<213> ORGANISM: Eucalyptus grandis

<400> SEQUENCE: 235
ctgtgtgtta agctagtagt cagtcaagca ttgaaggcat gaacaccttaa a agacatgaa   60 cagatgaaga tttggagtct caattatact gtgtgttaag ctagtagtca g tcaagcatt   120 gaaggcatga acaccttaaa gacatgaaca gatgaagatt tggagtctca a tggtattat  180 tgcctacctt atctccagtc acagcagagt cgcttctaga aaccgatcga g ttcgccgga  240 aaacaccgcg cctccgccgt gaaaaccact cagagatggc tgcgaagagc a aggtcctgg  300 tgatcggagg cactggatac atcggaaagt tcatcgtgga agcagtgcta a gtccggtc   360 gccctacctt cgctctcgcg agggagtcca ctctctccaa ccccgccaag g ccaagatcg  420
```

```
tcgaaggttt caagagcctc ggcgtcactt tagttcacgg agacatatac g atcaagaga    480 gtctattgaa tgcgatcaag caggtcgatg tggtaatctc tgctgtgggg c gagcacaaa    540 tagaggacca agacaggatt gttgctgcca tcaaagcagc cgggaatatc a agagatttg    600 tgccttcaga gtttggaaac aacgtggatc gtgtccatgc                           640

<210> SEQ ID NO 236
<211> LENGTH: 464
<212> TYPE: DNA
<213> ORGANISM: Eucalyptus grandis

<400> SEQUENCE: 236
gtctcgagtt ttttcttatt taattaattt tcttttaga gattcttgcc t tcagagttt     60 ggaaatgatg tggatcgtgt ccatgctgtg gagccagtaa aaactggatt t gctctcaag    120 gccaagatcc gccgcctcgt tgaggccgag ggaatcccct taacctatgt g tcttctaac    180 tcttttgcag gttactacct tcaaacattg tcacagcccg gggctacagc t cccctaga    240 gataacgttg ttatcttagg ggatggaaat gccaaagtgg tgtttaacaa g gaggatgac    300 atcggcacct ataccatcaa agctgtggat gatccaagga ccttgaacaa a attctgtac    360 atcaggcctc ctgccaacac ctactcaatg aatgagctcg tgtctttgtg g gagagaaag    420 atcggcaagg ctctggagag ggtgtatgtt ccagaggagc aaat              464

<210> SEQ ID NO 237
<211> LENGTH: 315
<212> TYPE: DNA
<213> ORGANISM: Eucalyptus grandis

<400> SEQUENCE: 237
cttctagaaa ccgatcgagt tcgccggaaa acaccgcgcc tccgccgtga a aaccacttc     60 agagatggcc gcgaagagca aggtcctggt gatcggaggc actggttaca t cggaaagtt    120 catcgtggaa gccagtgcta agtccggtcg ccctaccttc gttctcgcga g ggagtccac    180 tctctccaac cccgccaagg ccaagatcgt ccaaggtttc aagagcctcg g cgtcacttt    240 agttcacgga gacatatacg atcaagagag tctgttgaat gcgatcaagc a ggtcgatgt    300 ggtaatctct gctga                                              315

<210> SEQ ID NO 238
<211> LENGTH: 376
<212> TYPE: DNA
<213> ORGANISM: Eucalyptus grandis

<400> SEQUENCE: 238
caaagtcacg tcagagaccg atcaagttcg ccggaaaaca ccacgcgcgc t atgaaaaga     60 ccctccaaga tggcagagat gagcagagtc ttggtgattg gaggcgccgg a tacatcgga    120 aagttcattg tgaaagcgtg tgctaagtcc ggtcacccta cctttgttct c gagacggag    180 tccactctct ccaaccccgc caacgccgaa atcatcaaag gtttcaagag c ttaggcgtg    240 aacctagtcc atggagacat atacgatcaa aaaagtctgt tgagtgcgat t aagcaagtt    300 gatgtggtaa tatctactgt ggggcaagca cagctagaag accaagacag g attgttgca    360 gccatcaaag cagccg                                             376

<210> SEQ ID NO 239
<211> LENGTH: 297
<212> TYPE: DNA
<213> ORGANISM: Eucalyptus grandis
```

<400> SEQUENCE: 239

```
atcaagttcg ccggaaaaca ccacgcccgc tgtgaaaaga ccctccaaga t ggcagagat        60
gagcagagtc ttggtgatcg gaggcgccgg atacatcgga aagttcatcg t gaaagcgtg       120
tgctaagtcc ggtcacccta cctttgttct cgagacggag tccactctct c caaccccgc      180
caacgccgaa atcatcaaag gtttcaagag cttaggcgtg aacctagtcc a tggagacat      240
atacgatcaa aagagtctgt tgagtgcgat taagcaagtt gatgtggtaa t ctctac         297
```

<210> SEQ ID NO 240
<211> LENGTH: 951
<212> TYPE: DNA
<213> ORGANISM: Pinus radiata

<400> SEQUENCE: 240

```
tctcgcacag ttgacgacgt tttcttgtat ttgtagcgtt cggcacgatc g gggaaaaac        60
gatggcatgc gctactgatg ttgcacgtca gtttctgcca tgcgtccaac c cgtgccgtc       120
cagcatggga ggagagaccg cccggtcgat caacctcacc tgcaatggcc t ctcccgcc       180
tcaaccgcag tacaacgccg agaacaacca tgatcaggac accacagttg c cacaagggt      240
tctcattatt ggcgccaccg ggttcatcgg tcggtttgtt gcagaggcca g tgtgaaatc      300
cgggcgccca acttatgccc ttgtgcggcc gacaacatta gttcgaagc c caaggtcat       360
tcagtctctg gtggattcgg gtattcaagt tgtttatgga tgtctacatg a tcacaattc      420
tttggtgaaa gccatcaggc aggttgacgt tgttatttct actgttggtg g agccctaat     480
tcttgatcag ctcaagattg tggatgccat caaggaagtt ggcactgtca a gagatttct     540
tccttcagag tttggacacg atgtagaccg agcagatccc gtagagcctg c tcttagttt    600
ttacatagaa aagagaaaag tccggcgtgc agtggaggaa gcaaagattc c ttacacata    660
catctgctgc aactccatag ctggctggcc atactattat cacacacatc c aactgagct    720
cccccccacca aggaacagt ttgagatcta tggggatgga agcgttaaag c cttttttcgt    780
tactggggac gatattggcg cgtataccat gaaagctgtg gatgaccctc g tactctgaa    840
caagtctatt catttcagac caccaaagaa ttttctcaac ttaaacgaac t cgcagacat    900
atgggagaat aagattaaca gaactctgcc aagagtatct gtctcagcag a              951
```

<210> SEQ ID NO 241
<211> LENGTH: 371
<212> TYPE: DNA
<213> ORGANISM: Pinus radiata

<400> SEQUENCE: 241

```
tttagctgac attttattaa ttcaaagtgg caagatgaca ggtctcaagg a ctctgctaa        60
tagggttttg ataataggag gcacgggata cattgggaaa tacatggcaa a gccagcgt       120
ttcacagggc tatccaacct acgttcttgt ccgtcctgct acagcagctg c ccctgattc      180
cttcaaagca aagctacttc agcaattcaa agatattggc attcatattc t tgaaggatc      240
attagatgat cacaacagcc ttgtggatgc aatcaagcaa gtagacatag t aatatccgc      300
agttgccatt cctcagcatt tggatcagtt taatatcata acgccatta a ggatgttgg      360
aatggaaata t                                                           371
```

<210> SEQ ID NO 242
<211> LENGTH: 687
<212> TYPE: DNA

<213> ORGANISM: Eucalyptus grandis

<400> SEQUENCE: 242

| taatggcgag | ctccacccgt | ctcactactg | tgagagggac | ctgctcaaag | t ggtcgaccg | 60 |
| cgagcatgtg | ttcacctacg | ctgatgacgc | ctgcagcgcc | acctacccgc | t gatgcagaa | 120 |
| gctgaggcaa | gtcctggtcg | accaggcact | ggtgaatggc | gagagcgagc | t gaacccgag | 180 |
| cacttcgatc | ttccaaaaga | tcgtggcctt | cgaggaggag | ctcaaggccc | a gttgccgaa | 240 |
| ggacgtcgag | ggcgttcgag | tccagtacga | gacaggcaac | ctcgccatcc | c caaccagat | 300 |
| caaggaatgc | aggtcctatc | cattgtacaa | gctggtgagg | gaggagctgg | g gactgccct | 360 |
| gctcacgggc | gagggcgtga | tatcccctgg | cgaggacttc | gacaaggtct | t cactgcgat | 420 |
| ctgtgctgga | aaactgattg | atccgctgct | ggagtgccta | agcggttgga | a cggtgctcc | 480 |
| tcttcccatc | tcttaggaat | tgtcctatat | tctttctcct | tcttttccc | t ttccgttac | 540 |
| ttgccaagta | aatctcatgt | atccaatctt | ttctatcaag | agacaattgt | a tttcttgtt | 600 |
| ttctgtttgg | tccttttgt | ctcctcccaa | gtgaagaaat | tggagaatat | a agtaattga | 660 |
| gtaaattttt | acatggaaaa | aaaaaaa | | | | 687 |

<210> SEQ ID NO 243
<211> LENGTH: 344
<212> TYPE: DNA
<213> ORGANISM: Eucalyptus grandis

<400> SEQUENCE: 243

| tcctggtcga | ccaggcactg | gtgaatggcg | agagcgagct | gaacccgagc | a cttcgatct | 60 |
| tccaaaagat | cgtggccttc | gaggaggagc | tcaaggccca | gttgccgaag | g acgtcgagg | 120 |
| gcgttcgagt | ccagtacgag | acaggaaacc | tcgccatccc | caaccagatc | a aggaatgca | 180 |
| ggtcctatcc | attgtacaag | ctggtgaggg | aggagctggg | gactgccctg | c tcacgggcg | 240 |
| agggcgtgat | atcccctggc | gaggacttcg | acaaggtctt | cactgcgatc | t gtgctggaa | 300 |
| aactgattga | tccgctgctg | gagtgcctaa | gcggttggaa | cggt | | 344 |

<210> SEQ ID NO 244
<211> LENGTH: 681
<212> TYPE: DNA
<213> ORGANISM: Eucalyptus grandis

<400> SEQUENCE: 244

| cccaagcctg | gattacggct | tcaagggagc | tgagatcgcc | atggcctcat | a ctgctcgga | 60 |
| gctgcagttc | cttgccaacc | ctgtgaccaa | ccatgtccag | agcgcggagc | a acacaacca | 120 |
| ggacgtgaac | tccttgggcc | tgatctcgtc | gaggaagact | gccgaggcca | t cgatgtgct | 180 |
| gaagctcatg | tcctccacct | tcctggtcgc | cctgtgccag | gccatcgacc | t gaggcacct | 240 |
| ggaagagaac | ctcaagagcg | tggtcaagaa | cacggtgaac | caagtggcca | a gaaggtcct | 300 |
| ctacgtcggg | tccaacggcg | agctccaccc | gtcgcggttc | agcgagaaag | a cctgatcaa | 360 |
| ggtggtcgac | cgggagtacg | tcttcgccta | catcgatgac | ccctgcagcg | c cacgtaccc | 420 |
| cctgatgcag | aaactgaggc | aggtcctcgt | ggacgatgcg | ctggacgacg | t cgaccggga | 480 |
| gaagaacccc | agcacctcca | tcttccagaa | gattgggct | tcgaggagg | a gctcaaggc | 540 |
| actcctcccg | aaggaggtcg | agaacgcgag | agctcagttc | gagagcggga | a ctcggcgat | 600 |
| cgctaacaag | atcagggggt | gcaggtcgta | cccattgtac | aggttcgtga | g ggaagagct | 660 |
| cgggaccggt | ttgctcacgg | g | | | | 681 |

<210> SEQ ID NO 245
<211> LENGTH: 1455
<212> TYPE: DNA
<213> ORGANISM: Eucalyptus grandis

<400> SEQUENCE: 245

| | | | | | |
|---|---|---|---|---|---|
| tttgcaatcc | tctgaattttt | ccctaactag | aaataaagag | attatataca t | acacgagca | 60 |
| aagcgctctc | ctccagttgt | cttccttcgt | tcgctcatct | ctcctcgtac a | ttattagca | 120 |
| tacgacctct | tgtatcggac | ccggatccgc | tatcgttaac | gtacacacgt t | ctagtgctg | 180 |
| aatggagatg | gagagcacca | ccggcaccgg | caacggcctt | cacagcctct g | cgccgccgg | 240 |
| gagccaccat | gccgacccac | tgaactgggg | gcggcggca | gcagcccctca c | aggagcca | 300 |
| cctcgacgag | gtgaagcgga | tggtcgagga | gtaccggagg | ccggcggtgc g | cctcggcgg | 360 |
| ggagtccctc | acgatagccc | agtggcggc | ggtggcgagt | caggagggg t | aggggtcga | 420 |
| gctctcggag | gcggcccgtc | ccagggtcaa | ggccagcagc | gactgggtca t | ggagagcat | 480 |
| gaacaaggga | actgacagct | acggggtcac | caccgggttc | ggcgccactt c | tcaccggag | 540 |
| gacgaagcaa | ggcggtgctt | tgcagaagga | acttataagg | ttcttgaatg c | cgggatctt | 600 |
| cggcaacgga | acggagtcgt | gccacaccct | gcctcaatcc | tccacccgag c | cgccatgct | 660 |
| cgtccgggtc | aacaccctcc | tccagggcta | ctccggcatc | cgttttgaga t | cctcgaggc | 720 |
| catcaccaag | ttcctcaacc | acaacatcac | ccgtgcctg | cccctcaggg g | caccatcac | 780 |
| tgcctcaggc | gacttggtcc | ccctctccta | cattgccggg | ctcctgacgg g | ccggcccaa | 840 |
| ctccaaggcc | gtcgggcctg | atgggaagtc | cctggacgct | gtcgaggcct t | ccggctcgc | 900 |
| cgggattgac | acgggcttct | tcgagctgca | gccaaaggaa | gggttggcgc t | cgtgaacgg | 960 |
| cacggcagtc | gggtctggcc | tggcttccat | cgtcctcttc | gaggccaaca t | actcgcggt | 1020 |
| cctgtccgag | gtcctgtcag | cgatcttcgc | agaggtgatc | caggggaagc c | ggagttcac | 1080 |
| agaccacttg | acgcataaat | tgaagcacca | tcccgggcag | attgagtctg c | ggctataat | 1140 |
| ggagcacatt | ttggatggaa | gcgcttacgt | gaaggctgct | aaaaagttgc a | cgagatgga | 1200 |
| tccgctccag | aagccaaagc | aggacaggta | cgctctcagg | acttctcccc a | gtggctagg | 1260 |
| gccccagatt | gaggtgatcc | gagcggcaac | caagatgatt | gagagggaaa t | caattcggt | 1320 |
| caatgacaac | ccgctgatcg | atgtcgcgag | gaacaaggcc | ctgcacggtg g | gaacttcca | 1380 |
| ggggaccccg | attggtgtct | ccatggacaa | cactcgcctg | gcggttgcgt c | catagggaa | 1440 |
| gctcatgttc | gcgca | | | | 1455 |

<210> SEQ ID NO 246
<211> LENGTH: 294
<212> TYPE: DNA
<213> ORGANISM: Eucalyptus grandis

<400> SEQUENCE: 246

| | | | | | |
|---|---|---|---|---|---|
| caacagtggc | atcacgccgt | gcttgccgct | ccgcggctcg | atctccgcct c | tggtgactt | 60 |
| ggtaccctttt | tcctacatcg | cgggtctttt | gacgggacgt | cccaattcca a | agcggtcgg | 120 |
| acccgctggg | gagaccctca | cggccaaaca | agcctttgag | ctcgctggga t | cagtggtgg | 180 |
| attcttcgag | ttgcagccga | aggaaggact | tgcccttgtg | aatgggacgg g | agttgggtc | 240 |
| tgccttagct | gccatagtgc | tttttgaagc | taatatgctc | actgtcctct c | aga | 294 |

<210> SEQ ID NO 247

```
<211> LENGTH: 1520
<212> TYPE: DNA
<213> ORGANISM: Pinus radiata

<400> SEQUENCE: 247
gtgatctggt tcccctgtct tatattgctg ggctcttgac cgggaggcct a attccagag      60
tcagatccag agatggaatt gaaatgagcg gagccgaagc gctcaagaaa g tgggcctgg     120
aaaagccctt tgaattgcag cctaaagaag gtctggccat tgtcaatggc a cttcagtgg    180
gagcagcact ggcttccatt gtgtgtttcg atgccaatgt tcttgctctg c tctctgaag    240
taatctctgc catgttctgc gaggttatga atgggaagcc tgagtttaca g atccattaa    300
ctcacaagct gaagcaccat cctggccaaa tggaagctgc agcgatcatg g agtatgtct    360
tggacgggag tcttatatga aacacgctgc taagctccat gagatgaatc c tctgcagaa    420
gccaaagcag gatcgctatg cgcttcgcac ttcgcctcag tggctcggcc c tcaggtgga    480
gattatcaga tctgcaactc acatgattga gcgggaaatc aattctgtga a tgacaatcc    540
agtaattgat gttgccagag acaaagctct acatggaggg aatttccagg g cacacctat    600
tggtgtttcc atggataatc ttcgtctgtc aatttcagca attgggaaat t gatgttcgc    660
tcaattctca gagcttgtga atgattacta caatggaggc ttgccttcga a tctgagtgg    720
tgggcctaat cccagcctgg attatggact gaaagggggcc gagatcgcta t ggcttctta    780
cacttctgag cttctttacc tggcaaatcc tgtcaccagc catgtacaga g cgccgaaca    840
gcataaccag gatgtcaatt ctctgggtct cgtttcagct agaaaatctg c cgaggccat    900
cgatattctg aagctgatgc tctccacata cctgacagct ctgtgccagg c tgtggattt    960
aaggcatctg gaggaaaaca tgctggccac tgtgaagcag attgtttctc a ggtagccaa   1020
gaaaaccctg agcacagggc tcaacgggga gcttttgcca ggccgtttct g cgaaaagga   1080
tttgctccag gtagtggata cgaacatgt tttctcttac attgacgatc c gtgcaatgc   1140
cagctaccca ttgactcaga aactgagaaa catcctggtg gaacatgcct t caagaacgc   1200
agaaggtgag aaggatccca acacttccat tttcaataag attcctgtgt t tgaagccga   1260
gctgaaggca cagcttgaac cgcaagttag tctggccaga gaaagttatg a caaagggac   1320
cagccctctg cccaacagga tccaggaatg caggtcttat cctctctatg a atttgtgag   1380
aaaccagctc ggtaccttc aggcatggtt attccatata aatattgtaa t gagatgttt   1440
aattatttac tgctctcttt tttttccgga gcttgcgacc gccttcgatt c cgtgcacta   1500
cgcgaggacg aagcctctgt                                                152 0

<210> SEQ ID NO 248
<211> LENGTH: 449
<212> TYPE: DNA
<213> ORGANISM: Pinus radiata

<400> SEQUENCE: 248
ctctcattct gaggttcatc tggctgaagt ttgaactgtg ctcgaattct g aggttcatc     60
gtgcagaagt ttgattcgtg aattatttgt ttgtttaatt atagtgcaca t ggcgcctca    120
ggaattcaca ggcgaagtga aattctgtgc gggaaatggc ggtacggcgt c tttgaacga    180
tccgctgaat tgggcagccg cagcggagtc catgaaggga tctcacttcg a ggaagttaa    240
acgaatgtgg gaggagtttc gttctccagt tgtgaggctc cagggatccg g tctcacgat    300
tgcccaggtg gcagccgtgg ccaggagaac gggatccgtg agagtcgaac t tgagaccgg    360
cgcgaaggcg cgggtagatg agagcagtaa ttgggtgatg gacagtatgg c gaacgggac    420
```

```
ggatagctat ggcgttacga cggggttcg                                      449
```

<210> SEQ ID NO 249
<211> LENGTH: 512
<212> TYPE: DNA
<213> ORGANISM: Eucalyptus grandis

<400> SEQUENCE: 249

```
gaacttggtg aagttaggaa gtatactagg catggccatc ggtgttgcac t cttcagctc    60
gcttcttgta ctttcatttg tctctccaat ctcttcacta agttccaatt a ctacgacaa   120
gacctgtccc aatgctgagt tgatcgtcgc aaatgctgtc aagaatgcgg c aatgaagga   180
caaaaccgtt ccggctgctc ttctgcggat gcattttcac gactgtttca t tagggggtg   240
cgatgcgtcg gtgcttttaa actccaaagg aagcaacaaa gcggagaagg a tggacctcc   300
taatgtctct ctgcactcat tttttgtaat cgacaatgcc aaaaaggagt t ggaagcttc   360
ttgccccggc gtggtttcat gtgcggacat cttggcacta gctgctagag a ttccgtcgt   420
actgtccgga gtccgacttt gggatgtgcc caagggaagg aaggatggaa g aacatcaaa   480
agccagcgag acgactcaac tcccagcacc ac                                  512
```

<210> SEQ ID NO 250
<211> LENGTH: 354
<212> TYPE: DNA
<213> ORGANISM: Eucalyptus grandis

<400> SEQUENCE: 250

```
ctggtaatca ccatagttgt cttctttggg cacataggag actcagaagg a ggggacttg    60
aggaagaatt tctacaagag cgcatgtcct cttgctgagg aaatagtgaa g aatgtcacg   120
tggaagcatg ccgccagtaa ctcagctttg cccgccaagt tcctgaggat g catttccac   180
gattgcttcg ttaggggttg cgatggctca gttttgctag actcgacggc g aacaacaag   240
gcggagaagg tggcggttcc gaaccagtcg ctaaccgggt tcgacgtaat a gacgagatc   300
aaggagaagc tggaggaaac atgccctggg gtcgtctctt gtgccgacat c ctg         354
```

<210> SEQ ID NO 251
<211> LENGTH: 195
<212> TYPE: DNA
<213> ORGANISM: Pinus radiata

<400> SEQUENCE: 251

```
aacgctgacc ctatcgcggt tatagacgaa gcactcagca ctggtggtgc g cccaatttg    60
tcggatgcat atacccctaaa tggacagcca ggagacctgt ataactgctc t agggcagga   120
acattccggt ttctggtcaa acaaggagaa acttaccttc tacggatggt c aatgctgca   180
ctcaatagtg cccac                                                     195
```

<210> SEQ ID NO 252
<211> LENGTH: 377
<212> TYPE: DNA
<213> ORGANISM: Pinus radiata

<400> SEQUENCE: 252

```
ccaaacccca tggagaaact ccgctcataa taggagaatg gtggaacgct g accctattg    60
cggttataga tgaagcactc cgcactggtg gtgcgcccaa tttgtcggat g catatatccc  120
taaatggaca gccaggagac ctgtataact gctctagggc aggaacattt c ggtttcctg   180
```

| | |
|---|---|
| taaaacaagg agaaacttac cttctccgga tggtcaatgc tgcactcaat a gtgcccact | 240 |
| ttttcaagat cgcaggccac aaatttacag tagtagctgt ggatgcttcc t acaccaagc | 300 |
| catacaaaca gatgtaatcg ccattgctcc cggtcagact actgatgttc t cgtcacggc | 360 |
| cgaccaacct gtgggca | 377 |

<210> SEQ ID NO 253
<211> LENGTH: 387
<212> TYPE: DNA
<213> ORGANISM: Pinus radiata

<400> SEQUENCE: 253

| | |
|---|---|
| gatgcccaca ccattaatgg aaagccaggg ccactcttca aatgccctac c aaagatact | 60 |
| tttgtggttc cagtggaaca tgggaagact taccttcttc gaatcatcaa c gcagctctc | 120 |
| aatgacgagc tctttttga tgttgcaaac catcatctga aagtggtgga g attgacgca | 180 |
| gtatacacaa agccactaat aacgaactca atagtaattg ctccaggcca g accacaaat | 240 |
| gccttgatcc acaccaacaa aaggagtggc aggtatttca tggctgctcg c tcattcatg | 300 |
| gacgcgcccg tctccgtcga caataaaacc gccacagcca ttttgcagta c gtcaattca | 360 |
| atacaaattc tgttataatg cccagca | 387 |

<210> SEQ ID NO 254
<211> LENGTH: 534
<212> TYPE: DNA
<213> ORGANISM: Pinus radiata

<400> SEQUENCE: 254

| | |
|---|---|
| aacatgatgg cgcccatggc cggagcagag tacggaataa agctgattat t cagttgctt | 60 |
| gttgtactac ttgctgttca acttgttgca gggaaaacga ccagacatta c tcattccat | 120 |
| gtgaggttga agaacgttac tcgtctctgc cacacaaagc cattgattac a gtcaatggg | 180 |
| aaatctcctg gacctaaagt agtcgtccgt gagggagata gagtcatcat c aaagttcat | 240 |
| aatcatgtta gcaataatgt ctcaattcac tggcatggag ttcgacaatt g aggtctggt | 300 |
| tgggcagatg gccctgctta cataacccaa tgcccaattc aaacgggaca g acttatgtt | 360 |
| tataacttca ctgtcacagg acagagggga actctctggt ggcacgctca c atctcttgg | 420 |
| ctaagagcga gcgtatatgg cgctttcatc atctatccta aacgccatgt t ccttatcca | 480 |
| tttccaaagc catacaaaga agtccctctg attctcgggg aatggtggaa t gca | 534 |

<210> SEQ ID NO 255
<211> LENGTH: 1076
<212> TYPE: DNA
<213> ORGANISM: Pinus radiata

<400> SEQUENCE: 255

| | |
|---|---|
| gcccaattcc accaggtggt cgttacacat atagattcaa catctctggt c aagaaggaa | 60 |
| cggtttggtg gcatgcccat tactcatggc tccgagctac tgtgcatgga g cttttgtaa | 120 |
| tccttcctaa gaaaggaagc tcatatccct tttctaaacc gcatgctgaa a ttcctatta | 180 |
| taataggtga atggtggaac gctaaccca tcgccgttat agacgaagcg g ttcgcacag | 240 |
| gtggtgcgcc taatttatcc gatgccttca ccataaatgg acagccagga g atctgttta | 300 |
| actgctctac ctcgggaaca tttcgcctcc ctgtagaaag cggagaaacg t accttctgc | 360 |
| ggattgtgaa tgctgcactc aatagcgggc acttttcaa gatagcaggc c acgaattta | 420 |
| cagtggtagc tgtggatgct tgttacacca agccatacaa aacagatgta c tcgtcatat | 480 |

```
ctgccggcca gacgacagat gttcttatca cggccaacca gtctgtgggc a gatactata      540 tggccgcccg agcgtatcaa atcaggcgg caggcgattt cactaacacc a caacaactg      600 ccattctaga gtacattgga agtgaaaatt ctactcgccc aattttgcct a gccttccag      660 cctacaacga cactgccact gtcactagat ttagcagagc actgcgaagt c tggcatccc      720 aggagcaccc tgtgaatgtt ccgcacacaa tagatgaaag cctcatctca c tgttggac      780 tggggctact ccgtgtggc gctgggaata cctgtgaagg tcccaacgga a cgaggctga      840 gtgcaagtat caacaacata tcgtatgtag agcccacgat ctcgttgctt c aagcatatt      900 attacactgc caatggtatc tttacggggg attttccatc aaaacctgaa g ttagattca      960 actacacggg ggacgatata ccccgaaaat tttgggctcc ggaccccgca a caaaagtga     1020 aggtgctcga atacaactcc acagtgcagc tcgtttttca gtcaacaaac a tcttc        1076
```

<210> SEQ ID NO 256
<211> LENGTH: 483
<212> TYPE: DNA
<213> ORGANISM: Pinus radiata

<400> SEQUENCE: 256

```
atttcgcagg gaaactgtaa tacagcatat ttcaagaagc tttctttcga a aatggtgat       60 ctcaaaatat gcagcagcga tgtcgtgctt gctcatcgca gtagttgcat t agaggttgg      120 ggcagaaacg agacattaca aatttgacat aaaattcaag aacgttactc g tttatgcca      180 cacaaagccg atagttacag cgaatggcaa gttcccaggc ccaacaatat a tgcacgaga      240 aggagacaca gtcactgtga aagtaaccaa tcacgtgaca tacaacgtgt c catacactg      300 gcacgggata aggcagttgc ggactgggtg ggctgatggg cctgcttata t tacgcagtg      360 ccccattcaa acaggccaaa cttatgtata aactttaca atcacagggc a gcgaggcac      420 acttttctgg cacgctcaca ttctctggtt acgtgcaaca ttgaatgggc c catcgtcat      480 tct                                                                    483
```

<210> SEQ ID NO 257
<211> LENGTH: 470
<212> TYPE: DNA
<213> ORGANISM: Pinus radiata

<400> SEQUENCE: 257

```
ggttgttgtt taagtacaag gatgaacatg tcgagatcaa aggcgttgct c tgcccttcc       60 ccagctcatg tgaagtacgt gctaattgtc atcctgttga ttattatgat t cagtgcccg      120 gatatagtag caggaaagca tgcgcagaca accaggcatt acaagttcaa c gtgaggcta      180 agcaatgtga cacgtctttg ccgcacgaaa cctttgatta cagtgaatgg a aagtatcca      240 ggacctacag ttgttgctcg cgagggagat cgggtaatta taaaacttgt a aaccacgtg      300 aaggacaacg tcactattca ctggcatggc gttcgacagc tgagatcggg a tgggcggat      360 ggtcctggtt atatcactca atgtccactt caaaccggaa tgagttacgt t tataatttc      420 accatcgtag ggcagagagg aactctatgg tggcacgcac acatttcttg                 470
```

<210> SEQ ID NO 258
<211> LENGTH: 472
<212> TYPE: DNA
<213> ORGANISM: Pinus radiata

<400> SEQUENCE: 258

```
agttatccag caggctcttc aaacaggagg tggtccaaat gtatctgatg c ctatactat    60 aaatggactt cctggaccac tttacaactg ttccaatgag acatttgttt t gaaagtgca   120 tcctggacaa acatatcttc ttcgtatcat caatgctgca ctcaatgatg a actcttcct   180 tgccattgca aatcacagtt taacagttgt ggaggtggat gcagtgtatg t caagccttt   240 ccagacagat actcttctta taccccagg gcagactacc aatgttttac t tactgctaa   300 tgctactagt ggtaaaaata aacaatttgt catagctgct agtccttttg t taccggttc   360 agggacattt gataattcca ctgttgcagg aattgtgagt tataattctc a taagtttaa   420 aaattcttcc accattattc tgccaaaact cccatccttc aatgatacaa a t           472

<210> SEQ ID NO 259
<211> LENGTH: 405
<212> TYPE: DNA
<213> ORGANISM: Pinus radiata

<400> SEQUENCE: 259
caggacaaac cacgaatgtt ttgctcgagg ctaacaaaag atctggaagt t atttcgtgg    60 ctgctcggcc attcatggat gcacctgtga cagtgaacaa caagaccgca a ctgccattt   120 tgcactacat cggcaggaat tctgaatcag atattcccgc cgttaatcct c tcatgccac   180 gacttcctct cctcaacgac actgcgtttg caacgagttt cacctccaag c tcagaagct   240 tgaattctgt tcagtttccc gcaaaagtcc cgcagacaat agatcgcaat c tcttcttcg   300 cagtggggct tgcgacggag tcttgtcaga cctgtaacgg tggcctccgt g cttccgcat   360 caatcaacaa cataagcttc gtcatgccca gcatttctct tctgg              405

<210> SEQ ID NO 260
<211> LENGTH: 1352
<212> TYPE: DNA
<213> ORGANISM: Pinus radiata

<400> SEQUENCE: 260
acaccactta tcccttacc tttaccaggc cgcatcgcca gattcccatt c ttctaggag     60 aatggtggaa taggaatccc atggacgttg tgaatcaagc aacccaaaca g gagctgccc   120 ccaacgtttc agatgcattt actataaatg gacaaccagg cgacctatac a aatgttcta   180 cttcagatac ctttagcgtg tcgatgaaag gtggggaaac taatcttcta c gtgttatca   240 acgctgcact caatactgac ctattcttct ccattgctag ccacacaatg a cagttgtcg   300 ctgtggatgc cttgtataca aaaccttttc agacgaatgt tctgatgctc g ccccggcc    360 agacaacaga catacttctc actgccaatc aggctacagg tagatactac a tggctgctc   420 gagcatattc cagcgggcaa ggagttccct tcgataacac cactaccact g ccatttag    480 aatacgaggg aagctctaag acttcaactc cagtcatgcc taatcttcca t tctataacg   540 acaccaacag tgctactagc ttcgctaatg gtcttagaag cttgggctca c acgaccacc   600 cagtcttcgt tcctcagagt gtggaggaga atctgttcta caccatcggt t tggggttga   660 tcaaatgtcc ggggcagtct tgtggaggtc ccaacggatc aagatttgca g caagtatga   720 ataacatatc atttgtcccg ccaaccactt cttccatcct tcaagctcag c attttggca   780 tgaaaggagt attctccgcg gacttccccg ataacccttc cgtgggattt g attataccg   840 cacagaacat cagcagagac ctctggtccc ctgtgaaagc cacaagagtg a aagttctta   900 aatataactc gacggtgcaa gtaattcttc aaggaaccaa tatatttgcg g gtgaaagcc   960 atcctatcca tctccatggt tatgacttct acatcgtggg agcaggcttt g gcaattata  1020
```

```
acgcacaaac cgatcctcac aagttcaacc tggtggatcc tcctatgcgc a acactgtga   1080 acgttccagt caatggctgg gctgcaataa gattcgtggc tgacaatcct g gagcttggg   1140 tgatgcactg ccacttggac gtgcacataa catgggggatt ggccatggtg t tgtggtta   1200 acaatggacc tgacgctctt ttgagtctcc agtcacctcc cagagatctt c cgctatgct   1260 gaggaaaact gtgatgcata cgatcctct attggtccca cttcattctt t ttccttctc   1320 gtcactttgc tccttccatc gtttatgtct at                                 1352
```

<210> SEQ ID NO 261
<211> LENGTH: 337
<212> TYPE: DNA
<213> ORGANISM: Pinus radiata

<400> SEQUENCE: 261

```
ttcttaacta taacgcgaca gttcaagtaa ttctccaggg aacaaatata t ttgctggtg    60 aaagccatcc tatccatctc catggttatg acttttacat cgtgggagca g ggtttggta   120 attataatgc acaaacagat cctcagaagt tcaacctggt ggatcctcct a tgcgcaaca   180 ctgtgaacgt tccagtcaat ggctgggctg ccataagatt cgttgctgac a atcctggag   240 cttgggtgat gcactgccac ttagacgtgc acataacatg ggggttggcg a tggttttttg   300 tggttaacaa tggacctgat cctcttttga gtctcca                             337
```

<210> SEQ ID NO 262
<211> LENGTH: 279
<212> TYPE: DNA
<213> ORGANISM: Pinus radiata

<400> SEQUENCE: 262

```
acaagagtga aagttcttaa ttataacaca acggtgcaag taattcttca a ggaacaaat    60 atatttgcgg gtgaaagcca tcctattcat ctccatggtt atgacttcta c atagtggga   120 gcaggatttg gcaattataa tccacaaaac cgatcctcaa a agttcaacct g gcggatcct   180 cctatgcgca acactgtaaa cgttccagtt aatggctggg ctgcaataag a ttcgtggcc   240 gacaatcctg gcgcttgggt gatgcactgc cacttggac                           279
```

<210> SEQ ID NO 263
<211> LENGTH: 279
<212> TYPE: DNA
<213> ORGANISM: Pinus radiata

<400> SEQUENCE: 263

```
aaaaccttt cagacgaatg ttctgatgct cggccccggc cagacaacag a catagcggc    60 cgcgtcgacc aacttgcaga tacctttagc gtgtcgatga aggtggggga a actaatctt   120 ctacgtgtta tcaacgctgc actcaatact gacctattct tctccattgc t agccacaca   180 atgacagttg tcgctgtgga tgccttgtat acaaaacctt tcagacgaa t gttctgatg   240 ctcggccccg gccagacaac agacatagcg gccgcgaat                           279
```

<210> SEQ ID NO 264
<211> LENGTH: 474
<212> TYPE: DNA
<213> ORGANISM: Pinus radiata

<400> SEQUENCE: 264

```
ccctgactct acaatcaata cgtcgttcct gcaacagtta caagggcagt g tcctcgggc    60
```

| | |
|---|---|
| tggtggagac gagttgcctt cgtctcttga ctacgtaacg ccagcccgtt t tgataacac | 120 |
| ttactttgcc aacttgaagc agcagaaggg tgttctgcac tctgatcgca c gctatacga | 180 |
| tcccgcagcc tcagggtctg taactagcag tacagttgat catttctctt c tgatcagac | 240 |
| tgctttcttc gaaagcttca aaggagccat gatcaaaatg gggaacctca g cccttcggc | 300 |
| cggaacgcaa ggagaaatcc ggcgggactg cagaaaagta aattagagag c tcctagcct | 360 |
| tcatccagag gcatcaacca tgaggataag ttggataaat tatcttgtct t aatatcagg | 420 |
| ttggatttag tggtataata tcgggttgga tttagtggta aaaaaaaaaa a aaa | 474 |

<210> SEQ ID NO 265
<211> LENGTH: 1790
<212> TYPE: DNA
<213> ORGANISM: Pinus radiata

<400> SEQUENCE: 265

| | |
|---|---|
| ggcacgaggc aaacttggtc gtttgtttag gttttgctgc aggtgaacac t aatatggaa | 60 |
| ggccagattg cagcattaag caaagaagat gagttcattt ttcacagccc t tttcctgca | 120 |
| gtacctgttc cagagaatat aagtcttttc cagtttgttc tggaaggtgc t gagaaatac | 180 |
| cgtgataagg tggccctcgt ggaggcctcc acagggaagg agtacaacta t ggtcaggtg | 240 |
| atttcgctca aaggaatgt tgcagctggg ctcgtggaca aaggcattca a aagggcgat | 300 |
| gttgtatttg ttctgcttcc aaatatggca gaatacccca ttattgtgct g ggaataatg | 360 |
| ttggccggcg cagtgttttc tggggcaaat ccttctgcac acatcaatga a gttgaaaaa | 420 |
| catatccagg attctggagc aaagattgtt gtgacagttg gtctgcttta t gagaaggtg | 480 |
| aggcaagtga aactgcctgt tattattgca gataacgagc atgtcatgaa c acaattcca | 540 |
| ttgcaggaaa tttttgagag aaactatgag gccgcagggc ttttgtaca a atttgtcag | 600 |
| gatgatctgt gtgcactccc ttattcctct ggcaccacag gggcctctaa a ggtgtcatg | 660 |
| ctcactcaca gaaatctgat tgcaaatctg tgctctagct tgtttgatgt c catgaatct | 720 |
| cttgtaggaa atttccaccac gttggggctg atgccattct tcacatata t ggcatcacg | 780 |
| ggcatctgtt gcgccactct tcgcaacgga ggcaaggtcg tggtcatgtc c agattcgat | 840 |
| ctccgacact tatcagttc tttgattact tatgaggtca acttcgcgcc t attgtcccg | 900 |
| cctataatgc tctccctcgt taaaaatcct atcgttaacg agttcgatct c agccgcttg | 960 |
| aaactcaaag ctgtcatgac tgcggctgct ccactggcgc cggatctact g cgagcgttc | 1020 |
| gaggaaaaat tccctggggt tgaggttcaa gaggcctatg gtcttacgga a cacagttgc | 1080 |
| atcacattga ctcattgcgc tcccggaaac atacgtggga gagccaagaa g agttcggtt | 1140 |
| ggttttatta ttcccaatct ggaggtgaag tttattgatc ccgaaactgg a aagtcattg | 1200 |
| cccaggaatt ccatcgggga ggtgtgcgtc agaagccaat gtgtcatgcg a gggtattac | 1260 |
| aagaaaccga cagaaaccga gaaacagtg gacagcgacg gctggctgca t actggggat | 1320 |
| gtcggtttca tagatgatga cgacgacgta ttcatcgtcg acagaattaa a gagctgatc | 1380 |
| aaatacaaag ttttcaggt tgctcctgca gaactggaag ccattctact t tctcatcca | 1440 |
| tcagtggaag acgcagcagt ggttccttta cctgatgagg aagcagggga g attccagcg | 1500 |
| gcgtgcgtgg tgatggcagc cagtgctacg gagacgagg acgacatttc g aagtttgtg | 1560 |
| gcgtcgcagg tggctacata caagagggtg agactggtga agtttgtgtc c accattcct | 1620 |
| aaatcttctt ccggaaagat cctgcgcaga cttctgagag ataatctccg t gaaacgctc | 1680 |
| aaaaaccagc accaaccatt gtccacttag gctttgcagc gttatatata a ataaataat | 1740 |

-continued

```
caaacatcta gggatgggat tatagcccca taacatacat tttgaaattc            1790

<210> SEQ ID NO 266
<211> LENGTH: 2043
<212> TYPE: DNA
<213> ORGANISM: Eucalyptus grandis

<400> SEQUENCE: 266
gcgccaccac caaacgctca ccttctcatc atcagccctc tgtctctgtc t ctgtctctc    60
gattctccgc cccgccacga caatggaggc gaagccgtcg gagcagcccc g cgagttcat   120
cttccggtcg aagctccccg acatctacat tcccgacaac ctctccctcc a cgcctactg   180
cttcgagaac atctccgagt tcgccgaccg ccctgcgtc atcaacgggg c caccggccg    240
gacctacacc tatgccgagg tcgagctgat ctcccgccgg gtctcagccg g cctcaacgg   300
gctcggcgtc ggacagggcg acgtgatcat gctgctcctc cagaactgcc c tgagttcgt   360
gttcgcgttc ctcggcgcgt cctaccgggg cgccatcagc acgaccgcga a cccgttcta   420
caccccgggc gagatcgcca agcaggcctc agctgcccgg ccaagatcg t gatcacgca    480
ggccgcgttc gccgacaagg tgaggccgtt cgcggaggag aacggggtga a ggtcgtgtg   540
catcgatacc gcgccggagg gctgcctgca cttctcggaa ttgatgcagg c ggacgagaa   600
cgccgccccc gcggcggacg tcaagccgga cgacgtcttg gcgctcccct a ttcgtcggg   660
cacgacgggg cttcccaagg gagtgatgct tacgcacagg ggtcaagtga c cagcgtggc   720
gcagcaggtc gacggagaca accccaactt gtacttccac aaggaggacg t gatcctgtg   780
cacgctcccc ttgttccaca tatactccct caactcggtg atgttctgcg c gctccgtgt   840
cggcgccgcc atcctgatca tgcagaagtt cgagatcgtg gcgctgatgg a gctcgtgca   900
gcggtaccgg gtgacgatcc tgcccattgt cccgccgatc gtgctggaga t cgccaagag   960
cgccgaggtg gaccggtacg acctgtcgtc gatccggacc atcatgtcgg g tgcggcccc  1020
gatggggaag gagctcgagg acaccgtgcg agccaagctg cccaatgcca a gctcggaca  1080
gggctatggg atgacggagg cgggcccggt gctggcaatg tgcccggcat t tgcaaagga  1140
gccgttcgag atcaagtcag cgcatgcgg gaccgtcgtg aggaacgcgg a gatgaagat  1200
cgtcgacccg gagacagggg cctcgctccc gcggaaccag gccggcgaga t ctgcatccg  1260
gggtcaccag atcatgaaag gttatctgaa cgacgccgag cgaccgcaa a taccataga   1320
caaagaaggg tggctgcaca ccggcgacat cggctacata gacgatgacg a cgagctctt  1380
cattgtcgat cggttgaagg aactcatcaa gtacaagggc ttccaggttg c tccggccga  1440
gctagaggca atgctgattg cacacccaag tatctcggat gccgctgttg t gccgatgaa  1500
ggatgaggtt gccggtgagg ttcctgttgc attcgtggtg aaatccaatg g ttccgtaat  1560
caccgaggac gaaatcaagc aatacatctc gaagcaggtc gtgttttaca a gaggatcaa  1620
gcgggttttc ttcacggacg caattccgaa agccccctcc ggaaaaatct t gaggaagga  1680
cctaagagca aagttggcct ctggtgttta caattaattt ctcatacct t ttcttttc    1740
aaccctgccc ctgtacttgc ttaaagaccc atgtagttga atgaatgta a cctcttcgg   1800
agggccaaa tatggaaggg ggaaagaaag acatatggcg atgatttgat t tcacatgct   1860
attgtaatgt atttattgtt tcaattccga attagacaaa gtgcttaaag c tctcttttc  1920
ggattttttt tttcattaat gtataataat tgcggacatt acaatatact g tacaacgtg  1980
atttgagctt gatgaattac aagattggaa gaacttcgaa gacaaaaaaa a aaaaaaaaa  2040
```

-continued aaa  2043

<210> SEQ ID NO 267
<211> LENGTH: 92
<212> TYPE: PRT
<213> ORGANISM: Pinus radiata

<400> SEQUENCE: 267

Lys Glu Thr Gly Leu Leu Asn Gln Phe Val Asp Ile Tyr Gln Glu Met
1               5                   10                  15

Asp Asp Ser Val Gln Glu Val Ser Lys Glu Gly Asn Gln Trp Ala Gly
            20                  25                  30

Phe Ile Glu Gly Glu Asn Val Ile Arg Arg Gly Arg Glu Ile Leu Leu
        35                  40                  45

Gln His Asp Asn Arg Glu Ala His Asn Trp Glu Ser His Lys His Lys
    50                  55                  60

Trp Trp Pro His Leu Glu Lys Ile Pro His Ile Ala Lys Ala Gly
65                  70                  75                  80

Phe Thr Ser Ile Trp Leu Pro Pro Ala Phe Asp Ser
                85                  90

<210> SEQ ID NO 268
<211> LENGTH: 182
<212> TYPE: PRT
<213> ORGANISM: Pinus radiata

<400> SEQUENCE: 268

Leu Leu His Gln Phe Val Tyr Ser Phe Arg Lys Met Gly Tyr Pro Val
1               5                   10                  15

Gln Glu Val Ser Lys Glu His Asp Gln Trp Ala Gly Phe Val Glu Gly
            20                  25                  30

Glu Ser Val Leu Gln Arg Gly Arg Glu Ile Leu Leu Gln Gly Phe Asn
        35                  40                  45

Trp Glu Ser His Lys Tyr Lys Trp Trp Pro Asn Leu Glu Glu Lys Ile
    50                  55                  60

Pro His Ile Ala Lys Ala Gly Phe Thr Ser Val Trp Leu Pro Pro Ala
65                  70                  75                  80

Phe Asp Ser Ala Ala Pro Gln Gly Tyr Leu Pro Arg Asn Ile Tyr Ser
                85                  90                  95

Leu Asn Ser Ala Tyr Gly Ser Glu Tyr Gln Leu Lys Ser Leu Leu Met
            100                 105                 110

Thr Met Arg Lys Lys Asn Val Arg Ala Met Ala Asp Ile Val Ile Asn
        115                 120                 125

His Arg Met Gly Ser Ser Gln Gly Phe Gly Gly Leu Tyr Asn Arg Tyr
    130                 135                 140

Tyr Gly Cys Leu Pro Trp Asp Glu Arg Ala Val Thr Arg Cys Ser Gly
145                 150                 155                 160

Gly Leu Gly Asn Trp Ser Thr Gly Asp Asn Phe His Gly Val Pro Asn
                165                 170                 175

Val Asp His Thr Gln Asp
            180

<210> SEQ ID NO 269
<211> LENGTH: 218
<212> TYPE: PRT
<213> ORGANISM: Pinus radiata

<400> SEQUENCE: 269

```
Arg Met Ala Lys Phe Arg Ser Leu Ser Leu Leu Trp Phe Ser Cys
  1               5                  10                  15

Ile Ile Val Asn Ala Ala Ser Pro Ala Gln Ala Glu Ala Thr Thr Pro
                 20                  25                  30

Pro Leu Asn Thr Leu Leu Leu Gln Gly Phe Asn Trp Asp Ser Ala Gln
             35                  40                  45

Ser Ser Thr Pro Trp Tyr Asn Val Leu Lys Gly Ile Val Asp Asp Ala
     50                  55                  60

Ala Asp Ala Gly Ile Thr Tyr Val Trp Phe Pro Pro Pro Ser Gln Ser
 65                  70                  75                  80

Gly Ala Pro Gln Gly Tyr Leu Pro Ala Lys Leu Tyr Asp Leu Asp Ser
                 85                  90                  95

Ser Tyr Gly Ser Glu Gln Leu Lys Asp Ala Val Asn Ala Phe His
                100                 105                 110

Gln Lys Gly Ile Ala Ile Met Gly Asp Ile Val Ile Asn His Arg Asn
                115                 120                 125

Gly Thr Lys Gln Asp Asp Lys Gly Tyr Trp Cys Val Phe Glu Gly Gly
        130                 135                 140

Lys Gly Asp Gly Thr Leu Asp Trp Gly Pro Trp Ala Val Thr Val Lys
145                 150                 155                 160

Asp Gln Pro Tyr Pro Leu Cys Gly Ser Gly Gln Ala Asp Thr Gly Gly
                165                 170                 175

Asp Phe Lys Tyr Ala Pro Asp Val Asp His Thr Asn Pro Lys Ile Gln
            180                 185                 190

Gln Asp Leu Ser Glu Trp Met Asn Trp Leu Lys Ser Met Ser Asp Leu
                195                 200                 205

Met Ala Gly Gly Ser Thr Thr Ser Arg Leu
        210                 215

<210> SEQ ID NO 270
<211> LENGTH: 145
<212> TYPE: PRT
<213> ORGANISM: Eucalyptus grandis

<400> SEQUENCE: 270

Gly Val Gly Arg Leu Val Asp Val Gly Gly Ser Ala Gly Asp Cys Leu
  1               5                  10                  15

Arg Met Ile Met Gly Lys His Thr His Val Arg Glu Gly Ile Asn Phe
                 20                  25                  30

Asp Leu Pro Glu Val Val Ala Lys Ala Pro Pro Ile Pro Gly Val Thr
             35                  40                  45

His Val Gly Gly Asp Met Phe Lys Ser Ile Pro Ala Gly Asp Ala Ile
     50                  55                  60

Phe Met Arg Trp Ile Leu Thr Thr Trp Thr Asp Asp Glu Cys Lys Gln
 65                  70                  75                  80

Ile Leu Glu Asn Cys Phe Lys Ala Leu Pro Ala Gly Gly Lys Leu Ile
                 85                  90                  95

Ala Cys Glu Pro Val Leu Pro Gln His Ser Asp Asp Ser His Arg Thr
                100                 105                 110

Arg Ala Leu Leu Glu Gly Asp Ile Phe Val Met Thr Ile Tyr Arg Ala
            115                 120                 125

Lys Gly Lys His Arg Thr Glu Gln Glu Phe Gln Gln Leu Gly Leu Ser
    130                 135                 140

Thr
```

<210> SEQ ID NO 271
<211> LENGTH: 198
<212> TYPE: PRT
<213> ORGANISM: Eucalyptus grandis

<400> SEQUENCE: 271

Pro Thr Met Ala Asp Asn Gln Glu Arg Glu Gly Arg Asp Gln Glu Glu
1               5                   10                  15

Glu Val Gly Lys Leu Ala Val Gln Leu Ala Ser Ala Val Val Leu Pro
            20                  25                  30

Met Thr Leu Lys Ser Ala Leu Glu Leu Gly Ile Ile Asp Ala Leu Val
        35                  40                  45

Ser Ala Gly Gly Phe Leu Ser Ala Ala Glu Ile Ala Ser Arg Val Gly
    50                  55                  60

Ala Lys Asn Pro Gly Ala Pro Val Leu Val Asp Arg Met Met Arg Leu
65                  70                  75                  80

Leu Ala Ser His Gly Val Ile Glu Trp Arg Leu Arg Arg Gly Asp Gly
                85                  90                  95

Asn Gly Asp Gly Gly Glu Arg Glu Tyr Gly Pro Gly Pro Met Cys Arg
            100                 105                 110

Phe Phe Ala Lys Asp Gln Glu Gly Gly Asp Val Gly Pro Leu Phe Leu
        115                 120                 125

Leu Ile His Asp Lys Val Phe Met Glu Ser Trp Tyr His Leu Asn Asp
    130                 135                 140

Val Ile Met Glu Gly Gly Val Pro Phe Glu Arg Ala Tyr Gly Met Thr
145                 150                 155                 160

Ala Phe Glu Tyr Pro Ala Val Asp Asp Arg Phe Asn Gln Val Phe Asn
                165                 170                 175

Arg Ala Met Ala Ser His Thr Ser Leu Ile Met Lys Lys Ile Leu Asp
            180                 185                 190

Val Tyr Arg Gly Phe Glu
        195

<210> SEQ ID NO 272
<211> LENGTH: 156
<212> TYPE: PRT
<213> ORGANISM: Eucalyptus grandis

<400> SEQUENCE: 272

Pro Thr Pro Leu Tyr Met Asn Lys Ile Leu Glu Ser Tyr Arg Gly Phe
1               5                   10                  15

Glu Gly Ala Lys Thr Ile Ala Asp Leu Gly Gly Gly Val Gly Gln Asn
            20                  25                  30

Leu Arg Leu Ile Leu Asp Lys Phe Pro Asn Leu Arg Gly Ile Leu Tyr
        35                  40                  45

Asp Leu Pro His Val Ile Lys Asp Ala Pro Ala His Pro Arg Met Glu
    50                  55                  60

Arg Val Gly Gly Asp Leu Leu Lys Ser Val Pro Lys Ala Asp Ile Leu
65                  70                  75                  80

Phe Met Lys Trp Leu Phe His Gly Leu Arg Asp Asp Phe Cys Lys Met
                85                  90                  95

Leu Leu Gln Asn Cys Tyr Glu Ala Leu Pro Pro Asn Gly Lys Val Val
            100                 105                 110

Ile Val Asp Pro Ile Leu Pro Glu Tyr Pro Glu Thr Asp Ile Val Ser

```
                115                 120                 125
Arg Asn Ser Phe Thr Ser Asp Met Ile Met L eu Tyr Thr Ser Pro Gly
        130                 135                 140

Glu Asp Arg Thr Arg Lys Glu Leu Glu Val L eu Ala
145                 150                 155

<210> SEQ ID NO 273
<211> LENGTH: 166
<212> TYPE: PRT
<213> ORGANISM: Eucalyptus grandis

<400> SEQUENCE: 273

Ser Ser Phe Gln Pro Cys Tyr Glu Glu Ala A sn Ser Leu Asp Arg Trp
1               5                   10                  15

Ile Gln Pro Pro Ser Asp Leu Leu His Asn M et Ser Asp Lys Glu Leu
            20                  25                  30

Phe Trp Arg Ala Thr Leu Val Pro Lys Ile L ys Lys Tyr Pro Phe Arg
        35                  40                  45

Arg Val Pro Lys Ile Ala Phe Met Phe Leu T hr Lys Gly Pro Leu Pro
    50                  55                  60

Leu Ala Pro Leu Trp Glu Arg Phe Phe Lys G ly His Glu Gly Leu Tyr
65                  70                  75                  80

Ser Ile Tyr Ile His Ser His Pro Ser Phe H is Ala His Phe His Pro
                85                  90                  95

Trp Ser Val Phe Asn Arg Arg Gln Ile Pro S er Gln Val Ser Glu Trp
            100                 105                 110

Gly Arg Met Ser Met Cys Asp Ala Glu Lys A rg Leu Leu Ala Asn Ala
        115                 120                 125

Leu Leu Asp Ile Ser Asn Glu Arg Phe Ile L eu Leu Ser Glu Ser Cys
    130                 135                 140

Ile Pro Leu Tyr Asn Phe Ser Leu Ile Tyr H is Tyr Ile Met Lys Ser
145                 150                 155                 160

Gly Tyr Ser Phe Met Gly
                165

<210> SEQ ID NO 274
<211> LENGTH: 328
<212> TYPE: PRT
<213> ORGANISM: Eucalyptus grandis

<400> SEQUENCE: 274

Ile Leu Ser Arg Lys Pro Lys Glu Lys Thr V al Gly Arg Lys Asn Ile
1               5                   10                  15

Lys Lys Asn Met Ser Ser Lys Glu Ala Pro V al Ile Thr Thr Ser His
            20                  25                  30

Glu Asp Glu Glu Ile Leu Asn Ala Phe Glu V al Pro Ser Met Ala Phe
        35                  40                  45

Val Pro Met Val Leu Lys Gly Val His Glu L eu Gly Ile Leu Glu Leu
    50                  55                  60

Leu Ala Lys Gly Asp Gln Leu Ser Pro Leu A sp Ile Val Ala Arg Leu
65                  70                  75                  80

Ser Ile Asp Asn Pro Ala Ala Pro Asp Thr I le Asp Arg Met Leu Arg
                85                  90                  95

Leu Leu Ala Ser Tyr Ser Ile Leu Ser Cys T hr Leu Val Glu Asp Lys
            100                 105                 110

Glu Gly Arg Pro Gln Arg Leu Tyr Gly Leu G ly Pro Arg Ser Lys Phe
```

```
            115                 120                 125
Phe Leu Asp Gln Asn Gly Ala Ser Thr Leu Pro Thr His Met Leu Leu
130                 135                 140
Gln Glu Lys Thr Leu Leu Glu Cys Trp Asn Cys Leu Lys Asp Ala Val
145                 150                 155                 160
Lys Glu Gly Gly Ala Asp Pro Phe Thr Arg Arg His Gly Met Asn Val
                165                 170                 175
Phe Asp Tyr Met Gly Gln Asp Pro Arg Phe Asn Asp Leu Tyr Asn Lys
                180                 185                 190
Ser Met Arg Thr Gly Ser Ala Ile Tyr Met Pro Lys Ile Ala Gln His
                195                 200                 205
Tyr Arg Gly Phe Ser Lys Ala Lys Thr Val Val Asn Val Gly Gly Gly
                210                 215                 220
Ile Gly Glu Thr Leu Lys Thr Ile Leu Ser Lys Asn Pro His Ile Arg
225                 230                 235                 240
Ala Ile Asn Tyr Asp Leu Pro His Val Ile Ala Thr Ala Pro Pro Ile
                245                 250                 255
Pro Gly Ile Thr His Val Gly Gly Asp Ile Leu Lys Ser Val Pro Lys
                260                 265                 270
Ala Asp Val His Phe Leu Lys Ser Val Leu His Arg Gly Asp Asp Glu
                275                 280                 285
Phe Cys Val Lys Val Leu Lys Asn Cys Trp Glu Ala Leu Pro Pro Thr
290                 295                 300
Gly Lys Val Val Ile Val Glu Glu Val Thr Pro Glu Tyr Pro Gly Thr
305                 310                 315                 320
Asp Asp Val Ser Gln Thr Thr Leu
                325

<210> SEQ ID NO 275
<211> LENGTH: 160
<212> TYPE: PRT
<213> ORGANISM: Pinus radiata

<400> SEQUENCE: 275

Asp Val Gly Gly Gly Ile Gly Ser Ala Leu Ser Ile Ile Val Lys Glu
1               5                   10                  15
His Pro His Ile Arg Gly Ile Asn Leu Asp Leu Pro His Val Ile Ala
                20                  25                  30
Thr Ala Pro Leu Ile Thr Gly Val Glu His Met Glu Gly Asn Met Phe
                35                  40                  45
Glu His Ile Pro Ser Ala Asp Ala Val Met Met Lys Trp Ile Leu His
50                  55                  60
Asp Trp Ala Asp Glu Glu Cys Val Lys Leu Leu Arg Arg Ser Tyr Asp
65                  70                  75                  80
Ala Thr Pro Ala Lys Gly Lys Val Leu Ile Val Glu Ala Val Val Glu
                85                  90                  95
Gly Asp Lys Glu Gly Glu Ser Met Ser Arg Arg Leu Gly Leu Leu Tyr
                100                 105                 110
Asp Ile Ser Met Met Ala Tyr Thr Thr Gly Gly Lys Glu Arg Thr Glu
                115                 120                 125
Glu Glu Phe Lys Gly Leu Phe Gln Arg Ala Gly Phe Lys Ser His Thr
                130                 135                 140
Ile Ile Lys Leu Pro Phe Leu Gln Ser Leu Ile Val Leu Ser Lys Ala
145                 150                 155                 160
```

```
<210> SEQ ID NO 276
<211> LENGTH: 112
<212> TYPE: PRT
<213> ORGANISM: Eucalyptus grandis

<400> SEQUENCE: 276

Ser Leu Arg Thr Tyr Ser Asn Met Glu Gln Gly Trp Asp Lys Gly Glu
1               5                   10                  15

Ile Leu Ala Ser Lys Ala Leu Ser Lys Tyr Ile Leu Glu Thr Asn Ala
            20                  25                  30

Tyr Pro Arg Glu His Glu Gln Leu Lys Glu Leu Arg Glu Ala Thr Val
        35                  40                  45

Gln Lys Tyr Gln Ile Arg Ser Ile Met Asn Val Pro Val Asp Glu Gly
    50                  55                  60

Gln Leu Ile Ser Met Met Leu Lys Leu Met Asn Ala Lys Lys Thr Ile
65                  70                  75                  80

Glu Ile Gly Val Phe Thr Gly Tyr Ser Leu Leu Thr Thr Ala Leu Ala
                85                  90                  95

Leu Pro Ala Asp Gly Lys Ile Ile Ala Ile Asp Gln Asp Lys Glu Ala
            100                 105                 110

<210> SEQ ID NO 277
<211> LENGTH: 133
<212> TYPE: PRT
<213> ORGANISM: Eucalyptus grandis

<400> SEQUENCE: 277

Arg Thr Tyr Ser Asp Met Glu Arg Gly Gly Asp Lys Gly Glu Ile Leu
1               5                   10                  15

Ala Ser Lys Ala Leu Ser Lys Tyr Ile Leu Glu Thr Asn Ala Tyr Pro
            20                  25                  30

Arg Glu His Glu Gln Leu Lys Glu Leu Arg Glu Ala Thr Val Gln Lys
        35                  40                  45

Tyr Gln Met Arg Ser Ile Met Ser Val Pro Ala Asp Glu Gly Gln Leu
    50                  55                  60

Ile Ser Met Met Leu Lys Leu Met Asn Ala Lys Lys Thr Ile Glu Ile
65                  70                  75                  80

Gly Val Phe Thr Gly Tyr Ser Leu Leu Thr Thr Ala Leu Ala Leu Pro
                85                  90                  95

Ala Asp Gly Lys Ile Ile Ala Ile Asp Pro Asp Lys Glu Ala Tyr Glu
            100                 105                 110

Ile Gly Leu Pro Tyr Ile Lys Lys Ala Gly Val Asp His Lys Ile Asn
        115                 120                 125

Phe Ile Gln Ser Asp
    130

<210> SEQ ID NO 278
<211> LENGTH: 98
<212> TYPE: PRT
<213> ORGANISM: Eucalyptus grandis

<400> SEQUENCE: 278

Leu Gln Tyr Ile Leu Glu Thr Asn Ala Tyr Pro Arg Glu His Glu Gln
1               5                   10                  15

Leu Lys Glu Leu Arg Glu Ala Thr Val Gln Lys Tyr Gln Ile Arg Ser
            20                  25                  30

Ile Met Asn Val Pro Ala Asp Glu Gly Gln Leu Ile Ser Met Met Leu
```

```
                35                  40                  45
Lys Leu Met Asn Ala Lys Lys Thr Ile Glu Ile Gly Val Phe Thr Gly
         50                  55                  60
Cys Ser Leu Leu Thr Thr Ala Leu Ala Leu Pro Ala Asp Gly Lys Ile
 65                  70                  75                  80
Ile Ala Ile Asp Pro Asp Lys Glu Ala Tyr Glu Ile Gly Leu Pro Tyr
                 85                  90                  95
Ile Arg

<210> SEQ ID NO 279
<211> LENGTH: 157
<212> TYPE: PRT
<213> ORGANISM: Eucalyptus grandis

<400> SEQUENCE: 279

Arg His His Gln Thr Leu Thr Phe Ser Ser Ala Leu Cys Leu Cys
  1               5                  10                  15

Leu Cys Leu Ser Ile Leu Arg Pro Ala Thr Thr Met Glu Ala Lys Pro
                 20                  25                  30

Ser Glu Gln Pro Arg Glu Phe Ile Phe Arg Ser Lys Leu Pro Asp Ile
             35                  40                  45

Tyr Ile Pro Asp Asn Leu Ser Leu His Ala Tyr Cys Phe Glu Asn Ile
         50                  55                  60

Ser Glu Phe Ala Asp Arg Pro Cys Val Ile Asn Gly Ala Thr Gly Arg
 65                  70                  75                  80

Thr Tyr Thr Tyr Ala Glu Val Glu Leu Ile Ser Arg Arg Val Ser Ala
                 85                  90                  95

Gly Leu Asn Gly Leu Gly Val Gly Gln Gly Asp Val Ile Met Leu Leu
                100                 105                 110

Leu Gln Asn Cys Pro Glu Phe Val Phe Ala Phe Leu Gly Ala Ser Tyr
             115                 120                 125

Arg Gly Ala Ile Ser Thr Thr Ala Asn Pro Phe Tyr Thr Pro Gly Glu
         130                 135                 140

Ile Ala Lys Gln Ala Ser Ala Ala Arg Ala Lys Ile Val
145                 150                 155

<210> SEQ ID NO 280
<211> LENGTH: 180
<212> TYPE: PRT
<213> ORGANISM: Eucalyptus grandis

<400> SEQUENCE: 280

Phe Ala Asp Lys Val Arg Pro Phe Ala Glu Glu Asn Gly Val Lys Val
  1               5                  10                  15

Val Cys Ile Asp Thr Ala Pro Glu Gly Cys Leu His Phe Ser Glu Leu
                 20                  25                  30

Met Gln Ala Asp Glu Asn Ala Ala Pro Ala Ala Asp Val Lys Pro Asp
             35                  40                  45

Asp Val Leu Ala Leu Pro Tyr Ser Ser Gly Thr Thr Gly Leu Pro Lys
         50                  55                  60

Gly Val Met Leu Thr His Arg Gly Gln Val Thr Ser Val Ala Gln Gln
 65                  70                  75                  80

Val Asp Gly Asp Asn Pro Asn Leu Tyr Phe His Lys Glu Asp Val Ile
                 85                  90                  95

Leu Cys Thr Leu Pro Leu Phe His Ile Tyr Ser Leu Asn Ser Val Met
                100                 105                 110
```

```
Phe Cys Ala Leu Arg Val Gly Ala Ala Ile Leu Ile Met Gln Lys Phe
            115                 120                 125

Glu Ile Val Ala Leu Met Glu Leu Val Gln Arg Tyr Arg Val Thr Ile
        130                 135                 140

Leu Pro Ile Val Pro Pro Ile Val Leu Glu Ile Ala Lys Ser Ala Glu
145                 150                 155                 160

Val Asp Arg Tyr Asp Leu Ser Ser Ile Arg Thr Ile Met Ser Gly Ala
                165                 170                 175

Ala Arg Trp Gly
            180

<210> SEQ ID NO 281
<211> LENGTH: 180
<212> TYPE: PRT
<213> ORGANISM: Eucalyptus grandis

<400> SEQUENCE: 281

Gly Gln Leu Val Ala Gly Val Glu Ala Gln Val Ile Ser Val Asp Thr
1               5                   10                  15

Leu Lys Ser Leu Pro Pro Asn Gln Leu Gly Glu Ile Trp Val Arg Gly
            20                  25                  30

Pro Asn Met Met Lys Gly Tyr Tyr Asn Asn Pro Gln Ala Thr Lys Leu
        35                  40                  45

Thr Ile Asp Asn Lys Gly Trp Val His Thr Gly Asp Leu Gly Tyr Phe
    50                  55                  60

Asp Glu Glu Gly Gln Leu Tyr Val Val Asp Arg Ile Lys Glu Leu Ile
65                  70                  75                  80

Lys Tyr Lys Gly Phe Gln Ile Ala Pro Ala Glu Leu Glu Gly Leu Leu
                85                  90                  95

Leu Ser His Pro Glu Ile Leu Asp Ala Val Val Ile Pro Phe Pro Asp
            100                 105                 110

Ala Glu Ala Gly Glu Val Pro Ile Ala Tyr Val Val Arg Ser Pro Thr
        115                 120                 125

Ser Ser Leu Thr Glu Glu Val Gln Lys Phe Ile Ala Asn Gln Val
    130                 135                 140

Ala Pro Phe Lys Arg Leu Arg Val Thr Phe Val Asn Ser Val Pro
145                 150                 155                 160

Lys Ser Ala Ser Gly Lys Ile Leu Arg Arg Glu Leu Ile Ala Lys Val
                165                 170                 175

Arg Ala Lys Ile
            180

<210> SEQ ID NO 282
<211> LENGTH: 119
<212> TYPE: PRT
<213> ORGANISM: Pinus radiata

<400> SEQUENCE: 282

Gly Tyr Phe Asp Glu Glu Gly Gly Leu Phe Ile Val Asp Arg Ile Lys
1               5                   10                  15

Glu Leu Ile Lys Tyr Lys Gly Phe Gln Val Ala Pro Ala Glu Leu Glu
            20                  25                  30

Gly Ile Leu Leu Thr His Pro Gln Ile Ala Asp Ala Gly Val Ile Pro
        35                  40                  45

Leu Pro Asp Leu Lys Ala Gly Glu Val Pro Ile Ala Tyr Val Val Arg
    50                  55                  60
```

-continued

Thr Pro Gly Ser Ser Leu Thr Glu Lys Asp A la Met Asp Tyr Val Ala
65                  70                  75                  80

Lys Gln Val Ala Pro Phe Lys Arg Leu His A rg Val Asn Phe Val Asp
                85                  90                  95

Ser Ile Pro Lys Ser Ala Ser Gly Lys Ile L eu Arg Arg Glu Leu Ile
            100                 105                 110

Ala Lys Ala Lys Ser Lys Leu
        115

<210> SEQ ID NO 283
<211> LENGTH: 152
<212> TYPE: PRT
<213> ORGANISM: Pinus radiata

<400> SEQUENCE: 283

Asp Phe Pro Phe Phe Phe Leu Arg Val A la Met Ile Glu Val Gln
1               5                   10                  15

Ser Ala Pro Pro Met Ala Arg Ser Thr Glu A sn Glu Asn Gln His
            20                  25                  30

Asp Ala Glu Glu Gly Ala Val Leu Asn Glu G ly Gly Met Asp Phe Leu
        35                  40                  45

Tyr Arg Ser Lys Leu Pro Asp Ile Asp Ile P ro Tyr His Leu Pro Leu
    50                  55                  60

His Ser Tyr Cys Phe Glu Lys Leu Asp Glu L eu Arg Glu Lys Pro Cys
65                  70                  75                  80

Leu Ile Gln Gly Ser Asn Gly Lys Ile Tyr S er Tyr Gly Glu Val Glu
                85                  90                  95

Leu Ile Ser Arg Lys Val Ala Ser Gly Leu A la Lys Leu Gly Phe Lys
            100                 105                 110

Lys Gly Asp Val Val Met Leu Leu Pro A sn Cys Pro Glu Phe Val
        115                 120                 125

Phe Val Phe Leu Gly Ala Ser Met Ala Gly A la Ile Ala Thr Thr Ala
    130                 135                 140

Asn Pro Phe Tyr Thr Pro Ser Asp
145                 150

<210> SEQ ID NO 284
<211> LENGTH: 330
<212> TYPE: PRT
<213> ORGANISM: Eucalyptus grandis

<400> SEQUENCE: 284

Asp His Pro Pro Ala Met Ala Leu His Ile L eu Phe Thr Trp Leu Ala
1               5                   10                  15

Leu Ser Leu Pro Leu Leu Leu Leu Leu L eu Ser Val Lys Asn Phe
            20                  25                  30

Asn Asn Lys Lys Lys Asn Leu Pro Pro Gly P ro Pro Ser Leu Pro Ile
        35                  40                  45

Ile Gly Asn Phe His Gln Leu Gly Pro Leu P ro His Gln Ser Leu Trp
    50                  55                  60

Lys Leu Ser Arg Arg Tyr Gly Pro Val Met L eu Ile Arg Leu Gly Gly
65                  70                  75                  80

Thr Pro Thr Ile Val Ile Ser Ser Pro Asp A la Ala Arg Glu Val Leu
                85                  90                  95

Lys Thr His Asp Leu Asp Ser Cys Ser Arg P ro Gln Met Val Gly Pro
            100                 105                 110

```
Gly Arg Leu Ser Tyr Asp Ser Leu Asp Met Ala Phe Val Glu Tyr Gly
            115                 120                 125
Asp Tyr Trp Arg Glu Leu Arg Thr Leu Cys Val Leu Glu Leu Phe Ser
        130                 135                 140
Met Lys Arg Val Gln Ser Phe Arg Tyr Ile Arg Glu Glu Val Gly
145                 150                 155                 160
Ser Met Ile Glu Ser Ile Ala Lys Ser Ala Glu Ser Gly Thr Pro Val
                165                 170                 175
Asn Met Ser Glu Lys Phe Met Ala Leu Thr Ala Asn Phe Thr Cys Arg
            180                 185                 190
Val Ala Phe Gly Lys Pro Phe Gln Gly Thr Glu Leu Glu Asp Glu Gly
            195                 200                 205
Phe Met Asp Met Val His Glu Gly Met Ala Met Leu Gly Ser Phe Ser
        210                 215                 220
Ala Ser Asp Tyr Phe Pro Arg Leu Gly Trp Ile Val Asp Arg Phe Thr
225                 230                 235                 240
Gly Leu His Ser Arg Leu Glu Lys Ser Phe Arg Asn Leu Asp Asp Leu
            245                 250                 255
Tyr Gln Lys Val Ile Glu Glu His Arg Asn Ala Asn Lys Ser Asn Glu
            260                 265                 270
Gly Lys Glu Asp Ile Val Asp Val Leu Leu Lys Met Glu Lys Asp Gln
        275                 280                 285
Thr Glu Leu Ala Gly Val Arg Leu Lys Glu Asp Asn Ile Lys Ala Ile
        290                 295                 300
Leu Met Asn Ile Phe Leu Gly Gly Val Asp Thr Gly Ala Val Ser Trp
305                 310                 315                 320
Thr Gly Gln Trp Leu Ser Ser Leu Gly Thr
                325                 330

<210> SEQ ID NO 285
<211> LENGTH: 115
<212> TYPE: PRT
<213> ORGANISM: Eucalyptus grandis

<400> SEQUENCE: 285

Thr Glu Leu Glu Asp Glu Gly Phe Met Asp Met Val His Glu Gly Met
  1               5                   10                  15
Ala Met Leu Gly Ser Phe Ser Ala Ser Asp Tyr Phe Pro Arg Leu Gly
                20                  25                  30
Trp Ile Val Asp Arg Phe Thr Gly Leu His Ser Arg Leu Glu Lys Ser
            35                  40                  45
Phe Arg Asn Leu Asp Asp Leu Tyr Gln Lys Val Ile Glu Glu His Arg
        50                  55                  60
Asn Ala Asn Lys Ser Asn Glu Gly Lys Glu Asp Ile Val Asp Val Leu
65                  70                  75                  80
Leu Lys Met Glu Lys Asp Gln Thr Glu Leu Ala Gly Val Arg Leu Lys
                85                  90                  95
Glu Asp Asn Ile Lys Ala Ile Leu Met Val Tyr His Thr Ile Ser Thr
            100                 105                 110
Tyr Tyr Leu
        115

<210> SEQ ID NO 286
<211> LENGTH: 143
<212> TYPE: PRT
```

<213> ORGANISM: Eucalyptus grandis

<400> SEQUENCE: 286

```
Leu Val Val Ala Ala Leu Leu Ile Val Leu L eu Arg Ser Lys Ser Arg
  1               5                  10                  15

Lys Arg Lys Ser Asn Leu Pro Ser Pro P ro Lys Leu Pro Ile Ile
             20                  25                  30

Gly Asn Leu His Gln Leu Gly Lys Ser Pro H is Ile Ser Leu His Arg
             35                  40                  45

Leu Ala Arg Asn Tyr Gly Pro Ile Met Ser L eu Gln Leu Gly Glu Val
         50                  55                  60

Pro Thr Ile Val Val Ser Ser Ala Ala Met A la Lys Glu Val Met Lys
 65                  70                  75                  80

Thr His Asp Leu Val Leu Ala Asn Arg Pro G ln Ile Phe Ser Ala Lys
                 85                  90                  95

His Leu Phe Tyr Asp Cys Thr Asp Met Ala P he Ser Pro Tyr Gly Ala
            100                 105                 110

Tyr Trp Arg His Ile Arg Lys Ile Cys Ile L eu Glu Val Leu Ser Ala
            115                 120                 125

Lys Arg Val Gln Ser Phe Ser His Val Arg G lu Glu Glu Val Ala
        130                 135                 140
```

<210> SEQ ID NO 287
<211> LENGTH: 135
<212> TYPE: PRT
<213> ORGANISM: Eucalyptus grandis

<400> SEQUENCE: 287

```
 eu Thr Phe Lys Cys Leu Arg Phe Leu Phe Ser Ser Ala Ala Ala Thr
  1               5                  10                  15 sn Leu His Leu Pro Pro Ser Pro Pro Lys Le u Pro Ile Ile Gly Asn
             20                  25                  30

Leu His Gln Leu Ser Asp His Pro His Arg S er Leu Gln Ala Leu Ser
             35                  40                  45

Arg Arg Tyr Gly Pro Leu Met Met Leu His P he Gly Ser Val Pro Val
         50                  55                  60

Leu Val Val Ser Ser Ala Asp Cys Ala Arg A sp Ile Leu Lys Thr His
 65                  70                  75                  80

Asp Leu Ile Phe Ser Asp Arg Pro Arg Ser T hr Leu Ser Glu Arg Leu
                 85                  90                  95

Leu Tyr His Arg Lys Asp Val Ala Leu Ala P ro Phe Gly Glu Tyr Trp
            100                 105                 110

Arg Glu Met Arg Ser Ile Cys Val Leu L eu Leu Ser Asn Lys Arg
            115                 120                 125

Val His Ser Phe Arg Thr Val
        130                 135
```

<210> SEQ ID NO 288
<211> LENGTH: 128
<212> TYPE: PRT
<213> ORGANISM: Eucalyptus grandis

<400> SEQUENCE: 288

```
Gly Lys Leu Pro His Arg Ser Leu Asp Arg L eu Ser Lys Thr Tyr Gly
  1               5                  10                  15

Pro Leu Met Tyr Met Arg Leu Gly Ser Met P ro Cys Val Val Gly Ser
             20                  25                  30
```

```
Ser Ala Glu Met Ala Arg Glu Phe Leu Lys Thr His Asp Leu Thr Phe
            35                  40                  45

Ser Ser Arg Pro Arg Val Ala Ala Gly Lys Tyr Thr Val Tyr Asn Tyr
        50                  55                  60

Ser Asp Ile Thr Trp Ser Pro Tyr Gly Glu His Trp Arg Leu Ala Arg
 65                  70                  75                  80

Lys Ile Cys Leu Met Glu Leu Phe Ser Ala Lys Arg Leu Glu Ser Phe
                    85                  90                  95

Glu Tyr Ile Arg Val Glu Glu Val Ala Arg Met Leu Ser Ser Val Phe
                100                 105                 110

Glu Thr Ser Arg Gln Gly Leu Pro Val Glu Ile Arg Glu Glu Thr Thr
            115                 120                 125

<210> SEQ ID NO 289
<211> LENGTH: 179
<212> TYPE: PRT
<213> ORGANISM: Eucalyptus grandis

<400> SEQUENCE: 289

Ile Arg Met Val Asn Glu Leu Gly Ser Glu Lys Pro Phe Leu Val Cys
 1               5                  10                  15

Leu Glu Phe Tyr Met Lys Leu Ala Ile Ala Leu Val Ala Leu Val Val
                20                  25                  30

Ala Trp Ser Phe Phe Val Lys Gly Arg Asn Arg Lys Leu Pro Pro Gly
            35                  40                  45

Pro Phe Ser Leu Pro Ile Ile Gly Asn Leu His Leu Leu Gly Gln Leu
        50                  55                  60

Pro His Arg Ala Leu Thr Ala Leu Ser Leu Lys Phe Gly Pro Leu Met
 65                  70                  75                  80

Ser Leu Arg Leu Gly Ser Ala Leu Thr Leu Val Val Ser Ser Pro Asp
                    85                  90                  95

Met Ala Lys Glu Phe Leu Lys Thr His Asp Leu Leu Phe Ala Ser Arg
                100                 105                 110

Pro Pro Ser Ala Ala Thr Asn Tyr Phe Trp Tyr Asn Cys Thr Asp Ile
            115                 120                 125

Gly Phe Ala Pro Tyr Gly Ala Tyr Trp Arg Gln Val Arg Lys Val Cys
        130                 135                 140

Val Leu Gln Leu Leu Ser Ser Arg Arg Leu Asp Tyr Phe Arg Phe Ile
145                 150                 155                 160

Arg Glu Glu Glu Val Ser Ala Met Ile His Ser Ile Ala His Ser Asp
                165                 170                 175

His Pro Val

<210> SEQ ID NO 290
<211> LENGTH: 440
<212> TYPE: PRT
<213> ORGANISM: Eucalyptus grandis

<400> SEQUENCE: 290

Ser Ser Leu Ala Phe Gly Gln His Ile Ile Ala Thr Ser Tyr Ser Cys
 1               5                  10                  15

Asn Leu His Gln Ile Gly Glu Met Ser Phe Gln Asn Gln Leu Phe Ile
                20                  25                  30

Phe Cys Thr Leu Leu Leu Gly Phe Leu Lys Leu Ala Glu Gly Lys Thr
            35                  40                  45
```

```
Arg His Tyr Thr Phe His Ile Asp Ser His Asn Met Thr Arg Leu Cys
 50                  55                  60
His Thr Arg Ser Val Leu Ser Val Asn Lys Gln Tyr Pro Gly Pro Pro
 65                  70                  75                  80
Leu Val Ala Arg Glu Gly Asp Asn Ile Leu Val Lys Val Val Asn His
                 85                  90                  95
Val Ala Ala Asn Val Thr Ile His Trp His Gly Val Arg Gln Leu Arg
            100                 105                 110
Thr Gly Trp Ala Asp Gly Pro Ala Tyr Val Thr Gln Cys Pro Ile Gln
        115                 120                 125
Thr Asn Gln Ser Tyr Thr Tyr Asn Phe Thr Leu Thr Gly Gln Arg Gly
130                 135                 140
Thr Leu Leu Trp His Ala His Val Ser Trp Leu Arg Ser Ser Ile His
145                 150                 155                 160
Gly Pro Ile Ile Ile Leu Pro Lys Arg Asn Glu Ser Tyr Pro Phe Glu
                165                 170                 175
Lys Pro Ser Lys Glu Val Pro Ile Ile Phe Gly Glu Trp Phe Asn Val
            180                 185                 190
Asp Pro Glu Ala Val Ile Ala Gln Ala Leu Gln Ser Gly Gly Gly Pro
        195                 200                 205
Asn Val Ser Asp Ala Tyr Thr Ile Asn Gly Leu Pro Gly Pro Leu Tyr
210                 215                 220
Asn Cys Ser Ser Lys Asp Thr Phe Lys Leu Lys Val Lys Pro Gly Lys
225                 230                 235                 240
Thr Tyr Leu Leu Arg Leu Ile Asn Ala Ala Leu Asn Asp Glu Leu Phe
                245                 250                 255
Phe Ser Ile Ala Asn His Ala Val Thr Val Val Glu Val Asp Ala Val
            260                 265                 270
Tyr Thr Lys Pro Phe Ser Ala Gly Cys Leu His Leu Thr Pro Gly Gln
        275                 280                 285
Thr Met Asn Val Leu Leu Lys Thr Lys Thr Asp Phe Pro Asn Ser Thr
290                 295                 300
Phe Leu Met Ala Ala Trp Pro Tyr Phe Thr Gly Met Gly Thr Phe Asp
305                 310                 315                 320
Asn Ser Thr Val Ala Gly Ile Leu Glu Tyr Glu His Pro Lys Ser Ser
                325                 330                 335
Asn Tyr Pro Pro Leu Lys Lys Leu Pro Gln Tyr Lys Pro Thr Leu Pro
            340                 345                 350
Pro Met Asn Ser Thr Gly Phe Val Ala Lys Phe Thr Gly Gln Leu Arg
        355                 360                 365
Ser Leu Ala Ser Ala Lys Phe Pro Ala Asn Val Pro Gln Lys Val Asp
370                 375                 380
Arg Lys Phe Phe Phe Thr Val Gly Leu Gly Thr Ser Pro Cys Pro Lys
385                 390                 395                 400
Asn Thr Thr Cys Gln Gly Pro Asn Gly Thr Lys Phe Ala Ala Ser Val
                405                 410                 415
Asn Asn Ile Ser Phe Val Leu Pro Ser Val Ala Leu Leu Gln Ala His
            420                 425                 430
Phe Phe Gly Gln Ser Asn Gly Val
        435                 440

<210> SEQ ID NO 291
<211> LENGTH: 326
<212> TYPE: PRT
```

-continued

<213> ORGANISM: Eucalyptus grandis

<400> SEQUENCE: 291

```
Pro Ala Val Val Glu Gly Arg Val Arg Asn Tyr Thr Phe Asn Val Val
  1               5                  10                  15

Met Lys Asn Thr Thr Arg Leu Cys Ser Ser Lys Pro Ile Val Thr Val
             20                  25                  30

Asn Gly Met Phe Pro Gly Pro Thr Leu Tyr Ala Arg Glu Asp Asp Thr
         35                  40                  45

Val Leu Val Arg Val Ser Asn Arg Val Lys Tyr Asn Val Thr Ile His
     50                  55                  60

Trp His Gly Ile Arg Gln Leu Arg Thr Gly Trp Ala Asp Gly Pro Ala
 65                  70                  75                  80

Tyr Ile Thr Gln Cys Pro Ile Gln Pro Gly Gln Ser Tyr Val Tyr Asn
                 85                  90                  95

Phe Thr Ile Thr Gly Gln Arg Gly Thr Leu Leu Trp His Ala His Ile
            100                 105                 110

Leu Trp Leu Arg Ala Thr Leu His Gly Ala Ile Val Ile Leu Pro Lys
        115                 120                 125

Arg Gly Val Pro Tyr Pro Phe Pro Lys Pro His Lys Glu Val Val Val
    130                 135                 140

Val Leu Gly Glu Trp Trp Lys Ser Asp Thr Glu Gly Val Ile Ser Gln
145                 150                 155                 160

Ala Ile Lys Ser Gly Leu Ala Pro Asn Val Ser Asp Ala His Thr Ile
                165                 170                 175

Asn Gly His Pro Gly Pro Ser Ser Asn Cys Pro Ser Gln Gly Gly Phe
            180                 185                 190

Thr Leu Pro Val Glu Ser Gly Lys Lys Tyr Met Leu Arg Ile Ile Asn
        195                 200                 205

Ala Ala Leu Asn Glu Glu Leu Phe Phe Lys Ile Ala Gly His Gln Leu
    210                 215                 220

Thr Ile Val Glu Val Asp Ala Thr Tyr Val Lys Pro Phe Lys Thr Asp
225                 230                 235                 240

Thr Ile Val Ile Ala Pro Gly Gln Thr Thr Asn Ala Leu Ile Ser Thr
                245                 250                 255

Asp Gln Ser Ser Gly Lys Tyr Met Val Ala Ala Ser Pro Phe Met Asp
            260                 265                 270

Ser Pro Ile Ala Val Asp Asn Met Thr Ala Thr Ala Thr Leu His Tyr
        275                 280                 285

Ser Gly Thr Leu Ala Ala Thr Ser Thr Thr Leu Thr Lys Thr Pro Pro
    290                 295                 300

Gln Asn Ala Thr Ala Val Ala Asn Asn Phe Val Asn Ser Leu Arg Ser
305                 310                 315                 320

Leu Asn Ser Lys Arg Tyr
                325
```

<210> SEQ ID NO 292
<211> LENGTH: 101
<212> TYPE: PRT
<213> ORGANISM: Eucalyptus grandis

<400> SEQUENCE: 292

```
Arg Leu Cys Ser Ser Lys Pro Ile Val Thr Val Asn Gly Met Phe Pro
  1               5                  10                  15

Gly Pro Thr Leu Tyr Ala Arg Glu Asp Asp Thr Val Leu Val Arg Val
```

```
                20                  25                  30
Ser Asn Arg Val Lys Tyr Asn Val Thr Ile H is Trp His Gly Ile Arg
             35                  40                  45

Gln Leu Arg Ser Gly Trp Ala Asp Gly Pro A la Tyr Ile Thr Gln Cys
     50                  55                  60

Pro Ile Gln Pro Gly Gln Ser Tyr Val Tyr A sn Phe Thr Ile Thr Gly
 65                  70                  75                  80

Gln Arg Gly Thr Leu Leu Trp His Ala His I le Leu Trp Leu Arg Ala
             85                  90                  95

Thr Leu His Gly Ala
            100

<210> SEQ ID NO 293
<211> LENGTH: 136
<212> TYPE: PRT
<213> ORGANISM: Eucalyptus grandis

<400> SEQUENCE: 293

Thr Val Asp His Ser Leu Leu Phe Thr Val G ly Leu Gly Ile Asn Pro
  1               5                  10                  15

Cys Pro Ser Cys Lys Ala Gly Asn Gly Ser A rg Val Val Ala Ser Met
             20                  25                  30

Asn Asn Val Thr Phe Val Met Pro Thr Thr A la Ile Leu Gln Ala His
             35                  40                  45

Phe Phe Asn Lys Ser Gly Val Phe Thr Ser A sp Phe Pro Gly Asn Pro
     50                  55                  60

Pro Thr Ile Phe Asn Tyr Thr Gly Ser Pro P ro Ser Asn Leu Arg Thr
 65                  70                  75                  80

Thr Ser Gly Thr Lys Val Tyr Arg Leu Arg T yr Asn Ser Thr Val Gln
             85                  90                  95

Leu Val Phe Gln Asp Thr Gly Ile Ile Ala P ro Glu Asn His Pro Ile
            100                 105                 110

His Leu His Gly Phe Asn Phe Phe Ala Ile G ly Lys Gly Leu Gly Asn
            115                 120                 125

Tyr Asn Pro Lys Val Asp Gln Lys
            130                 135

<210> SEQ ID NO 294
<211> LENGTH: 104
<212> TYPE: PRT
<213> ORGANISM: Eucalyptus grandis

<400> SEQUENCE: 294

His Lys Glu Val Val Val Leu Gly Glu T rp Trp Lys Ser Asp Thr
  1               5                  10                  15

Glu Ala Val Ile Asn Gln Ala Ile Lys Ser G ly Leu Ala Pro Asn Val
             20                  25                  30

Ser Asp Ala His Thr Ile Asn Gly His Pro G ly Pro Ser Ser Asn Cys
             35                  40                  45

Pro Ser Gln Gly Gly Phe Thr Leu Pro Val G lu Ser Gly Lys Lys Tyr
     50                  55                  60

Met Leu Arg Ile Ile Asn Ala Ala Leu Asn G lu Leu Phe Phe Lys
 65                  70                  75                  80

Ile Ala Gly His Gln Leu Thr Ile Val Glu V al Asp Ala Thr Tyr Val
             85                  90                  95

Lys Pro Phe Lys Thr Asn Thr Gly
```

```
                    100
```

<210> SEQ ID NO 295
<211> LENGTH: 110
<212> TYPE: PRT
<213> ORGANISM: Eucalyptus grandis

<400> SEQUENCE: 295

Arg Gly Val Pro Tyr Pro Phe Pro Lys Pro His Lys Glu Val Val Val
 1               5                  10                  15

Val Leu Gly Glu Trp Trp Lys Ser Asp Thr Glu Ala Val Ile Asn Gln
            20                  25                  30

Ala Ile Lys Ser Gly Leu Ala Pro Asn Val Ser Asp Ala His Thr Ile
        35                  40                  45

Asn Gly His Pro Gly Pro Ser Ser Asn Cys Pro Ser Gln Gly Gly Phe
    50                  55                  60

Thr Leu Pro Val Glu Ser Gly Lys Lys Tyr Met Leu Arg Ile Ile Asn
65                  70                  75                  80

Ala Ala Leu Asn Glu Glu Leu Phe Phe Lys Ile Ala Gly His Gln Leu
                85                  90                  95

Thr Ile Val Glu Val Asp Ala Thr Tyr Val Lys Pro Phe Lys
            100                 105                 110

<210> SEQ ID NO 296
<211> LENGTH: 384
<212> TYPE: PRT
<213> ORGANISM: Eucalyptus grandis

<400> SEQUENCE: 296

Pro Asn Val Ser Asp Ala Tyr Thr Ile Asn Gly Gln Pro Gly Asp Leu
 1               5                  10                  15

Tyr Asn Cys Ser Ser Lys Asp Thr Val Ile Val Pro Ile Asp Ser Gly
            20                  25                  30

Glu Thr His Leu Leu Arg Val Ile Asn Ala Ala Leu Asn Gln Glu Leu
        35                  40                  45

Phe Phe Thr Val Ala Asn His Arg Phe Thr Val Val Gly Ala Asp Ala
    50                  55                  60

Ser Tyr Leu Lys Pro Phe Thr Thr Ser Val Ile Met Leu Gly Pro Gly
65                  70                  75                  80

Gln Thr Thr Asp Val Leu Ile Ser Gly Asp Gln Pro Pro Ala Arg Tyr
                85                  90                  95

Tyr Met Ala Ala Glu Pro Tyr Gln Ser Ala Gln Gly Ala Pro Phe Asp
            100                 105                 110

Asn Thr Thr Thr Ala Ile Leu Glu Tyr Lys Ser Ala Pro Cys Pro
        115                 120                 125

Ala Lys Gly Ile Ser Ser Lys Pro Val Met Pro Thr Leu Pro Ala Phe
    130                 135                 140

Asn Asp Thr Ala Thr Val Thr Ala Phe Ile Gln Ser Phe Arg Ser Pro
145                 150                 155                 160

Asn Lys Val Asp Val Pro Thr Asp Ile Asp Glu Asn Leu Phe Ile Thr
                165                 170                 175

Val Gly Leu Gly Leu Phe Asn Cys Pro Lys Asn Phe Gly Ser Ser Arg
            180                 185                 190

Cys Gln Gly Pro Asn Gly Thr Arg Phe Thr Ala Ser Met Asn Asn Val
        195                 200                 205

Ser Phe Val Leu Pro Ser Asn Val Ser Ile Leu Gln Ala Tyr Lys Gln

```
                   210                 215                 220
Gly Val Pro Gly Val Phe Thr Thr Asp Phe Pro Ala Asn Pro Pro Val
225                 230                 235                 240

Gln Phe Asp Tyr Thr Gly Asn Val Ser Arg Ser Leu Trp Gln Pro Val
                245                 250                 255

Pro Gly Thr Lys Val Tyr Lys Leu Lys Tyr Gly Ser Arg Val Gln Ile
                260                 265                 270

Val Leu Gln Gly Thr Asn Ile Gln Thr Ala Glu Asn His Pro Ile His
            275                 280                 285

Ile His Gly Tyr Asp Phe Tyr Ile Leu Ala Thr Gly Phe Gly Asn Phe
        290                 295                 300

Asn Pro Gln Lys Asp Thr Ala Lys Phe Asn Leu Val Asp Pro Pro Met
305                 310                 315                 320

Arg Asn Thr Val Gly Val Ser Val Asn Gly Trp Ala Val Ile Arg Phe
                325                 330                 335

Val Ala Asp Asn Pro Gly Ala Trp Leu Met His Cys His Leu Asp Val
            340                 345                 350

His Ile Thr Trp Gly Leu Ala Val Val Phe Leu Val Glu Asn Gly Val
        355                 360                 365

Gly Glu Leu Gln Ser Leu Gln Pro Pro Ala Asp Leu Pro Pro Cys
    370                 375                 380

<210> SEQ ID NO 297
<211> LENGTH: 139
<212> TYPE: PRT
<213> ORGANISM: Eucalyptus grandis

<400> SEQUENCE: 297

Ser Cys Leu Ser Leu His His His Leu Arg Gln Val Thr Ser Asp Phe
1               5                   10                  15

Glu Glu Asp Glu Arg Lys Met Gly Ser Ala Thr Ala Ala Gly Ala
            20                  25                  30

Ser Val Ser Ser Arg Met Ile Leu Met Arg Ala Ala Phe Phe Thr Leu
        35                  40                  45

Cys Ala Leu Val Phe Leu Pro Ala Leu Ala Gln Ala Lys His Gly Gly
    50                  55                  60

Val Thr Arg His Tyr Lys Phe Asp Ile Lys Met Gln Asn Val Thr Arg
65                  70                  75                  80

Leu Cys Gln Thr Lys Ser Ile Val Thr Val Asn Gly Gln Leu Pro Gly
                85                  90                  95

Pro Arg Ile Ile Ala Arg Glu Gly Asp Arg Leu Leu Ile Lys Val Val
            100                 105                 110

Asn Asn Val Gln Tyr Asn Val Thr Ile His Trp His Gly Val Arg Gln
        115                 120                 125

Leu Arg Ser Gly Trp Ala Asp Gly Pro Ala Tyr
    130                 135

<210> SEQ ID NO 298
<211> LENGTH: 155
<212> TYPE: PRT
<213> ORGANISM: Eucalyptus grandis

<400> SEQUENCE: 298

Pro Asp Arg Val Ile Ser Thr Ser Ser Ile Leu Tyr Gln Gly Glu Arg
1               5                   10                  15

Gly Thr Met Gly Thr Phe Leu Gly Phe Ala Val Thr Ala Thr Leu Leu
```

-continued

```
                    20                  25                  30
Phe Cys Val Ala Gln Gly Glu Val Leu Phe Tyr Asp Phe Val Asn
                35                  40                  45
Glu Thr Pro Ile Glu Met Leu Cys Glu Thr Asn Arg Ser Val Leu Thr
 50                  55                  60
Val Asn Gly Leu Phe Pro Gly Pro Glu Ile His Ala His Lys Gly Asp
 65                  70                  75                  80
Thr Ile Tyr Val Asn Val Thr Asn Leu Gly Pro Tyr Gly Val Thr Ile
                85                  90                  95
His Trp His Gly Val Arg Gln Ile Arg Tyr Pro Trp Ser Asp Gly Pro
               100                 105                 110
Glu Tyr Val Thr Gln Cys Pro Ile Pro Thr Asn Ser Ser Phe Leu Gln
               115                 120                 125
Lys Ile Lys Leu Thr Glu Glu Gly Thr Val Trp Trp His Ala His
           130                 135                 140
Ser Asp Trp Ser Arg Ala Thr Ile His Gly Leu
145                 150                 155
```

<210> SEQ ID NO 299
<211> LENGTH: 179
<212> TYPE: PRT
<213> ORGANISM: Eucalyptus grandis

<400> SEQUENCE: 299

```
Leu Leu Gln Val His Phe Ser Leu Val Glu Arg Glu Arg Glu Met Gly
 1               5                  10                  15
Thr Phe Leu Gly Phe Val Val Thr Met Thr Leu Leu Phe Cys Met Ala
                20                  25                  30
Gln Gly Glu Val Ile Tyr Tyr Asp Phe Val Val Lys Glu Thr Pro Ile
            35                  40                  45
Gln Met Leu Cys Gly Thr Asn Gln Thr Val Leu Thr Val Asn Gly Leu
 50                  55                  60
Phe Pro Gly Pro Glu Ile His Ala His Lys Gly Asp Thr Ile Tyr Val
 65                  70                  75                  80
Asn Val Thr Asn Thr Gly Pro Tyr Gly Val Thr Ile His Trp His Gly
                85                  90                  95
Val Arg Gln Ile Arg Tyr Pro Trp Ser Asp Gly Pro Glu Tyr Ile Thr
           100                 105                 110
Gln Cys Pro Ile Pro Thr Asn Ser Ser Phe Leu Gln Lys Ile Ile Leu
           115                 120                 125
Thr Glu Glu Gly Thr Leu Trp Trp His Ala His Ser Asp Trp Thr
130                 135                 140
Arg Ala Thr Ile His Gly Pro Ile Ile Leu Pro Val Asn Gly Thr
145                 150                 155                 160
Asn Tyr Pro Tyr Lys Phe Asp Glu Gln His Thr Ile Val Ile Ser Glu
                165                 170                 175
Trp Tyr Ala
```

<210> SEQ ID NO 300
<211> LENGTH: 62
<212> TYPE: PRT
<213> ORGANISM: Eucalyptus grandis

<400> SEQUENCE: 300

```
Glu Arg Glu Met Gly Thr Phe Leu Gly Phe Val Val Thr Met Thr Leu
 1               5                  10                  15
```

Leu Phe Cys Met Ala Gln Gly Glu Val Leu Tyr Tyr Asp Phe Val Val
                    20                  25                  30

Lys Glu Thr Pro Ile Gln Met Leu Cys Gly Thr Asn Gln Thr Val Leu
            35                  40                  45

Thr Val Asn Gly Leu Phe Pro Gly Pro Glu Ile His Ala His
    50                  55                  60

<210> SEQ ID NO 301
<211> LENGTH: 190
<212> TYPE: PRT
<213> ORGANISM: Pinus radiata

<400> SEQUENCE: 301

Leu Ala Val Met Ser Asn Glu Gln Leu Leu Glu Phe Ala Trp Gly Leu
 1               5                  10                  15

Ala Ser Ser Asn Gln Ser Phe Leu Trp Val Val Arg Ser Asp Ile Val
                20                  25                  30

His Gly Glu Ser Ala Ile Leu Pro Lys Glu Phe Ile Glu Glu Thr Lys
            35                  40                  45

Asp Arg Gly Met Leu Val Gly Trp Ala Pro Gln Ile Lys Val Leu Ser
        50                  55                  60

His Pro Ser Val Gly Gly Phe Leu Thr His Ser Gly Trp Asn Ser Thr
65                  70                  75                  80

Leu Glu Ser Ile Ser Ala Gly Val Pro Met Met Cys Trp Pro Phe Phe
                85                  90                  95

Ala Glu Gln Glu Thr Asn Ala Lys Phe Val Cys Glu Glu Trp Gly Ile
            100                 105                 110

Gly Met Gln Val Lys Lys Met Val Lys Arg Glu Glu Leu Ala Ile Leu
        115                 120                 125

Val Arg Asn Ser Ile Lys Gly Glu Glu Gly Asp Glu Met Arg Lys Arg
    130                 135                 140

Ile Gly Lys Leu Lys Glu Thr Ala Lys Arg Ala Val Ser Glu Gly Gly
145                 150                 155                 160

Ser Ser Lys Asn Asn Leu Asp Lys Leu Leu His His Ile Phe Leu Lys
                165                 170                 175

Gly Met His Gln Met Ile Val Gln Asn Val Glu Ala Asn Asn
            180                 185                 190

<210> SEQ ID NO 302
<211> LENGTH: 365
<212> TYPE: PRT
<213> ORGANISM: Eucalyptus grandis

<400> SEQUENCE: 302

Pro Met Glu Ser Cys Ser Ile Ser Leu Phe Trp Leu Gly Leu Leu Leu
 1               5                  10                  15

Pro Ala Leu Leu Val Phe Leu Leu Asn Arg Arg Lys Arg Thr Lys Leu
                20                  25                  30

Pro Pro Gln Pro Pro Ala Trp Pro Val Ile Gly Asn Ile Phe Asp Leu
            35                  40                  45

Gly Thr Met Pro His Gln Asn Leu His Asn Leu Arg Ala Lys His Gly
        50                  55                  60

Pro Val Leu Trp Leu Lys Leu Gly Ser Val Asn Thr Met Val Ile Gln
65                  70                  75                  80

Ser Ala Arg Ala Ala Met Glu Leu Phe Lys Gly His Asp Phe Val Phe
                85                  90                  95

```
Ala Asp Arg Lys Cys Ser Gln Ala Phe Thr Ala Leu Gly Tyr Asp Gln
            100                 105                 110

Gly Ser Leu Ala Leu Gly Arg His Gly Asp Tyr Trp Arg Ala Leu Arg
        115                 120                 125

Arg Leu Cys Ser Ala Glu Leu Val Asn Lys Arg Val Asn Asp Thr
    130                 135                 140

Ala His Leu Arg Gln Lys Cys Val Asp Ser Met Ile Met Tyr Ile Glu
145                 150                 155                 160

Glu Glu Met Ala Val Lys Gln Ala Thr Lys Gly Gln Gly Ile Asp Leu
                165                 170                 175

Ser His Phe Leu Phe Leu Leu Ala Phe Asn Val Val Gly Asn Met Val
            180                 185                 190

Leu Ser Arg Asp Leu Leu Asp Pro Lys Ser Lys Asp Gly Pro Glu Phe
        195                 200                 205

Tyr Asp Ala Met Asn Arg Phe Met Glu Trp Ala Gly Lys Pro Asn Val
    210                 215                 220

Ala Asp Phe Met Pro Trp Leu Lys Trp Leu Asp Pro Gln Gly Ile Lys
225                 230                 235                 240

Ala Gly Met Ala Lys Asp Met Gly Arg Ala Met Arg Ile Ala Glu Gly
                245                 250                 255

Phe Val Lys Glu Arg Leu Glu Glu Arg Lys Leu Arg Gly Glu Met Arg
            260                 265                 270

Thr Thr Asn Asp Phe Leu Asp Ala Val Leu Asp Tyr Glu Gly Asp Gly
        275                 280                 285

Lys Glu Gly Pro His Asn Ile Ser Ser Gln Asn Ile Asn Ile Ile Ile
    290                 295                 300

Leu Glu Met Phe Phe Ala Gly Ser Glu Ser Thr Ser Ser Thr Ile Glu
305                 310                 315                 320

Trp Ala Met Ala Glu Leu Leu Arg Gln Pro Glu Ser Met Lys Lys Ala
                325                 330                 335

Lys Asp Glu Ile Asp Gln Val Val Gly Leu Asn Arg Lys Leu Glu Glu
            340                 345                 350

Asn Asp Thr Glu Lys Met Pro Phe Leu Gln Ala Val Val
        355                 360                 365

<210> SEQ ID NO 303
<211> LENGTH: 183
<212> TYPE: PRT
<213> ORGANISM: Eucalyptus grandis

<400> SEQUENCE: 303

Pro Met Glu Ser Cys Ser Ile Ser Leu Phe Trp Leu Gly Leu Leu Leu
1               5                   10                  15

Pro Ala Leu Leu Val Phe Leu Leu Asn Arg Arg Lys Arg Thr Lys Leu
            20                  25                  30

Pro Pro Gln Pro Pro Ala Trp Pro Val Ile Gly Asn Ile Phe Asp Leu
        35                  40                  45

Gly Thr Met Pro His Gln Asn Leu His Asn Leu Arg Ala Lys His Gly
    50                  55                  60

Pro Val Leu Trp Leu Lys Leu Gly Ser Val Asn Thr Met Val Ile Gln
65                  70                  75                  80

Ser Ala Gln Ala Ala Met Glu Leu Phe Lys Gly His Asp Phe Val Phe
                85                  90                  95
```

```
Ala Asp Arg Lys Cys Ser Gln Ala Phe Thr Ala Leu Gly Tyr Asp Gln
            100                 105                 110

Gly Ser Leu Ala Leu Gly Arg His Gly Asp Tyr Trp Arg Ala Leu Arg
        115                 120                 125

Arg Leu Cys Ser Ala Glu Leu Leu Val Asn Lys Arg Val Asn Glu Thr
    130                 135                 140

Ala His Leu Arg Gln Lys Cys Val Asp Ser Met Ile Met Tyr Ile Glu
145                 150                 155                 160

Glu Glu Met Ala Val Lys Gln Ala Thr Lys Gly Gln Gly Ile Asp Leu
                165                 170                 175

Ser His Phe Leu Phe Leu Leu
            180

<210> SEQ ID NO 304
<211> LENGTH: 148
<212> TYPE: PRT
<213> ORGANISM: Eucalyptus grandis

<400> SEQUENCE: 304

Met Lys Ala Gln Asp Glu Ile Asp Ser Met Ile Gly His Asp Ser Leu
1               5                   10                  15

Leu Glu Glu Ser Asp Val Ser Lys Leu Pro Tyr Leu Gln Cys Ile Ile
            20                  25                  30

Leu Glu Thr Leu Arg Leu Asn Thr Thr Ala Pro Leu Leu Leu Pro His
        35                  40                  45

Ala Ser Ser Ala Asp Cys Thr Ile Gly Gly Tyr Phe Val Pro Arg Asp
    50                  55                  60

Thr Ile Val Met Val Asn Ala Trp Ala Ile His Lys Asp Pro Gln Leu
65                  70                  75                  80

Trp Glu Asp Pro Leu Ser Phe Lys Pro Glu Arg Phe Glu Gly Asn Gly
                85                  90                  95

Ser Glu Lys Gln Gln Lys Leu Leu Pro Phe Gly Leu Gly Arg Arg
            100                 105                 110

Ala Cys Pro Gly Ala Pro Leu Ala His Arg Val Met Gly Trp Thr Leu
        115                 120                 125

Gly Leu Leu Ile Gln Cys Phe Asp Trp Lys Arg Val Ser Glu Glu Glu
    130                 135                 140

Ile Asp Met Thr
145

<210> SEQ ID NO 305
<211> LENGTH: 164
<212> TYPE: PRT
<213> ORGANISM: Eucalyptus grandis

<400> SEQUENCE: 305

Tyr Leu Gly Asp Phe Leu Pro Ile Leu Lys Leu Val Asp Tyr Asn Gly
1               5                   10                  15

Val Lys Lys Arg Val Val Glu Leu Lys Glu Lys Phe Asp Ala Phe Ile
            20                  25                  30

Gln Gly Leu Ile Asn Glu His Arg Arg Lys Lys Gly Asp Pro Glu Leu
        35                  40                  45

Ala Asp Ser Met Ile Ser His Leu Leu His Leu Gln Glu Ser Gln Pro
    50                  55                  60

Glu Asp Tyr Ser Asp Ser Met Ile Lys Gly Leu Val Leu Val Leu Leu
65                  70                  75                  80
```

-continued

```
Val Ala Gly Thr Asp Thr Ser Ser Leu Thr Leu Glu Trp Ile Met Thr
                85                  90                  95

Asn Leu Leu Asn Asn Pro Glu Lys Leu Glu Lys Ala Arg Asn Glu Ile
            100                 105                 110

Asp Ser Val Ile Gly His Asp Arg Leu Val Glu Glu Ser Asp Val Ser
        115                 120                 125

Asn Leu Pro Tyr Leu Gln Cys Ile Ile Leu Glu Thr Leu Arg Leu Asn
    130                 135                 140

Thr Thr Val Pro Leu Leu Val Pro His Ala Ser Ser Ala Asp Cys Thr
145                 150                 155                 160

Ile Gly Gly Tyr

<210> SEQ ID NO 306
<211> LENGTH: 163
<212> TYPE: PRT
<213> ORGANISM: Eucalyptus grandis

<400> SEQUENCE: 306

Leu Ser Asp Ala Ile Pro Ala Leu Gly Trp Leu Asp Ser Gly Gly Tyr
1               5                   10                  15

Arg Arg Ser Met Asp Glu Thr Ala Lys Glu Leu Asp Val Leu Ala Gln
            20                  25                  30

Gly Trp Leu Glu Glu His Arg Arg Lys Arg Leu Ser Cys Pro Lys Asp
        35                  40                  45

Asp Arg Glu Gln Asp Phe Met Asp Trp Met Ile Asn Ala Leu Glu Gly
    50                  55                  60

Arg Asn Phe Pro Asp Phe Asp Ala Asp Thr Val Ile Lys Ala Thr Cys
65                  70                  75                  80

Leu Asn Met Ile Ile Ala Gly Thr Asp Thr Ser Thr Val Ala Ile Thr
                85                  90                  95

Trp Ala Leu Ser Leu Leu Met Asn Asn Arg Arg Ala Leu Lys Lys Ala
            100                 105                 110

Gln Gln Glu Leu Asp Thr His Val Gly Arg Ser Arg Pro Val Glu Glu
        115                 120                 125

Ser Asp Val Lys Asn Leu Thr Tyr Leu Gln Ala Ile Val Lys Glu Ala
    130                 135                 140

Leu Arg Leu Tyr Pro Pro Val Pro Val Asn Gly Leu Arg Ser Ser Met
145                 150                 155                 160

Glu Glu Cys

<210> SEQ ID NO 307
<211> LENGTH: 129
<212> TYPE: PRT
<213> ORGANISM: Pinus radiata

<400> SEQUENCE: 307

Arg Leu Pro Pro Gly Pro Pro Gly Trp Pro Ile Val Gly Asn Leu Phe
1               5                   10                  15

Gln Leu Gly Asn Lys Pro His Glu Ala Leu Phe His Leu Ala Gln Lys
            20                  25                  30

Tyr Gly Pro Leu Met Cys Val Ser Leu Gly Met Lys Thr Thr Val Val
        35                  40                  45

Val Ser Ser Pro Ala Met Ala Lys Gln Val Leu Lys Thr His Asp His
    50                  55                  60

Val Phe Ala Gly Arg Thr Val Ile Gln Ser Val Gln Cys Leu Ser Tyr
65                  70                  75                  80
```

```
Asp Lys Ser Ser Val Ile Trp Ala Gln Tyr Gly Ser His Trp Arg Leu
                85                  90                  95

Leu Arg Arg Ile Ser Asn Thr Lys Leu Phe Ser Val Lys Arg Leu Glu
            100                 105                 110

Ala Leu Glu His Leu Arg Arg Asp Glu Val Phe Arg Thr Ile Lys Gln
        115                 120                 125

Ile

<210> SEQ ID NO 308
<211> LENGTH: 166
<212> TYPE: PRT
<213> ORGANISM: Pinus radiata

<400> SEQUENCE: 308

Leu Val Tyr Leu Gln Ala Ala Val Lys Glu Thr Leu Arg Leu His Pro
  1               5                  10                  15

Ser Gly Pro Leu Leu Val Arg His Leu Phe Gly Thr Ala Ser Cys Asn
             20                  25                  30

Val Leu Gly Tyr Glu Ile Pro Gln Asn Thr Leu Val Leu Val Asn Val
         35                  40                  45

Trp Ala Ile Gly Arg Asn Pro Lys Ser Trp Glu Asp Ala Glu Val Phe
     50                  55                  60

Lys Pro Glu Arg Phe Met Glu Lys Val Gly Ser Glu Val Asp Ala Asn
 65                  70                  75                  80

Gly Asp Gln Asn Phe Gly Cys Leu Leu Phe Gly Ala Gly Arg Arg Arg
                 85                  90                  95

Cys Pro Gly Gln Gln Leu Gly Thr Leu Leu Val Glu Phe Gly Leu Ala
            100                 105                 110

Gln Leu Leu His Cys Phe Asn Trp Arg Leu Pro Leu Asp Asp Ile Asn
        115                 120                 125

Gly Glu Asn Gln Glu Val Asp Met Asn Glu Met Phe Asn Gly Val Thr
    130                 135                 140

Leu Arg Lys Ala Arg Glu Leu Ser Ala Ile Pro Thr Pro Arg Leu Glu
145                 150                 155                 160

Cys Ile Ala His Leu Lys
                165

<210> SEQ ID NO 309
<211> LENGTH: 123
<212> TYPE: PRT
<213> ORGANISM: Pinus radiata

<400> SEQUENCE: 309

Ser Cys Trp Arg Cys Val Ala Glu Pro Asn His Ala Trp Ser Asn Leu
  1               5                  10                  15

Ser Arg Lys Arg Lys Gly Arg Leu Pro Gly Pro Phe Ser Leu Pro
             20                  25                  30

Ile Ile Gly Asn Leu His Met Leu Gly Lys Ile Pro His Arg Ser Leu
         35                  40                  45

Ala Glu Leu Ser Met Lys Tyr Gly Pro Leu Leu Ser Leu Arg Leu Gly
     50                  55                  60

Ser Thr Pro Ala Leu Val Val Ser Ser Pro Glu Ile Ala Ser Glu Phe
 65                  70                  75                  80

Leu Lys Thr His Asp Gln Leu Phe Ala Ser Arg Ile Pro Ser Ala Ala
                 85                  90                  95
```

```
Ile Lys Val Leu Thr Tyr Asn Leu Ser Gly Leu Ile Phe Ser Pro Tyr
            100                 105                 110
Gly Pro Cys Trp Arg Gln Val Arg Lys Leu Cys
            115                 120
```

<210> SEQ ID NO 310
<211> LENGTH: 114
<212> TYPE: PRT
<213> ORGANISM: Pinus radiata

<400> SEQUENCE: 310

```
Tyr Ser Glu Pro Ser Lys Lys Leu Ala Met Glu Phe Val Glu Phe Cys
 1               5                  10                  15
Ile Thr Leu Val Thr Ala Leu Leu Phe Val Val Leu Val Ala Ala Trp
            20                  25                  30
Ser Asn Leu Phe Arg Lys Arg Lys Gly Arg Leu Pro Pro Gly Pro Phe
        35                  40                  45
Ser Leu Pro Ile Ile Gly Asn Leu His Met Leu Gly Lys Ile Pro His
    50                  55                  60
Arg Ser Leu Ala Glu Leu Ser Met Lys Tyr Gly Pro Leu Leu Ser Leu
65                  70                  75                  80
Arg Leu Gly Ser Thr Pro Ala Leu Val Val Ser Ser Pro Glu Ile Ala
                85                  90                  95
Ser Glu Phe Leu Lys Thr His Asp Gln Leu Phe Ala Ser Arg Ile Pro
            100                 105                 110
Ser Ala
```

<210> SEQ ID NO 311
<211> LENGTH: 154
<212> TYPE: PRT
<213> ORGANISM: Pinus radiata

<400> SEQUENCE: 311

```
Glu Leu Leu Ser Ala Cys Pro Val His Glu Cys Pro Tyr Phe Tyr Phe
 1               5                  10                  15
Asn Leu Ala Thr Val Ile Leu Leu Gly Val Val Thr Gly Trp Gly Phe
            20                  25                  30
Leu Phe Arg Gly Arg Lys Gln Lys Leu Pro Pro Gly Pro Phe Gln Trp
        35                  40                  45
Pro Ile Val Gly Asn Leu His Met Met Gly Glu Leu Pro His Gln Ala
    50                  55                  60
Ile Thr Ala Leu Ser Met Lys Tyr Gly Pro Leu Met Ser Leu Arg Leu
65                  70                  75                  80
Gly Ser Tyr Leu Thr Leu Val Val Ser Pro Asp Val Ala Glu Glu
                85                  90                  95
Phe Leu Lys Thr His Asp Leu Ala Phe Ala Ser Arg Pro Pro Thr Ile
            100                 105                 110
Gly Thr Lys Tyr Phe Trp Tyr Asn Ser Ser Asp Val Ala Phe Ser Pro
            115                 120                 125
Tyr Gly Pro Tyr Trp Arg Gln Met Arg Lys Ile Cys Val Leu Gln Leu
    130                 135                 140
Leu Ser Ser Arg Arg Ile Asp Ser Phe Arg
145                 150
```

<210> SEQ ID NO 312
<211> LENGTH: 116
<212> TYPE: PRT

<213> ORGANISM: Pinus radiata

<400> SEQUENCE: 312

Cys Asp Gln Asp Leu Ile Gly Gly Ile Gly Ile Lys Ser Met Ile Lys
1               5                   10                  15

Glu Thr Phe Val Leu Ala Gly Ser Leu Asn Met Gly Asp Phe Ile Pro
            20                  25                  30

Tyr Leu Ala Trp Ile Asp Leu Gln Gly Leu Asn Arg Arg Leu Lys Asn
        35                  40                  45

Ile His Lys Ile Gln Asp Asp Leu Leu Gly Lys Ile Leu Glu Glu His
    50                  55                  60

Ala Ser Pro Pro Gln Asn Asn Pro Asn Tyr Met Pro Asp Leu Val Asp
65                  70                  75                  80

Val Leu Leu Ala Ala Ser Ala Asp Glu Asp Leu Glu Phe Glu Ile Thr
            85                  90                  95

Arg Asp Asn Ile Lys Ser Val Ile Tyr Val Tyr Ile Val His Ala Ile
            100                 105                 110

Ile Arg Phe Gln
        115

<210> SEQ ID NO 313
<211> LENGTH: 180
<212> TYPE: PRT
<213> ORGANISM: Pinus radiata

<400> SEQUENCE: 313

Ala Pro Asp Glu Leu Glu Arg Val Val Gly Leu Gly Arg Met Val Arg
1               5                   10                  15

Glu Ser Asp Leu Pro Arg Leu Val Tyr Leu Gln Ala Val Val Lys Glu
            20                  25                  30

Thr Leu Arg Leu Tyr Pro Gln Gly Pro Ile Leu Phe Arg His Leu Ser
        35                  40                  45

Ser Glu Pro Cys Asn Val Leu Gly Tyr Glu Ile Ser Gln Asn Thr Gln
    50                  55                  60

Val Leu Val Asn Ile Trp Ala Ile Gly Arg Asn Ser Glu Ser Trp Glu
65                  70                  75                  80

Asp Ala Gly Ser Phe Lys Pro Glu Arg Phe Met Glu Arg Val Gly Ser
            85                  90                  95

Glu Val Asp Thr Asn Gly Asp Gln Asn Ser Ala Trp Leu Pro Phe Gly
            100                 105                 110

Ala Gly Arg Arg Arg Cys Pro Gly Gln Gln Leu Gly Thr Leu Val Ala
        115                 120                 125

Glu Ile Gly Leu Ala Gln Leu Leu His Cys Phe Lys Trp Arg Leu Pro
    130                 135                 140

Glu Ala Asp Met Asp Gly Pro Asn Gln Glu Leu Asp Met Met Glu Arg
145                 150                 155                 160

Phe Asn Gly Ile Thr Ser Pro Arg Ala Lys Glu Leu Phe Ala Ile Pro
            165                 170                 175

Thr Pro Arg Leu
        180

<210> SEQ ID NO 314
<211> LENGTH: 127
<212> TYPE: PRT
<213> ORGANISM: Pinus radiata

<400> SEQUENCE: 314

```
Gly Ile Leu Phe Asp Met Leu Leu Gly Gly Ser Asp Thr Ala Pro Thr
 1               5                  10                  15

Ile Ile Glu Trp Ala Ile Ser Glu Ala Leu Ile Asn Pro Pro Val Met
            20                  25                  30

Lys Lys Leu Gln Asp Glu Leu Glu Arg Val Val Gly Leu Asp Arg Met
            35                  40                  45

Ala Cys Glu Ser Asp Leu Pro Gln Leu Val Tyr Leu Gln Ala Met Val
 50                  55                  60

Lys Glu Thr Leu Arg Leu His Pro Ala Gly Pro Leu Leu Asn Arg Arg
 65                  70                  75                  80

Leu Ser Ala Glu Ser Cys Asn Val Leu Gly Tyr Glu Phe Pro Lys Asn
            85                  90                  95

Thr Arg Val Leu Val Asn Ala Trp Ala Ile Gly Arg Asn Pro Lys Leu
            100                 105                 110

Trp Glu Asp Ala Glu Thr Phe Lys Pro Glu Arg Phe Thr Gly Arg
            115                 120                 125
```

<210> SEQ ID NO 315
<211> LENGTH: 127
<212> TYPE: PRT
<213> ORGANISM: Pinus radiata

<400> SEQUENCE: 315

```
Thr Ser Ala Thr Val Glu Trp Ala Met Ala Glu Leu Ile Arg Lys Pro
 1               5                  10                  15

Thr Leu Leu Lys Lys Ala Gln Ala Glu Leu Asp Glu Val Val Gly Arg
            20                  25                  30

Glu Lys Arg Met Glu Glu Ser Asp Ile Ala Lys Leu Pro Tyr Leu Gln
            35                  40                  45

Ala Val Val Lys Glu Val Leu Arg Leu His Pro Ala Ala Pro Leu Ile
 50                  55                  60

Ile Pro Arg Arg Ala Asp Asn Ser Ala Glu Ile Gly Gly Tyr Val Val
 65                  70                  75                  80

Pro Glu Asn Thr Gln Val Phe Val Asn Ile Trp Gly Ile Gly Arg Asp
            85                  90                  95

Pro Asn Val Trp Lys Glu Pro Leu Lys Phe Lys Pro Glu Arg Phe Leu
            100                 105                 110

Asp Cys Asn Thr Asp Tyr Arg Gly Gln Asp Phe Glu Leu Ile Pro
            115                 120                 125
```

<210> SEQ ID NO 316
<211> LENGTH: 134
<212> TYPE: PRT
<213> ORGANISM: Pinus radiata

<400> SEQUENCE: 316

```
Glu Asp Glu Val Ser Ala Met Ile Arg Ser Ile Val Asn Ser Asp Ala
 1               5                  10                  15

His Lys Asp Ser Arg Pro Val Asn Ile Lys Gln Leu Ala Ser Ser Leu
            20                  25                  30

Val Thr Ala Ile Val Leu Arg Met Thr Phe Gly Lys Lys Tyr Ser Asp
            35                  40                  45

Arg Asp Ser Gly Ala Phe Ser Ser Met Ile Lys Glu Ser Leu Leu Leu
 50                  55                  60

Leu Gly Ser Phe Asn Ile Gly Glu Tyr Ile Pro Tyr Leu Asn Trp Met
 65                  70                  75                  80
```

-continued

```
Asp Leu Gln Gly Leu Asn Arg Arg Leu Lys Leu Arg Thr Thr Gln
                 85                  90                  95

Asp Gln Leu Leu Glu Lys Val Ile Glu His Ala Ala Gln Asn Arg
            100                 105                 110

Ser Asn Met Thr His Asp Leu Val Asp Ala Leu Leu Ala Ala Ser Ala
        115                 120                 125

Asp Lys Asp Arg Glu Leu
    130

<210> SEQ ID NO 317
<211> LENGTH: 115
<212> TYPE: PRT
<213> ORGANISM: Eucalyptus grandis

<400> SEQUENCE: 317

Ile Tyr Asp Gln Glu Ser Leu Leu Asn Ala Ile Lys Gln Val Asp Val
  1               5                  10                  15

Val Ile Ser Ala Val Gly Gln Ala Gln Thr Glu Asp Gln Asp Arg Ile
             20                  25                  30

Val Ala Ala Ile Lys Ala Ala Gly Asn Ile Lys Arg Phe Leu Pro Ser
         35                  40                  45

Glu Phe Gly Asn Asp Val Asp Arg Val His Ala Val Glu Pro Val Lys
     50                  55                  60

Thr Gly Phe Ala Leu Lys Ala Lys Ile Arg Arg Leu Val Glu Ala Glu
 65                  70                  75                  80

Gly Ile Pro Tyr Thr Tyr Val Ser Ser Asn Ser Phe Ala Gly Tyr Tyr
                 85                  90                  95

Leu Gln Thr Leu Ser Gln Pro Gly Ala Thr Ala Pro Pro Arg Asp Asn
            100                 105                 110

Val Val Ile
    115

<210> SEQ ID NO 318
<211> LENGTH: 161
<212> TYPE: PRT
<213> ORGANISM: Eucalyptus grandis

<400> SEQUENCE: 318

Arg Phe Gly Val Ser Met Val Leu Leu Pro Thr Leu Ser Pro Val Thr
  1               5                  10                  15

Ala Glu Ser Leu Leu Glu Thr Asp Arg Val Arg Arg Lys Thr Pro Arg
             20                  25                  30

Leu Arg Arg Glu Asn His Ser Glu Met Ala Ala Lys Ser Lys Val Leu
         35                  40                  45

Val Ile Gly Gly Thr Gly Tyr Ile Gly Lys Phe Ile Val Glu Ala Ser
     50                  55                  60

Ala Lys Ser Gly Arg Pro Thr Phe Ala Leu Ala Arg Glu Ser Thr Leu
 65                  70                  75                  80

Ser Asn Pro Ala Lys Ala Lys Ile Val Glu Gly Phe Lys Ser Leu Gly
                 85                  90                  95

Val Thr Leu Val His Gly Asp Ile Tyr Asp Gln Glu Ser Leu Leu Asn
            100                 105                 110

Ala Ile Lys Gln Val Asp Val Val Ile Ser Ala Val Gly Arg Ala Gln
        115                 120                 125

Ile Glu Asp Gln Asp Arg Ile Val Ala Ile Lys Ala Ala Gly Asn
    130                 135                 140
```

```
Ile Lys Arg Phe Val Pro Ser Glu Phe Gly A sn Asn Val Asp Arg Val
145                 150                 155                 160

His
```

<210> SEQ ID NO 319
<211> LENGTH: 141
<212> TYPE: PRT
<213> ORGANISM: Eucalyptus grandis

<400> SEQUENCE: 319

```
Arg Phe Leu Pro Ser Glu Phe Gly Asn Asp V al Asp Arg Val His Ala
  1               5                  10                  15

Val Glu Pro Val Lys Thr Gly Phe Ala Leu L ys Ala Lys Ile Arg Arg
             20                  25                  30

Leu Val Glu Ala Glu Gly Ile Pro Tyr Thr T yr Val Ser Ser Asn Ser
         35                  40                  45

Phe Ala Gly Tyr Tyr Leu Gln Thr Leu Ser G ln Pro Gly Ala Thr Ala
     50                  55                  60

Pro Pro Arg Asp Asn Val Val Ile Leu Gly A sp Gly Asn Ala Lys Val
 65                  70                  75                  80

Val Phe Asn Lys Glu Asp Asp Ile Gly Thr T yr Thr Ile Lys Ala Val
                 85                  90                  95

Asp Asp Pro Arg Thr Leu Asn Lys Ile Leu T yr Ile Arg Pro Pro Ala
             100                 105                 110

Asn Thr Tyr Ser Met Asn Glu Leu Val Ser L eu Trp Glu Arg Lys Ile
         115                 120                 125

Gly Lys Ala Leu Glu Arg Val Tyr Val Pro G lu Glu Gln
     130                 135                 140
```

<210> SEQ ID NO 320
<211> LENGTH: 102
<212> TYPE: PRT
<213> ORGANISM: Eucalyptus grandis

<400> SEQUENCE: 320

```
Lys Pro Ile Glu Phe Ala Gly Lys His Arg A la Ser Ala Val Lys Thr
  1               5                  10                  15

Thr Ser Glu Met Ala Ala Lys Ser Lys Val L eu Val Ile Gly Gly Thr
             20                  25                  30

Gly Tyr Ile Gly Lys Phe Ile Val Glu Ala S er Ala Lys Ser Gly Arg
         35                  40                  45

Pro Thr Phe Val Leu Ala Arg Glu Ser Thr L eu Ser Asn Pro Ala Lys
     50                  55                  60

Ala Lys Ile Val Gln Gly Phe Lys Ser Leu G ly Val Thr Leu Val His
 65                  70                  75                  80

Gly Asp Ile Tyr Asp Gln Glu Ser Leu Leu A sn Ala Ile Lys Gln Val
                 85                  90                  95

Asp Val Val Ile Ser Ala
             100
```

<210> SEQ ID NO 321
<211> LENGTH: 125
<212> TYPE: PRT
<213> ORGANISM: Eucalyptus grandis

<400> SEQUENCE: 321

```
Gln Ser His Val Arg Asp Arg Ser Ser Ser P ro Glu Asn Thr Thr Arg
```

```
                1               5                   10                  15
            Ala Met Lys Arg Pro Ser Lys Met Ala Glu M et Ser Arg Val Leu Val
                            20                  25                  30

Ile Gly Gly Ala Gly Tyr Ile Gly Lys Phe I le Val Lys Ala Cys Ala
                        35                  40                  45

Lys Ser Gly His Pro Thr Phe Val Leu Glu T hr Glu Ser Thr Leu Ser
                    50                  55                  60

Asn Pro Ala Asn Ala Glu Ile Ile Lys Gly P he Lys Ser Leu Gly Val
            65                  70                  75                  80

Asn Leu Val His Gly Asp Ile Tyr Asp Gln L ys Ser Leu Leu Ser Ala
                            85                  90                  95

Ile Lys Gln Val Asp Val Val Ile Ser Thr V al Gly Gln Ala Gln Leu
                        100                 105                 110

Glu Asp Gln Asp Arg Ile Val Ala Ala Ile L ys Ala Ala
                    115                 120                 125

<210> SEQ ID NO 322
<211> LENGTH: 98
<212> TYPE: PRT
<213> ORGANISM: Eucalyptus grandis

<400> SEQUENCE: 322

Ser Ser Ser Pro Glu Asn Thr Thr Pro Ala V al Lys Arg Pro Ser Lys
1               5                   10                  15

Met Ala Glu Met Ser Arg Val Leu Val Ile G ly Gly Ala Gly Tyr Ile
            20                  25                  30

Gly Lys Phe Ile Val Lys Ala Cys Ala Lys S er Gly His Pro Thr Phe
        35                  40                  45

Val Leu Glu Thr Glu Ser Thr Leu Ser Asn P ro Ala Asn Ala Glu Ile
    50                  55                  60

Ile Lys Gly Phe Lys Ser Leu Gly Val Asn L eu Val His Gly Asp Ile
65                  70                  75                  80

Tyr Asp Gln Lys Ser Leu Leu Ser Ala Ile L ys Gln Val Asp Val Val
                85                  90                  95

Ile Ser

<210> SEQ ID NO 323
<211> LENGTH: 319
<212> TYPE: PRT
<213> ORGANISM: Pinus radiata

<400> SEQUENCE: 323

Lys Asp Pro Leu Ala Gln Leu Thr Thr Phe S er Cys Ile Cys Ser Val
1               5                   10                  15

Arg His Asp Arg Gly Lys Thr Met Ala Cys A la Thr Asp Val Ala Arg
            20                  25                  30

Gln Phe Leu Pro Cys Val Gln Pro Val Pro S er Ser Met Gly Gly Glu
        35                  40                  45

Thr Ala Arg Ser Ile Asn Leu Thr Cys Asn G ly Leu Ser Pro Pro Gln
    50                  55                  60

Pro Gln Tyr Asn Ala Glu Asn Asn His Asp G ln Asp Thr Thr Val Ala
65                  70                  75                  80

Thr Arg Val Leu Ile Ile Gly Ala Thr Gly P he Ile Gly Arg Phe Val
                85                  90                  95

Ala Glu Ala Ser Val Lys Ser Gly Arg Pro T hr Tyr Ala Leu Val Arg
            100                 105                 110
```

-continued

```
Pro Thr Thr Leu Ser Ser Lys Pro Lys Val Ile Gln Ser Leu Val Asp
            115                 120                 125
Ser Gly Ile Gln Val Val Tyr Gly Cys Leu His Asp His Asn Ser Leu
        130                 135                 140
Val Lys Ala Ile Arg Gln Val Asp Val Ile Ser Thr Val Gly Gly
145                 150                 155                 160
Ala Leu Ile Leu Asp Gln Leu Lys Ile Val Asp Ala Ile Lys Glu Val
                165                 170                 175
Gly Thr Val Lys Arg Phe Leu Pro Ser Glu Phe Gly His Asp Val Asp
            180                 185                 190
Arg Ala Asp Pro Val Glu Pro Ala Leu Ser Phe Tyr Ile Glu Lys Arg
        195                 200                 205
Lys Val Arg Arg Ala Val Glu Glu Ala Lys Ile Pro Tyr Thr Tyr Ile
    210                 215                 220
Cys Cys Asn Ser Ile Ala Gly Trp Pro Tyr Tyr Tyr His Thr His Pro
225                 230                 235                 240
Thr Glu Leu Pro Pro Pro Lys Glu Gln Phe Glu Ile Tyr Gly Asp Gly
                245                 250                 255
Ser Val Lys Ala Phe Phe Val Thr Gly Asp Asp Ile Gly Ala Tyr Thr
            260                 265                 270
Met Lys Ala Val Asp Asp Pro Arg Thr Leu Asn Lys Ser Ile His Phe
        275                 280                 285
Arg Pro Pro Lys Asn Phe Leu Asn Leu Asn Glu Leu Ala Asp Ile Trp
    290                 295                 300
Glu Asn Lys Ile Asn Arg Thr Leu Pro Arg Val Ser Val Ser Ala
305                 310                 315

<210> SEQ ID NO 324
<211> LENGTH: 126
<212> TYPE: PRT
<213> ORGANISM: Pinus radiata

<400> SEQUENCE: 324

Leu Asn Ser Leu Ala Asp Ile Leu Leu Ile Gln Ser Gly Lys Met Thr
 1               5                  10                  15
Gly Leu Lys Asp Ser Ala Asn Arg Val Leu Ile Ile Gly Gly Thr Gly
            20                  25                  30
Tyr Ile Gly Lys Tyr Met Ala Lys Ala Ser Val Ser Gln Gly Tyr Pro
        35                  40                  45
Thr Tyr Val Leu Val Arg Pro Ala Thr Ala Ala Pro Asp Ser Phe
    50                  55                  60
Lys Ala Lys Leu Leu Gln Gln Phe Lys Asp Ile Gly Ile His Ile Leu
65                  70                  75                  80
Glu Gly Ser Leu Asp Asp His Asn Ser Leu Val Asp Ala Ile Lys Gln
                85                  90                  95
Val Asp Ile Val Ile Ser Ala Val Ala Ile Pro Gln His Leu Asp Gln
            100                 105                 110
Phe Asn Ile Ile Asn Ala Ile Lys Asp Val Gly Met Glu Ile
        115                 120                 125

<210> SEQ ID NO 325
<211> LENGTH: 164
<212> TYPE: PRT
<213> ORGANISM: Eucalyptus grandis

<400> SEQUENCE: 325
```

Asn Gly Glu Leu His Pro Ser His Tyr Cys Glu Arg Asp Leu Leu Lys
1               5                   10                  15

Val Val Asp Arg Glu His Val Phe Thr Tyr Ala Asp Asp Ala Cys Ser
                20                  25                  30

Ala Thr Tyr Pro Leu Met Gln Lys Leu Arg Gln Val Leu Val Asp Gln
            35                  40                  45

Ala Leu Val Asn Gly Glu Ser Glu Leu Asn Pro Ser Thr Ser Ile Phe
    50                  55                  60

Gln Lys Ile Val Ala Phe Glu Glu Leu Lys Ala Gln Leu Pro Lys
65                  70                  75                  80

Asp Val Glu Gly Val Arg Val Gln Tyr Glu Thr Gly Asn Leu Ala Ile
                85                  90                  95

Pro Asn Gln Ile Lys Glu Cys Arg Ser Tyr Pro Leu Tyr Lys Leu Val
            100                 105                 110

Arg Glu Leu Gly Thr Ala Leu Leu Thr Gly Glu Gly Val Ile Ser
            115                 120                 125

Pro Gly Glu Asp Phe Asp Lys Val Phe Thr Ala Ile Cys Ala Gly Lys
130                 135                 140

Leu Ile Asp Pro Leu Leu Glu Cys Leu Ser Gly Trp Asn Gly Ala Pro
145                 150                 155                 160

Leu Pro Ile Ser

<210> SEQ ID NO 326
<211> LENGTH: 114
<212> TYPE: PRT
<213> ORGANISM: Eucalyptus grandis

<400> SEQUENCE: 326

Leu Val Asp Gln Ala Leu Val Asn Gly Glu Ser Glu Leu Asn Pro Ser
1               5                   10                  15

Thr Ser Ile Phe Gln Lys Ile Val Ala Phe Glu Glu Glu Leu Lys Ala
                20                  25                  30

Gln Leu Pro Lys Asp Val Glu Gly Val Arg Val Gln Tyr Glu Thr Gly
            35                  40                  45

Asn Leu Ala Ile Pro Asn Gln Ile Lys Glu Cys Arg Ser Tyr Pro Leu
    50                  55                  60

Tyr Lys Leu Val Arg Glu Glu Leu Gly Thr Ala Leu Leu Thr Gly Glu
65                  70                  75                  80

Gly Val Ile Ser Pro Gly Glu Asp Phe Asp Lys Val Phe Thr Ala Ile
                85                  90                  95

Cys Ala Gly Lys Leu Ile Asp Pro Leu Leu Glu Cys Leu Ser Gly Trp
            100                 105                 110

Asn Gly

<210> SEQ ID NO 327
<211> LENGTH: 226
<212> TYPE: PRT
<213> ORGANISM: Eucalyptus grandis

<400> SEQUENCE: 327

Pro Ser Leu Asp Tyr Gly Phe Lys Gly Ala Glu Ile Ala Met Ala Ser
1               5                   10                  15

Tyr Cys Ser Glu Leu Gln Phe Leu Ala Asn Pro Val Thr Asn His Val
                20                  25                  30

Gln Ser Ala Glu Gln His Asn Gln Asp Val Asn Ser Leu Gly Leu Ile

-continued

```
Ser Ser Arg Lys Thr Ala Glu Ala Ile Asp Val Leu Lys Leu Met Ser
    50                  55                  60
Ser Thr Phe Leu Val Ala Leu Cys Gln Ala Ile Asp Leu Arg His Leu
 65                 70                  75                  80
Glu Glu Asn Leu Lys Ser Val Val Lys Asn Thr Val Asn Gln Val Ala
                85                  90                  95
Lys Lys Val Leu Tyr Val Gly Ser Asn Gly Glu Leu His Pro Ser Arg
            100                 105                 110
Phe Ser Glu Lys Asp Leu Ile Lys Val Val Asp Arg Glu Tyr Val Phe
        115                 120                 125
Ala Tyr Ile Asp Asp Pro Cys Ser Ala Thr Tyr Pro Leu Met Gln Lys
    130                 135                 140
Leu Arg Gln Val Leu Val Asp Asp Ala Leu Asp Asp Val Asp Arg Glu
145                 150                 155                 160
Lys Asn Pro Ser Thr Ser Ile Phe Gln Lys Ile Gly Ala Phe Glu Glu
                165                 170                 175
Glu Leu Lys Ala Leu Leu Pro Lys Glu Val Glu Asn Ala Arg Ala Gln
            180                 185                 190
Phe Glu Ser Gly Asn Ser Ala Ile Ala Asn Lys Ile Arg Gly Cys Arg
        195                 200                 205
Ser Tyr Pro Leu Tyr Arg Phe Val Arg Glu Glu Leu Gly Thr Gly Leu
    210                 215                 220
Leu Thr
225

<210> SEQ ID NO 328
<211> LENGTH: 424
<212> TYPE: PRT
<213> ORGANISM: Eucalyptus grandis

<400> SEQUENCE: 328

Met Glu Met Glu Ser Thr Thr Gly Thr Gly Asn Gly Leu His Ser Leu
  1               5                  10                  15
Cys Ala Ala Gly Ser His His Ala Asp Pro Leu Asn Trp Gly Ala Ala
                20                  25                  30
Ala Ala Ala Leu Thr Gly Ser His Leu Asp Glu Val Lys Arg Met Val
            35                  40                  45
Glu Glu Tyr Arg Arg Pro Ala Val Arg Leu Gly Gly Glu Ser Leu Thr
        50                  55                  60
Ile Ala Gln Val Ala Ala Val Ala Ser Gln Glu Gly Val Gly Val Glu
 65                 70                  75                  80
Leu Ser Glu Ala Ala Arg Pro Arg Val Lys Ala Ser Ser Asp Trp Val
                85                  90                  95
Met Glu Ser Met Asn Lys Gly Thr Asp Ser Tyr Gly Val Thr Thr Gly
            100                 105                 110
Phe Gly Ala Thr Ser His Arg Arg Thr Lys Gln Gly Gly Ala Leu Gln
        115                 120                 125
Lys Glu Leu Ile Arg Phe Leu Asn Ala Gly Ile Phe Gly Asn Gly Thr
    130                 135                 140
Glu Ser Cys His Thr Leu Pro Gln Ser Ser Thr Arg Ala Ala Met Leu
145                 150                 155                 160
Val Arg Val Asn Thr Leu Leu Gln Gly Tyr Ser Gly Ile Arg Phe Glu
                165                 170                 175
```

-continued

```
Ile Leu Glu Ala Ile Thr Lys Phe Leu Asn His Asn Ile Thr Pro Cys
            180                 185                 190

Leu Pro Leu Arg Gly Thr Ile Thr Ala Ser Gly Asp Leu Val Pro Leu
        195                 200                 205

Ser Tyr Ile Ala Gly Leu Leu Thr Gly Arg Pro Asn Ser Lys Ala Val
        210                 215                 220

Gly Pro Asp Gly Lys Ser Leu Asp Ala Val Glu Ala Phe Arg Leu Ala
225                 230                 235                 240

Gly Ile Asp Thr Gly Phe Phe Glu Leu Gln Pro Lys Glu Gly Leu Ala
                245                 250                 255

Leu Val Asn Gly Thr Ala Val Gly Ser Gly Leu Ala Ser Ile Val Leu
            260                 265                 270

Phe Glu Ala Asn Ile Leu Ala Val Leu Ser Glu Val Leu Ser Ala Ile
        275                 280                 285

Phe Ala Glu Val Met Gln Gly Lys Pro Glu Phe Thr Asp His Leu Thr
        290                 295                 300

His Lys Leu Lys His His Pro Gly Gln Ile Glu Ser Ala Ala Ile Met
305                 310                 315                 320

Glu His Ile Leu Asp Gly Ser Ala Tyr Val Lys Ala Ala Lys Lys Leu
                325                 330                 335

His Glu Met Asp Pro Leu Gln Lys Pro Lys Gln Asp Arg Tyr Ala Leu
            340                 345                 350

Arg Thr Ser Pro Gln Trp Leu Gly Pro Gln Ile Glu Val Ile Arg Ala
        355                 360                 365

Ala Thr Lys Met Ile Glu Arg Glu Ile Asn Ser Val Asn Asp Asn Pro
        370                 375                 380

Leu Ile Asp Val Ala Arg Asn Lys Ala Leu His Gly Gly Asn Phe Gln
385                 390                 395                 400

Gly Thr Pro Ile Gly Val Ser Met Asp Asn Thr Arg Leu Ala Val Ala
                405                 410                 415

Ser Ile Gly Lys Leu Met Phe Ala
            420
```

<210> SEQ ID NO 329
<211> LENGTH: 97
<212> TYPE: PRT
<213> ORGANISM: Eucalyptus grandis

<400> SEQUENCE: 329

```
Asn Ser Gly Ile Thr Pro Cys Leu Pro Leu Arg Gly Ser Ile Ser Ala
 1               5                  10                  15

Ser Gly Asp Leu Val Pro Phe Ser Tyr Ile Ala Gly Leu Leu Thr Gly
            20                  25                  30

Arg Pro Asn Ser Lys Ala Val Gly Pro Ala Gly Glu Thr Leu Thr Ala
        35                  40                  45

Lys Gln Ala Phe Glu Leu Ala Gly Ile Ser Gly Gly Phe Phe Glu Leu
    50                  55                  60

Gln Pro Lys Glu Gly Leu Ala Leu Val Asn Gly Thr Gly Val Gly Ser
65                  70                  75                  80

Ala Leu Ala Ala Ile Val Leu Phe Glu Ala Asn Met Leu Thr Val Leu
                85                  90                  95

Ser
```

<210> SEQ ID NO 330
<211> LENGTH: 412

```
<212> TYPE: PRT
<213> ORGANISM: Pinus radiata

<400> SEQUENCE: 330

Val Tyr Arg Ser Ile Asn Ser Gln Ala Glu Ala Pro Ser Trp Pro Asn
  1               5                  10                  15

Gly Ser Cys Ser Asp His Gly Val Cys Leu Gly Arg Glu Ser Tyr Met
             20                  25                  30

Lys His Ala Ala Lys Leu His Glu Met Asn Pro Leu Gln Lys Pro Lys
             35                  40                  45

Gln Asp Arg Tyr Ala Leu Arg Thr Ser Pro Gln Trp Leu Gly Pro Gln
 50                  55                  60

Val Glu Ile Ile Arg Ser Ala Thr His Met Ile Glu Arg Glu Ile Asn
 65                  70                  75                  80

Ser Val Asn Asp Asn Pro Val Ile Asp Val Ala Arg Asp Lys Ala Leu
                 85                  90                  95

His Gly Gly Asn Phe Gln Gly Thr Pro Ile Gly Val Ser Met Asp Asn
                100                 105                 110

Leu Arg Leu Ser Ile Ser Ala Ile Gly Lys Leu Met Phe Ala Gln Phe
            115                 120                 125

Ser Glu Leu Val Asn Asp Tyr Tyr Asn Gly Gly Leu Pro Ser Asn Leu
130                 135                 140

Ser Gly Gly Pro Asn Pro Ser Leu Asp Tyr Gly Leu Lys Gly Ala Glu
145                 150                 155                 160

Ile Ala Met Ala Ser Tyr Thr Ser Glu Leu Leu Tyr Leu Ala Asn Pro
                165                 170                 175

Val Thr Ser His Val Gln Ser Ala Glu Gln His Asn Gln Asp Val Asn
            180                 185                 190

Ser Leu Gly Leu Val Ser Ala Arg Lys Ser Ala Glu Ala Ile Asp Ile
            195                 200                 205

Leu Lys Leu Met Leu Ser Thr Tyr Leu Thr Ala Leu Cys Gln Ala Val
210                 215                 220

Asp Leu Arg His Leu Glu Glu Asn Met Leu Ala Thr Val Lys Gln Ile
225                 230                 235                 240

Val Ser Gln Val Ala Lys Lys Thr Leu Ser Thr Gly Leu Asn Gly Glu
                245                 250                 255

Leu Leu Pro Gly Arg Phe Cys Glu Lys Asp Leu Leu Gln Val Val Asp
            260                 265                 270

Asn Glu His Val Phe Ser Tyr Ile Asp Asp Pro Cys Asn Ala Ser Tyr
            275                 280                 285

Pro Leu Thr Gln Lys Leu Arg Asn Ile Leu Val Glu His Ala Phe Lys
            290                 295                 300

Asn Ala Glu Gly Glu Lys Asp Pro Asn Thr Ser Ile Phe Asn Lys Ile
305                 310                 315                 320

Pro Val Phe Glu Ala Glu Leu Lys Ala Gln Leu Glu Pro Gln Val Ser
                325                 330                 335

Leu Ala Arg Glu Ser Tyr Asp Lys Gly Thr Ser Pro Leu Pro Asn Arg
                340                 345                 350

Ile Gln Glu Cys Arg Ser Tyr Pro Leu Tyr Glu Phe Val Arg Asn Gln
            355                 360                 365

Leu Gly Thr Leu Gln Ala Trp Leu Phe His Ile Asn Ile Val Met Arg
        370                 375                 380

Cys Leu Ile Ile Tyr Cys Ser Leu Phe Phe Pro Glu Leu Ala Thr Ala
385                 390                 395                 400
```

```
Phe Asp Ser Val His Tyr Ala Arg Thr Lys Pro Leu
                405                 410

<210> SEQ ID NO 331
<211> LENGTH: 132
<212> TYPE: PRT
<213> ORGANISM: Pinus radiata

<400> SEQUENCE: 331

Gly Ser Ser Cys Arg Ser Leu Ile Arg Glu Leu Phe Val Cys Leu Ile
  1               5                  10                  15

Ile Val His Met Ala Pro Gln Glu Phe Thr Gly Glu Val Lys Phe Cys
             20                  25                  30

Ala Gly Asn Gly Gly Thr Ala Ser Leu Asn Asp Pro Leu Asn Trp Ala
         35                  40                  45

Ala Ala Ala Glu Ser Met Lys Gly Ser His Phe Glu Glu Val Lys Arg
     50                  55                  60

Met Trp Glu Glu Phe Arg Ser Pro Val Val Arg Leu Gln Gly Ser Gly
 65                  70                  75                  80

Leu Thr Ile Ala Gln Val Ala Val Ala Arg Arg Thr Gly Ser Val
                 85                  90                  95

Arg Val Glu Leu Glu Thr Gly Ala Lys Ala Arg Val Asp Glu Ser Ser
            100                 105                 110

Asn Trp Val Met Asp Ser Met Ala Asn Gly Thr Asp Ser Tyr Gly Val
        115                 120                 125

Thr Thr Gly Phe
        130

<210> SEQ ID NO 332
<211> LENGTH: 170
<212> TYPE: PRT
<213> ORGANISM: Eucalyptus grandis

<400> SEQUENCE: 332

Asn Leu Val Lys Leu Gly Ser Ile Leu Gly Met Ala Ile Gly Val Ala
  1               5                  10                  15

Leu Phe Ser Ser Leu Leu Val Leu Ser Phe Val Ser Pro Ile Ser Ser
             20                  25                  30

Leu Ser Ser Asn Tyr Tyr Asp Lys Thr Cys Pro Asn Ala Glu Leu Ile
         35                  40                  45

Val Ala Asn Ala Val Lys Asn Ala Ala Met Lys Asp Lys Thr Val Pro
     50                  55                  60

Ala Ala Leu Leu Arg Met His Phe His Asp Cys Phe Ile Arg Gly Cys
 65                  70                  75                  80

Asp Ala Ser Val Leu Leu Asn Ser Lys Gly Ser Asn Lys Ala Glu Lys
                 85                  90                  95

Asp Gly Pro Pro Asn Val Ser Leu His Ser Phe Phe Val Ile Asp Asn
            100                 105                 110

Ala Lys Lys Glu Leu Glu Ala Ser Cys Pro Gly Val Val Ser Cys Ala
        115                 120                 125

Asp Ile Leu Ala Leu Ala Ala Arg Asp Ser Val Val Leu Ser Gly Gly
    130                 135                 140

Pro Thr Trp Asp Val Pro Lys Gly Arg Lys Asp Gly Arg Thr Ser Lys
145                 150                 155                 160

Ala Ser Glu Thr Thr Gln Leu Pro Ala Pro
                165                 170
```

<210> SEQ ID NO 333
<211> LENGTH: 118
<212> TYPE: PRT
<213> ORGANISM: Eucalyptus grandis

<400> SEQUENCE: 333

Leu Val Ile Thr Ile Val Val Phe Phe Gly His Ile Gly Asp Ser Glu
1               5                   10                  15

Gly Gly Asp Leu Arg Lys Asn Phe Tyr Lys Ser Ala Cys Pro Leu Ala
            20                  25                  30

Glu Glu Ile Val Lys Asn Val Thr Trp Lys His Ala Ala Ser Asn Ser
        35                  40                  45

Ala Leu Pro Ala Lys Phe Leu Arg Met His Phe His Asp Cys Phe Val
    50                  55                  60

Arg Gly Cys Asp Gly Ser Val Leu Leu Asp Ser Thr Ala Asn Asn Lys
65                  70                  75                  80

Ala Glu Lys Val Ala Val Pro Asn Gln Ser Leu Thr Gly Phe Asp Val
                85                  90                  95

Ile Asp Glu Ile Lys Glu Lys Leu Glu Glu Thr Cys Pro Gly Val Val
                100                 105                 110

Ser Cys Ala Asp Ile Leu
            115

<210> SEQ ID NO 334
<211> LENGTH: 65
<212> TYPE: PRT
<213> ORGANISM: Pinus radiata

<400> SEQUENCE: 334

Asn Ala Asp Pro Ile Ala Val Ile Asp Glu Ala la Leu Ser Thr Gly Gly
1               5                   10                  15

Ala Pro Asn Leu Ser Asp Ala Tyr Thr Leu Asn Gly Gln Pro Gly Asp
            20                  25                  30

Leu Tyr Asn Cys Ser Arg Ala Gly Thr Phe Arg Phe Leu Val Lys Gln
        35                  40                  45

Gly Glu Thr Tyr Leu Leu Arg Met Val Asn Ala Ala Leu Asn Ser Ala
    50                  55                  60

His
65

<210> SEQ ID NO 335
<211> LENGTH: 104
<212> TYPE: PRT
<213> ORGANISM: Pinus radiata

<400> SEQUENCE: 335

Lys Pro His Gly Glu Thr Pro Leu Ile Ile Gly Glu Trp Trp Asn Ala
1               5                   10                  15

Asp Pro Ile Ala Val Ile Asp Gly Ala Leu Arg Thr Gly Gly Ala Pro
            20                  25                  30

Asn Leu Ser Asp Ala Tyr Thr Leu Asn Gly Gln Pro Gly Asp Leu Tyr
        35                  40                  45

Asn Cys Ser Arg Ala Gly Thr Phe Arg Phe Pro Val Lys Gln Gly Glu
    50                  55                  60

Thr Tyr Leu Leu Arg Met Val Asn Ala Ala Leu Asn Ser Ala His Phe
65                  70                  75                  80

```
Phe Lys Ile Ala Gly His Lys Phe Thr Val Val Ala Val Asp Ala Ser
                85                  90                  95

Tyr Thr Lys Pro Tyr Lys Gln Met
                100
```

<210> SEQ ID NO 336
<211> LENGTH: 125
<212> TYPE: PRT
<213> ORGANISM: Pinus radiata

<400> SEQUENCE: 336

```
Asp Ala His Thr Ile Asn Gly Lys Pro Gly Pro Leu Phe Lys Cys Pro
1               5                   10                  15

Thr Lys Asp Thr Phe Val Val Pro Val Glu His Gly Lys Thr Tyr Leu
                20                  25                  30

Leu Arg Ile Ile Asn Ala Ala Leu Asn Asp Glu Leu Phe Phe Asp Val
            35                  40                  45

Ala Asn His His Leu Lys Val Val Glu Ile Asp Ala Val Tyr Thr Lys
        50                  55                  60

Pro Leu Ile Thr Asn Ser Ile Val Ile Ala Pro Gly Gln Thr Thr Asn
65                  70                  75                  80

Ala Leu Ile His Thr Asn Lys Arg Ser Gly Arg Tyr Phe Met Ala Ala
                85                  90                  95

Arg Ser Phe Met Asp Ala Pro Val Ser Val Asp Asn Lys Thr Ala Thr
                100                 105                 110

Ala Ile Leu Gln Tyr Val Asn Ser Ile Gln Ile Leu Leu
            115                 120                 125
```

<210> SEQ ID NO 337
<211> LENGTH: 178
<212> TYPE: PRT
<213> ORGANISM: Pinus radiata

<400> SEQUENCE: 337

```
Asn Met Met Ala Pro Met Ala Gly Ala Glu Tyr Gly Ile Lys Leu Ile
1               5                   10                  15

Ile Gln Leu Leu Val Val Leu Leu Ala Val Gln Leu Val Ala Gly Lys
                20                  25                  30

Thr Thr Arg His Tyr Ser Phe His Val Arg Leu Lys Asn Val Thr Arg
            35                  40                  45

Leu Cys His Thr Lys Pro Leu Ile Thr Val Asn Gly Lys Ser Pro Gly
        50                  55                  60

Pro Lys Val Val Arg Glu Gly Asp Arg Val Ile Ile Lys Val His
65                  70                  75                  80

Asn His Val Ser Asn Val Ser Ile His Trp His Gly Val Arg Gln
                85                  90                  95

Leu Arg Ser Gly Trp Ala Asp Gly Pro Ala Tyr Ile Thr Gln Cys Pro
                100                 105                 110

Ile Gln Thr Gly Gln Thr Tyr Val Tyr Asn Phe Thr Val Thr Gly Gln
            115                 120                 125

Arg Gly Thr Leu Trp Trp His Ala His Ile Ser Trp Leu Arg Ala Ser
        130                 135                 140

Val Tyr Gly Ala Phe Ile Ile Tyr Pro Lys Arg His Val Pro Tyr Pro
145                 150                 155                 160

Phe Pro Lys Pro Tyr Lys Glu Val Pro Leu Ile Leu Gly Glu Trp Trp
                165                 170                 175
```

Asn Ala

<210> SEQ ID NO 338
<211> LENGTH: 358
<212> TYPE: PRT
<213> ORGANISM: Pinus radiata

<400> SEQUENCE: 338

```
Pro Ile Pro Pro Gly Gly Arg Tyr Thr Tyr Arg Phe Asn Ile Ser Gly
 1               5                  10                  15

Gln Glu Gly Thr Val Trp Trp His Ala His Tyr Ser Trp Leu Arg Ala
            20                  25                  30

Thr Val His Gly Ala Phe Val Ile Leu Pro Lys Lys Gly Ser Ser Tyr
        35                  40                  45

Pro Phe Ser Lys Pro His Ala Glu Ile Pro Ile Ile Gly Glu Trp
 50                  55                  60

Trp Asn Ala Asn Pro Ile Ala Val Ile Asp Glu Ala Val Arg Thr Gly
 65                  70                  75                  80

Gly Ala Pro Asn Leu Ser Asp Ala Phe Thr Ile Asn Gly Gln Pro Gly
                85                  90                  95

Asp Leu Phe Asn Cys Ser Thr Ser Gly Thr Phe Arg Leu Pro Val Glu
                100                 105                 110

Ser Gly Glu Thr Tyr Leu Leu Arg Ile Val Asn Ala Ala Leu Asn Ser
            115                 120                 125

Gly His Phe Phe Lys Ile Ala Gly His Glu Phe Thr Val Val Ala Val
        130                 135                 140

Asp Ala Cys Tyr Thr Lys Pro Tyr Lys Thr Asp Val Leu Val Ile Ser
145                 150                 155                 160

Ala Gly Gln Thr Thr Asp Val Leu Ile Thr Ala Asn Gln Ser Val Gly
                165                 170                 175

Arg Tyr Tyr Met Ala Ala Arg Ala Tyr Gln Asn Gln Ala Ala Gly Asp
            180                 185                 190

Phe Thr Asn Thr Thr Thr Thr Ala Ile Leu Glu Tyr Ile Gly Ser Glu
        195                 200                 205

Asn Ser Thr Arg Pro Ile Leu Pro Ser Leu Pro Ala Tyr Asn Asp Thr
    210                 215                 220

Ala Thr Val Thr Arg Phe Ser Arg Ala Leu Arg Ser Leu Ala Ser Gln
225                 230                 235                 240

Glu His Pro Val Asn Val Pro His Thr Ile Asp Glu Ser Leu Ile Ser
                245                 250                 255

Thr Val Gly Leu Gly Leu Leu Pro Cys Gly Ala Gly Asn Thr Cys Glu
            260                 265                 270

Gly Pro Asn Gly Thr Arg Leu Ser Ala Ser Ile Asn Asn Ile Ser Tyr
        275                 280                 285

Val Glu Pro Thr Ile Ser Leu Leu Gln Ala Tyr Tyr Thr Ala Asn
    290                 295                 300

Gly Ile Phe Thr Gly Asp Phe Pro Ser Lys Pro Glu Val Arg Phe Asn
305                 310                 315                 320

Tyr Thr Gly Asp Asp Ile Pro Arg Lys Phe Trp Ala Pro Asp Pro Ala
                325                 330                 335

Thr Lys Val Lys Val Leu Glu Tyr Asn Ser Thr Val Gln Leu Val Phe
            340                 345                 350

Gln Ser Thr Asn Ile Phe
        355
```

<210> SEQ ID NO 339
<211> LENGTH: 160
<212> TYPE: PRT
<213> ORGANISM: Pinus radiata

<400> SEQUENCE: 339

```
Phe Arg Arg Glu Thr Val Ile Gln His Ile Ser Arg Ser Phe Leu Ser
  1               5                  10                  15

Lys Met Val Ile Ser Lys Tyr Ala Ala Met Ser Cys Leu Leu Ile
             20                  25                  30

Ala Val Ala Leu Glu Val Gly Ala Glu Thr Arg His Tyr Lys Phe
         35                  40                  45

Asp Ile Lys Phe Lys Asn Val Thr Arg Leu Cys His Thr Lys Pro Ile
 50                  55                  60

Val Thr Ala Asn Gly Lys Phe Pro Gly Pro Thr Ile Tyr Ala Arg Glu
 65                  70                  75                  80

Gly Asp Thr Val Thr Val Lys Val Thr Asn His Val Thr Tyr Asn Val
                 85                  90                  95

Ser Ile His Trp His Gly Ile Arg Gln Leu Arg Thr Gly Trp Ala Asp
                100                 105                 110

Gly Pro Ala Tyr Ile Thr Gln Cys Pro Ile Gln Thr Gly Gln Thr Tyr
             115                 120                 125

Val Tyr Asn Phe Thr Ile Thr Gly Gln Arg Gly Thr Leu Phe Trp His
130                 135                 140

Ala His Ile Leu Trp Leu Arg Ala Thr Leu Asn Gly Pro Ile Val Ile
145                 150                 155                 160
```

<210> SEQ ID NO 340
<211> LENGTH: 156
<212> TYPE: PRT
<213> ORGANISM: Pinus radiata

<400> SEQUENCE: 340

```
Gly Cys Cys Leu Ser Thr Arg Met Asn Met Ser Arg Ser Lys Ala Leu
  1               5                  10                  15

Leu Cys Pro Ser Pro Ala His Val Lys Tyr Val Leu Ile Val Ile Leu
             20                  25                  30

Leu Ile Ile Met Ile Gln Cys Pro Asp Ile Val Ala Gly Lys His Ala
         35                  40                  45

Gln Thr Thr Arg His Tyr Lys Phe Asn Val Arg Leu Ser Asn Val Thr
 50                  55                  60

Arg Leu Cys Arg Thr Lys Pro Leu Ile Thr Val Asn Gly Lys Tyr Pro
 65                  70                  75                  80

Gly Pro Thr Val Val Ala Arg Glu Gly Asp Arg Val Ile Ile Lys Leu
                 85                  90                  95

Val Asn His Val Lys Asp Asn Val Thr Ile His Trp His Gly Val Arg
                100                 105                 110

Gln Leu Arg Ser Gly Trp Ala Asp Gly Pro Gly Tyr Ile Thr Gln Cys
             115                 120                 125

Pro Leu Gln Thr Gly Met Ser Tyr Val Tyr Asn Phe Thr Ile Val Gly
130                 135                 140

Gln Arg Gly Thr Leu Trp Trp His Ala His Ile Ser
145                 150                 155
```

<210> SEQ ID NO 341
<211> LENGTH: 157

```
<212> TYPE: PRT
<213> ORGANISM: Pinus radiata

<400> SEQUENCE: 341

Val Ile Gln Gln Ala Leu Gln Thr Gly Gly Pro Asn Val Ser Asp
 1               5                  10                  15

Ala Tyr Thr Ile Asn Gly Leu Pro Gly Pro Leu Tyr Asn Cys Ser Asn
                20                  25                  30

Glu Thr Phe Val Leu Lys Val His Pro Gly Gln Thr Tyr Leu Leu Arg
            35                  40                  45

Ile Ile Asn Ala Ala Leu Asn Asp Glu Leu Phe Leu Ala Ile Ala Asn
 50                  55                  60

His Ser Leu Thr Val Val Glu Val Asp Ala Val Tyr Val Lys Pro Phe
 65                  70                  75                  80

Gln Thr Asp Thr Leu Leu Ile Thr Pro Gly Gln Thr Thr Asn Val Leu
                85                  90                  95

Leu Thr Ala Asn Ala Thr Ser Gly Lys Asn Lys Gln Phe Val Ile Ala
                100                 105                 110

Ala Ser Pro Phe Val Thr Gly Ser Gly Thr Phe Asp Asn Ser Thr Val
            115                 120                 125

Ala Gly Ile Val Ser Tyr Asn Ser His Lys Phe Lys Asn Ser Ser Thr
130                 135                 140

Ile Ile Leu Pro Lys Leu Pro Ser Phe Asn Asp Thr Asn
145                 150                 155

<210> SEQ ID NO 342
<211> LENGTH: 134
<212> TYPE: PRT
<213> ORGANISM: Pinus radiata

<400> SEQUENCE: 342

Gly Gln Thr Thr Asn Val Leu Leu Glu Ala Asn Lys Arg Ser Gly Ser
 1               5                  10                  15

Tyr Phe Val Ala Ala Arg Pro Phe Met Asp Ala Pro Val Thr Val Asn
                20                  25                  30

Asn Lys Thr Ala Thr Ala Ile Leu His Tyr Ile Gly Arg Asn Ser Glu
            35                  40                  45

Ser Asp Ile Pro Ala Val Asn Pro Leu Met Pro Arg Leu Pro Leu Leu
 50                  55                  60

Asn Asp Thr Ala Phe Ala Thr Ser Phe Thr Ser Lys Leu Arg Ser Leu
 65                  70                  75                  80

Asn Ser Val Gln Phe Pro Ala Lys Val Pro Gln Thr Ile Asp Arg Asn
                85                  90                  95

Leu Phe Phe Ala Val Gly Leu Ala Thr Glu Ser Cys Gln Thr Cys Asn
                100                 105                 110

Gly Gly Leu Arg Ala Ser Ala Ser Ile Asn Asn Ile Ser Phe Val Met
            115                 120                 125

Pro Ser Ile Ser Leu Leu
        130

<210> SEQ ID NO 343
<211> LENGTH: 419
<212> TYPE: PRT
<213> ORGANISM: Pinus radiata

<400> SEQUENCE: 343

Thr Thr Tyr Pro Phe Thr Phe Thr Arg Pro His Arg Gln Ile Pro Ile
```

-continued

```
  1               5                  10                  15
Leu Leu Gly Glu Trp Trp Asn Arg Asn Pro Met Asp Val Val Asn Gln
                20                  25                  30
Ala Thr Gln Thr Gly Ala Ala Pro Asn Val Ser Asp Ala Phe Thr Ile
                35                  40                  45
Asn Gly Gln Pro Gly Asp Leu Tyr Lys Cys Ser Thr Ser Asp Thr Phe
 50                  55                  60
Ser Val Ser Met Lys Gly Glu Thr Asn Leu Leu Arg Val Ile Asn
 65                  70                  75                  80
Ala Ala Leu Asn Thr Asp Leu Phe Phe Ser Ile Ala Ser His Thr Met
                85                  90                  95
Thr Val Val Ala Val Asp Ala Leu Tyr Thr Lys Pro Phe Gln Thr Asn
                100                 105                 110
Val Leu Met Leu Gly Pro Gly Gln Thr Thr Asp Ile Leu Leu Thr Ala
                115                 120                 125
Asn Gln Ala Thr Gly Arg Tyr Tyr Met Ala Ala Arg Ala Tyr Ser Ser
                130                 135                 140
Gly Gln Gly Val Pro Phe Asp Asn Thr Thr Thr Ala Ile Leu Glu
145                 150                 155                 160
Tyr Glu Gly Ser Ser Lys Thr Ser Thr Pro Val Met Pro Asn Leu Pro
                165                 170                 175
Phe Tyr Asn Asp Thr Asn Ser Ala Thr Ser Phe Ala Asn Gly Leu Arg
                180                 185                 190
Ser Leu Gly Ser His Asp His Pro Val Phe Val Pro Gln Ser Val Glu
                195                 200                 205
Glu Asn Leu Phe Tyr Thr Ile Gly Leu Gly Leu Ile Lys Cys Pro Gly
                210                 215                 220
Gln Ser Cys Gly Gly Pro Asn Gly Ser Arg Phe Ala Ala Ser Met Asn
225                 230                 235                 240
Asn Ile Ser Phe Val Pro Pro Thr Thr Ser Ser Ile Leu Gln Ala Gln
                245                 250                 255
His Phe Gly Met Lys Gly Val Phe Ser Ala Asp Phe Pro Asp Asn Pro
                260                 265                 270
Ser Val Gly Phe Asp Tyr Thr Ala Gln Asn Ile Ser Arg Asp Leu Trp
                275                 280                 285
Ser Pro Val Lys Ala Thr Arg Val Lys Val Leu Lys Tyr Asn Ser Thr
 290                 295                 300
Val Gln Val Ile Leu Gln Gly Thr Asn Ile Phe Ala Gly Glu Ser His
305                 310                 315                 320
Pro Ile His Leu His Gly Tyr Asp Phe Tyr Ile Val Gly Ala Gly Phe
                325                 330                 335
Gly Asn Tyr Asn Ala Gln Thr Asp Pro His Lys Phe Asn Leu Val Asp
                340                 345                 350
Pro Pro Met Arg Asn Thr Val Asn Val Pro Val Asn Gly Trp Ala Ala
                355                 360                 365
Ile Arg Phe Val Ala Asp Asn Pro Gly Ala Trp Val Met His Cys His
                370                 375                 380
Leu Asp Val His Ile Thr Trp Gly Leu Ala Met Val Phe Val Val Asn
385                 390                 395                 400
Asn Gly Pro Asp Ala Leu Leu Ser Leu Gln Ser Pro Pro Arg Asp Leu
                405                 410                 415
Pro Leu Cys
```

```
<210> SEQ ID NO 344
<211> LENGTH: 111
<212> TYPE: PRT
<213> ORGANISM: Pinus radiata

<400> SEQUENCE: 344

Leu Asn Tyr Asn Ala Thr Val Gln Val Ile L eu Gln Gly Thr Asn Ile
  1               5                  10                  15

Phe Ala Gly Glu Ser His Pro Ile His Leu H is Gly Tyr Asp Phe Tyr
             20                  25                  30

Ile Val Gly Ala Gly Phe Gly Asn Tyr Asn A la Gln Thr Asp Pro Gln
         35                  40                  45

Lys Phe Asn Leu Val Asp Pro Pro Met Arg A sn Thr Val Asn Val Pro
 50                  55                  60

Val Asn Gly Trp Ala Ala Ile Arg Phe Val A la Asp Asn Pro Gly Ala
 65                  70                  75                  80

Trp Val Met His Cys His Leu Asp Val His I le Thr Trp Gly Leu Ala
                 85                  90                  95

Met Val Phe Val Val Asn Asn Gly Pro Asp P ro Leu Leu Ser Leu
            100                 105                 110

<210> SEQ ID NO 345
<211> LENGTH: 93
<212> TYPE: PRT
<213> ORGANISM: Pinus radiata

<400> SEQUENCE: 345

Thr Arg Val Lys Val Leu Asn Tyr Asn Thr T hr Val Gln Val Ile Leu
  1               5                  10                  15

Gln Gly Thr Asn Ile Phe Ala Gly Glu Ser H is Pro Ile His Leu His
             20                  25                  30

Gly Tyr Asp Phe Tyr Ile Val Gly Ala Gly P he Gly Asn Tyr Asn Pro
         35                  40                  45

Gln Thr Asp Pro Gln Lys Phe Asn Leu Ala A sp Pro Pro Met Arg Asn
 50                  55                  60

Thr Val Asn Val Pro Val Asn Gly Trp Ala A la Ile Arg Phe Val Ala
 65                  70                  75                  80

Asp Asn Pro Gly Ala Trp Val Met His Cys H is Leu Asp
                 85                  90

<210> SEQ ID NO 346
<211> LENGTH: 93
<212> TYPE: PRT
<213> ORGANISM: Pinus radiata

<400> SEQUENCE: 346

Lys Thr Phe Ser Asp Glu Cys Ser Asp Ala A rg Pro Arg Pro Asp Asn
  1               5                  10                  15

Arg His Ser Gly Arg Val Asp Gln Leu Ala A sp Thr Phe Ser Val Ser
             20                  25                  30

Met Lys Gly Gly Glu Thr Asn Leu Leu Arg V al Ile Asn Ala Ala Leu
         35                  40                  45

Asn Thr Asp Leu Phe Phe Ser Ile Ala Ser H is Thr Met Thr Val Val
 50                  55                  60

Ala Val Asp Ala Leu Tyr Thr Lys Pro Phe G ln Thr Asn Val Leu Met
 65                  70                  75                  80

Leu Gly Pro Gly Gln Thr Thr Asp Ile Ala A la Ala Asn
```

<210> SEQ ID NO 347
<211> LENGTH: 114
<212> TYPE: PRT
<213> ORGANISM: Pinus radiata

<400> SEQUENCE: 347

Pro Asp Ser Thr Ile Asn Thr Ser Phe Leu Gln Gln Leu Gln Gly Gln
1               5                   10                  15

Cys Pro Arg Ala Gly Gly Asp Glu Leu Pro Ser Ser Leu Asp Tyr Val
            20                  25                  30

Thr Pro Ala Arg Phe Asp Asn Thr Tyr Phe Ala Asn Leu Lys Gln Gln
        35                  40                  45

Lys Gly Val Leu His Ser Asp Arg Thr Leu Tyr Asp Pro Ala Ala Ser
50                  55                  60

Gly Ser Val Thr Ser Thr Val Asp His Phe Ser Ser Asp Gln Thr
65                  70                  75                  80

Ala Phe Phe Glu Ser Phe Lys Gly Ala Met Ile Lys Met Gly Asn Leu
                85                  90                  95

Ser Pro Ser Ala Gly Thr Gln Gly Glu Ile Arg Arg Asp Cys Arg Lys
            100                 105                 110

Val Asn

<210> SEQ ID NO 348
<211> LENGTH: 551
<212> TYPE: PRT
<213> ORGANISM: Pinus radiata

<400> SEQUENCE: 348

Met Glu Gly Gln Ile Ala Ala Leu Ser Lys Glu Asp Glu Phe Ile Phe
1               5                   10                  15

His Ser Pro Phe Pro Ala Val Pro Val Pro Glu Asn Ile Ser Leu Phe
            20                  25                  30

Gln Phe Val Leu Glu Gly Ala Glu Lys Tyr Arg Asp Lys Val Ala Leu
        35                  40                  45

Val Glu Ala Ser Thr Gly Lys Glu Tyr Asn Tyr Gly Gln Val Ile Ser
50                  55                  60

Leu Thr Arg Asn Val Ala Ala Gly Leu Val Asp Lys Gly Ile Gln Lys
65                  70                  75                  80

Gly Asp Val Val Phe Val Leu Leu Pro Asn Met Ala Glu Tyr Pro Ile
                85                  90                  95

Ile Val Leu Gly Ile Met Leu Ala Gly Ala Val Phe Ser Gly Ala Asn
            100                 105                 110

Pro Ser Ala His Ile Asn Glu Val Glu Lys His Ile Gln Asp Ser Gly
        115                 120                 125

Ala Lys Ile Val Val Thr Val Gly Ser Ala Tyr Glu Lys Val Arg Gln
130                 135                 140

Val Lys Leu Pro Val Ile Ile Ala Asp Asn Glu His Val Met Asn Thr
145                 150                 155                 160

Ile Pro Leu Gln Glu Ile Phe Glu Arg Asn Tyr Glu Ala Ala Gly Pro
                165                 170                 175

Phe Val Gln Ile Cys Gln Asp Asp Leu Cys Ala Leu Pro Tyr Ser Ser
            180                 185                 190

Gly Thr Thr Gly Ala Ser Lys Gly Val Met Leu Thr His Arg Asn Leu
        195                 200                 205

```
Ile Ala Asn Leu Cys Ser Ser Leu Phe Asp Val His Glu Ser Leu Val
    210                 215                 220

Gly Asn Phe Thr Thr Leu Gly Leu Met Pro Phe Phe His Ile Tyr Gly
225                 230                 235                 240

Ile Thr Gly Ile Cys Cys Ala Thr Leu Arg Asn Gly Gly Lys Val Val
                245                 250                 255

Val Met Ser Arg Phe Asp Leu Arg His Phe Ile Ser Ser Leu Ile Thr
                260                 265                 270

Tyr Glu Val Asn Phe Ala Pro Ile Val Pro Pro Ile Met Leu Ser Leu
            275                 280                 285

Val Lys Asn Pro Ile Val Asn Glu Phe Asp Leu Ser Arg Leu Lys Leu
        290                 295                 300

Lys Ala Val Met Thr Ala Ala Pro Leu Ala Pro Asp Leu Leu Arg
305                 310                 315                 320

Ala Phe Glu Glu Lys Phe Pro Gly Val Glu Val Gln Glu Ala Tyr Gly
                325                 330                 335

Leu Thr Glu His Ser Cys Ile Thr Leu Thr His Cys Ala Pro Gly Asn
            340                 345                 350

Ile Arg Gly Arg Ala Lys Lys Ser Ser Val Gly Phe Ile Ile Pro Asn
        355                 360                 365

Leu Glu Val Lys Phe Ile Asp Pro Glu Thr Gly Lys Ser Leu Pro Arg
    370                 375                 380

Asn Ser Ile Gly Glu Val Cys Val Arg Ser Gln Cys Val Met Arg Gly
385                 390                 395                 400

Tyr Tyr Lys Lys Pro Thr Glu Thr Glu Lys Thr Val Asp Ser Asp Gly
                405                 410                 415

Trp Leu His Thr Gly Asp Val Gly Phe Ile Asp Asp Asp Asp Val
            420                 425                 430

Phe Ile Val Asp Arg Ile Lys Glu Leu Ile Lys Tyr Lys Gly Phe Gln
        435                 440                 445

Val Ala Pro Ala Glu Leu Glu Ala Ile Leu Leu Ser His Pro Ser Val
    450                 455                 460

Glu Asp Ala Ala Val Val Pro Leu Pro Asp Glu Glu Ala Gly Glu Ile
465                 470                 475                 480

Pro Ala Ala Cys Val Val Met Ala Ala Ser Ala Thr Glu Thr Glu Asp
                485                 490                 495

Asp Ile Ser Lys Phe Val Ala Ser Gln Val Ala Thr Tyr Lys Arg Val
            500                 505                 510

Arg Leu Val Lys Phe Val Ser Thr Ile Pro Lys Ser Ser Ser Gly Lys
        515                 520                 525

Ile Leu Arg Arg Leu Leu Arg Asp Asn Leu Arg Glu Thr Leu Lys Asn
    530                 535                 540

Gln His Gln Pro Leu Ser Thr
545                 550

<210> SEQ ID NO 349
<211> LENGTH: 544
<212> TYPE: PRT
<213> ORGANISM: Pinus radiata

<400> SEQUENCE: 349

Met Glu Ala Lys Pro Ser Glu Gln Pro Arg Glu Phe Ile Phe Arg Ser
1               5                   10                  15

Lys Leu Pro Asp Ile Tyr Ile Pro Asp Asn Leu Ser Leu His Ala Tyr
```

-continued

```
                  20                  25                  30
Cys Phe Glu Asn Ile Ser Glu Phe Ala Asp A rg Pro Cys Val Ile Asn
                35                  40                  45
Gly Ala Thr Gly Arg Thr Tyr Thr Tyr Ala G lu Val Glu Leu Ile Ser
 50                  55                  60
Arg Arg Val Ser Ala Gly Leu Asn Gly L eu G ly Val Gly Gln Gly Asp
 65                  70                  75                  80
Val Ile Met Leu Leu Leu Gln Asn Cys Pro G lu Phe Val Phe Ala Phe
                85                  90                  95
Leu Gly Ala Ser Tyr Arg Gly Ala Ile Ser T hr Thr Ala Asn Pro Phe
                100                 105                 110
Tyr Thr Pro Gly Glu Ile Ala Lys Gln Ala S er Ala Ala Arg Ala Lys
                115                 120                 125
Ile Val Ile Thr Gln Ala Ala Phe Ala Asp L ys Val Arg Pro Phe Ala
                130                 135                 140
Glu Glu Asn Gly Val Lys Val Val Cys Ile A sp Thr Ala Pro Glu Gly
145                 150                 155                 160
Cys Leu His Phe Ser Glu Leu Met Gln Ala A sp Glu Asn Ala Ala Pro
                165                 170                 175
Ala Ala Asp Val Lys Pro Asp Asp Val Leu A la Leu Pro Tyr Ser Ser
                180                 185                 190
Gly Thr Thr Gly Leu Pro Lys Gly Val Met L eu Thr His Arg Gly Gln
                195                 200                 205
Val Thr Ser Val Ala Gln Gln Val Asp Gly A sp Asn Pro Asn Leu Tyr
                210                 215                 220
Phe His Lys Glu Asp Val Ile Leu Cys Thr L eu Pro Leu Phe His Ile
225                 230                 235                 240
Tyr Ser Leu Asn Ser Val Met Phe Cys Ala L eu Arg Val Gly Ala Ala
                245                 250                 255
Ile Leu Ile Met Gln Lys Phe Glu Ile Val A la Leu Met Glu Leu Val
                260                 265                 270
Gln Arg Tyr Arg Val Thr Ile Leu Pro Ile V al Pro Pro Ile Val Leu
                275                 280                 285
Glu Ile Ala Lys Ser Ala Glu Val Asp Arg T yr Asp Leu Ser Ser Ile
                290                 295                 300
Arg Thr Ile Met Ser Gly Ala Ala Pro Met G ly Lys Glu Leu Glu Asp
305                 310                 315                 320
Thr Val Arg Ala Lys Leu Pro Asn Ala Lys L eu Gly Gln Gly Tyr Gly
                325                 330                 335
Met Thr Glu Ala Gly Pro Val Leu Ala Met C ys Pro Ala Phe Ala Lys
                340                 345                 350
Glu Pro Phe Glu Ile Lys Ser Gly Ala Cys G ly Thr Val Val Arg Asn
                355                 360                 365
Ala Glu Met Lys Ile Val Asp Pro Glu Thr G ly Ala Ser Leu Pro Arg
                370                 375                 380
Asn Gln Ala Gly Glu Ile Cys Ile Arg Gly H is Gln Ile Met Lys Gly
385                 390                 395                 400
Tyr Leu Asn Asp Ala Glu Ala Thr Ala Asn T hr Ile Asp Lys Glu Gly
                405                 410                 415
Trp Leu His Thr Gly Asp Ile Gly Tyr Ile A sp Asp Asp Glu Leu
                420                 425                 430
Phe Ile Val Asp Arg Leu Lys Glu Leu Ile L ys Tyr Lys Gly Phe Gln
                435                 440                 445
```

```
Val Ala Pro Ala Glu Leu Glu Ala Met Leu Ile Ala His Pro Ser Ile
    450                 455                 460
Ser Asp Ala Ala Val Pro Met Lys Asp Glu Val Ala Gly Glu Val
465                 470                 475                 480
Pro Val Ala Phe Val Lys Ser Asn Gly Ser Val Ile Thr Glu Asp
                485                 490                 495
Glu Ile Lys Gln Tyr Ile Ser Lys Gln Val Phe Tyr Lys Arg Ile
                500                 505                 510
Lys Arg Val Phe Phe Thr Asp Ala Ile Pro Lys Ala Pro Ser Gly Lys
                515                 520                 525
Ile Leu Arg Lys Asp Leu Arg Ala Lys Leu Ala Ser Gly Val Tyr Asn
    530                 535                 540
```

<210> SEQ ID NO 350
<211> LENGTH: 717
<212> TYPE: DNA
<213> ORGANISM: Eucalyptus grandis

<400> SEQUENCE: 350

```
cctgttttgg caacaactcc agcagctctc tgctcttttt actataaaaa a acccatctt      60
cacttcttct gtacttgcac acgaacatta agcgcttgat cagaacttgt a tcagctccc    120
caccaccacc aaacagaaga gaaacagaag aaaaggaaaa gttcgaacaa c ttcgaacga    180
tgcgagccct gctgttgtg ctcggttctg ctatcttgct ggcgtatgtc g cgagcagtg     240
cgggtgcgct gagcttggat tactatgacc agacgtgccc gaagctcgag t tttcggtga    300
gggggggctgt gaagaaagcg atgaagaacg acaacaccgt tcctgctgct t tacttcgca   360
tgcacttcca cgactgcttc atcagaggat gtgacggttc cgtgctcttg a actcgacgg    420
caaagaacac agccgaaaaa gacgggccgc cgaacatctc actccacgca t tctatgtga    480
tcgaccttgc gaaggaagcg gtggaagctc agtgccctgg ggtcgtctct t gcgccgaca    540
tcttggcctt ggccgctcgg gatgctgtcg ctctgtctgg aggaccgcat t gggatgtgc    600
cgaaaggaag aaaagatggg aggattcgaa agcgaatgac acaaggcaat t accagctcc    660
gaccttcaac atctctcaac tacagcaagc ttctctcaag aggcctttcc a tggaga      717
```

<210> SEQ ID NO 351
<211> LENGTH: 369
<212> TYPE: DNA
<213> ORGANISM: Eucalyptus grandis

<400> SEQUENCE: 351

```
ggcgtctctc ctctgtctag tcatgtttct gaaatacctc tccgccgcac t catctctct      60
tgcaacgatt cgctctgctt acggtgcctc cactccgaag cgaagagcaa c atgcgcggg    120
cgggcagacc gtgaaaaacg aggcctgttg cgcctggttc cccgtcctgg a agacattct    180
gcccaacatg ttcgacaacg aatgtggcga cgacgcccat ggcgctctgc g tctgagctt    240
ccacgacgcg atcggtttct ctccttctca aggtggagga ggcgcggacg g atccatttt    300
gtcttcagtg acaccgaact gcagttcccc gcgaacgctg gcctcgacga c ccgatcgac    360
actgagctt                                                             369
```

<210> SEQ ID NO 352
<211> LENGTH: 1391
<212> TYPE: DNA
<213> ORGANISM: Eucalyptus grandis

<400> SEQUENCE: 352

```
gaaaaactgt ggtggtgaag ctgcctcgca aagatgtgac gttatctaat c agcgtctcc      60
ctgcccggaa aaagccggaa aaggaactgt tattttcaag cttttatttc a ccacaatca     120
cggagttata tattatacca agatttccgc gttaaccttA cgccggagaa a cttcatctg    180
agtgtgtgct cttgctggtt ttcaacagga acatatcgat aatttatgtc a tggctacac    240
acgatatggt cggcttttcc gtcgtcgttg tcctccttgc cacttcggtt a tcaccactg    300
cccgttgtaa gctctcaccg agtcattatc aatcaacatg tccgaaagca t tgtcgattg   360
ttcgagctgg agtagcaaaa gcaatcaaga atgagacccg gacgggcgcg t ccttgcttc   420
ggctgcactt ccatgactgc ttcgtcaatg ggtgcgatgc gtcgatattg t tggatgaca  480
cgcctagctt cgtgggcgag aaaacagcag ctccgaacaa caattccgtg a gagggttcg   540
aagtgatcga ccgcatcaag gctagtctgg agaaggagtg ccctggagtg g tttcctgtg   600
cagatatcgt tgccctggct gctcgcgact cagtcgttca tttgggaggt c cttcatgga    660
ccgtaagctt agggagaaag gattccatta ctgctagcag gagccttgct a acacctcca    720
tacctccacc tacttctaat ctcagtgctc tcataaccag cttcgctgct c agggtcttt    780
cagtcaagaa catggtggct ctttctggtt cacataccat tggcctagcg a gatgcactt    840
ccttccgaag acggatctac aacgactcga acatagatac atccttcgcc c ataaattgc   900
agaagatatg tcccaggatt ggaaatgata gtgtccttca aaggctagac a tccaaacgc   960
cgaccttctt tgacaacctt tactaccaca atttactgca gaagagggc c ttcttcact   1020
ctgatcaaga gctcttcaat ggcagttctg tggattcact ggtcaagaag t atgcatgcg  1080
acacaggaaa attttttccga gattttgcca aggcaatgat caaaatgagc g aaattaagc  1140
cccccaaagg aagcaatggt caaataagga aaaattgcag gaaagtgaac t aagtatgaa   1200
gctcatatat gcaatttgaa actgccacat atgaacacgg tagtgaaatc a gggctcgat   1260
aatgtcccct gacaatttgt cgtcatgtat ctgtcttctt gactaatttg t ggttgctgc  1320
ttgaaaaata aaggagctcg tctcagtttc tgtaaaaaaa aaaaaaaaaa a aaaaaaaa  1380
aaaaaaaaaa a                                                         1391
```

<210> SEQ ID NO 353
<211> LENGTH: 337
<212> TYPE: DNA
<213> ORGANISM: Eucalyptus grandis

<400> SEQUENCE: 353

```
cagaatgcct agtcgtcatc cgatttgggt aattgtcgcc atagcttttg t aaccgcact      60
cgggtgggga agtgcctccg cacaactctc tacaaacttc tactccaaaa g ttgtcccaa    120
tgttttgagc acggtgaaat ctgttgtccg gtccgcggtg tcgaaagagc g ccgcatggg   180
tgcttctctc ctgcgcctct tctttcatga ttgcttcgtc aatgggtgcg a tggctcgat    240
actcctggac gacacatcct cgttccaagg ggagaagacg gccggcccaa a taataagtc   300
tttgagagga tacaacgtca ttgaccggat caagtcc                                337
```

<210> SEQ ID NO 354
<211> LENGTH: 368
<212> TYPE: DNA
<213> ORGANISM: Eucalyptus grandis

<400> SEQUENCE: 354

```
ctcacttccg agcgcgccat gcagttcacc ttttccgccg ctttcctcgc t ctcgtcaca     60
```

```
gtcgcggccg ctatgcccac caagcgtgcg gcgtgcagca acggacgaac g gccactcat      120 gcctcgtgct gtgtgtggtt cgacgtcctc gacgatattc aagagaatct g ttcgacggt      180 ggagagtgcg gagaggaaac acacgagtct ctgcggctca ctttccacga t gccatcggc      240 ttctccccga gcctgtttct cgagggaaaa ttcggtggtc tcggcgctga t ggttccatc      300 atggctcact ctgacatcga gaccgtgttc cccgccaaca atggaattga t gatatcgtc      360 gacgcgca                                                                368
```

<210> SEQ ID NO 355
<211> LENGTH: 955
<212> TYPE: DNA
<213> ORGANISM: Eucalyptus grandis

<400> SEQUENCE: 355

```
aagaaactca gacccagacc cagaccacat catggcctcc cgtttcagct c tttcgtttt      60 ggtttctttt cttgtgatag ctgcatcaca tgttcatgtt acgagctctg c tcacttggt     120 gaagggctc tcgtggtcct tctacgagaa gagctgtccc aaggtggagt c cgtcatcaa     180 gaaacatctc aagaaggtgt tcgaggagga tattggccaa gctgctgggc t gcttcgtct     240 gcacttccat gactgctttg ttaagggatg tgatgcttcg gtgttgctgg a tggatcagc     300 cagtggacca agtgagcagg acgctccacc gaaccggagc ttgagaccat c agcattcaa     360 gatcatcgat gacctccgtg agctcgtgga caagaagtgt ggtcgagtag t ctcttgtgc     420 tgatatcgca gccattgccg ctcgtgactc cgttgtcctg tcaggcggac c tgagtatga     480 tgtgccgttg ggaaggcggg atggactcac gtttgcgact caaaatgtga c cttagagaa     540 tttacctgca ccaactgaga acgccagtgc aattctctcc gccctagcca a gaaaaactt     600 agacgctacc gacgtggtgg ccctctctgg aggccacacc atcgggcttg g gcactgcac     660 ctcctttgag aatcggctct acccgaccca agaccccacg atggagaaga c ctttgccca     720 tgatctcaag ggcgtgtgcc ccaccacaaa ctccaccaac actacggtct t ggacatccg     780 atcacccaac cgattcgaca acaagtactt tgtcgatttg gtgaaccgcc a aggcctgtt     840 cacctcagac caagatctgt atgaggatcc cacaaccagg acattgtca c tagctttgc     900 cgaggaccag gaattgttct ttgagaagtt tgtcctagcc atgacgaaga t gggg          955
```

<210> SEQ ID NO 356
<211> LENGTH: 308
<212> TYPE: DNA
<213> ORGANISM: Eucalyptus grandis

<400> SEQUENCE: 356

```
ctgtgtctag tcatgttcct gaagtatctc tccggcgccc tcgtctccct t gcaacgatc      60 cgcggtgttt gcggtgcttc cgctccgatg cgaagagcaa catgtgcggg t gggcagact     120 gtcaaaaatg cggcatgttg tgcatggttc ccagtactcg acgacatcag g gaaaacttt     180 ttcgacaacg aatgcggcga tgacgcccat gctgccctgc gtctgagttt c cacgatgca     240 atcggtttct ctcgttcgaa aggtggagga ggcgcggacg gatccatcat t gccttcaat     300 aagactga                                                                308
```

<210> SEQ ID NO 357
<211> LENGTH: 373
<212> TYPE: DNA
<213> ORGANISM: Eucalyptus grandis -continued

```
<400> SEQUENCE: 357
tcaggtcctt gtcaacatgg cattcaaact cgtggttaat cttgttagtc t tgctctcgc      60
cgtcagtgct gcaaacttca agcgagttgc ttgcccaggt actacggcca c agctcgcaa    120
tccggcgtgc tgcgcattct tctcactgag agatgacttg cttacaaatc t cttcggggg    180
tgtgtgcggc gaagaggcgc acgagtctct ccgattgtct ttccatgatg c cattgcgtt    240
ttcgcccgca ttaattaggc aaggcaaacc gggaggtgga ggtgctgatg g ctctatgat    300
tactttccca aacgtcgagc ccaattttaa tgccaacaac ggcattattg a ttctgtcga    360
cttttttgaca cca                                                       373

<210> SEQ ID NO 358
<211> LENGTH: 417
<212> TYPE: DNA
<213> ORGANISM: Eucalyptus grandis

<400> SEQUENCE: 358
ctcttgtcct gggaccgtgt cttgcgccga cattctcgcc ctcggtgctc a agcttctgt     60
cgttctgtca ggaggtccat cttggagggt gctctcgggg aggagggaca g cttgacggc   120
gaaccaagca ggagcgaaca catcgatacc tagcccttt gattccttgg c taacctcac    180
ttccaaattc gccgctgttg gcttggacac caatgacctt gtcactcttt c cggagctca   240
cacctttgga cgtgcacagt gcaggacatt cagccctagg ctctacaact t caacgcgag   300
tggcagccca gatccaacca taagtccttc atacttgacc actctccaac a actttgccc   360
acagaatgga agcggctccg tcctcgccaa cctcgacccg acgaccgtga a cacatt     417

<210> SEQ ID NO 359
<211> LENGTH: 659
<212> TYPE: DNA
<213> ORGANISM: Pinus radiata

<400> SEQUENCE: 359
cacaatggaa atagtttagg tcagtaatgg aacggatgaa acatattccc g gccttacac     60
tgcagtttca gtctgtgctg atcactggag cggcattgtt tctatggatc c agacatcgg   120
atgctcagga ctgtaatggt ctgagtcatc actattatca gaagtcctgt c caaatgccc   180
aggctatcat taaatctgta gtttcagatg ctgtcaaaaa ggaagcgaga a tggctgctt   240
ccttgcttcg tctgcatttt catgactgtt ttgttcaggg ctgtgatgct t caattctgc   300
ttgatgacac tgctagtttc acaggggaga agacagcatt acctaacaga a attctgtaa   360
gaggctttga ggtagtggat aagatcaaaa gcaaattgga ggaagcatgt c ctggagtgg   420
tctcatgtgc tgacattctt gctgtggcag cccgtgattc agtaggcttt a gtgtgggtc   480
cgtattggga ggttctactg gcaggaggg actcaaagac tgcaagcaag a gcggtgcaa    540
acaacgacat tcctgcaccc aactcaaccc atcagactct ggaaaccaaa t tcaacctca   600
aaggtctcaa tgtgcttgac ctagttgctc tatcaaggtc ccataacaat a gggttagc    659

<210> SEQ ID NO 360
<211> LENGTH: 669
<212> TYPE: DNA
<213> ORGANISM: Pinus radiata

<400> SEQUENCE: 360
gcggcacgag cggcaaaaact aaagctattc gcagcctccc tctatggcga c attagggat     60
ccctctcggc tcactcagcc tgctcctcct cttcttctgc tgcgcacaac g cagtgtggg   120
```

```
actgaaggaa aattactacg caacgtcgtg tccgagagca gagcacatag t gaaggagca      180 ggtctacaat ctctaccagg agcacggcaa cactgccgtt tcatggatca g acttatctt      240 ccatgactgc atagttcagt cgtgcgatgc ctccattcta ttagacagta g tggagacgt      300 gcagacagag aaacaatcgg accgaaactt cggaatgcga aacttcaagt a tgtggacac      360 cattaaggag gccatcgagg tggaatgtcc tggagtggtg tcgtgtgctg a cattattgt      420 tctcgccgca aaggaggcag ctgcaatgct aggaggtcca cgcatcgcgg t gaaaacagg      480 gagacgagac agcagaaaaa gcagtgcagc agtggtggaa aaatacgttc c gctgcataa      540 tggcagcatc tcatctcttc tctctgcctt tgcctctgtg ggcatcgatg c ggaaggagc      600 tgtggcccct ttaggtttga tacttatcca ttctgtatta cattatacat a aataaaaaa      660 aaaaaaaaa                                                               669

<210> SEQ ID NO 361
<211> LENGTH: 916
<212> TYPE: DNA
<213> ORGANISM: Pinus radiata

<400> SEQUENCE: 361
agcaaattgg ttgcttttgg agcgcttgtt ccaacagcaa aaatggctgt t ttgatgaag      60 agctttccgt gcattgctgt cattgtgttc attatctgtt cgattactga t actgtgaat     120 gggaaactga gctccacgtt ttatgataag tcttgtccca aggccctgtc t atagtgcaa     180 gccggggtga agcaagcagt ggctaaggaa aaacgtatgg gggcatcgct t ctccgcctt     240 catttccacg actgcttcgt taatggctgc gatgggtctg tactgttgga c aattccacg     300 accttcacta gcgagaaata tgctcttccc aataacaatt ccgcgagggg t ttcgaggtg     360 atcgatagca taaagagcca actcgagaat gcttgcaccg gcgtcgtttc t tgtgcagac     420 attctcacga ttgctgctcg tgattctgtt gttcagttgg gtggaccttc g tggaaggtg     480 atgttgggga ggcgagactc aacaacagcg agcattagcg gtgcaaacaa t aacattccg     540 cctcccactt ccaatctgac gaaactcatt tcactatttc aggcacaggg c ctctccaca     600 aaggaaatgg ttgcactctc tggtggtcat accatcgggc aggcgcaatg c aagaatttc     660 agagcccata tttacaacga caccaacata gatactacgt acgccacttc a ttgcgttca     720 aagtgtccta gtaccacagg ctccggagac agcaacctgt cgccactgga t tatacgact     780 cccactgtgt ttgacaaaaa ctattactac aatctgaaaa gcaaagagg a cttctccac      840 tccgaccagg aactcttcaa cggaggctcc actgattcgc atgtgactaa g tacgcctcc     900 aaccagaata ccttct                                                       916

<210> SEQ ID NO 362
<211> LENGTH: 586
<212> TYPE: DNA
<213> ORGANISM: Pinus radiata

<400> SEQUENCE: 362
gcaaacagca accttccctc gccagcttcc agtctcagca cactcatgac a gcatttcaa      60 aaacagggtc tctctaccaa ggacctcgtc gcactctcag gtgctcatac a attggtcaa     120 gcacggtgca ccacattcag aactcgcatc tacaacgata ccaacattaa c gctgccttc     180 gctacatctg cgaaggcgaa ctgccccagc actggtggcg acaacaccct c tctcccttg     240 gatgttctca cccctaccac atttgacaac aagtattaca ctaatctgaa a agccaaaag     300
```

| | | |
|---|---|---|
| ggactttttcc actccgatca ggagctattt aatggaggtt ccacagactc t agagttagt | 360 | |
| atctacagca ccagtcaagc catttctctt actgactttg cagccgccat g gtgaatatg | 420 | |
| ggtaatatta gtcccctcac tggcaccaac ggcgagatcc gcacaaactg c aggaaagtc | 480 | |
| aattaaaatt tgtaaagatt gtattatcta tagcttttct ctgaagttat a agcgaagct | 540 | |
| ttacaagaaa gcaataaatt actgtttaat taaaaaaaaa aaaaaa | 586 | |

<210> SEQ ID NO 363
<211> LENGTH: 1224
<212> TYPE: DNA
<213> ORGANISM: Pinus radiata

<400> SEQUENCE: 363

| | | |
|---|---|---|
| ctaccactca atttcgctct tatcttctgt gtttcatcgt tttcttccaa a tatgatgat | 60 | |
| gaggactcta gtgtgcattg ggttaatggc tgtgtttgta gccttcatac a tataaacgc | 120 | |
| tgtgaatggg cagctgagct caacgtttta tgccaaatcg tgtccgaggt t gccatcgat | 180 | |
| agtgaaatca gtggtgaagc aagcggtagc taaggagaaa agaatgggag c gtccttggt | 240 | |
| ccgccttcac tttcacgatt gcttcgtcaa cgggtgcgat ggttcaatct t attggatga | 300 | |
| caacgctacg tttaccggag aaaagactgc aggcccaaac gccaattctg c gagaggctt | 360 | |
| cgaggtaatt gacagcatta aaactcaagt ggaggcagcc tgcagtggag t cgtgtcgtg | 420 | |
| tgcagacatt ctcaccattg ctgctcgtga ctctattgtt gaacttcaag g cccaacatg | 480 | |
| gacggtaatg cttggaaggc gagactccac gactgcgagt ttaagcgctg c aaacaacaa | 540 | |
| cattccatct cccgcttcca gtctgagcac actcatctca tctttcaag c tcacggtct | 600 | |
| ttctaccaaa gaccttgttg cactctcagg tgctcataca attggtcaat c acgatgcgc | 660 | |
| cttttttcaga actcggatct acaacgaaac gaacattaac gctgctttcg c tacatctgt | 720 | |
| aaaggcaaac tgccccagcg ctggtggcga cagcaacctc tctcccttag a tgcggtcac | 780 | |
| ctcaatcaca tttgacaaca agtattactc taatcttaaa atacagaaag g acttctcca | 840 | |
| ctccgaccag cagctcttta atggaggttc tacagattct caggttactg c gtacagcag | 900 | |
| caatcagaac agcttctttta tagactttac agctgccatg gtgaagatgg g aaatattag | 960 | |
| ccctctcact ggcactaacg ggcaaatccg caaaaactgc aggaagtcca a ttagtctct | 1020 | |
| ctgaagattg tattctccgt actctttcag cttattttt ctttgtaaca t tgattttcg | 1080 | |
| atcggctagt gagccttcaa atcgaagctc taaagaaag caataaacta c atttctgag | 1140 | |
| attatgttca gagttgtatg cagttcagac cataattcca attttgcttc c aaaaaaaa | 1200 | |
| aagacttgta aaaaaaaaa aaaa | 1224 | |

<210> SEQ ID NO 364
<211> LENGTH: 519
<212> TYPE: DNA
<213> ORGANISM: Pinus radiata

<400> SEQUENCE: 364

| | | |
|---|---|---|
| aaactgccca agtcaggagg cgacaataac ctgtcaccgt tggatctact g actccaaca | 60 | |
| acgttcgaca ataaatacta cacaaatctg aagagccaaa agggtcttct c cactcagac | 120 | |
| cagcagctgt ttaatggcgg ctctgcagat tcccaggtta ctacctacag c accactcag | 180 | |
| agcaccttct ttaccgactt cgcagcttcc atgttgaata tgggtaatat c agtcccctc | 240 | |
| actggcacca gcggacaaat ccgcaaaaac tgcagaaaac ctaattgatg c ctctcttag | 300 | |
| gccatatgta ctttactgtt ctcatgggat tatattttga ttgtagaatt a tatagatag | 360 | |

```
ttgggagacc tacggctgcg ttagacacta gcaagcctcc aattggatct g tgcgtccct    420 agtttgttga ctatttggtt gatttcgatg taccaagtac aaagtttctc a acagattaa    480 tccaatgaat taggttttat aaaaaaaaaa aaaaaaaa                              519

<210> SEQ ID NO 365
<211> LENGTH: 646
<212> TYPE: DNA
<213> ORGANISM: Pinus radiata

<400> SEQUENCE: 365
aaaccattca aacccaccga agatttcatt gcgtcgcagc atcatgactt c ctttacagc     60 aatggcgtca gtcgtgtgca tcgctctgct cttttttttcg accgttgctt t tgctcaact   120 caactcaacg tattatgata cgtcgtgtcc caaactcctg gcaacggtga a ggctgcagt   180 gaagacggcg gtggccaatg agaaacgcat gggggcatca ttgctccgtc t tcactttca   240 tgattgtttc gtcaatggtt gcgatgggtc agtgttgttg gacgactctt c gagtctaac   300 tggggaaaag actgctcttc ccaacaacaa ttcgttgagg ggtttcgacg t catagacac   360 catcaaatca caagtggaag cagtttgcag cggaatcgta tcgtgcgctg a cattttggc   420 tattacggct agagattctg tcgtcgaatt gggaggacca acatgdacag t gctgcttgg   480 aaggagagac tcagcaactg ccagcctaag cgccgcaaac accaacattc c cgctcccac   540 ttccaatctc agtggtctca tctcatcttt tcaagcacag ggcctttcaa c caaggatat   600 gattgtccta tcaggtgcac ataccattgg ccaagctcga tgcaca                    646

<210> SEQ ID NO 366
<211> LENGTH: 364
<212> TYPE: DNA
<213> ORGANISM: Pinus radiata

<400> SEQUENCE: 366
ccttaatctc ctcttttaca gcccatggtc tttccacaaa ggatctcggt g cactctcgg    60 gagctcatac gattggccaa gcgcggtgca ccacattcag agctcgcgtc t acaacgaat   120 ccaacattga cacttccttc gccacttcgg tgaaggcaaa ctggccaagc g ctggtggcg   180 acaacaccct ctcgcccttta gatctggcca cgcctaccac atttgacaac a agtattaca   240 ctgatttgag aagccaaaag ggacttctgc actccgatca gcaaatgttt a gcggagggt   300 ctacaaaattc tcaagtcacc acctatagct ccaatcaaaa cacctttctt t acagacttt   360 acag                                                                 364

<210> SEQ ID NO 367
<211> LENGTH: 364
<212> TYPE: DNA
<213> ORGANISM: Pinus radiata

<400> SEQUENCE: 367
ggaaaaggat caactttcac ttaaaggagg acatcaccca agcggctggt t tgctgcgcg    60 tccatttcca tgactgcttc gttcagggtt gcgacggatc ggttctgttg g acggttctg   120 ccagcggtcc tagcgaacaa gacgctccac cgaacttaac gctgagagca a aagcctttg   180 aaataattaa cgacatcaag aaacatgtgg aaaaggcttg cagcggcgtt g tctcttgcg   240 cggacttgac tgctctcgca gctcgcgagt cggtcagagc agttggagga c cagagtatc   300 gagtgcctct ggggcgcagg gacagcctga aattcgccac acgaaaagtg a ccccttgcca   360
``` acct                                                                    364

<210> SEQ ID NO 368
<211> LENGTH: 801
<212> TYPE: DNA
<213> ORGANISM: Pinus radiata

<400> SEQUENCE: 368

| | | | | | |
|---|---|---|---|---|---|
| gtcatggctt | cgtttacagc | aatgcgatct | ctggccttta | tcgccttgtt g | atgtgttcg | 60 |
| accgttgcgt | acgcgcagct | tagcgcaacg | ttttataata | catcatgtcc c | aaactactc | 120 |
| tcaacggtgc | aggccgctgt | gaagcaagcg | gtggccaacg | agaagcgcat g | ggggcatcg | 180 |
| ctcctccgcc | ttcactttca | cgactgcttc | gttaatggtt | gcgatgggtc t | gtgctgctg | 240 |
| gacgactctt | cgactctaac | tggagagaag | accgccgttc | ccaacaacaa t | tcggcaagg | 300 |
| ggtttcgatg | tgatagacac | catcaagtct | caagtggaag | cagtttgcag t | ggagttgtg | 360 |
| tcgtgcgcag | atattttggc | tattgctgct | agagattctg | ttgtccagtt g | ggaggccca | 420 |
| acatggacag | tgcagctggg | gaggagagac | tccaggactg | ccagcctaag t | ggtgcaaac | 480 |
| aacaacattc | cggctcctac | ttctaatctc | agtgctctca | tctcattatt t | caagctcag | 540 |
| ggtcttttcca | cgaaggacat | ggttgtccta | tcaggtgcgc | acaccatagg c | caagcgcgg | 600 |
| tgcacaagct | tcagggcccg | catctacaac | gaatcccaaca | ttaatgcagc a | tacgcaact | 660 |
| tccctgaaga | caaactgtcc | gactacagga | agcgacaaca | acctgtcacc a | ttggatcgt | 720 |
| gttactccca | ctacgtttga | catcaactac | tactcaaatc | tgagaagcca a | aagggactt | 780 |
| ctccactccg | accagcagct | g | | | | 801 |

<210> SEQ ID NO 369
<211> LENGTH: 1171
<212> TYPE: DNA
<213> ORGANISM: Pinus radiata

<400> SEQUENCE: 369

| | | | | | |
|---|---|---|---|---|---|
| gccaaataaa | gttatctttt | ggctttattc | cacaagaaaa | aaatggctta c | ctaaggaag | 60 |
| agtttcgcct | gtatagctgt | aatggtgttt | atcgtgtgtt | ctattacaga t | actgtgaat | 120 |
| gggcagctga | gctccacgtt | ttacgacaaa | tcttgcccga | cggcactgtc g | gtagtgaag | 180 |
| gccgcagtga | agcaagcggt | cgctaacgag | aaacggatgg | gtgcgtcttt g | ctccgcctg | 240 |
| cactttcacg | actgcttcgt | taatggttgc | gatgggtccg | ttctgttgga c | gattcttcg | 300 |
| accattactg | gcgagaagac | agctaatccc | aatgccaatt | ctgcgagggg a | ttcgacgta | 360 |
| atagatacca | taaagagcaa | tgtcgagaaa | gcttgcagtg | gagtcgtttc c | tgtgcagac | 420 |
| attctcgcca | ttgctgctcg | tgattctgtt | gttgaactgg | gcggtccttc a | tggacagta | 480 |
| atgttgggaa | ggcgagactc | gacaacagct | agcaaaagcg | gtgcaaacag t | aatattccg | 540 |
| cctccgactt | ccagtctgag | caacctcatc | tcactattcc | aagcgcaggg a | ctctccgca | 600 |
| aaggaaatgg | ttgcactttc | tggcggtcat | accatcgggc | aggcgcaatg c | aagaatttc | 660 |
| agagcccata | tttacaacga | gaccaacata | gacagtgcgt | acgccacttc a | ttgcgttca | 720 |
| aagtgtccga | gtaccacagg | ctccggagac | agcaacttgt | cgccattgga t | tatatgact | 780 |
| cccactgtgt | ttgacaaaaa | ctattacagc | gacctgaaaa | gccaaaaagg a | cttctccac | 840 |
| tccgaccagg | aactcttcaa | cggaggctcc | actgattcac | aggtgactac g | tacgcctcc | 900 |
| aaccagaaca | ccttcttctc | cgattttgct | gcggccatgt | ttaagatggg a | aatatcaaa | 960 |
| cctcttaccg | gcaccagcgg | acagatccca | aagaactgca | ggaagccaaa c | taattatga | 1020 |

```
tcactgtcga attatcatca ctccgttgca ctgccttta attgtaaaag t aacgtttcg    1080 actgatttca gtctatggat accatatgct gatggagctt gtcatgaata a ataagttca    1140 taactttacc atcattaaaa aaaaaaaaaa a                                    1171

<210> SEQ ID NO 370
<211> LENGTH: 1073
<212> TYPE: DNA
<213> ORGANISM: Pinus radiata

<400> SEQUENCE: 370
atcagattaa gagtgcactt gagaaggagt gcccaaaaac tgtatcgtgt g cagatattc    60 tcgctattgc atctcgtgat tcagtggtcc tgagtggagg gctgggctgg g aagttttac   120 tggggaggag agattcgaag agtgcaagtt tgagtgggtc caacaacaat a tcccggcgc   180 ccaactcaac tctgcagacg cttactacca agttcaaact acaaggtcta g atgaggtag   240 acttggtatc cctttcaggg agtcacacca tcggcctatc tcgatgcaca a gtttcaggc   300 agaggcttta caaccagagt ggaaatgggc tgccagactt cactctaaac a ggggttact   360 atgctcggct gaaatccgga tgtccaaaat ctggaggaga taataacttg t tcccattgg   420 atttcgtgac tcctaccaaa ttcgataact actacttcaa gagcttgctg a gcggtcaag   480 ggctgttgaa cacagacgaa gaattgttcg caaagggctc agggaagacg a aggagctag   540 ttaaacttta tgcagcaaat gaggagctct ttctcaaaca gtttgcatta t ctatggtga   600 agatgggaaa catcaagcct cttacaggca ccgtgggaga aatcagggtc a actgtcgta   660 aggttaacag ttgatcgttt taatttaatc attttccatc tcttgcattg c attttgtta   720 catctcccct cttagctgcc atcaaattgc attactagat catccttccc a tggctttca   780 gttgtaacag gttgaataaa attgccactt ctgaattatt aaacttctga t tgggctgga   840 cgatagaggg aaacttcaac gtcccaatca aattgtcatg taagaaatat c tcgggcagt   900 aaactcagag tggtaaatca agattgttga ataaaatgtt agctcttcgt t aatggctgt   960 ggagaaggtc aacactcctc gtgtgtttag ctatgtgtct gtttattaac g cttgcgagt  1020 tttgatgtaa tggaaatcgt gtcttcaaca agaataaaaa aaaaaaaaaa a aa         1073

<210> SEQ ID NO 371
<211> LENGTH: 1522
<212> TYPE: DNA
<213> ORGANISM: Pinus radiata

<400> SEQUENCE: 371
gaaaggcctg tcgatttcct ccatttgaat cgacaggatc gaagaatcta t tttacatca    60 aagcaaagcc aaagctgtgg ccgacatggg caagtttatc acggctctgg c ttctgttat   120 tctctgcgtg tttgtgatct atggcggcgc tgtcaatgct ctgcccagtc c cgtggctgg   180 tctttcttgg acgttctaca gctcgagttg cccgtccttg gagtccatag t gtgggagcg   240 catggaagcc tatttgagtg cagacatcac acaggctgca ggattgttga g gctccactt   300 ccacgactgc tttgtccagg gatgcgatgg gtcggtgttg ttgaacgcaa c gtcaggtga   360 gcaaacggct cccccaaact tatcactcag agcgcaggct ttaaagatta t taacgacat   420 caaagagaac gtcgaagccg cctgcagcgg aattgtgtcg tgtgccgaca t tgttacttt   480 agcagctcgt gactccgttg taatggctgg aggaccgttc tacccettac c actcggccg   540 cagggacagc cttaccttcg ccaatcgatc gaccgttctc gccaatttgc c atccccaac   600
```

-continued

```
ctccaatgta acggggctca tcagtgtttt gggtcccaaa ggcttgaatt t cacagatct      660 ggtggccctc tcaggaggac atacaattgg cagaagcaac tgctcctcct t cgacaacag     720 actatataac agcaccaccg gtacacaaat gcgggatccc acgatggacc a gagtttcgc     780 taagaatctt tatctcacct gccctaccag taccaccgtt aacaccacca a attggatat     840 tcgcactcca aatgtgttcg acaacaaata ctacgtcgat ctcctcaacc g acagaccct    900 cttcacttct gaccagactc tttacaccga cactcgaacc cgcgacattg t gatcaattt    960 tgcggtgaat cagagcctct tctttgaaca gtttgtgctg agcatgctca a aatggggca   1020 gctggatgtg ctcacaggaa gcgagggaga gatccgtaag aactgctggg c tgcgaatcc   1080 ttcaacattt tcgattatgg atccagaggc gtctcaagaa tcaacatctt a ctctatgtg   1140 agattagggt tatgagcgaa tctcaaatat aagcaagcag cgttaattcc c agcaaagtc   1200 taataaaatat atatataacc ggcatcttgt aaacccttg caatgctggt t ctacaaatt   1260 acttttcccc ttttgacctt ctgaaagagc agaaatcaag cctgaataca g tgcattctc   1320 gttgaaaata aatagcgttt cttgttgata atcagatttc caaccgattc c ggcaatttc   1380 caataagaaa ctttactgaa tttaaactca aatgctggcc aattttgttt a gggcgtttt   1440 tgaaatcgtt ggactgttat ctttggaaac ctacattaga cttatattta t ctaaaatat   1500 tgcacccaaa aaaaaaaaaa aa                                              1522
```

<210> SEQ ID NO 372
<211> LENGTH: 311
<212> TYPE: DNA
<213> ORGANISM: Pinus radiata

<400> SEQUENCE: 372

```
ctcaatttcg ctcttatctt ctgtgtttca tcgttttctt cccaatatga t gatgaggac       60 tctagtgtgc attgggttaa tggctgtgtt tgtagccttc atacatataa a cgcttgaat     120 gggcagctga gctcaacgtt ttatgccaaa tcgtgtccga ggttgccatc g atagtgaaa     180 tcagtggtga agcaagcggt cgctaaggag aaaagaatgg gagcgtcctt g gtccgcctt     240 cactttcacg attgcttcgt caatgggtgc gatggttcaa tcttattgga t gacaacgcg     300 acgtttaccg g                                                           311
```

<210> SEQ ID NO 373
<211> LENGTH: 474
<212> TYPE: DNA
<213> ORGANISM: Pinus radiata

<400> SEQUENCE: 373

```
catcgatgct atcaagacag ccctcgagag ttcttgcaac gccactgttt c ttgcgcaga       60 tattctcgct attgcagcgc gggattcagt ataccttagc ggtgggcctt a ctggcaagt     120 gcagatgggg agaagagatg gcaccactgc cagcaaaagt gcagcaaatg c cgacatccc     180 ttctcctatt gagtcgcttg gttcactcat atcccaattc caaggtgttg g ctttctgt      240 tcatgatctt gtagtgcttt caggggctca caccataggc cgtgcccact g tggcacctt     300 cagctcacgc ctattcaatt tcagcggctc aaacagtgcg gacccaacta t tcaccaatc     360 tctactgcaa gacctgcata gtttatgccc agatggaaac agtgatccaa t accctggc     420 gccactggac cctgtgacca aagacaagct ccataatgtg tatttcagaa a tct           474
```

<210> SEQ ID NO 374
<211> LENGTH: 353

```
<212> TYPE: DNA
<213> ORGANISM: Pinus radiata

<400> SEQUENCE: 374
ctttctgtta cggatgtcgt tgctttgtca gggggacata caattgggcg a gctcggtgc    60 acagtgttca gcggtagact ctacaatttc agcggaacgg gcagtccgga t ccgacactg   120 aattcctcct atctatccac cttgcaaagc acgtgcccgc agaatggaag c gcgaatacg   180 ttaacgtcac tggatccagg gactccaaat acgttcgaca caactactt t gcaaatctg   240 cagattgaga tgggtctgct tcagtcgatc aagaacttct ttccacatcg g gagcaagca   300 ccatctctac tgtcaatgat tatgccagta gtcaatccga tttcttcttc a ac          353

<210> SEQ ID NO 375
<211> LENGTH: 461
<212> TYPE: DNA
<213> ORGANISM: Pinus radiata

<400> SEQUENCE: 375
caaagcagag ttgcgtttga agcgcaagaa atggccgctt taatgaaaag c tccgcatgc    60 attgctgtaa ttgtgtttat tgtgtgttcg attaataaca ctgtgcatgg g cagctgagc   120 tcaacatttt atgacaaatc ttgcccgacg gtgctgtcgg tagtgaaagc c ggggtgaag   180 caagcggtcg ccaaggagca aaggatgggg gcgtcgcttc tccgacttca c ttccacgac   240 tgcttcgtta atggttgcga tgggtccgtt ctgttggatg actcttcgaa a attactggc   300 gagaaaacgg ctattcccaa tgccaattcg gcgagggggt tcgatgtgat c gataccata   360 aagagtcagg tcgagaaatc ttgcagcgca gtcgtttcct gttctgacat t ctagccatt   420 gctgctcgtg attctgttgt tgaactgggc ggcccttcat g              461

<210> SEQ ID NO 376
<211> LENGTH: 179
<212> TYPE: PRT
<213> ORGANISM: Eucalyptus grandis

<400> SEQUENCE: 376

Met Arg Ala Leu Ala Val Val Leu Gly Ser A la Ile Leu Leu Ala Tyr
 1               5                  10                  15

Val Ala Ser Ser Ala Gly Ala Leu Ser Leu A sp Tyr Tyr Asp Gln Thr
                20                  25                  30

Cys Pro Lys Leu Glu Phe Ser Val Arg Gly A la Val Lys Lys Ala Met
            35                  40                  45

Lys Asn Asp Asn Thr Val Pro Ala Ala Leu L eu Arg Met His Phe His
        50                  55                  60

Asp Cys Phe Ile Arg Gly Cys Asp Gly Ser V al Leu Leu Asn Ser Thr
65                  70                  75                  80

Ala Lys Asn Thr Ala Glu Lys Asp Gly Pro P ro Asn Ile Ser Leu His
                85                  90                  95

Ala Phe Tyr Val Ile Asp Leu Ala Lys Glu A la Val Glu Ala Gln Cys
            100                 105                 110

Pro Gly Val Val Ser Cys Ala Asp Ile Leu A la Leu Ala Ala Arg Asp
        115                 120                 125

Ala Val Ala Leu Ser Gly Gly Pro His Trp A sp Val Pro Lys Gly Arg
    130                 135                 140

Lys Asp Gly Arg Ile Arg Lys Met Thr G ln Gly Asn Tyr Gln Leu
145                 150                 155                 160
```

```
Arg Pro Ser Thr Ser Leu Asn Tyr Ser Lys Leu Leu Ser Arg Gly Leu
            165                 170                 175

Ser Met Glu

<210> SEQ ID NO 377
<211> LENGTH: 115
<212> TYPE: PRT
<213> ORGANISM: Eucalyptus grandis

<400> SEQUENCE: 377

Met Phe Leu Lys Tyr Leu Ser Ala Ala Leu Ile Ser Leu Ala Thr Ile
  1               5                  10                  15

Arg Ser Ala Tyr Gly Ala Ser Thr Pro Lys Arg Arg Ala Thr Cys Ala
             20                  25                  30

Gly Gly Gln Thr Val Lys Asn Glu Ala Cys Cys Ala Trp Phe Pro Val
         35                  40                  45

Leu Glu Asp Ile Leu Pro Asn Met Phe Asp Asn Glu Cys Gly Asp Asp
 50                  55                  60

Ala His Gly Ala Leu Arg Leu Ser Phe His Asp Ala Ile Gly Phe Ser
 65                  70                  75                  80

Pro Ser Gln Gly Gly Gly Ala Asp Gly Ser Ile Leu Ser Ser Val
             85                  90                  95

Thr Pro Asn Cys Ser Ser Pro Arg Thr Leu Ala Ser Thr Thr Arg Ser
            100                 105                 110

Thr Leu Ser
        115

<210> SEQ ID NO 378
<211> LENGTH: 315
<212> TYPE: PRT
<213> ORGANISM: Eucalyptus grandis

<400> SEQUENCE: 378

Met Val Gly Phe Ser Val Val Val Leu Leu Ala Thr Ser Val Ile
  1               5                  10                  15

Thr Thr Ala Arg Cys Lys Leu Ser Pro Ser His Tyr Gln Ser Thr Cys
             20                  25                  30

Pro Lys Ala Leu Ser Ile Val Arg Ala Gly Val Ala Lys Ala Ile Lys
         35                  40                  45

Asn Glu Thr Arg Thr Gly Ala Ser Leu Leu Arg Leu His Phe His Asp
 50                  55                  60

Cys Phe Val Asn Gly Cys Asp Ala Ser Ile Leu Leu Asp Asp Thr Pro
 65                  70                  75                  80

Ser Phe Val Gly Glu Lys Thr Ala Ala Pro Asn Asn Ser Val Arg
             85                  90                  95

Gly Phe Glu Val Ile Asp Arg Ile Lys Ala Ser Leu Glu Lys Glu Cys
            100                 105                 110

Pro Gly Val Val Ser Cys Ala Asp Ile Val Ala Leu Ala Ala Arg Asp
            115                 120                 125

Ser Val His Leu Gly Gly Pro Ser Trp Thr Val Ser Leu Gly Arg
            130                 135                 140

Lys Asp Ser Ile Thr Ala Ser Arg Ser Leu Ala Asn Thr Ser Ile Pro
145                 150                 155                 160

Pro Pro Thr Ser Asn Leu Ser Ala Leu Ile Thr Ser Phe Ala Ala Gln
            165                 170                 175

Gly Leu Ser Val Lys Asn Met Val Ala Leu Ser Gly Ser His Thr Ile
```

```
                    180                 185                 190
Gly Leu Ala Arg Cys Thr Ser Phe Arg Arg A rg Ile Tyr Asn Asp Ser
                195                 200                 205
Asn Ile Asp Thr Ser Phe Ala His Lys Leu G ln Lys Ile Cys Pro Arg
        210                 215                 220
Ile Gly Asn Asp Ser Val Leu Gln Arg Leu A sp Ile Gln Thr Pro Thr
225                 230                 235                 240
Phe Phe Asp Asn Leu Tyr Tyr His Asn Leu L eu Gln Lys Lys Gly Leu
                245                 250                 255
Leu His Ser Asp Gln Glu Leu Phe Asn Gly S er Ser Val Asp Ser Leu
                260                 265                 270
Val Lys Lys Tyr Ala Cys Asp Thr Gly Lys P he Phe Arg Asp Phe Ala
                275                 280                 285
Lys Ala Met Ile Lys Met Ser Glu Ile Lys P ro Pro Lys Gly Ser Asn
        290                 295                 300
Gly Gln Ile Arg Lys Asn Cys Arg Lys Val A sn
305                 310                 315

<210> SEQ ID NO 379
<211> LENGTH: 111
<212> TYPE: PRT
<213> ORGANISM: Eucalyptus grandis

<400> SEQUENCE: 379

Met Pro Ser Arg His Pro Ile Trp Val Ile V al Ala Ile Ala Phe Val
1               5                   10                  15
Thr Ala Leu Gly Trp Gly Ser Ala Ser Ala G ln Leu Ser Thr Asn Phe
            20                  25                  30
Tyr Ser Lys Ser Cys Pro Asn Val Leu Ser T hr Val Lys Ser Val Val
        35                  40                  45
Arg Ser Ala Val Ser Lys Glu Arg Arg Met G ly Ala Ser Leu Leu Arg
    50                  55                  60
Leu Phe Phe His Asp Cys Phe Val Asn Gly C ys Asp Gly Ser Ile Leu
65                  70                  75                  80
Leu Asp Asp Thr Ser Ser Phe Gln Gly Glu L ys Thr Ala Gly Pro Asn
                85                  90                  95
Asn Lys Ser Leu Arg Gly Tyr Asn Val Ile A sp Arg Ile Lys Ser
            100                 105                 110

<210> SEQ ID NO 380
<211> LENGTH: 116
<212> TYPE: PRT
<213> ORGANISM: Eucalyptus grandis

<400> SEQUENCE: 380

Met Gln Phe Thr Phe Ser Ala Ala Phe Leu A la Leu Val Thr Val Ala
1               5                   10                  15
Ala Ala Met Pro Thr Lys Arg Ala Ala Cys S er Asn Gly Arg Thr Ala
            20                  25                  30
Thr His Ala Ser Cys Cys Val Trp Phe Asp V al Leu Asp Asp Ile Gln
        35                  40                  45
Glu Asn Leu Phe Asp Gly Gly Glu Cys Gly G lu Glu Thr His Glu Ser
    50                  55                  60
Leu Arg Leu Thr Phe His Asp Ala Ile Gly P he Ser Pro Ser Leu Phe
65                  70                  75                  80
Leu Glu Gly Lys Phe Gly Gly Leu Gly Ala A sp Gly Ser Ile Met Ala
```

```
                    85                   90                    95
His Ser Asp Ile Glu Thr Val Phe Pro Ala Asn Asn Gly Ile Asp Asp
                100                  105                   110

Ile Val Asp Ala
        115

<210> SEQ ID NO 381
<211> LENGTH: 308
<212> TYPE: PRT
<213> ORGANISM: Eucalyptus grandis

<400> SEQUENCE: 381

Met Ala Ser Arg Phe Ser Ser Phe Val Leu Val Ser Phe Leu Val Ile
 1               5                  10                   15

Ala Ala Ser His Val His Val Thr Ser Ser Ala His Leu Val Lys Gly
                20                  25                   30

Leu Ser Trp Ser Phe Tyr Glu Lys Ser Cys Pro Lys Val Glu Ser Val
                35                  40                   45

Ile Lys Lys His Leu Lys Lys Val Phe Glu Glu Asp Ile Gly Gln Ala
         50                  55                  60

Ala Gly Leu Leu Arg Leu His Phe His Asp Cys Phe Val Lys Gly Cys
65                   70                  75                   80

Asp Ala Ser Val Leu Leu Asp Gly Ser Ala Ser Gly Pro Ser Glu Gln
                85                  90                   95

Asp Ala Pro Pro Asn Arg Ser Leu Arg Pro Ser Ala Phe Lys Ile Ile
               100                 105                  110

Asp Asp Leu Arg Glu Leu Val Asp Lys Lys Cys Gly Arg Val Val Ser
        115                 120                 125

Cys Ala Asp Ile Ala Ala Ile Ala Ala Arg Asp Ser Val Val Leu Ser
130                 135                 140

Gly Gly Pro Glu Tyr Asp Val Pro Leu Gly Arg Arg Asp Gly Leu Thr
145                 150                 155                 160

Phe Ala Thr Gln Asn Val Thr Leu Glu Asn Leu Pro Ala Pro Thr Glu
                165                 170                 175

Asn Ala Ser Ala Ile Leu Ser Ala Leu Ala Lys Lys Asn Leu Asp Ala
                180                 185                 190

Thr Asp Val Val Ala Leu Ser Gly Gly His Thr Ile Gly Leu Gly His
        195                 200                 205

Cys Thr Ser Phe Glu Asn Arg Leu Tyr Pro Thr Gln Asp Pro Thr Met
        210                 215                 220

Glu Lys Thr Phe Ala His Asp Leu Lys Gly Val Cys Pro Thr Thr Asn
225                 230                 235                 240

Ser Thr Asn Thr Thr Val Leu Asp Ile Arg Ser Pro Asn Arg Phe Asp
                245                 250                 255

Asn Lys Tyr Phe Val Asp Leu Val Asn Arg Gln Gly Leu Phe Thr Ser
                260                 265                 270

Asp Gln Asp Leu Tyr Glu Asp Pro Thr Thr Arg Asp Ile Val Thr Ser
        275                 280                 285

Phe Ala Glu Asp Gln Glu Leu Phe Phe Glu Lys Phe Val Leu Ala Met
        290                 295                 300

Thr Lys Met Gly
305

<210> SEQ ID NO 382
<211> LENGTH: 98
```

```
<212> TYPE: PRT
<213> ORGANISM: Eucalyptus grandis

<400> SEQUENCE: 382

Met Phe Leu Lys Tyr Leu Ser Gly Ala Leu Val Ser Leu Ala Thr Ile
1               5                   10                  15

Arg Gly Val Cys Gly Ala Ser Ala Pro Met Arg Arg Ala Thr Cys Ala
            20                  25                  30

Gly Gly Gln Thr Val Lys Asn Ala Ala Cys Cys Ala Trp Phe Pro Val
        35                  40                  45

Leu Asp Asp Ile Arg Glu Asn Phe Phe Asp Asn Glu Cys Gly Asp Asp
    50                  55                  60

Ala His Ala Ala Leu Arg Leu Ser Phe His Asp Ala Ile Gly Phe Ser
65                  70                  75                  80

Arg Ser Lys Gly Gly Gly Ala Asp Gly Ser Ile Ile Ala Phe Asn
                85                  90                  95

Lys Thr

<210> SEQ ID NO 383
<211> LENGTH: 119
<212> TYPE: PRT
<213> ORGANISM: Eucalyptus grandis

<400> SEQUENCE: 383

Met Ala Phe Lys Leu Val Val Asn Leu Val Ser Leu Ala Leu Ala Val
1               5                   10                  15

Ser Ala Ala Asn Phe Lys Arg Val Ala Cys Pro Gly Thr Thr Ala Thr
            20                  25                  30

Ala Arg Asn Pro Ala Cys Cys Ala Phe Phe Ser Leu Arg Asp Asp Leu
        35                  40                  45

Leu Thr Asn Leu Phe Gly Gly Val Cys Gly Glu Glu Ala His Glu Ser
    50                  55                  60

Leu Arg Leu Ser Phe His Asp Ala Ile Ala Phe Ser Pro Ala Leu Ile
65                  70                  75                  80

Arg Gln Gly Lys Pro Gly Gly Gly Ala Asp Gly Ser Met Ile Thr
                85                  90                  95

Phe Pro Asn Val Glu Pro Asn Phe Asn Ala Asn Asn Gly Ile Ile Asp
            100                 105                 110

Ser Val Asp Phe Leu Thr Pro
        115

<210> SEQ ID NO 384
<211> LENGTH: 138
<212> TYPE: PRT
<213> ORGANISM: Eucalyptus grandis

<400> SEQUENCE: 384

Ser Cys Pro Gly Thr Val Ser Cys Ala Asp Ile Leu Ala Leu Gly Ala
1               5                   10                  15

Gln Ala Ser Val Val Leu Ser Gly Gly Pro Ser Trp Arg Val Leu Ser
            20                  25                  30

Gly Arg Arg Asp Ser Leu Thr Ala Asn Gln Ala Gly Ala Asn Thr Ser
        35                  40                  45

Ile Pro Ser Pro Phe Asp Ser Leu Ala Asn Leu Thr Ser Lys Phe Ala
    50                  55                  60

Ala Val Gly Leu Asp Thr Asn Asp Leu Val Thr Leu Ser Gly Ala His
65                  70                  75                  80
```

```
Thr Phe Gly Arg Ala Gln Cys Arg Thr Phe Ser Pro Arg Leu Tyr Asn
                85                  90                  95

Phe Asn Ala Ser Gly Ser Pro Asp Pro Thr Ile Ser Pro Ser Tyr Leu
            100                 105                 110

Thr Thr Leu Gln Gln Leu Cys Pro Gln Asn Gly Ser Gly Ser Val Leu
        115                 120                 125

Ala Asn Leu Asp Pro Thr Thr Val Asn Thr
    130                 135
```

<210> SEQ ID NO 385
<211> LENGTH: 208
<212> TYPE: PRT
<213> ORGANISM: Pinus radiata

<400> SEQUENCE: 385

```
Met Lys His Ile Pro Gly Leu Thr Leu Gln Phe Gln Ser Val Leu Ile
1               5                   10                  15

Thr Gly Ala Ala Leu Phe Leu Trp Ile Gln Thr Ser Asp Ala Gln Asp
            20                  25                  30

Cys Asn Gly Leu Ser His His Tyr Tyr Gln Lys Ser Cys Pro Asn Ala
        35                  40                  45

Gln Ala Ile Ile Lys Ser Val Val Ser Asp Ala Val Lys Lys Glu Ala
    50                  55                  60

Arg Met Ala Ala Ser Leu Leu Arg Leu His Phe His Asp Cys Phe Val
65                  70                  75                  80

Gln Gly Cys Asp Ala Ser Ile Leu Leu Asp Asp Thr Ala Ser Phe Thr
                85                  90                  95

Gly Glu Lys Thr Ala Leu Pro Asn Arg Asn Ser Val Arg Gly Phe Glu
            100                 105                 110

Val Val Asp Lys Ile Lys Ser Lys Leu Glu Glu Ala Cys Pro Gly Val
        115                 120                 125

Val Ser Cys Ala Asp Ile Leu Ala Val Ala Ala Arg Asp Ser Val Gly
    130                 135                 140

Phe Ser Val Gly Pro Tyr Trp Glu Val Leu Leu Gly Arg Arg Asp Ser
145                 150                 155                 160

Lys Thr Ala Ser Lys Ser Gly Ala Asn Asn Asp Ile Pro Ala Pro Asn
                165                 170                 175

Ser Thr His Gln Thr Leu Glu Thr Lys Phe Asn Leu Lys Gly Leu Asn
            180                 185                 190

Val Leu Asp Leu Val Ala Leu Ser Arg Ser His Asn Asn Arg Val Ser
        195                 200                 205
```

<210> SEQ ID NO 386
<211> LENGTH: 202
<212> TYPE: PRT
<213> ORGANISM: Pinus radiata

<400> SEQUENCE: 386

```
Met Ala Thr Leu Gly Ile Pro Leu Gly Ser Leu Ser Leu Leu Leu Leu
1               5                   10                  15

Phe Phe Cys Cys Ala Gln Arg Ser Val Gly Leu Lys Glu Asn Tyr Tyr
            20                  25                  30

Ala Thr Ser Cys Pro Arg Ala Glu His Ile Val Lys Glu Gln Val Tyr
        35                  40                  45

Asn Leu Tyr Gln Glu His Gly Asn Thr Ala Val Ser Trp Ile Arg Leu
    50                  55                  60
```

Ile Phe His Asp Cys Ile Val Gln Ser Cys Asp Ala Ser Ile Leu Leu
65                  70                  75                  80

Asp Ser Ser Gly Asp Val Gln Thr Glu Lys Gln Ser Asp Arg Asn Phe
            85                  90                  95

Gly Met Arg Asn Phe Lys Tyr Val Asp Thr Ile Lys Glu Ala Ile Glu
            100                 105                 110

Val Glu Cys Pro Gly Val Val Ser Cys Ala Asp Ile Ile Val Leu Ala
            115                 120                 125

Ala Lys Glu Ala Ala Met Leu Gly Gly Pro Arg Ile Ala Val Lys
    130                 135                 140

Thr Gly Arg Arg Asp Ser Arg Lys Ser Ser Ala Ala Val Val Asp Lys
145                 150                 155                 160

Tyr Val Pro Leu His Asn Gly Ser Ile Ser Ser Leu Leu Ser Ala Phe
                165                 170                 175

Ala Ser Val Gly Ile Asp Ala Glu Gly Ala Val Ala Leu Leu Gly Leu
            180                 185                 190

Ile Leu Ile His Ser Val Leu His Tyr Thr
            195                 200

<210> SEQ ID NO 387
<211> LENGTH: 287
<212> TYPE: PRT
<213> ORGANISM: Pinus radiata

<400> SEQUENCE: 387

Met Lys Ser Phe Pro Cys Ile Ala Val Ile Val Phe Ile Ile Cys Ser
1               5                   10                  15

Ile Thr Asp Thr Val Asn Gly Lys Leu Ser Ser Thr Phe Tyr Asp Lys
            20                  25                  30

Ser Cys Pro Lys Ala Leu Ser Ile Val Gln Ala Gly Val Lys Gln Ala
            35                  40                  45

Val Ala Lys Glu Lys Arg Met Gly Ala Ser Leu Leu Arg Leu His Phe
    50                  55                  60

His Asp Cys Phe Val Asn Gly Cys Asp Gly Ser Val Leu Leu Asp Asn
65                  70                  75                  80

Ser Thr Thr Phe Thr Ser Glu Lys Tyr Ala Leu Pro Asn Asn Asn Ser
                85                  90                  95

Ala Arg Gly Phe Glu Val Ile Asp Ser Ile Lys Ser Gln Leu Glu Asn
            100                 105                 110

Ala Cys Thr Gly Val Val Ser Cys Ala Asp Ile Leu Thr Ile Ala Ala
            115                 120                 125

Arg Asp Ser Val Val Gln Leu Gly Gly Pro Ser Trp Lys Val Met Leu
    130                 135                 140

Gly Arg Arg Asp Ser Thr Thr Ala Ser Ile Ser Gly Ala Asn Asn Asn
145                 150                 155                 160

Ile Pro Pro Thr Ser Asn Leu Thr Lys Leu Ile Ser Leu Phe Gln
                165                 170                 175

Ala Gln Gly Leu Ser Thr Lys Glu Met Val Ala Leu Ser Gly Gly His
            180                 185                 190

Thr Ile Gly Gln Ala Gln Cys Lys Asn Phe Arg Ala His Ile Tyr Asn
            195                 200                 205

Asp Thr Asn Ile Asp Thr Thr Tyr Ala Thr Ser Leu Arg Ser Lys Cys
    210                 215                 220

Pro Ser Thr Thr Gly Ser Gly Asp Ser Asn Leu Ser Pro Leu Asp Tyr

-continued

```
              225                 230                 235                 240
Thr Thr Pro Thr Val Phe Asp Lys Asn Tyr Tyr Tyr Asn Leu Lys Ser
                    245                 250                 255

Lys Arg Gly Leu Leu His Ser Asp Gln Glu Leu Phe Asn Gly Gly Ser
                260                 265                 270

Thr Asp Ser His Val Thr Lys Tyr Ala Ser Asn Gln Asn Thr Phe
            275                 280                 285

<210> SEQ ID NO 388
<211> LENGTH: 161
<212> TYPE: PRT
<213> ORGANISM: Pinus radiata

<400> SEQUENCE: 388

Ala Asn Ser Asn Leu Pro Ser Pro Ala Ser Ser Leu Ser Thr Leu Met
  1               5                  10                  15

Thr Ala Phe Gln Lys Gln Gly Leu Ser Thr Lys Asp Leu Val Ala Leu
                 20                  25                  30

Ser Gly Ala His Thr Ile Gly Gln Ala Arg Cys Thr Thr Phe Arg Thr
             35                  40                  45

Arg Ile Tyr Asn Asp Thr Asn Ile Asn Ala Ala Phe Ala Thr Ser Ala
         50                  55                  60

Lys Ala Asn Cys Pro Ser Thr Gly Gly Asp Asn Thr Leu Ser Pro Leu
 65                  70                  75                  80

Asp Val Leu Thr Pro Thr Thr Phe Asp Asn Lys Tyr Tyr Thr Asn Leu
                 85                  90                  95

Lys Ser Gln Lys Gly Leu Phe His Ser Asp Gln Glu Leu Phe Asn Gly
                100                 105                 110

Gly Ser Thr Asp Ser Arg Val Ser Ile Tyr Ser Thr Ser Gln Ala Ile
            115                 120                 125

Phe Phe Thr Asp Phe Ala Ala Ala Met Val Asn Met Gly Asn Ile Ser
        130                 135                 140

Pro Leu Thr Gly Thr Asn Gly Glu Ile Arg Thr Asn Cys Arg Lys Val
145                 150                 155                 160

Asn

<210> SEQ ID NO 389
<211> LENGTH: 318
<212> TYPE: PRT
<213> ORGANISM: Pinus radiata

<400> SEQUENCE: 389

Met Arg Thr Leu Val Cys Ile Gly Leu Met Ala Val Phe Val Ala Phe
  1               5                  10                  15

Ile His Ile Asn Ala Val Asn Gly Gln Leu Ser Ser Thr Phe Tyr Ala
                 20                  25                  30

Lys Ser Cys Pro Arg Leu Pro Ser Ile Val Lys Ser Val Val Lys Gln
             35                  40                  45

Ala Val Ala Lys Glu Lys Arg Met Gly Ala Ser Leu Val Arg Leu His
         50                  55                  60

Phe His Asp Cys Phe Val Asn Gly Cys Asp Gly Ser Ile Leu Leu Asp
 65                  70                  75                  80

Asp Asn Ala Thr Phe Thr Gly Glu Lys Thr Ala Gly Pro Asn Ala Asn
                 85                  90                  95

Ser Ala Arg Gly Phe Glu Val Ile Asp Ser Ile Lys Thr Gln Val Glu
                100                 105                 110
```

-continued

```
Ala Ala Cys Ser Gly Val Val Ser Cys Asp Ile Leu Thr Ile Ala
        115                 120                 125

Ala Arg Asp Ser Ile Val Glu Leu Gln Gly Pro Thr Trp Thr Val Met
130                 135                 140

Leu Gly Arg Arg Asp Ser Thr Thr Ala Ser Leu Ser Ala Ala Asn Asn
145                 150                 155                 160

Asn Ile Pro Ser Pro Ala Ser Ser Leu Ser Thr Leu Ile Ser Ser Phe
                165                 170                 175

Gln Ala His Gly Leu Ser Thr Lys Asp Leu Val Ala Leu Ser Gly Ala
        180                 185                 190

His Thr Ile Gly Gln Ser Arg Cys Ala Phe Phe Arg Thr Arg Ile Tyr
        195                 200                 205

Asn Glu Thr Asn Ile Asn Ala Ala Phe Ala Thr Ser Val Lys Ala Asn
210                 215                 220

Cys Pro Ser Ala Gly Gly Asp Ser Asn Leu Ser Pro Leu Asp Ala Val
225                 230                 235                 240

Thr Ser Ile Thr Phe Asp Asn Lys Tyr Tyr Ser Asn Leu Lys Ile Gln
                245                 250                 255

Lys Gly Leu Leu His Ser Asp Gln Gln Leu Phe Asn Gly Gly Ser Thr
        260                 265                 270

Asp Ser Gln Val Thr Ala Tyr Ser Ser Asn Gln Asn Ser Phe Phe Ile
        275                 280                 285

Asp Phe Thr Ala Ala Met Val Lys Met Gly Asn Ile Ser Pro Leu Thr
        290                 295                 300

Gly Thr Asn Gly Gln Ile Arg Lys Asn Cys Arg Lys Ser Asn
305                 310                 315

<210> SEQ ID NO 390
<211> LENGTH: 95
<212> TYPE: PRT
<213> ORGANISM: Pinus radiata

<400> SEQUENCE: 390

Lys Leu Pro Lys Ser Gly Gly Asp Asn Asn Leu Ser Pro Leu Asp Leu
1               5                   10                  15

Leu Thr Pro Thr Thr Phe Asp Asn Lys Tyr Tyr Thr Asn Leu Lys Ser
                20                  25                  30

Gln Lys Gly Leu Leu His Ser Asp Gln Gln Leu Phe Asn Gly Gly Ser
        35                  40                  45

Ala Asp Ser Gln Val Thr Thr Tyr Ser Thr Thr Gln Ser Thr Phe Phe
50                  55                  60

Thr Asp Phe Ala Ala Ser Met Leu Asn Met Gly Asn Ile Ser Pro Leu
65                  70                  75                  80

Thr Gly Thr Ser Gly Gln Ile Arg Lys Asn Cys Arg Lys Pro Asn
                85                  90                  95

<210> SEQ ID NO 391
<211> LENGTH: 201
<212> TYPE: PRT
<213> ORGANISM: Pinus radiata

<400> SEQUENCE: 391

Met Thr Ser Phe Thr Ala Met Ala Ser Val Val Cys Ile Ala Leu Leu
1               5                   10                  15

Phe Phe Ser Thr Val Ala Phe Ala Gln Leu Asn Ser Thr Tyr Tyr Asp
                20                  25                  30
```

Thr Ser Cys Pro Lys Leu Leu Ala Thr Val Lys Ala Ala Val Lys Thr
            35                  40                  45

Ala Val Ala Asn Glu Lys Arg Met Gly Ala Ser Leu Leu Arg Leu His
 50                  55                  60

Phe His Asp Cys Phe Val Asn Gly Cys Asp Gly Ser Val Leu Leu Asp
65                  70                  75                  80

Asp Ser Ser Leu Thr Gly Glu Lys Thr Ala Leu Pro Asn Asn Asn
                85                  90                  95

Ser Leu Arg Gly Phe Asp Val Ile Asp Thr Ile Lys Ser Gln Val Glu
            100                 105                 110

Ala Val Cys Ser Gly Ile Val Ser Cys Ala Asp Ile Leu Ala Ile Thr
        115                 120                 125

Ala Arg Asp Ser Val Val Glu Leu Gly Gly Pro Thr Trp Thr Val Leu
    130                 135                 140

Leu Gly Arg Arg Asp Ser Ala Thr Ala Ser Leu Ser Ala Ala Asn Thr
145                 150                 155                 160

Asn Ile Pro Ala Pro Thr Ser Asn Leu Ser Gly Leu Ile Ser Ser Phe
                165                 170                 175

Gln Ala Gln Gly Leu Ser Thr Lys Asp Met Ile Val Leu Ser Gly Ala
            180                 185                 190

His Thr Ile Gly Gln Ala Arg Cys Thr
        195                 200

<210> SEQ ID NO 392
<211> LENGTH: 120
<212> TYPE: PRT
<213> ORGANISM: Pinus radiata

<400> SEQUENCE: 392

Leu Ile Ser Ser Phe Thr Ala His Gly Leu Ser Thr Lys Asp Leu Gly
 1               5                  10                  15

Ala Leu Ser Gly Ala His Thr Ile Gly Gln Ala Arg Cys Thr Thr Phe
            20                  25                  30

Arg Ala Arg Val Tyr Asn Glu Ser Asn Ile Asp Thr Ser Phe Ala Thr
        35                  40                  45

Ser Val Lys Ala Asn Trp Pro Ser Ala Gly Gly Asp Asn Thr Leu Ser
    50                  55                  60

Pro Leu Asp Leu Ala Thr Pro Thr Thr Phe Asp Asn Lys Tyr Tyr Thr
65                  70                  75                  80

Asp Leu Arg Ser Gln Lys Gly Leu Leu His Ser Asp Gln Met Phe
                85                  90                  95

Ser Gly Gly Ser Thr Asn Ser Gln Val Thr Thr Tyr Ser Ser Asn Gln
            100                 105                 110

Lys His Leu Leu Tyr Arg Leu Tyr
        115                 120

<210> SEQ ID NO 393
<211> LENGTH: 120
<212> TYPE: PRT
<213> ORGANISM: Pinus radiata

<400> SEQUENCE: 393

Lys Arg Ile Asn Phe His Leu Lys Glu Asp Ile Thr Gln Ala Ala Gly
 1               5                  10                  15

Leu Leu Arg Val His Phe His Asp Cys Phe Val Gln Gly Cys Asp Gly
            20                  25                  30

-continued

```
Ser Val Leu Leu Asp Gly Ser Ala Ser Gly Pro Ser Glu Gln Asp Ala
        35                  40                  45

Pro Pro Asn Leu Thr Leu Arg Ala Lys Ala Phe Glu Ile Ile Asn Asp
 50                  55                  60

Ile Lys Lys His Val Glu Lys Ala Cys Ser Gly Val Val Ser Cys Ala
 65                  70                  75                  80

Asp Leu Thr Ala Leu Ala Arg Glu Ser Val Arg Ala Val Gly Gly
                 85                  90                  95

Pro Glu Tyr Arg Val Pro Leu Gly Arg Arg Asp Ser Leu Lys Phe Ala
            100                 105                 110

Thr Arg Lys Val Thr Leu Ala Asn
        115                 120

<210> SEQ ID NO 394
<211> LENGTH: 266
<212> TYPE: PRT
<213> ORGANISM: Pinus radiata

<400> SEQUENCE: 394

Met Ala Ser Phe Thr Ala Met Arg Ser Leu Ala Phe Ile Ala Leu Leu
  1               5                  10                  15

Met Cys Ser Thr Val Ala Tyr Ala Gln Leu Ser Ala Thr Phe Tyr Asn
                 20                  25                  30

Thr Ser Cys Pro Lys Leu Leu Ser Thr Val Gln Ala Ala Val Lys Gln
        35                  40                  45

Ala Val Ala Asn Glu Lys Arg Met Gly Ala Ser Leu Leu Arg Leu His
 50                  55                  60

Phe His Asp Cys Phe Val Asn Gly Cys Asp Gly Ser Val Leu Leu Asp
 65                  70                  75                  80

Asp Ser Ser Thr Leu Thr Gly Glu Lys Thr Ala Val Pro Asn Asn Asn
                 85                  90                  95

Ser Ala Arg Gly Phe Asp Val Ile Asp Thr Ile Lys Ser Gln Val Glu
            100                 105                 110

Ala Val Cys Ser Gly Val Val Ser Cys Ala Asp Ile Leu Ala Ile Ala
        115                 120                 125

Ala Arg Asp Ser Val Val Gln Leu Gly Gly Pro Thr Trp Thr Val Gln
        130                 135                 140

Leu Gly Arg Arg Asp Ser Arg Thr Ala Ser Leu Ser Gly Ala Asn Asn
145                 150                 155                 160

Asn Ile Pro Ala Pro Thr Ser Asn Leu Ser Ala Leu Ile Ser Leu Phe
                165                 170                 175

Gln Ala Gln Gly Leu Ser Thr Lys Asp Met Val Val Leu Ser Gly Ala
            180                 185                 190

His Thr Ile Gly Gln Ala Arg Cys Thr Ser Phe Arg Ala Arg Ile Tyr
        195                 200                 205

Asn Glu Ser Asn Ile Asn Ala Ala Tyr Ala Thr Ser Leu Lys Thr Asn
    210                 215                 220

Cys Pro Thr Thr Gly Ser Asp Asn Asn Leu Ser Pro Leu Asp Arg Val
225                 230                 235                 240

Thr Pro Thr Thr Phe Asp Ile Asn Tyr Tyr Ser Asn Leu Arg Ser Gln
                245                 250                 255

Lys Gly Leu Leu His Ser Asp Gln Gln Leu
            260                 265
```

```
<210> SEQ ID NO 395
<211> LENGTH: 323
<212> TYPE: PRT
<213> ORGANISM: Pinus radiata

<400> SEQUENCE: 395

Met Ala Tyr Leu Arg Lys Ser Phe Ala Cys Ile Ala Val Met Val Phe
  1               5                  10                  15

Ile Val Cys Ser Ile Thr Asp Thr Val Asn Gly Gln Leu Ser Ser Thr
             20                  25                  30

Phe Tyr Asp Lys Ser Cys Pro Thr Ala Leu Ser Val Val Lys Ala Ala
         35                  40                  45

Val Lys Gln Ala Val Ala Asn Glu Lys Arg Met Gly Ala Ser Leu Leu
 50                  55                  60

Arg Leu His Phe His Asp Cys Phe Val Asn Gly Cys Asp Gly Ser Val
 65                  70                  75                  80

Leu Leu Asp Asp Ser Ser Thr Ile Thr Gly Glu Lys Thr Ala Asn Pro
                 85                  90                  95

Asn Ala Asn Ser Ala Arg Gly Phe Asp Val Ile Asp Thr Ile Lys Ser
            100                 105                 110

Asn Val Glu Lys Ala Cys Ser Gly Val Val Ser Cys Ala Asp Ile Leu
        115                 120                 125

Ala Ile Ala Ala Arg Asp Ser Val Val Glu Leu Gly Gly Pro Ser Trp
130                 135                 140

Thr Val Met Leu Gly Arg Arg Asp Ser Thr Thr Ala Ser Lys Ser Gly
145                 150                 155                 160

Ala Asn Ser Asn Ile Pro Pro Thr Ser Leu Ser Asn Leu Ile
                165                 170                 175

Ser Leu Phe Gln Ala Gln Gly Leu Ser Ala Lys Glu Met Val Ala Leu
            180                 185                 190

Ser Gly Gly His Thr Ile Gly Gln Ala Gln Cys Lys Asn Phe Arg Ala
        195                 200                 205

His Ile Tyr Asn Glu Thr Asn Ile Asp Ser Ala Tyr Ala Thr Ser Leu
    210                 215                 220

Arg Ser Lys Cys Pro Ser Thr Thr Gly Ser Gly Asp Ser Asn Leu Ser
225                 230                 235                 240

Pro Leu Asp Tyr Met Thr Pro Thr Val Phe Asp Lys Asn Tyr Tyr Ser
                245                 250                 255

Asp Leu Lys Ser Gln Lys Gly Leu Leu His Ser Asp Gln Glu Leu Phe
            260                 265                 270

Asn Gly Gly Ser Thr Asp Ser Gln Val Thr Thr Tyr Ala Ser Asn Gln
        275                 280                 285

Asn Thr Phe Phe Ser Asp Phe Ala Ala Ala Met Val Lys Met Gly Asn
    290                 295                 300

Ile Lys Pro Leu Thr Gly Thr Ser Gly Gln Ile Pro Lys Asn Cys Arg
305                 310                 315                 320

Lys Pro Asn

<210> SEQ ID NO 396
<211> LENGTH: 223
<212> TYPE: PRT
<213> ORGANISM: Pinus radiata

<400> SEQUENCE: 396

Gln Ile Lys Ser Ala Leu Glu Lys Glu Cys Pro Lys Thr Val Ser Cys
  1               5                  10                  15
```

```
Ala Asp Ile Leu Ala Ile Ala Ser Arg Asp Ser Val Val Leu Ser Gly
             20                  25                  30

Gly Leu Gly Trp Glu Val Leu Leu Gly Arg Arg Asp Ser Lys Ser Ala
         35                  40                  45

Ser Leu Ser Gly Ser Asn Asn Asn Ile Pro Ala Pro Asn Ser Thr Leu
     50                  55                  60

Gln Thr Leu Thr Thr Lys Phe Lys Leu Gln Gly Leu Asp Glu Val Asp
 65                  70                  75                  80

Leu Val Ser Leu Ser Gly Ser His Thr Ile Gly Leu Ser Arg Cys Thr
             85                  90                  95

Ser Phe Arg Gln Arg Leu Tyr Asn Gln Ser Gly Asn Gly Leu Pro Asp
            100                 105                 110

Phe Thr Leu Asn Arg Gly Tyr Tyr Ala Arg Leu Lys Ser Gly Cys Pro
            115                 120                 125

Lys Ser Gly Gly Asp Asn Asn Leu Phe Pro Leu Asp Phe Val Thr Pro
            130                 135                 140

Thr Lys Phe Asp Asn Tyr Tyr Phe Lys Ser Leu Leu Ser Gly Gln Gly
145                 150                 155                 160

Leu Leu Asn Thr Asp Glu Glu Leu Phe Ala Lys Gly Ser Gly Lys Thr
            165                 170                 175

Lys Glu Leu Val Lys Leu Tyr Ala Ala Asn Glu Glu Leu Phe Leu Lys
            180                 185                 190

Gln Phe Ala Leu Ser Met Val Lys Met Gly Asn Ile Lys Pro Leu Thr
            195                 200                 205

Gly Thr Val Gly Glu Ile Arg Val Asn Cys Arg Lys Val Asn Ser
            210                 215                 220

<210> SEQ ID NO 397
<211> LENGTH: 351
<212> TYPE: PRT
<213> ORGANISM: Pinus radiata

<400> SEQUENCE: 397

Met Gly Lys Phe Ile Thr Ala Leu Ala Ser Val Ile Leu Cys Val Phe
  1               5                  10                  15

Val Ile Tyr Gly Gly Ala Val Asn Ala Leu Pro Ser Pro Val Ala Gly
             20                  25                  30

Leu Ser Trp Thr Phe Tyr Ser Ser Cys Pro Ser Leu Glu Ser Ile
         35                  40                  45

Val Trp Glu Arg Met Glu Ala Tyr Leu Ser Ala Asp Ile Thr Gln Ala
 50                  55                  60

Ala Gly Leu Leu Arg Leu His Phe His Asp Cys Phe Val Gln Gly Cys
 65                  70                  75                  80

Asp Gly Ser Val Leu Leu Asn Ala Thr Ser Gly Glu Gln Thr Ala Pro
             85                  90                  95

Pro Asn Leu Ser Leu Arg Ala Gln Ala Leu Lys Ile Ile Asn Asp Ile
            100                 105                 110

Lys Glu Asn Val Glu Ala Ala Cys Ser Gly Ile Val Ser Cys Ala Asp
            115                 120                 125

Ile Val Thr Leu Ala Ala Arg Asp Ser Val Val Met Ala Gly Gly Pro
            130                 135                 140

Phe Tyr Pro Leu Pro Leu Gly Arg Arg Asp Ser Leu Thr Phe Ala Asn
145                 150                 155                 160

Arg Ser Thr Val Leu Ala Asn Leu Pro Ser Pro Thr Ser Asn Val Thr
```

-continued

```
                165                 170                 175
Gly Leu Ile Ser Val Leu Gly Pro Lys Gly Leu Asn Phe Thr Asp Leu
                180                 185                 190

Val Ala Leu Ser Gly Gly His Thr Ile Gly Arg Ser Asn Cys Ser Ser
            195                 200                 205

Phe Asp Asn Arg Leu Tyr Asn Ser Thr Thr Gly Thr Gln Met Arg Asp
        210                 215                 220

Pro Thr Met Asp Gln Ser Phe Ala Lys Asn Leu Tyr Leu Thr Cys Pro
225                 230                 235                 240

Thr Ser Thr Thr Val Asn Thr Thr Lys Leu Asp Ile Arg Thr Pro Asn
                245                 250                 255

Val Phe Asp Asn Lys Tyr Tyr Val Asp Leu Leu Asn Arg Gln Thr Leu
            260                 265                 270

Phe Thr Ser Asp Gln Thr Leu Tyr Thr Asp Thr Arg Thr Arg Asp Ile
        275                 280                 285

Val Ile Asn Phe Ala Val Asn Gln Ser Leu Phe Phe Glu Gln Phe Val
    290                 295                 300

Leu Ser Met Leu Lys Met Gly Gln Leu Asp Val Leu Thr Gly Ser Glu
305                 310                 315                 320

Gly Glu Ile Arg Lys Asn Cys Trp Ala Ala Asn Pro Ser Thr Phe Ser
                325                 330                 335

Ile Met Asp Pro Glu Ala Ser Gln Glu Ser Thr Ser Tyr Ser Met
            340                 345                 350
```

<210> SEQ ID NO 398
<211> LENGTH: 103
<212> TYPE: PRT
<213> ORGANISM: Pinus radiata

<400> SEQUENCE: 398

```
Leu Asn Phe Ala Leu Ile Phe Cys Val Ser Ser Phe Ser Ser Gln Tyr
1               5                   10                  15

Asp Asp Glu Asp Ser Ser Val His Trp Val Asn Gly Cys Val Cys Ser
            20                  25                  30

Leu His Thr Tyr Lys Arg Leu Asn Gly Gln Leu Ser Ser Thr Phe Tyr
        35                  40                  45

Ala Lys Ser Cys Pro Arg Leu Pro Ser Ile Val Lys Ser Val Val Lys
    50                  55                  60

Gln Ala Val Ala Lys Glu Lys Arg Met Gly Ala Ser Leu Val Arg Leu
65                  70                  75                  80

His Phe His Asp Cys Phe Val Asn Gly Cys Asp Gly Ser Ile Leu Leu
                85                  90                  95

Asp Asp Asn Ala Thr Phe Thr
            100
```

<210> SEQ ID NO 399
<211> LENGTH: 157
<212> TYPE: PRT
<213> ORGANISM: Pinus radiata

<400> SEQUENCE: 399

```
Ile Asp Ala Ile Lys Thr Ala Leu Glu Ser Ser Cys Asn Ala Thr Val
1               5                   10                  15

Ser Cys Ala Asp Ile Leu Ala Ile Ala Ala Arg Asp Ser Val Tyr Leu
            20                  25                  30

Ser Gly Gly Pro Tyr Trp Gln Val Gln Met Gly Arg Arg Asp Gly Thr
```

-continued

```
                     35                  40                  45
Thr Ala Ser Lys Ser Ala Ala Asn Ala Asp I le Pro Ser Pro Ile Glu
                 50                  55                  60
Ser Leu Gly Ser Leu Ile Ser Gln Phe Gln G ly Val Gly Leu Ser Val
 65                  70                  75                  80
His Asp Leu Val Val Leu Ser Gly Ala His T hr Ile Gly Arg Ala His
                     85                  90                  95
Cys Gly Thr Phe Ser Ser Arg Leu Phe Asn P he Ser Gly Ser Asn Ser
                100                 105                 110
Ala Asp Pro Thr Ile His Gln Ser Leu Leu G ln Asp Leu His Ser Leu
                115                 120                 125
Cys Pro Asp Gly Asn Ser Asp Pro Asn Thr L eu Ala Pro Leu Asp Pro
            130                 135                 140
Val Thr Lys Asp Lys Leu His Asn Val Tyr P he Arg Asn
145                 150                 155

<210> SEQ ID NO 400
<211> LENGTH: 117
<212> TYPE: PRT
<213> ORGANISM: Pinus radiata

<400> SEQUENCE: 400

Leu Ser Val Thr Asp Val Val Ala Leu Ser G ly Gly His Thr Ile Gly
  1               5                  10                  15
Arg Ala Arg Cys Thr Val Phe Ser Gly Arg L eu Tyr Asn Phe Ser Gly
                 20                  25                  30
Thr Gly Ser Pro Asp Pro Thr Leu Asn Ser S er Tyr Leu Ser Thr Leu
             35                  40                  45
Gln Ser Thr Cys Pro Gln Asn Gly Ser Ala A sn Thr Leu Thr Ser Leu
         50                  55                  60
Asp Pro Gly Thr Pro Asn Thr Phe Asp Asn A sn Tyr Phe Ala Asn Leu
 65                  70                  75                  80
Gln Ile Glu Met Gly Leu Leu Gln Ser Ile L ys Asn Phe Phe Pro His
                 85                  90                  95
Arg Glu Gln Ala Pro Ser Leu Leu Ser Met I le Met Pro Val Val Asn
                100                 105                 110
Pro Ile Ser Ser Ser
            115

<210> SEQ ID NO 401
<211> LENGTH: 143
<212> TYPE: PRT
<213> ORGANISM: Pinus radiata

<400> SEQUENCE: 401

Met Ala Ala Leu Met Lys Ser Ser Ala Cys I le Ala Val Ile Val Phe
  1               5                  10                  15
Ile Val Cys Ser Ile Asn Asn Thr Val His G ly Gln Leu Ser Ser Thr
                 20                  25                  30
Phe Tyr Asp Lys Ser Cys Pro Thr Val Leu S er Val Val Lys Ala Gly
             35                  40                  45
Val Lys Gln Ala Val Ala Lys Glu Gln Arg M et Gly Ala Ser Leu Leu
         50                  55                  60
Arg Leu His Phe His Asp Cys Phe Val Asn G ly Cys Asp Gly Ser Val
 65                  70                  75                  80
Leu Leu Asp Asp Ser Ser Lys Ile Thr Gly G lu Lys Thr Ala Ile Pro
```

```
                  85                   90                    95
Asn Ala Asn Ser Ala Arg Gly Phe Asp Val Ile Asp Thr Ile Lys Ser
               100                    105                    110

Gln Val Glu Lys Ser Cys Ser Ala Val Ser Cys Ser Asp Ile Leu
       115                   120                    125

Ala Ile Ala Ala Arg Asp Ser Val Val Glu Leu Gly Gly Pro Ser
   130                   135                    140
```

<210> SEQ ID NO 402
<211> LENGTH: 1474
<212> TYPE: DNA
<213> ORGANISM: Pinus radiata

<400> SEQUENCE: 402

```
gaattcggca cgagaaaacg tccatagctt ccttgccaac tgcaagcaat a cagtacaag      60
agccagacga tcgaatcctg tgaagtggtt ctgaagtgat gggaagcttg g aatctgaaa     120
aaactgttac aggatatgca gctcgggact ccagtggcca cttgtcccct t acacttaca    180
atctcagaaa gaaaggacct gaggatgtaa ttgtaaaggt catttactgc g aatctgcc     240
actctgattt agttcaaatg cgtaatgaaa tggacatgtc tcattaccca a tggtccctg     300
ggcatgaagt ggtggggatt gtaacagaga ttggcagcga ggtgaagaaa t caaagtgg     360
gagagcatgt aggggttggt tgcattgttg ggtcctgtcg cagttgcggt a attgcaatc     420
agagcatgga acaatactgc agcaagagga tttggaccta caatgatgtg a accatgacg     480
gcacacctac tcagggcgga tttgcaagca gtatggtggt tgatcagatg t ttgtggttc     540
gaatcccgga gaatcttcct ctggaacaag cggcccctct gttatgtgca g gggttacag     600
ttttcagccc aatgaagcat tcgccatga cagagcccgg aagaaatgt g ggattttgg     660
gtttaggagg cgtggggcac atgggtgtca agattgccaa agcctttgga c tccacgtga     720
cggttatcag ttcgtctgat aaaagaaag aagaagccat ggaagtcctc g gcgccgatg     780
cttatcttgt tagcaaggat actgaaaaga tgatggaagc agcagagagc c tagattaca     840
taatggacac cattccagtt gctcatcctc tggaaccata tcttgccctt c tgaagacaa     900
atggaaagct agtgatgctg ggcgttgttc cagagccgtt gcacttcgtg a ctcctctct     960
taatacttgg gagaaggagc atagctggaa gtttcattgg cagcatggag g aaacacagg   1020
aaactctaga tttctgtgca gagaagaagg tatcatcgat gattgaggtt g tgggcctgg   1080
actacatcaa cacggccatg gaaaggttgg agaagaacga tgtccgttac a gatttgtgg   1140
tggatgttgc tagaagcaag ttggataatt agtctgcaat caatcaatca g atcaatgcc   1200
tgcatgcaag atgaatagat ctggactagt agcttaacat gaaagggaaa t taaatttt   1260
atttaggaac tcgatactgg tttttgttac tttagtttag cttttgtgag g ttgaaacaa   1320
ttcagatgtt tttttaactt gtatatgtaa agatcaattt ctcgtgacag t aataataa   1380
tccaatgtct tctgccaaat taatatatgt attcgtattt ttatatgaaa a aaaaaaaa   1440
aaaaaaaaaa aaaaaaaaaa aaaaaaaaaa aaaa                                 1474
```

<210> SEQ ID NO 403
<211> LENGTH: 414
<212> TYPE: DNA
<213> ORGANISM: eucalyptus grandis

<400> SEQUENCE: 403

```
cacgctcgac gaattcggta ccccgggttc gaaatcgata agcttggatc c aaagcaaca      60
```

-continued

| | |
|---|---|
| cattgaactc tctctctctc tctctctctc tctctctctc tcccccaccc c cccttccca | 120 |
| accccacccca catacagaca agtagatacg cgcacacaga agaagaaaag a tgggggttt | 180 |
| caatgcagtc aatcgcacta gcgacggttc tggccgtcct aacgacatgg g cgtggaggg | 240 |
| cggtgaactg ggtgtggctg aggccgaaga ggctcgagag gcttctgaga c agcaaggtc | 300 |
| tctccggcaa gtcctacacc ttcctggtcg gcgacctcaa ggagaacctg c ggatgctca | 360 |
| aggaagccaa gtccaagccc atcgccgtct ccgatgacat caagcctcgt c tct | 414 |

<210> SEQ ID NO 404
<211> LENGTH: 2013
<212> TYPE: DNA
<213> ORGANISM: Eucalyptus grandis

<400> SEQUENCE: 404

| | |
|---|---|
| gataagttg cgcttaaatc ctctccaaaa gagctaatcc atggatattt tc tatttcta | 60 |
| tcccaactc cagtctcttg ttcaaactca actccagcaa tctcccatga cc tcctcct | 120 |
| tccgtcgtc cctcttctcc tcttcctcgg gctcgtggct cggctccggc gc aagccgcc | 180 |
| ttcccaccg ggcccgaggg gcctcccggt catcgggaac atgctcatga tg ggcgagct | 240 |
| acccaccgc ggcctcgcga gtctggcgaa gaagtatggc gggatcttcc ac ctccgcat | 300 |
| ggcttcctg cacatggttg ccgtgtcgtc ccccgacgtg gcccgccagg tc ctccaggt | 360 |
| cacgacggg atcttctcga accggcctgc caccatcgcg atcagctacc tc acgtatga | 420 |
| cgggccgac atggccttcg cgcactacgg cccgttctgg cggcagatgc gg aagctgtg | 480 |
| gtgatgaag ctcttcagcc ggaagcgggc tgagtcgtgg gagtcggtcc gc gatgaggt | 540 |
| gacacgatg gtgcgcaccg tcgcgggcag cgaggggacc gccgtgaaca tc ggcgagct | 600 |
| gtgttcgag ctcacgcggg acatcatcta ccgcgcggcc ttcggcacga gc tcgaccga | 660 |
| ggccaggac gagttcatca gcatactgca ggagttctcg aaattatttg gc gccttcaa | 720 |
| atagccgat tttatcccgt acctgagctg gatcgatccg caagggctca cc gccaggct | 780 |
| gtcaaggcg cgccagtcgc tggacggggtt catcgaccac attatagatg at cacatgga | 840 |
| aagaagaga aacaagacga gttccggtgg aggcgatcaa gatgtcgata cc gacatggt | 900 |
| gacgatctg ctggccttct acagcgacga agcgaaggtg aacgagtccg ac gatttgca | 960 |
| gaactcgatc aggctaacga gagacaacat caaggccatc atcatggacg t gatgttcgg | 1020 |
| cgggacggag actgtggcgt cggctatcga gtgggccatg gcggagctca t gcgaagccc | 1080 |
| cgaggacctg aagaaggtcc agcaagaact cgcggatgtc gtgggcctag a ccggagagt | 1140 |
| cgaggagagc gacttcgaga agctgaccta tctcaagtgc tgcctcaaag a gaccctccg | 1200 |
| cctccacccg ccgatcccgc tgctcctcca cgagacggca gaggacgccg t gatctccgg | 1260 |
| ctaccgcatc cccgcacggt cccgggtcat gatcaatgca tgggccatcg g gcgtgaccc | 1320 |
| cggctcgtgg accgaacctg acaagttcaa accgtcccgg ttcctggagt c aggcatgcc | 1380 |
| cgactacaag gggagcaact tcgagttcat ccctttcggg tcgggccgga g gtcgtgccc | 1440 |
| agggatgcag ctcgggctct acgcgctcga catggccgtg gcccacctcc t gcactgctt | 1500 |
| cacgtgggaa ctgcccgacg ggatgaagcc gagcgagatg gacatgggcg a cgtcttcgg | 1560 |
| gctcaccgcg ccgaggtcca cccggctcgt ggcggtgccg actccgaggt t ggtgggggc | 1620 |
| tctatattga gcaagcaaat ggagggtcgg gttgggggt gcgaggaggg g aacgtattt | 1680 |
| ttcagctcct ggagggctgc aagatttgga gtgcataaac ccatccatac a agggcaaaa | 1740 |
| gagggtggtg ccaaaatgat ttgcatggat ttttcgattt tgttttgta t tataaaaaa | 1800 |

-continued

```
ggtcaaataa ccgaagagga caagaaagac aagaaaaaga attgagacgg a acttgaatc   1860 aatgttgttc tgttctctct ttctatttct ttgtggatat tacaagactt a tctcatttg  1920 gtgggctttt cttttcttgt gatttctttg atcttgtcat acacaaataa a tatggaatg  1980 aagaaacctt tccatcaaaa aaaaaaaaaa aaa                                 2013
```

<210> SEQ ID NO 405
<211> LENGTH: 529
<212> TYPE: PRT
<213> ORGANISM: Eucalyptus grandis

<400> SEQUENCE: 405

```
Met Asp Ile Phe Tyr Phe Tyr Ser Gln Leu G ln Ser Leu Val Gln Thr
 1               5                  10                  15

Gln Leu Gln Gln Ser Pro Met Thr Leu L eu Ser Val Val Pro Leu
             20                  25                  30

Leu Leu Phe Leu Gly Leu Val Ala Arg Leu A rg Arg Lys Pro Pro Phe
         35                  40                  45

Pro Pro Gly Pro Arg Gly Leu Pro Val Ile G ly Asn Met Leu Met Met
     50                  55                  60

Gly Glu Leu Thr His Arg Gly Leu Ala Ser L eu Ala Lys Lys Tyr Gly
 65                  70                  75                  80

Gly Ile Phe His Leu Arg Met Gly Phe Leu H is Met Val Ala Val Ser
                 85                  90                  95

Ser Pro Asp Val Ala Arg Gln Val Leu Gln V al His Asp Gly Ile Phe
            100                 105                 110

Ser Asn Arg Pro Ala Thr Ile Ala Ile Ser T yr Leu Thr Tyr Asp Arg
        115                 120                 125

Ala Asp Met Ala Phe Ala His Tyr Gly Pro P he Trp Arg Gln Met Arg
    130                 135                 140

Lys Leu Cys Val Met Lys Leu Phe Ser Arg L ys Arg Ala Glu Ser Trp
145                 150                 155                 160

Glu Ser Val Arg Asp Glu Val Asp Thr Met V al Arg Thr Val Ala Gly
                165                 170                 175

Ser Glu Gly Thr Ala Val Asn Ile Gly Glu L eu Val Phe Glu Leu Thr
            180                 185                 190

Arg Asp Ile Ile Tyr Arg Ala Ala Phe Gly T hr Ser Ser Thr Glu Gly
        195                 200                 205

Gln Asp Glu Phe Ile Ser Ile Leu Gln Glu P he Ser Lys Leu Phe Gly
    210                 215                 220

Ala Phe Asn Ile Ala Asp Phe Ile Pro Tyr L eu Ser Trp Ile Asp Pro
225                 230                 235                 240

Gln Gly Leu Thr Ala Arg Leu Val Lys Ala A rg Gln Ser Leu Asp Gly
                245                 250                 255

Phe Ile Asp His Ile Ile Asp Asp His Met A sp Lys Lys Arg Asn Lys
            260                 265                 270

Thr Ser Ser Gly Gly Gly Asp Gln Asp Val A sp Thr Asp Met Val Asp
        275                 280                 285

Asp Leu Leu Ala Phe Tyr Ser Asp Glu Ala L ys Val Asn Glu Ser Asp
    290                 295                 300

Asp Leu Gln Asn Ser Ile Arg Leu Thr Arg A sp Asn Ile Lys Ala Ile
305                 310                 315                 320

Ile Met Asp Val Met Phe Gly Gly Thr Glu T hr Val Ala Ser Ala Ile
                325                 330                 335
```

-continued

```
Glu Trp Ala Met Ala Glu Leu Met Arg Ser Pro Glu Asp Leu Lys Lys
            340                 345                 350
Val Gln Gln Glu Leu Ala Asp Val Val Gly Leu Asp Arg Arg Val Glu
        355                 360                 365
Glu Ser Asp Phe Glu Lys Leu Thr Tyr Leu Lys Cys Cys Leu Lys Glu
    370                 375                 380
Thr Leu Arg Leu His Pro Pro Ile Pro Leu Leu Leu His Glu Thr Ala
385                 390                 395                 400
Glu Asp Ala Val Ile Ser Gly Tyr Arg Ile Pro Ala Arg Ser Arg Val
                405                 410                 415
Met Ile Asn Ala Trp Ala Ile Gly Arg Asp Pro Gly Ser Trp Thr Glu
            420                 425                 430
Pro Asp Lys Phe Lys Pro Ser Arg Phe Leu Glu Ser Gly Met Pro Asp
        435                 440                 445
Tyr Lys Gly Ser Asn Phe Glu Phe Ile Pro Phe Gly Ser Gly Arg Arg
    450                 455                 460
Ser Cys Pro Gly Met Gln Leu Gly Leu Tyr Ala Leu Asp Met Ala Val
465                 470                 475                 480
Ala His Leu Leu His Cys Phe Thr Trp Glu Leu Pro Asp Gly Met Lys
                485                 490                 495
Pro Ser Glu Met Asp Met Gly Asp Val Phe Gly Leu Thr Ala Pro Arg
            500                 505                 510
Ser Thr Arg Leu Val Ala Val Pro Thr Pro Arg Leu Val Gly Ala Leu
        515                 520                 525
Tyr
```

MATERIALS AND METHODS FOR THE MODIFICATION OF PLANT LIGNIN CONTENT

CROSS-REFERENCE TO RELATED APPLICATIONS

This application is a continuation-in-part of U.S. application Ser. No. 09/169,789, filed Oct. 9, 1998, which is a continuation-in-part of U.S. patent application Ser. No. 08/975,316, now U.S. Pat. No. 5,952,486 filed Nov. 21, 1997, which is a continuation-in-part of U.S. patent application Ser. No. 08/713,000, now U.S. Pat. No. 5,850,020 filed Sept. 11, 1996. This application claims priority from U.S. application Ser. No. 60/143,811, filed Jul. 14, 1999.

TECHNICAL FIELD OF THE INVENTION

This invention relates to polynucleotides believed to be novel, including partial and extended sequences as well as probes and primers, constructs comprising the polynucleotides, biological materials (including plants, microorganisms and multicellular organisms) incorporating the polynucleotides, polypeptides encoded by the polynucleotides, and methods for using the polynucleotides and polypeptides. The invention relates, more particularly, to the modification of lignin content and composition in biological materials including plants, to polypeptides involved in the lignin biosynthetic pathway, and to polynucleotides encoding such enzymes.

BACKGROUND OF THE INVENTION

Lignin is an insoluble polymer that is primarily responsible for the rigidity of plant stems. Specifically, lignin serves as a matrix around the polysaccharide components of some plant cell walls. The higher the lignin content, the more rigid the plant. For example, tree species synthesize large quantities of lignin, with lignin constituting between 20% to 30% of the dry weight of wood. In addition to providing rigidity, lignin aids in water transport within plants by rendering cell walls hydrophobic and water impermeable. Lignin also plays a role in disease resistance of plants by impeding the penetration and propagation of pathogenic agents.

The high concentration of lignin in trees presents a significant problem in the paper industry wherein considerable resources must be employed to separate lignin from the cellulose fiber needed for the production of paper. Methods typically employed for the removal of lignin are highly energy- and chemical-intensive, resulting in increased costs and increased levels of undesirable waste products. In the U.S. alone, about 20 million tons of lignin are removed from wood per year.

Lignin is largely responsible for the digestibility, or lack thereof, of forage crops, with small increases in plant lignin content resulting in relatively high decreases in digestibility. For example, crops with reduced lignin content provide more efficient forage for cattle, with the yield of milk and meat being higher relative to the amount of forage crop consumed. During normal plant growth, the increase in dry matter content is accompanied by a corresponding decrease in digestibility. When deciding on the optimum time to harvest forage crops, farmers must therefore chose between a high yield of less digestible material and a lower yield of more digestible material.

For some applications, an increase in lignin content is desirable since increasing the lignin content of a plant would lead to increased mechanical strength of wood, changes in its color and increased resistance to rot. Mycorrhizal species composition and abundance may also be favorably manipulated by modifying lignin content and structural composition.

As discussed in detail below, lignin is formed by polymerization of at least three different monolignols that are synthesized in a multistep pathway, each step in the pathway being catalyzed by a different enzyme. It has been shown that manipulation of the number of copies of genes encoding certain enzymes, such as cinnamyl alcohol dehydrogenase (CAD) and caffeic acid 3-O-methyltransferase (COMT) results in modification of the amount of lignin produced; see, for example, U.S. Pat. No. 5,451,514 and PCT Publication No. WO 94/23044. Furthermore, it has been shown that antisense expression of sequences encoding CAD in poplar leads to the production of lignin having a modified composition (Grand C et al., *Planta* (Berl.) 163:232–237, 1985).

While polynucleotides encoding some of the enzymes involved in the lignin biosynthetic pathway have been isolated for certain species of plants, genes encoding, many of the enzymes in a wide range of plant species have not yet been identified. Thus there remains a need in the art for materials useful in the modification of lignin content and composition in plants and for methods for their use.

SUMMARY OF THE INVENTION

Briefly, the present invention provides isolated polynucleotides identified in the attached Sequence Listing as SEQ ID NOS: 1–266, 350–375 and 404, variants of those sequences, constructs comprising such sequences, extended sequences comprising the sequences of SEQ ID NOS: 1–266, 350–375 and 404, and their variants, probes and primers corresponding to the sequences set out in SEQ ID NOS: 1–266, 350–375 and 404, and their variants, and polynucleotides comprising at least a specified number of contiguous residues of any of the polynucleotides identified as SEQ ID NOS: 1–266, 350–375 and 404 (x-mers), all of which are referred to herein, collectively, as "polynucleotides of the present invention." Polynucleotides of the present invention are preferably obtainable from eucalyptus and pine species, and preferably comprise open reading frames or partial open reading frames encoding enzymes, or functional portions of enzymes, involved in the lignin biosynthetic pathway. Constructs incorporating such sequences, methods for using such sequences and constructs, and biological materials, including plant cells and plants having an altered genomic and/or lignin content and composition are provided. The present invention also provides isolated polypeptide sequences identified in the attached Sequence Listing as SEQ ID NOS: 267–349, 376–401 and 405; polypeptide variants of those sequences; and polypeptides comprising the polypeptide sequences and variants of those sequences.

In one aspect, the present invention provides isolated polynucleotides encoding the following enzymes, or portions of the following enzymes: cinnamate 4-hydroxylase (C4H), coumarate 3-hydroxylase (C3H), phenolase (PNL), O-methyl transferase (OMT), cinnamyl alcohol dehydrogenase (CAD), cinnamoyl-CoA reductase (CCR), phenylalanine ammonia-lyase (PAL), 4-coumarate: CoA ligase (4CL), coniferol glucosyl transferase (CGT), coniferin beta-glucosidase (CBG), laccase (LAC), peroxidase (POX), ferulate-5-hydroxylase (F5H), alpha amylase, caffeic acid methyl transferase, caffeoyl CoA methyl transferase, coumerate 6A ligase, cytochrome P450 LXX1A, diphenol oxidase, flavonol glucosyl transferase, flavonoid hydroxylase, and isoflavone reductase.

In one embodiment, polynucleotides of the present invention encompass polynucleotides comprising a nucleotide sequence selected from the group consisting of: (a) polynucleotides recited in SEQ ID NOS: 1–266, 350–375 and 404; (b) complements of the polynucleotides recited in SEQ ID NOS: 1–266, 350–375 and 404; (c) reverse complements of the sequences recited in SEQ ID NOS: 1–266, 350–375 and 404; (d) reverse sequences of the sequences recited in SEQ ID NOS: 1–266, 350–375 and 404; and (e) variants of the polynucleotides recited in SEQ ID NOS: 1–266, 350–375 and 404. In another embodiment of the present invention, polynucleotides comprise at least a specified number of contiguous residues (x-mers) of any of the polynucleotides of SEQ ID NOS: 1–266, 350–375 and 404. In yet another aspect, polynucleotides comprise probes and primers corresponding to any of the polynucleotides of SEQ ID NOS: 1–266, 350–375 and 404.

In another aspect, the present invention provides constructs comprising a polynucleotide of the present invention, either alone or in combination with one or more of the inventive sequences, or in combination with one or more known polynucleotides; together with host cells and transgenic cells comprising such constructs.

In a related aspect, the present invention provides constructs comprising, in the 5'-3' direction, a gene promoter sequence; an open reading frame coding for at least a functional portion of an enzyme encoded by a polynucleotide of the present invention; and a gene termination sequence. An open reading frame may be orientated in either a sense or antisense direction. DNA constructs comprising a non-coding region of a gene coding for an enzyme encoded by the above polynucleotides or a polynucleotide complementary to a non-coding region, together with a gene promoter sequence and a gene termination sequence, are also provided. Preferably, the gene promoter and termination sequences are functional in a host cell, such as a plant cell. Most preferably, the gene promoter and termination sequences are those of the original enzyme genes but others generally used in the art, such as the Cauliflower Mosaic Virus (CMV) promoter, with or without enhancers, such as the Kozak sequence or Omega enhancer, and *Agrobacterium tumefaciens* nopalin synthase terminator may be usefully employed in the present invention. Tissue-specific promoters may be employed in order to target expression to one or more desired tissues. In a preferred embodiment, the gene promoter sequence provides for transcription in xylem. The construct may further include a marker for the identification of transformed cells.

In a further aspect, transgenic cells, such as transgenic plant cells, comprising the constructs of the present invention are provided, together with plants comprising such transgenic cells, and fruits and seeds of such plants.

In yet another aspect, methods for modulating the lignin content and composition of a target organism such as a plant are provided, such methods including stably incorporating into the genome of the target plant a construct comprising a polynucleotide of the present invention. In a preferred embodiment, the target plant is a woody plant, preferably selected from the group consisting of eucalyptus and pine species, most preferably from the group consisting of *Eucalyptus grandis* and *Pinus radiata*. In a related aspect, a method for producing a plant having altered lignin content is provided, the method comprising transforming a plant cell with a construct comprising a polynucleotide of the present invention to provide a transgenic cell, and cultivating the transgenic cell under conditions conducive to regeneration and mature plant growth.

In yet a further aspect, the present invention provides methods for modifying the activity of an enzyme in a target organism such as a plant, comprising stably incorporating into the genome of the target organism a construct of the present invention. In a preferred embodiment, the target plant is a woody plant, preferably selected from the group consisting of eucalyptus and pine species, most preferably from the group consisting of *Eucalyptus grandis* and *Pinus radiata*.

The present invention also provides polypeptides comprising the isolated polypeptides identified as SEQ ID NOS: 267–349, 376–401 and 405, and variants of those polypeptides.

BRIEF DESCRIPTION OF THE FIGURES

The above-mentioned and additional features of the present invention and the manner of obtaining them will become apparent, and the invention will be best understood by reference to the following more detailed description, read in conjunction with the accompanying drawing.

DETAILED DESCRIPTION

Lignin is formed by polymerization of at least three different monolignols, primarily para-coumaryl alcohol, coniferyl alcohol and sinapyl alcohol. While these three types of lignin subunits are well known, it is possible that slightly different variants of these subunits may be involved in the lignin biosynthetic pathway in various plants. The relative concentration of these residues in lignin varies among different plant species and within species. In addition, the composition of lignin may also vary among different tissues within a specific plant. The three monolignols are derived from phenylalanine in a multistep process and are believed to be polymerized into lignin by a free radical mechanism.

Figure 1:
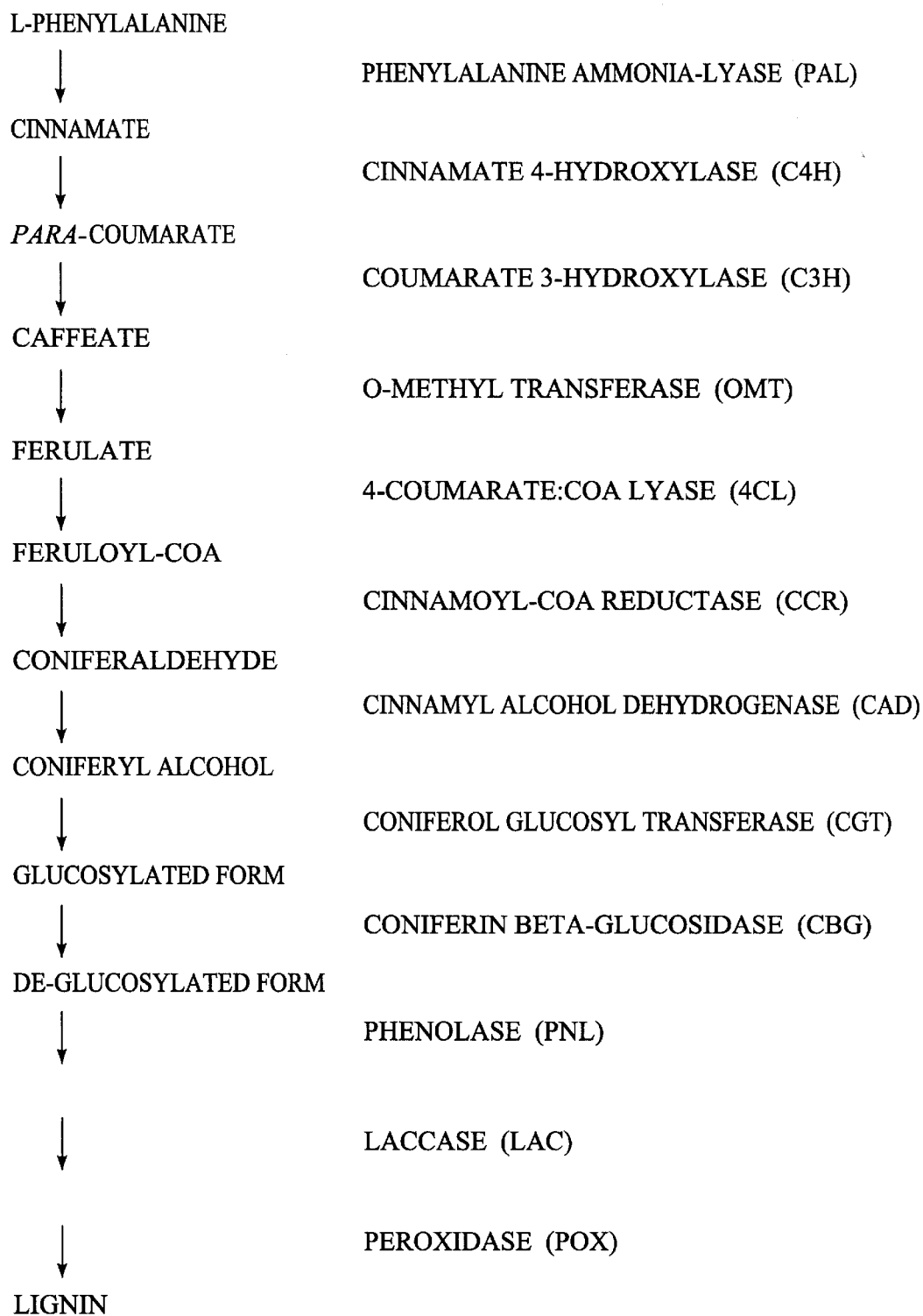
FIG. 1 is a schematic overview of the lignin biosynthetic pathway.

FIG. 1 shows different steps in the biosynthetic pathway for coniferyl alcohol together with the enzymes responsible for catalyzing each step. para-Coumaryl alcohol and sinapyl alcohol are synthesized by similar pathways. Phenylalanine is first deaminated by phenylalanine ammonia-lyase (PAL) to give cinnamate which is then hydroxylated by cinnamate 4-hydroxylase (C4H) to form p-coumarate. p-Coumarate is hydroxylated by coumarate 3-hydroxylase to give caffeate. The newly added hydroxyl group is then methylated by O-methyl transferase (OMT) to give ferulate which is conjugated to coenzyme A by 4-coumarate:CoA ligase (4CL) to form feruloyl-CoA. Reduction of feruloyl-CoA to coniferaldehyde is catalyzed by cinnamoyl-CoA reductase (CCR). Coniferaldehyde is further reduced by the action of cinnamyl alcohol dehydrogenase (CAD) to give coniferyl alcohol which is then converted into its glucosylated form for export from the cytoplasm to the cell wall by coniferol glucosyl transferase (CGT). Following export, the de-glucosylated form of coniferyl alcohol is obtained by the action of coniferin beta-glucosidase (CBG). Finally, polymerization of the three monolignols to provide lignin is catalyzed by phenolase (PNL), laccase (LAC) and peroxidase (POX).

The formation of sinapyl alcohol involves an additional enzyme, ferulate-5-hydroxylase (F5H). For a more detailed review of the lignin biosynthetic pathway, see Whetton R and Sederoff R, *The Plant Cell*, 7:1001–1013, 1995.

Quantitative and qualitative modifications in plant lignin content are known to be induced by external factors such as light stimulation, low calcium levels and mechanical stress. Synthesis of new types of lignins, sometimes in tissues not normally lignified, can also be induced by infection with pathogens. In addition to lignin, several other classes of plant products are derived from phenylalanine, including flavonoids, coumarins, stilbenes and benzoic acid derivatives, with the initial steps in the synthesis of all these compounds being the same. Thus modification of the action of PAL, C4H, 4CL and other enzymes involved in the lignin biosynthetic pathway may affect the synthesis of other plant products in addition to lignin.

Using the methods and materials of the present invention, the lignin content of a plant may be modulated by modulating expression of polynucleotides of the present invention, or by modifying the polypeptides encoded by polynucleotides or the polynucleotides. The lignin content of a target organism, such as a plant, may be modified, for example, by incorporating additional copies of genes encoding enzymes involved in the lignin biosynthetic pathway into the genome of the target plant. Similarly, a modified lignin content can be obtained by transforming the target plant with antisense copies of such genes. In addition, the number of copies of genes encoding for different enzymes in the lignin biosynthetic pathway can be manipulated to modify the relative amount of each monolignol synthesized, thereby leading to the formation of lignin having altered composition. The alteration of lignin composition would be advantageous, for example, in applications of wood processing for paper, and may also be effective in altering the palatability of wood materials to rotting fungi.

In a first aspect, the present invention provides isolated polynucleotide sequences identified in the attached Sequence Listing as SEQ ID NOS: 1–266, 350–375 and 404, variants of those sequences, extended sequences comprising the sequences set out in SEQ ID NOS: 1–266, 350–375 and 404, and their variants, probes and primers corresponding to the sequences set out in SEQ ID NOS: 1–266, 350–375 and 404, and their variants, polynucleotides comprising at least a specified number of contiguous residues of any of the polynucleotides identified as SEQ ID NOS: 1–266, 350–375 and 404 (x-mers), and extended sequences comprising portions of the sequences set out in SEQ ID NOS: 1–266, 350–375 and 404, all of which are referred to herein, collectively, as "polynucleotides of the present invention." The present invention also provides isolated polypeptide sequences identified in the attached Sequence Listing as SEQ ID NOS: 267–349, 376–401 and 405, polypeptide variants of those sequences, and polypeptides comprising the isolated polypeptide sequences and variants of those sequences.

The polynucleotides disclosed herein were derived from forestry plant sources, namely from *Eucalyptus grandis* and *Pinus radiata*. Some of the polynucleotides of the present invention are "partial" sequences, in that they do not represent a full length gene encoding a full length polypeptide. Such partial sequences may be extended by analyzing and sequencing various DNA libraries using primers and/or probes and well known hybridization and/or PCR techniques. Partial sequences may be extended until an open reading frame encoding a polypeptide, a full length polynucleotide and/or gene capable of expressing a polypeptide, or another useful portion of the genome is identified. Such extended sequences, including full length polynucleotides and genes, are described as "corresponding to" a sequence identified as one of the sequences of SEQ ID NOS: 1–266, 350–375 and 404, or a variant thereof, or a portion of one of the sequences of SEQ ID NOS: 1–266, 350–375 and 404, or a variant thereof, when the extended polynucleotide comprises an identified sequence or its variant, or an identified contiguous portion (x-mer) of one of the sequences of SEQ ID NOS: 1–266, 350–375 and 404, or a variant thereof. Similarly, RNA sequences, reverse sequences, complementary sequences, antisense sequences, and the like, corresponding to the polynucleotides of the present invention, may be routinely ascertained and obtained using the cDNA sequences identified as SEQ ID NOS: 1–266, 350–375 and 404.

The polynucleotides identified as SEQ ID NOS: 1–266, 350–375 and 404 contain open reading frames ("ORFs") or partial open reading frames encoding polypeptides and functional portions of polypeptides. Additionally, open reading frames encoding polypeptides may be identified in extended or full length sequences corresponding to the sequences set out as SEQ ID NOS: 1–266, 350–375 and 404. Open reading frames may be identified using techniques that are well known in the art. These techniques include, for example, analysis for the location of known start and stop codons, most likely reading frame identification based on codon frequencies, etc. Suitable tools and software for ORF analysis are available, for example, on the Internet. Additionally, tools ; and software for ORF analysis, for example, including GeneWise, available from The Sanger Center, Wellcome Trust Genome Campus, Hinxton, Cambridge, CB101 SA, United Kingdom; Diogenes, available from Computational Biology Centers, University of Minnesota, Academic Health Center, UMHG Box 43 Minneapolis Minn. 55455; and GRAIL, available from the Informatics Group, Oak Ridge National Laboratories, Oak Ridge, Tennessee Tenn., are suitable. Open reading frames and portions of open reading frames are present and may be identified in the polynucleotides of the present invention. Once a partial open reading frame is identified, the polynucleotide may be extended in the area of the partial open reading frame using techniques that are well known in the art until the polynucleotide for the full open reading frame is identified. Thus, open reading frames encoding polypeptides may be identified using the polynucleotides of the present invention.

Once open reading frames are identified in the polynucleotides of the present invention, the open reading frames may be isolated and/or synthesized. Expressible genetic constructs comprising the open reading frames and suitable promoters, initiators, terminators, etc., which are well known in the art, may then be constructed. Such genetic constructs may be introduced into a host cell to express the polypeptide encoded by the open reading frame. Suitable host cells may include various prokaryotic and eukaryotic cells, including plant cells, mammalian cells, bacterial cells, algae and the like.

Polypeptides encoded by the polynucleotides of the present invention may be expressed and used in various assays to determine their biological activity. Such polypeptides may be used to raise antibodies, to isolate corresponding interacting proteins or other compounds, and to quantitatively determine levels of interacting proteins or other compounds.

The present invention also contemplates methods for modulating the polynucleotide and/or polypeptide content and composition of a forestry species, such methods involving stably incorporating into the genome of the organism a genetic construct comprising one or more polynucleotides of the present invention. In one embodiment, the target organism is a forestry species, preferably a woody plant, more preferably a woody plant of the Pinus or Eucalyptus species, and most preferably *Eucalyptus grandis* or *Pinus radiata*. In a related aspect, a method for producing a forestry plant having an altered genotype or phenotype is provided, the method comprising transforming a plant cell with a genetic construct of the present invention to provide a transgenic cell, and cultivating the transgenic cell under conditions conducive to regeneration and mature plant growth. Forestry plants having an altered genotype or phenotype as a consequence of modulation of the level or content of a polynucleotide or polypeptide of the present invention compared to a wild-type organism, as well as components (seeds, etc.) of such forestry plants, and the progeny of such forestry plants, are contemplated by and encompassed within the present invention.

The isolated polynucleotides of the present invention also have utility in genome mapping, in physical mapping, and in positional cloning of genes. Additionally, the polynucleotide sequences identified as SEQ ID NOS: 1–266, 350–375 and 404, and their variants, may be used to design oligonucleotide probes and primers. Oligonucleotide probes and primers have sequences that are substantially complementary to the polynucleotide of interest over a certain portion of the polynucleotide. Oligonucleotide probes designed using the polynucleotides of the present invention may be used to detect the presence and examine the expression patterns of genes in any organism having sufficiently similar DNA and RNA sequences in their cells using techniques that are well known in the art, such as slot blot DNA hybridization techniques. Oligonucleotide primers designed using the polynucleotides of the present invention may be used for PCR amplifications. Oligonucleotide probes and primers designed using the polynucleotides of the present invention may also be used in connection with various microarray technologies, including the microarray technology used by Synteni (Palo Alto, Calif.).

The polynucleotides of the present invention may also be used to tag or identify an organism or reproductive material therefrom. Such tagging may be accomplished, for example, by stably introducing a non-disruptive non-functional heterologous polynucleotide identifier into an organism, the polynucleotide comprising one of the polynucleotides of the present invention.

The polypeptides of the present invention and the polynucleotides encoding the polypeptides have activity in lignin biosynthetic pathways in plants. The polynucleotides were putatively identified by DNA and polypeptide similarity searches. The polynucleotides and polypeptides of the present invention have demonstrated similarity to the following polypeptides that are known to be involved in lignin biosynthetic processes:

TABLE 1

| POLYPEPTIDE IDENTITY | POLYNUCLEOTIDE SEQ ID NO. | POLYPEPTIDE SEQ ID NO. |
| --- | --- | --- |
| Cinnamate 4-hydroxylase (C4H) | 2, 3, 17, 48, 49, 92, 124, 125, 153–163 | |
| Coumarate 3-hydroxylase (C3H) | 4, 18, 50–52, 93, 101, 126, 127, 149–152 | |
| Phenolase (PNL) | 5, 35, 36, 81, 116, 183 | |
| O-methyl transferase (OMT) | 6, 22–25, 53–55, 94, 104–107, 173–175 | |
| Cinnamyl alcohol dehydrogenase (CAD) | 1, 7, 30, 71, 95, 112, 164 | |
| Cinnamoyl-CoA reductase (CCR) | 8, 26–29, 58–70, 96, 108–111, 128–134, 167 | |
| Phenylalanine ammonia-lyase (PAL) | 9–11, 16, 45–47, 97, 98, 100, 122, 123, 176 242–248 | 325–331 |
| 4-coumarate: CoA ligase (4CL) | 2, 56–57, 90, 147, 158 265, 266 | 348–349 |
| Coniferol glucosyl transferase (CGT) | 31–33, 72, 113–115, 135, 168 | |
| Coniferin beta-glucosidase (CBG) | 34, 73–80, 1360141, 165, 166 | |
| Laccase (LAC) | 37–41, 82–84, 117, 118, 142–144, 172 | |
| Peroxidase (POX) | 13, 42–44, 85–89, 91, 119–121, 145, 146, 177–182, 249–250, 264, 350–375 | 332–333 347, 376–401 |
| Ferulate-5-hydroxylase (F5H) | 19–21, 102, 103, 169–171, 404 | 405 |
| Alpha amylase | 184–186 | 267–269 |
| Caffeic acid methyl transferase | 187–192 | 270–275 |
| Caffeoyl CoA methyl transferase | 193–195 | 276–278 |
| Coumerate CoA ligase | 196–200 | 279–283 |
| Cytochrome P450 LXXIA | 201–206 | 284–289 |
| Diphenol oxidase | 207–217 251–263 | 290–300 334–346 |
| Flavonol glucosyl transferase | 218 | 301 |
| Flavonoid hydroxylase | 219–233 | 302–316 |
| Isoflavone reductase | 234–241 | 317–324 |

In one embodiment, isolated polynucleotides of the present invention comprise a sequence selected from the group consisting of: (a) sequences recited in SEQ ID NOS: 1–266, 350–375 and 404; (b) complements of the sequences recited in SEQ ID NOS: 1–266, 350–375 and 404; (c) reverse complements of the sequences recited in SEQ ID NOS: 1–266, 350–375 and 404; (d) reverse sequences of the sequences recited in SEQ ID NOS: 1–266, 350–375 and 404; and (e) sequences having at least 50%, 75%, 90%, or 98% identity, as defined herein, to a sequence of (a)–(d) or a specified region of a sequence of (a)–(d).

In a further aspect, isolated polypeptides encoded by the polynucleotides of the present invention are provided. In one embodiment, such polypeptides comprise an amino acid sequence recited in SEQ ID NOS: 267–349, 376–401 and 405, and variants thereof, as well as polypeptides expressed by polynucleotides of the present invention, including polynucleotides comprising a sequence of SEQ ID NOS: 1–266, 350–375 and 404.

In another aspect, the invention provides genetic constructs comprising a polynucleotide of the present invention, either alone, in combination with one or more additional polynucleotides of the present invention, or in combination with one or more known polynucleotides, together with cells and target organisms comprising such constructs.

In a related aspect, the present invention provides genetic constructs comprising, in the 5'-3' direction, a gene promoter sequence, an open reading frame coding for at least a functional portion of a polypeptide encoded by a polynucleotide of the present invention, and a gene termination sequence. The open reading frame may be oriented in either a sense or antisense direction. Genetic constructs comprising a gene promoter sequence, a polynucleotide of the present invention, and a gene termination sequence are also contemplated, as are genetic constructs comprising a gene promoter sequence, an untranslated region of a polynucleotide of the present invention, or a nucleotide sequence complementary to an untranslated region, and a gene termination sequence. The genetic construct may further include a marker for the identification of transformed cells.

The gene promoter and termination sequences are preferably functional in a host plant and, most preferably, are those native to the host plant. Promoter and termination sequences that are generally used in the art, such as the Cauliflower Mosaic Virus (CMV) promoter, with or without enhancers such as the Kozak sequence or Omega enhancer, and *Agrobacterium tumefaciens* nopaline synthase terminator, are useful. Tissue-specific promoters may be employed in order to target expression to one or more desired tissues.

In a further aspect, methods for producing forestry plants having a modified content of a polynucleotide or polypeptide of the present invention compared to a native organism are provided. The methods involve transforming a target forestry plant with a genetic construct of the present invention to provide a transgenic cell, and cultivating the transgenic cell under conditions conducive to regeneration and mature plant growth. Cells comprising the genetic constructs of the present invention are provided, together with tissues and forestry plants comprising such transgenic cells, and fruits, seeds and other products, derivatives, or progeny of such forestry plants.

The word "polynucleotide(s)," as used herein, means a polymeric collection of nucleotides and includes DNA and corresponding RNA molecules and both single and double stranded molecules, including HnRNA and mRNA molecules, sense and anti-sense strands of DNA and RNA molecules, and cDNA, genomic DNA, and wholly or partially synthesized polynucleotides. An HnRNA molecule contains introns and "corresponds to" a DNA molecule in a generally one-to-one manner. An mRNA molecule "corresponds to" an HnRNA and DNA molecule from which the introns have been excised. A polynucleotide of the present invention may be an entire gene, or any portion thereof. A gene is a DNA sequence which codes for a functional protein or RNA molecule. Operable anti-sense polynucleotides may comprise a fragment of the corresponding polynucleotide, and the definition of "polynucleotide" therefore includes all operable anti-sense fragments. Anti-sense polynucleotides and techniques involving anti-sense polynucleotides are well known in the art and are described, for example, in Robinson-Benion et al., "Antisense techniques," *Methods in Enzymol.* 254(23):363–375, 1995; and Kawasaki et al., *Artific. Organs* 20(8):836–848, 1996.

Complements of such isolated polynucleotides, reverse complements of such isolated polynucleotides, and reverse sequences of such isolated polynucleotides, together with variants of such sequences, are also provided. The definition of the terms "complement", "reverse complement" and "reverse sequence", as used herein, is best illustrated by the following example. For the sequence 5' AGGACC 3', the complement, reverse complement and reverse sequence are as follows:

```
complement           3' TCCTGG 5'
reverse complement   3' GGTCCT 5'
reverse sequence     5' CCAGGA 3'.
```

As used herein, the term "oligonucleotide" refers to a relatively short segment of a polynucleotide sequence, generally comprising between 6 and 60 nucleotides, and comprehends both probes for use in hybridization assays and primers for use in the amplification of DNA by polymerase chain reaction.

Identification of genomic DNA and heterologous species DNAs can be accomplished by standard DNA/DNA hybridization techniques, under appropriately stringent conditions, using all or part of a cDNA sequence as a probe to screen an appropriate library. Alternatively, PCR techniques using oligonucleotide primers that are designed based on known genomic DNA, cDNA and protein sequences can be used to amplify and identify genomic and cDNA sequences. Synthetic DNAs corresponding to the identified sequences and variants may be produced by conventional synthesis methods. All of the polynucleotides described herein are isolated and purified, as those terms are commonly used in the art.

In another aspect, the present invention provides isolated polypeptides encoded, or partially encoded, by the above polynucleotides. As used herein, the term "polypeptide" encompasses amino acid chains of any length, including full length proteins, wherein the amino acid residues are linked by covalent peptide bonds. The term "polypeptide encoded by a polynucleotide" as used herein, includes polypeptides encoded by a polynucleotide which comprises an isolated DNA sequence or variant provided herein. In specific embodiments, the inventive polypeptides comprise an amino acid sequence selected from the group consisting of sequences provided in SEQ ID NOS: 267–349, 376–401 and 405, as well as variants of such sequences.

Polypeptides of the present invention may be produced recombinantly by inserting a DNA sequence that encodes the polypeptide into an expression vector and expressing the polypeptide in an appropriate host. Any of a variety of expression vectors known to those of ordinary skill in the art may be employed. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, insect, yeast or a mammalian cell line such as COS or CHO. The DNA sequences expressed in this manner may encode naturally occurring polypeptides, portions of naturally occurring polypeptides, or other variants thereof.

In a related aspect, polypeptides are provided that comprise at least a functional portion of a polypeptide having an amino acid sequence selected from the group consisting of sequences provided in SEQ ID NOS:267–349, 376–401 and 405, and variants thereof. As used herein, the "functional portion" of a polypeptide is that portion which contains the active site essential for affecting the function of the polypeptide, for example, the portion of the molecule that is capable of binding one or more reactants. The active site may be made up of separate portions present on one or more polypeptide chains and will generally exhibit high binding affinity.

Functional portions of a polypeptide may be identified by first preparing fragments of the polypeptide by either chemical or enzymatic digestion of the polypeptide, or by mutation analysis of the polynucleotide that encodes the polypeptide and subsequent expression of the resulting mutant polypeptides. The polypeptide fragments or mutant polypeptides are then tested to determine which portions retain biological activity, using, for example, the representative assays provided below.

A functional portion comprising an active site may be made up of separate portions present on one or more polypeptide chains and generally exhibits high substrate specificity. The term "polypeptide encoded by a polynucleotide" as used herein, includes polypeptides encoded by a polynucleotide comprising a partial isolated polynucleotide of the present invention.

Portions and other variants of the inventive polypeptides may also be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied Biosystems, Inc. (Foster City, Calif.), and may be operated according to the manufacturer's instructions. Variants of a native polypeptide may be prepared using standard mutagenesis techniques, such as oligonucleotide-directed site-specific mutagensis (Kunkel, T., *Proc. Natl. Acad. Sci. USA* 82: 488–492, 1985). Sections of DNA sequences may also be removed using standard techniques to permit preparation of truncated polypeptides.

In general, the polypeptides disclosed herein are prepared in an isolated, substantially pure form. Preferably, the polypeptides are at least about 80% pure; more preferably at least about 90% pure; and most preferably, at least about 99% pure. In certain preferred embodiments, described in detail below, the isolated polypeptides are incorporated into pharmaceutical compositions or vaccines for use in the treatment of skin disorders.

As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 50%; more preferably, at least 75%; and most preferably, at least 90% or 95% identity to a sequence of the present invention. The percentage identity is determined by aligning the two sequences to be compared as described below, determining the number of identical residues in the aligned portion, dividing that number by the total number of residues in the inventive (queried) sequence, and multiplying the result by 100.

Polynucleotide and polypeptide sequences may be aligned, and percentage of identical nucleotides in a specified region may be determined against another polynucleotide, using computer algorithms that are publicly available. Two exemplary algorithms for aligning and identifying the similarity of polynucleotide sequences are the BLASTN and FASTA algorithms. Polynucleotides may also be analyzed using the BLASTX algorithm, which compares the six-frame conceptual translation products of a nucleotide query sequence (both strands) against a protein sequence database. The similarity of polypeptide sequences may be examined using the BLASTP algorithm. The BLASTN, BLASTX and BLASTP programs are available on the NCBI anonymous FTP server under /blast/executables/ and are available from the National Center for Biotechnology Information (NCBI) National Library of Medicine, Building 38A, Room 8N805, Bethesda, Md. 20894 USA. The BLASTN algorithm Version 2.0.4 [Feb. 24, 1998] and Version 2.0.6 [Sep. 16, 1998], set to the default parameters described in the documentation and distributed with the algorithm, are preferred for use in the determination of polynucleotide variants according to the present invention. The BLASTP algorithm, set to the default parameters described in the documentation and distributed with the program, is preferred for use in the determination of polypeptide variants according to the present invention. The use of the BLAST family of algorithms, including BLASTN, BLASTP, and BLASTX, is described at NCBI's website and in the publication of Altschul Stephen F. et al., "Gapped BLAST and PSI-BLAST: a new generation of protein database search programs," *Nucleic Acids Res.* 25: 3389–3402, 1997.

The computer algorithm FASTA is available on the Internet, and the FASTA software package is available from the University of Virginia by contacting David Hudson, Assistant Provost for Research, University of Virginia, PO Box 9025, Charlottesville, Va. 22906-9025 USA. FASTA Version 2.0.4, February 1996, set to the default parameters described in the documentation and distributed with the algorithm, may be used in the determination of variants according to the present invention. The use of the FASTA algorithm is described in Pearson W R and Lipman D J, "Improved Tools for Biological Sequence Analysis," *Proc. Natl. Acad. Sci. USA* 85: 2444–2448, 1988; and Pearson W R, "Rapid and Sensitive Sequence Comparison with FASTP and FASTA," *Methods in Enzymology* 183: 63–98, 1990.

The following running parameters are preferred for determination of alignments and similarities using BLASTN that contribute to the E values and percentage identity for polynucleotide sequences: Unix running command: blastall -p blastn -d embldb -e 10-G0-E0-r 1-v 30-b 30-i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -r Reward for a nucleotide match (blastn only) [Integer]; -v Number of one-line descriptions (V) [Integer]; -b Number of alignments to show (B) [Integer]; -i Query File [File In]; and -o BLAST report Output File [File Out] Optional. The following running parameters are preferred for determination of alignments and similarities using BLASTP that contribute to the E values and percentage identity of polypeptide sequences: blastall -p blastp -d swissprotdb -e 10-G 0-E 0-v 30-b 30-i queryseq -o results;

the parameters are: -p Program Name [String]; -d Database [String]; -e Expectation value (E) [Real]; -G Cost to open a gap (zero invokes default behavior) [Integer]; -E- Cost to extend a gap (zero invokes default behavior) [Integer]; -v Number of one-line descriptions (v) [Integer]; -b Number of alignments to show (b) [Integer]; -I Query File [File In]; -o BLAST report Output File [File Out] Optional. The "hits" to one or more database sequences by a queried sequence produced by BLASTN, FASTA, BLASTP or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, FASTA, and BLASTP algorithms also produce "Expect" (E) values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the polynucleotide sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides and polypeptides, with reference to each of the polynucleotides and polypeptides of the present invention, preferably comprise sequences having the same number or fewer nucleic or amino acids than each of the polynucleotides or polypeptides of the present invention and producing an E value of 0.01 or less when compared to the polynucleotide or polypeptide of the present invention. That is, a variant polynucleotide or polypeptide is any sequence that has at least a 99% probability of being the same as the polynucleotide or polypeptide of the present invention, measured as having an E value of 0.01 or less using the BLASTN, FASTA, or BLASTP algorithms set at parameters described above. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN or FASTA algorithms set at parameters described above. Similarly, according to a preferred embodiment, a variant polypeptide is a sequence having the same number or fewer amino acids than a polypeptide of the present invention that has at least a 99% probability of being the same as a polypeptide of the present invention, measured as having an E value of 0.01 or less using the BLASTP algorithm set at the parameters described above.

Alternatively, variant polynucleotides or polypeptides of the present invention comprise a sequence exhibiting at least 50%; more preferably at least 75%; more preferably yet at least 90%; and most preferably at least 98% similarity to a polynucleotide or polypeptide of the present invention, determined as described below. Polynucleotides and polypeptides having a specified percentage similarity to a polynucleotide or polypeptide specified in one of the SEQ ID NOS. thus share a high degree of similarity in their primary structure. In addition to a specified percentage similarity to a polynucleotide of the present invention, variant polynucleotides and polypeptides preferably have additional structural and/or functional features in common with a polynucleotide of the present invention. Polynucleotides having a specified degree of similarity to or capable of hybridizing to a polynucleotide of the present invention preferably additionally have at least one of the following features: (1) they contain an open reading frame or partial open reading frame encoding a polypeptide, or a functional portion of a polypeptide, having substantially the same functional properties as the polypeptide, or functional portion thereof, encoded by a polynucleotide in a recited SEQ ID NO.; or (2) they contain identifiable domains in common. Similarly, polypeptides, or functional portions of polypeptides, having a specified degree of similarity to a polypeptide of the present invention shares a high degree of similarity in their primary structure and have substantially similar functional properties.

The percentage similarity is determined by aligning sequences using one of the BLASTN, FASTA, or BLASTP algorithms, set at the running parameters described above, and identifying the number of identical nucleic or amino acids over the aligned portions; dividing the number of identical nucleic or amino acids by the total number of nucleic or amino acids of the polynucleotide or polypeptide of the present invention; and then multiplying by 100 to determine the percentage similarity. For example, a polynucleotide of the present invention having 220 nucleic acids has a hit to a polynucleotide sequence in the EMBL database having 520 nucleic acids over a stretch of 23 nucleotides in the alignment produced by the BLASTN algorithm using the parameters described above. The 23 nucleotide hit includes 21 identical nucleotides, one gap and one different nucleotide. The percentage similarity of the polynucleotide of the present invention to the hit in the EMBL library is thus 21/220 times 100, or 9.5%. The polynucleotide sequence in the EMBL database is thus not a variant of a polynucleotide of the present invention.

Alternatively, variant polynucleotides of the present invention hybridize to the polynucleotide sequences recited in SEQ ID NOS: 1–266, 350–375 and 404, or complements, reverse sequences, or reverse complements of those sequences under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The present invention also encompasses polynucleotides that differ from the disclosed sequences but that, as a consequence of the discrepancy of the genetic code, encode a polypeptide having similar enzymatic activity as a polypeptide encoded by a polynucleotide of the present invention. Thus, polynucleotides comprising sequences that differ from the polynucleotide sequences recited in SEQ ID NOS: 1–266, 350–375 and 404, or complements, reverse sequences, or reverse complements of those sequences as a result of conservative substitutions are contemplated by and encompassed within the present invention. Additionally, polynucleotides comprising sequences that differ from the polynucleotide sequences recited in SEQ ID NOS: 1–266, 350–375 and 404, or complements, reverse complements, or reverse sequences as a result of deletions and/or insertions totaling less than 10% of the total sequence length are also contemplated by and encompassed within the present invention. Similarly, polypeptides comprising sequences that differ from the polypeptide sequences recited in SEQ ID NOS: 267–349, 376–401 and 405 as a result of amino acid substitutions, insertions, and/or deletions totaling less than 10% of the total sequence length are contemplated by and encompassed within the present invention, provided the variant polypeptide has activity in a lignin biosynthetic pathway.

The polynucleotides of the present invention, including variants, may be isolated from various libraries assembled from plant or non-plant organisms, or may be synthesized using techniques that are well known in the art. Polynucleotides of the present invention may be isolated by high throughput sequencing of cDNA libraries prepared from *Eucalyptus grandis* and *Pinus radiata* as described below in Examples 1 and 2. Alternatively, oligonucleotide probes based on the sequences provided in SEQ ID NO: 1–266, 350–375 and 404 may be synthesized and used to identify positive clones in either cDNA or genomic DNA libraries from *Eucalyptus grandis* and *Pinus radiata* by means of hybridization or PCR techniques. Probes may be shorter than the sequences provided herein but should be at least about 10, preferably at least about 15 and most preferably at least about 20 nucleotides in length. Hybridization and PCR techniques suitable for use with such oligonucleotide probes are well known in the art. Positive clones may be analyzed by restriction enzyme digestion, DNA sequencing or the like.

Variants of the polynucleotides of the present invention derived from other eucalyptus and pine species, as well as from other commercially important species utilized by the lumber industry, are contemplated. These include the following gymnosperms, by way of example: loblolly pine *Pinus taeda*, slash pine *Pinus elliotti*, sand pine *Pinus clausa*, longleaf pine *Pinus palustrus*, shortleaf pine *Pinus echinata*, ponderosa pine *Pinus ponderosa*, Jeffrey pine *Pinus Jeffrey*, red pine *Pinus resinosa*, pitch pine *Pinus rigida*, jack pine *Pinus banksiana*, pond pine *Pinus serotina*, Eastern white pine *Pinus strobus*, Western white pine *Pinus monticola*, sugar pine *Pinus lambertiana*, Virginia pine *Pinus virginiana*, lodgepole pine *Pinus contorta*, Caribbean pine *Pinus caribaea, P. pinaster*, Calabrian pine *P. brutia*, Afghan pine *P. eldarica*, Coulter pine *P. coulteri*, European pine *P. nigra* and *P. sylvestris*; Douglas-fir *Pseudotsuga menziesii*; the hemlocks which include Western hemlock *Tsuga heterophylla*, Eastern hemlock *Tsuga canadensis*, Mountain hemlock *Tsuga mertensiana*; the spruces which include the Norway spruce *Picea abies*, red spruce *Picea rubens*, white spruce *Picea glauca*, black spruce *Picea mariana*, Sitka spruce *Picea sitchensis*, Englemann spruce *Picea engelmanni*, and blue spruce *Picea pungens*; redwood *Sequoia sempervirens*; the true firs include the Alpine fir *Abies lasiocarpa*, silver fir *Abies amabilis*, grand fir *Abies grandis*, nobel fir *Abies procera*, white fir *Abies concolor*, California red fir *Abies magnifica*, and balsam fir *Abies balsamea*, the cedars which include the Western red cedar *Thuja plicata*, incense cedar *libocedrus decurrens*, Northern white cedar *Thuja occidentalis*, Port Orford cedar *Chamaecyparis lawsoniona*, Atlantic white cedar *Chamaecyparis thyoides*, Alaska yellow-cedar *Chamaecyparis nootkatensis*, and Eastern red cedar *Huniperus virginiana*; the larches which include Eastern larch *Larix laricina*, Western larch *Larix occidentalis*, European larch *Larix decidua*, Japanese larch *Larix leptolepis*, and Siberian larch *Larix siberica*; bold cypress *Taxodium distichum* and Giant sequoia *Sequoia gigantea*; and the following angiosperms, by way of example: *Eucalyptus alba, E. bancroftii, E. botyroides, E. bridgesiana, E. calophylla, E. camaldulensis, E. citriodora, E. cladocalyx, E. coccifera, E. curtisii, E. dalrympleana, E. deglupta, E. delagatensis, E. diversicolor, E. dunnii, E. ficifolia, E. globulus, E. gomphocephala, E. gunnii, E. henryi, E. laevopinea, E. macarthurii, E. macrorhyncha, E. maculata, E. marginata, E. megacarpa, E. melliodora, E. nicholii, E. nitens, E. nova-angelica, E. obliqua, E. obtusiflora, E. oreades, E. pauciflora, E. polybractea, E. regnans, E. resinifera, E. robusta, E. rudis, E. saligna, E. sideroxylon, E. stuartiana, E. tereticornis, E. torelliana, E. urnigera, E. urophylla, E. viminalis, E. viridis, E. wandoo* and *E. youmanni*.

The polynucleotides of the present invention may alternatively be synthesized, for example, using automated oligonucleotide synthesizers (e.g., Beckman Oligo 1000M DNA Synthesizer) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleic acids, and hybridizing that segment to a synthesized complementary 85 nucleic acid segment to produce a 5 nucleotide overhang. The next segment may then be synthesized in a similar fashion, with a 5 nucleotide overhang on the opposite strand. The "sticky" ends ensure proper ligation when the two portions are hybridized. In this way, a complete polynucleotide of the present invention may be synthesized entirely in vitro.

The polynucleotides identified as SEQ ID NOS: 1–266, 350–375 and 404 represent both "partial" and full length sequences. Partial sequences do not represent the full coding portion of a gene encoding a naturally occurring polypeptide. The partial polynucleotide sequences disclosed herein may be employed to obtain the corresponding full length genes for various species and organisms by, for example, screening DNA expression libraries using hybridization probes based on the polynucleotides of the present invention, or using PCR amplification with primers based upon the polynucleotides of the present invention. In this way one can, using methods well known in the art, extend a polynucleotide of the present invention upstream and downstream of the corresponding mRNA, as well as identify the corresponding genomic DNA, including the promoter and enhancer regions, of the complete gene.

The present invention thus comprehends isolated polynucleotides comprising a sequence identified in SEQ ID NOS: 1–266, 350–375 and 404, or a variant of one of the specified sequences, that encode a functional polypeptide, including full length genes. Such extended polynucleotides may have a length of from about 50 to about 4,000 nucleic acids or base pairs, and preferably have a length of less than about 4,000 nucleic acids or base pairs, more preferably a length of less than about 3,000 nucleic acids or base pairs, more preferably yet a length of less than about 2,000 nucleic acids or base pairs. Under some circumstances, extended polynucleotides of the present invention may have a length of less than about 1,800 nucleic acids or base pairs, preferably less than about 1,600 nucleic acids or base pairs, more preferably less than about 1,400 nucleic acids or base pairs, more preferably yet less than about 1,200 nucleic acids or base pairs, and most preferably less than about 1,000 nucleic acids or base pairs.

Polynucleotides of the present invention also comprehend polynucleotides comprising at least a specified number of contiguous residues (x-mers) of any of the polynucleotides identified as SEQ ID NOS: 1–266, 350–375 and 404 or their variants. According to preferred embodiments, the value of x is preferably at least 20, more preferably at least 40, more preferably yet at least 60, and most preferably at least 80. Thus, polynucleotides of the present invention include polynucleotides comprising a 20-mer, a 40-mer, a 60-mer, an 80-mer, a 100-mer, a 120-mer, a 150-mer, a 180-mer, a 220-mer a 250-mer, or a 300-mer, 400-mer, 500-mer or 600-mer of a polynucleotide identified as SEQ ID NOS: 1–266, 350–375 and 404, or a variant of any x-mer. That is, the definitions for variants described above in terms of E values, % similarity and hybridization, apply also to any x-mer of any polynucleotide of the present invention.

Polynucleotide probes and primers complementary to and/or corresponding to SEQ ID NOS: 1–266, 350–375 and 404, and variants of those sequences, are also comprehended by the present invention. Such oligonucleotide probes and primers are substantially complementary to the polynucleotide of interest. An oligonucleotide probe or primer is described as. "corresponding to" a polynucleotide of the present invention, including one of the sequences set out as SEQ ID NOS: 1–266, 350–375 and 404 or a variant, if the oligonucleotide probe or primer, or its complement, is contained within one of the sequences set out as SEQ ID NOS: 1–266, 350–375 and 404 or a variant of one of the specified sequences.

Two single stranded sequences are said to be substantially complementary when the nucleotides of one strand, optimally aligned and compared, with the appropriate nucleotide insertions and/or deletions, pair with at least 80%, preferably at least 90% to 95%, and more preferably at least 98% to 100%, of the nucleotides of the other strand. Alternatively, substantial complementarity exists when a first DNA strand will selectively hybridize to a second DNA strand under stringent hybridization conditions. Stringent hybridization conditions for determining complementarity include salt conditions of less than about 1 M, more usually less than about 500 mM and preferably less than about 200 mM. Hybridization temperatures can be as low as 5° C., but are generally greater than about 22° C., more preferably greater than about 30° C. and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone. The DNAs from plants or samples or products containing plant material can be either genomic DNA or DNAs derived by preparing cDNA from the RNAs present in the sample.

In addition to DNA—DNA hybridization, DNA-RNA or RNA—RNA hybridization assays are also possible. In the first case, the mRNAs from expressed genes would then be detected instead of genomic DNA or cDNA derived from mRNA of the sample. In the second case, RNA probes could be used. In addition, artificial analogs of DNA hybridizing specifically to target sequences could also be used.

In specific embodiments, the oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length or, preferably, from about 10 to 50 base pairs in length or, more preferably, from about 15 to 40 base pairs in length. The probes can be easily selected using procedures well known in the art, taking into account DNA—DNA hybridization stringencies, annealing and melting temperatures, potential for formation of loops and other factors, which are well known in the art. Tools and software suitable for designing probes, and especially suitable for designing PCR primers, are available on the Internet, for example, at http://www.horizonpress.com/pcr/. Preferred techniques for designing PCR primers are also disclosed in Dieffenbach CW and Dvksler GS, *PCR primer: a laboratory manual*, CSHL Press: Cold Spring Harbor, N.Y., 1995. A software program suitable for designing probes, and especially for designing PCR primers, is available from Premier Biosoft International, 3786 Corina Way, Palo Alto, Calif. 94303-4504.

A plurality of oligonucleotide probes or primers corresponding to polynucleotides of the present invention may be provided in a kit form. Such kits generally comprise multiple DNA or oligonucleotide probes, each probe being specific for a polynucleotide sequence. Kits of the present invention may comprise one or more probes or primers corresponding to a polynucleotide of the present invention, including a polynucleotide sequence identified in SEQ ID NOS: 1–266, 350–375 and 404.

In one embodiment useful for high-throughput assays, the oligonucleotide probe kits of the present invention comprise multiple probes in an array format, wherein each probe is immobilized in a predefined, spatially addressable location on the surface of a solid substrate. Array formats which may be usefully employed in the present invention are disclosed, for example, in U.S. Pat. Nos. 5,412,087, 5,545,531, and PCT Publication No. WO 95/00530, the disclosures of which are hereby incorporated by reference.

The significance of high-throughput screening systems is apparent for applications such as plant breeding and quality control operations in which there is a need to identify large numbers of seed lots and plant seedlings, to examine samples or products for unwanted plant materials, to identify plants or samples or products containing plant material for quarantine purposes etc. or to ascertain the true origin of plants or samples or products containing plant material. Screening for the presence or absence of polynucleotides of the present invention used as identifiers for tagging plants is valuable for later detecting the amount of gene flow in plant breeding, introgression of genes via dispersed pollen, etc.

In this manner, oligonucleotide probe kits of the present invention may be employed to examine the presence/absence (or relative amounts in case of mixtures) of polynucleotides of the present invention in different samples or products containing different materials rapidly and in a cost-effective manner. Examples of plant species that may be examined using the present invention, include forestry species, such as pine and eucalyptus species, other tree species, agricultural plants including crop and forage plants, and horticultural plants.

Another aspect of the present invention involves collections of polynucleotides of the present invention. A collection of polynucleotides of the present invention, particularly the polynucleotides identified as SEQ ID NOS: 1–266, 350–375 and 404, and variants and x-mers thereof, may be recorded and/or stored on a storage medium and subsequently accessed for purposes of analysis, comparison, etc. Suitable storage media include magnetic media such as magnetic diskettes, magnetic tapes, CD-ROM storage media, optical storage media, and the like. Suitable storage media and methods for recording and storing information, as well as accessing information such as polynucleotide sequences recorded on such media, are well known in the art. The polynucleotide information stored on the storage medium is preferably computer-readable and may be used for analysis and comparison of the polynucleotide information.

Another aspect of the present invention thus involves storage medium on which are recorded a collection of the polynucleotides of the present invention, particularly a collection of the polynucleotides identified as SEQ ID NOS: 1–266, 350–375 and 404, and variants thereof, as well as x-mers of the polynucleotides of SEQ ID NOS: 1–266, 350–375 and 404, and extended sequences, probes and primers comprising or correspond to a polynucleotide of SEQ ID NOS: 1–266, 350–375 and 404. According to one embodiment, the storage medium includes a collection of at least 20, preferably at least 50, more preferably at least 100, and most preferably at least 200 of the polynucleotides of the present invention, preferably the polynucleotides identified as SEQ ID NOS: 1–266, 350–375 and 404, or variants of those polynucleotides.

In another aspect, the present invention provides genetic constructs comprising, in the 5'-3' direction, a gene promoter sequence; an open reading frame coding for at least a functional portion of a polypeptide encoded by a polynucleotide of the present invention; and a gene termination sequence. As used herein, the "functional portion" of an enzyme is a portion that contains an active site essential for affecting a metabolic step, i.e. .a portion of the molecule that is capable of binding one or more reactants or is capable of improving or regulating the rate of reaction. An active site may be made up of separate portions present on one or more polypeptide chains and will generally exhibit high substrate specificity. The term "enzyme encoded by a nucleotide sequence" as used herein, includes enzymes encoded by a nucleotide sequence which includes the partial isolated polynucleotides of the present invention.

The open reading frame may be orientated in either a sense or antisense direction. For applications where amplification of lignin synthesis is desired, the open reading frame may be inserted in the construct in a sense orientation, such that transformation of a target organism with the construct will lead to an increase in the number of copies of the gene and therefore an increase in the amount of enzyme. When down-regulation of lignin synthesis is desired, the open reading frame may be inserted in the construct in an antisense orientation, such that the RNA produced by transcription of the polynucleotide is complementary to the endogenous mRNA sequence. This, in turn, will result in a decrease in the number of copies of the gene and therefore a decrease in the amount of enzyme. Alternatively, regulation may be achieved by inserting appropriate sequences or subsequences (e.g., DNA or RNA) in ribozyme constructs.

Genetic constructs comprising a non-coding region of a gene coding for an enzyme encoded by the above DNA sequences or a nucleotide sequence complementary to a non-coding region, together with a gene promoter sequence and a gene termination sequence, are also provided. As used herein the term "non-coding region" includes both transcribed sequences which are not translated, and non-transcribed sequences within about 2000 base pairs 5' or 3' of the translated sequences or open reading frames. Examples of non-coding regions which may be usefully employed in the inventive constructs include introns and 5'-non-coding leader sequences. Transformation of a target plant with such a DNA construct may lead to a reduction in the amount of lignin synthesized by the plant by the process of cosuppression, in a manner similar to that discussed, for example, by Napoli et al., *Plant Cell* 2:279–290, 1990; and de Carvalho Niebel et al., *Plant Cell* 7:347–358, 1995.

The genetic constructs of the present invention further comprise a gene promoter sequence and a gene termination sequence, operably linked to the polynucleotide to be transcribed, which control expression of the gene. The gene promoter sequence is generally positioned at the 5' end of the polynucleotide to be transcribed, and is employed to initiate transcription of the polynucleotide. Gene promoter sequences are generally found in the 5' non-coding region of a gene but they may exist in introns (Luehrsen K R, *Mol. Gen. Genet*. 225:81–93, 1991, or in the coding region, as for example in PAL of tomato (Bloksberg, *Studies on the Biology of Phenylalanine Ammonia Lyase and Plant Pathogen Interaction*, Ph.D. Thesis, University of California, Davis, 1991, University Microfilms International Order No. 9217564). When the construct includes an open reading frame in a sense orientation, the gene promoter sequence also initiates translation of the open reading frame. For DNA constructs comprising either an open reading frame in an antisense orientation or a non-coding region, the gene promoter sequence consists only of a transcription initiation site having a RNA polymerase binding site.

A variety of gene promoter sequences which may be usefully employed in the DNA constructs of the present invention are well known in the art. The promoter gene sequence, and also the gene termination sequence, may be endogenous to the target plant host or may be exogenous, provided the promoter is functional in the target host. For example, the promoter and termination sequences may be from other plant species, plant viruses, bacterial plasmids and the like. Preferably, gene promoter and termination sequences are from the inventive sequences themselves.

Factors influencing the choice of promoter include the desired tissue specificity of the construct, and the timing of transcription and translation. For example, constitutive promoters, such as the 35S Cauliflower Mosaic Virus (CaMV 35S) promoter, will affect the activity of the enzyme in all parts of the plant. Use of a tissue specific promoter will result in production of the desired sense or antisense RNA only in the tissue of interest. With DNA constructs employing inducible gene promoter sequences, the rate of RNA polymerase binding and initiation can be modulated by external stimuli, such as light, heat, anaerobic stress, alteration in nutrient conditions and the like. Temporally regulated promoters can be employed to effect modulation of the rate of RNA polymerase binding and initiation at a specific time during development of a transformed cell. Preferably, the original promoters from the enzyme gene in question, or promoters from a specific tissue-targeted gene in the organism to be transformed, such as eucalyptus or pine are used. Other examples of gene promoters which may be usefully employed in the present invention include, mannopine synthase (mas), octopine synthase (ocs) and those reviewed by Chua et al., *Science* 244:174–181, 1989.

The gene termination sequence, which is located 3' to the polynucleotide to be transcribed, may come from the same gene as the gene promoter sequence or may be from a different gene. Many gene termination sequences known in the art may be usefully employed in the present invention, such as the 3' end of the *Agrobacterium tumefaciens* nopaline synthase gene. However, preferred gene terminator sequences are those from the original enzyme gene or from the target species to be transformed.

The genetic constructs of the present invention may also contain a selection marker that is effective in plant cells, to allow for the detection of transformed cells containing the inventive construct. Such markers, which are well known in the art, typically confer resistance to one or more toxins. One example of such a marker is the NPTII gene whose expression results in resistance to kanamycin or hygromycin, antibiotics which are usually toxic to plant cells at a moderate concentration (Rogers et al., in Weissbach A and H, eds., *Methods for Plant Molecular Biology*, Academic Press Inc.: San Diego, Calif., 1988). Alternatively, the presence of the desired construct in transformed cells can be determined by means of other techniques well known in the art, such as Southern and Western blots.

Techniques for operatively linking the components of the inventive genetic constructs are well known in the art and include the use of synthetic linkers containing one or more restriction endonuclease sites as described, for example, by Maniatis et al., (*Molecular cloning: a laboratory manual*, CSHL Press: Cold Spring Harbor, N.Y., 1989). The DNA construct of the present invention may be linked to a vector having at least one replication system, for example, *E. coli*, whereby after each manipulation, the resulting construct can be cloned and sequenced and the correctness of the manipulation determined.

The genetic constructs of the present invention may be used to transform a variety of plants, both monocotyledonous (e.g., grasses, corn, grains, oat, wheat and barley), dicotyledonous (e.g., Arabidopsis, tobacco, legumes, alfalfa, oaks, eucalyptus, maple), and Gymnosperms (e.g., Scots pine; see Aronen, *Finnish Forest Res. Papers*, Vol. 595, 1996), white spruce (Ellis et al., *Biotechnology* 11:94–92, 1993), and larch (Huang et al., *In Vitro Cell* 27:201–207, 1991). In a preferred embodiment, the inventive genetic constructs are employed to transform woody plants, herein defined as a tree or shrub whose stem lives for a number of years and increases in diameter each year by the addition of woody tissue. Preferably the target plant is selected from the group consisting of eucalyptus and pine species, most preferably from the group consisting of *Eucalyptus grandis* and *Pinus radiata*. As discussed above, transformation of a plant with a genetic construct including an open reading frame coding for an enzyme encoded by an inventive polynucleotide wherein the open reading frame is orientated in a sense direction will produce a modified lignin content in the plant. Transformation of a plant with a genetic construct comprising an open reading frame in an antisense orientation or a non-coding (untranslated) region of a gene will also produced a modification in the lignin content of the transformed plant.

The production of RNA in target cells may be controlled by choice of the promoter sequence, or by selecting the number of functional copies or the site of integration of the polynucleotides incorporated into the genome of the target organism. A target plant may be transformed with more than one construct of the present invention, thereby modulating the lignin biosynthetic pathway for the activity of more than one enzyme, affecting enzyme activity in more than one tissue or affecting enzyme activity at more than one expression time. Similarly, a construct may be assembled containing more than one open reading frame coding for an enzyme encoded by a polynucleotide of the present invention or more than one non-coding region of a gene coding for such an enzyme. The polynucleotides of the present invention may also be employed in combination with other known sequences encoding enzymes involved in the lignin biosynthetic pathway. In this manner, it may be possible to add a lignin biosynthetic pathway to a non-woody plant to produce a new woody plant.

Techniques for stably incorporating DNA constructs into the genome of target plants are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by *Agrobacterium ti* plasmid technology, as described, for example by Bevan (*Nucl. Acid Res.* 12:8711–8721, 1984). Targets for the introduction of the DNA constructs of the present invention include tissues, such as leaf tissue, disseminated cells, protoplasts, seeds, embryos, meristematic regions; cotyledons, hypocotyls, and the like. One preferred method for transforming eucalyptus and pine is a biolistic method using pollen (see, for example, Aronen, *Finnish Forest Res. Papers*, Vol. 595:53, 1996) or easily regenerable embryonic tissues. Other transformation techniques which may be usefully employed in the inventive methods include those taught by Ellis et al. (*Plant Cell Reports*, 8:16–20, 1989), Wilson et al. (*Plant Cell Reports* 7:704–707, 1989) and Tautorus et al. (*Theor. Appl. Genet.* 78:531–536, 1989).

Once the cells are transformed, cells having the inventive DNA construct incorporated in their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. For a review of regeneration of forest trees, see Dunstan et al., "Somatic embryogenesis in woody plants," in Thorpe T A, ed., *In vitro embryogenesis of plants*, Current Plant Science and Biotechnology in Agriculture 20(12):471–540, 1995. Specific protocols for the regeneration of spruce are discussed by Roberts et al., ("Somatic embryogenesis of spruce," in Redenbaugh K, ed., *Synseed: applications of synthetic seed to crop improvement*, CRC Press: Chapter 23, pp. 427–449, 1993). The resulting transformed plants may be reproduced sexually or asexually, using methods well known in the art, to give successive generations of transgenic plants.

In yet a further aspect, the present invention provides methods for modifying the level (concentration) or activity of a polypeptide in a host organism, comprising stably incorporating into the genome of the plant a construct comprising a polynucleotide of the present invention. The genetic NA constructs of the present invention may be used to transform a variety of organisms. Such organisms include plants, such as monocotyledonous angiosperms (e.g., grasses, corn, grains, oat, wheat and barley), and dicotyledonous angiosperms (e.g., Arabidopsis, tobacco, legumes, alfalfa, oaks, eucalyptus, maple), and gymnosperms (e.g., Scots pine; see Aronen, *Finnish Forest Res. Papers*, Vol. 595, 1996), white spruce (Ellis et al., *Biotechnology* 11:94–92, 1993), and larch (Huang et al., *In Vitro Cell* 27:201–207, 1991).

In preferred embodiments, the genetic constructs of the present invention are employed to transform woody plants, herein defined as a tree or shrub having a stem that lives for a number of years and increases in diameter each year as a consequence of the addition of woody tissue. The target plant is preferably selected from the group consisting of eucalyptus and pine species, most preferably from the group consisting of *Eucalyptus grandis* and *Pinus radiata*, but also including any of the species in the following list:

Pines: *Pinus banksiana, Pinus brutia, Pinus caribaea, Pinus clausa, Pinus contorta, Pinus coulteri, Pinus echinata, Pinus eldarica, Pinus ellioti, Pinus jeffreyi, Pinus lambertiana, Pinus monticola, Pinus nigra, Pinus palustrus, Pinus pinaster, Pinus ponderosa, Pinus resinosa, Pinus rigida, Pinus serotina, Pinus strobus, Pinus sylvestris, Pinus taeda, Pinus virginiana.*

Other gymnosperms: *Abies amabilis, Abies balsamea, Abies concolor, Abies grandis, Abies lasiocarpa, Abies magnifica, Abies procera, Chamaecyparis lawsoniona, Chamaecyparis nootkatensis, Chamaecyparis thyoides, Huniperus virginiana, Larix decidua, Larix laricina, Larix leptolepis, Larix occidentalis, Larix siberica, Libocedrus decurrens, Picea abies, Picea engelmanni, Picea glauca, Picea mariana, Picea pungens, Picea rubens, Picea sitchensis, Pseudotsuga menziesii, Sequoia gigantea, Sequoia sempervirens, Taxodium distichum, Tsuga canadensis, Tsuga heterophylla, Tsuga mertensiana, Thuja occidentalis, Thuja plicata.*

Eucalypts. *Eucalyptus alba, Eucalyptus bancroftii, Eucalyptus botyroides, Eucalyptus bridgesiana, Eucalyptus calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus globulus, Eucalyptus gomphocephala, Eucalyptus gunnii, Eucalyptus henryi, Eucalyptus laevopinea, Eucalyptus macarthurii, Eucalyptus macrorhyncha, Eucalyptus maculata, Eucalyptus marginata, Eucalyptus megacarpa, Eucalyptus melliodora, Eucalyptus nicholii, Eucalyptus nitens, Eucalyptus nova-anglica, Eucalyptus obliqua, Eucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptus stuartiana, Eucalyptus tereticornis, Eucalyptus torelliana, Eucalyptus urnigera, Eucalyptus urophylla, Eucalyptus viminalis, Eucalyptus viridis, Eucalyptus wandoo, Eucalyptus youmanni*; and hybrids of any of the above species.

Further, the polynucleotides of the present invention have particular application for use as non-disruptive tags for marking organisms, particularly plants. Other organisms may, however, be tagged with the polynucleotides of the present invention, including commercially valuable animals, fish, bacteria and yeasts. Constructs comprising polynucleotides of the present invention may be stably introduced into an organism as heterologous, non-functional, non-disruptive tags. It is then possible to identify the origin or source of the organism at a later date by determining the presence or absence of the tag(s) in a sample of material.

Detection of the tag(s) may be accomplished using a variety of conventional techniques, and will generally involve the use of nucleic acid probes. Sensitivity in assaying the presence of probe can be usefully increased by using branched oligonucleotides, as described in Horn T, Chang C A and Urdea M S, "Chemical synthesis and characterization of branched oligodeoxyribonucleotides (bDNA) for use as signal amplifiers in nucleic acid quantification assays," *Nucleic Acids Research* 25(23):4842–4849, 1997), enabling detection of as few as 50 DNA molecules in the sample.

The following examples are offered by way of illustration and not by way of limitation.

EXAMPLE 1

Isolation and Characterization of cDNA Clones from *Eucalyptus grandis*

Two *Eucalyptus grandis* cDNA expression libraries (one from a mixture of various tissues from a single tree and one from leaves of a single tree) were constructed and screened as follows.

mRNA was extracted from the plant tissue using the protocol of Chang et al. (*Plant Molecular Biology Reporter* 11:113–116, 1993) with minor modifications. Specifically, samples were dissolved in CPC-RNAXB (100 mM Tris-Cl, pH 8,0; 25 mM EDTA; 2.0 M NaCl; 2% CTAB; 2% PVP and 0.05% Spermidine*3 HCl) and extracted with chloroform:isoamyl alcohol, 24:1. mRNA was precipitated with ethanol and the total RNA preparate was purified using a Poly(A) Quik mRNA Isolation Kit (Stratagene, La Jolla, Calif.). A cDNA expression library was constructed from the purified mRNA by reverse transcriptase synthesis followed by insertion of the resulting cDNA clones in Lambda ZAP using a ZAP Express cDNA Synthesis Kit (Stratagene), according to the manufacturer's protocol. The resulting cDNAs were packaged using a Gigapack II Packaging Extract (Stratagene) employing 1 µl of sample DNA from the 5 µl ligation mix. Mass excision of the library was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing X-gal and isopropylthio-beta-galactoside (IPTG).

Of the colonies plated and picked for DNA miniprep, 99% contained an insert suitable for sequencing. Positive colonies were cultured in NZY broth with kanamycin and cDNA was purified by means of alkaline lysis and polyethylene glycol (PEG) precipitation. Agarose gel at 1% was used to screen sequencing templates for chromosomal contamination. Dye primer sequences were prepared using a Turbo Catalyst 800 machine (Perkin Elmer/Applied Biosystems, Foster City, Calif.) according to the manufacturer's protocol.

DNA sequences for positive clones were obtained using a Perkin Elmer/Applied Biosystems Prism 377 sequencer. cDNA clones were sequenced first from the 5' end and, in some cases, also from the 3' end. For some clones, internal sequence was obtained using subcloned fragments. Subcloning was performed using standard procedures of restriction mapping and subcloning to pBluescript II SK+ vector.

The determined cDNA sequences were compared to known sequences in the EMBL database (release 46, March 1996) using the FASTA algorithm of February 1996 (Version 2.0.4) (available on the Internet) or the BLASTN algorithm Version 2.0.4 [Feb. 24, 1998], or Version 2.0.6 [Sep. 16, 1998], set to the preferred parameters described above. Multiple alignments of redundant sequences were used to build up reliable consensus sequences. Based on similarity to known sequences from other plant species, the isolated polynucleotides of the present invention were identified as encoding a specified enzyme.

Using the procedures described above, cDNA sequences derived from the *Eucalyptus grandis* library encoding the following polypeptides were isolated: PAL (SEQ ID NOS: 16, 100, 242–246); C4H (SEQ ID NOS: 17, 153, 154, and 161); C3H (SEQ ID NOS: 18, 101, 149 and 150); F5H (SEQ ID NOS: 19–21, 102, 103, 169–171 and 404); OMT (SEQ ID NOS: 22–25, 104–107, 173 and 174); CCR (SEQ ID NOS: 26–29 and 108–111); CAD (SEQ ID NOS: 1, 30 and 112); CGT (SEQ ID NOS: 31–33 and 113–115); CBG (SEQ ID NOS: 34, 165 and 166); PNL (SEQ ID NOS: 35, 36 and 116); LAC (SEQ ID NOS: 37–41, 117 and 118); POX (SEQ ID NOS: 42–44, 119–121, 179, 249–250 and 350–358); 4CL (SEQ ID NO: 266); caffeic acid methyl transferase (SEQ ID NOS: 187–192); caffeoyl CoA methyl transferase (SEQ ID NOS: 193–195); coumarate Co-A ligase (SEQ ID NOS: 196–198); cytochrome P450 LXX1A (SEQ ID NOS: 201–206); diphenol oxidase (SEQ ID NOS: 207–217); flavonol glucosyl transferase (SEQ ID NO: 218); flavonoid hydroxylase (SEQ ID NOS: 219–223); and isoflavone reductase (SEQ ID NOS: 234–240).

EXAMPLE 2

Isolation and Characterization of cDNA Clones from *Pinus radiata* a) Isolation of cDNA Clones by High Through-put Screening

A *Pinus radiata* cDNA expression library was constructed from xylem and screened as described above in Example 1. DNA sequences for positive clones were obtained using forward and reverse primers on a Perkin Elmer/Applied Biosystems Prism 377 sequencer and the determined sequences were compared to known sequences in the EMBL database as described above.

Based on similarity to known sequences from other plant species, the isolated DNA sequences were identified as encoding the enzymes C4H (SEQ ID NOS: 2, 3, 48, 49, 92, 124, 125, 155–160, 162 and 163); C3H (SEQ ID NOS: 4, 50–52, 93, 126, 127, 151 and 152); PNL (SEQ ID NOS: 5, 81 and 183); OMT (SEQ ID NOS: 6, 53–55, 94 and 175); CAD (SEQ ID NOS: 7, 71, 95 and 164); CCR (SEQ ID NOS: 8, 58–70, 96, 128–134 and 167); PAL (SEQ ID NOS: 9–11, 45–47, 97, 98, 122, 123 and 176, 247 and 248); 4CL (SEQ ID NOS: 12, 56, 57, 90, 99, 147, 148 and 265); CGT (SEQ ID NOS: 72, 135 and 168); CBG (SEQ ID NOS: 73–80 and 136–141); LAC (SEQ ID NOS: 82–84, 142–144 and 172); POX (SEQ ID NOS: 85–89, 91, 145, 146, 177, 178, 180–182, 264, 359–375); alpha amylase (SEQ ID NOS: 184–186); coumarate 6A ligase (SEQ ID NOS: 199 and 200); flavonoid hydroxylase (SEQ ID NOS: 224–233); isoflavone reductase (SEQ ID NO: 241); and diphenol oxidase (SEQ ID NOS: 251–263).

b) Isolation of cDNA Clones by PCR

Two PCR probes, hereinafter referred to as LNB010 and LNB011 (SEQ ID NO: 14 and 15, respectively) were designed based on conserved domains in the following peroxidase sequences previously identified in other species: vanpox, hvupox6, taepox, hvupox1, osapox, ntopox2, ntopox1, lespox, pokpox, luspox, athpox, hrpox, spopox, and tvepox (Genbank Accession Nos. D11337, M83671, X56011, X58396, X66125, J02979, D11396, X71593, D11102, L07554, M58381, X57564, Z22920, and Z31011, respectively).

RNA was isolated from pine xylem and first strand cDNA was synthesized as described above. This cDNA was subjected to PCR using 4 $\mu$M LNB010, 4 $\mu$M LNB011, 1×Kogen's buffer, 0.1 mg/ml BSA, 200 mM dNTP, 2 mM $Mg^{2+}$, and 0.1 U/$\mu$l of Taq polymerase (Gibco BRL). Conditions were 2 cycles of 2 min at 94° C., 1 min at 55° C. and 1 min at 72° C.; 25 cycles of 1 min at 94° C., 1 min at 55° C., and 1 min at 72° C.; and 18 cycles of 1 min at 94° C., 1 min at 55° C., and 3 min at 72° C. in a Stratagene Robocycler. The gene was re-amplified in the same manner. A band of about 200 bp was purified from a TAE agarose gel using a Schleicher & Schuell Elu-Quik DNA purification kit and clones into a T-tailed pBluescript vector (Marchuk D et al., *Nucleic Acids Res.* 19:1154, 1991). Based on similarity to known sequences, the isolated gene (SEQ ID NO: 13) was identified as encoding pine peroxidase (POX).

EXAMPLE 3

Use of an O-methyltransferase (OMT) Gene to Modify Lignin Biosynthesis a) Transformation of Tobacco Plants with a *Pinus radiata* OMT Gene Sense and anti-sense constructs containing a polynucleotide including the coding region of OMT (SEQ ID NO: 53) from *Pinus radiata* were inserted into *Agrobacterium tumefaciens* LBA4301 (provided as a gift by Dr. C. Kado, University of California, Davis, Calif.) by direct transformation using published methods (see, An G, Ebert P R, Mitra A, Ha S B, "Binary Vectors," in Gelvin S B, Schilperoort R A, eds., *Plant Molecular Biology Manual*, Kluwer Academic Publishers: Dordrecht, 1988). The presence and integrity of the transgenic constructs were verified by restriction digestion and DNA sequencing.

Tobacco (*Nicotiana tabacum* cv. *samsun*) leaf sections were transformed using the method of Horsch et al. (*Science*, 227:1229–1231, 1985). Five independent transformed plant lines were established for the sense construct and eight independent transformed plant lines were established for the anti-sense construct for OMT. Transformed plants containing the appropriate lignin gene construct were verified using Southern blot experiments. A "+" in the column labeled "Southern" in Table 2 below indicates that the transformed plant lines were confirmed as independent transformed lines.

b) Expression of Pinus OMT in Transformed Plants

Total RNA was isolated from each independent transformed plant line created with the OMT sense and anti-sense constructs. The RNA samples were analysed in Northern blot experiments to determine the level of expression of the transgene in each transformed line. The data shown in the column labeled "Northern" in Table 2 shows that the transformed plant lines containing the sense and anti-sense constructs for OMT all exhibited high levels of expression, relative to the background on the Northern blots. OMT expression in sense plant line number 2 was not measured because the RNA sample showed signs of degradation. There was no detectable hybridisation to RNA samples from empty vector-transformed control plants.

c) Modulation of OMT Enzyme Activity in Transformed Plants

The total activity of OMT enzyme, encoded by the Pinus OMT gene and by the endogenous tobacco OMT gene, in transformed tobacco plants was analysed for each transformed plant line created with the OMT sense and anti-sense constructs. Crude protein extracts were prepared from each transformed plant and assayed using the method of Zhang et al. (*Plant Physiol.*, 113:65–74, 1997). The data contained in the column labeled "Enzyme" in Table 1 shows that the transformed plant lines containing the OMT sense construct generally had elevated OMT enzyme activity, with a maximum of 199%, whereas the transformed plant lines containing the OMT anti-sense construct generally had reduced OMT enzyme activity, with a minimum of 35%, relative to empty vector-transformed control plants. OMT enzyme activity was not estimated in sense plant line number 3.

d) Effects of Pinus OMT on Lignin Concentration in Transformed Plants

The concentration of lignin in the transformed tobacco plants was determined using the well-established procedure of thioglycolic acid extraction (see, Freudenberg et al., *Constitution and Biosynthesis of Lignin*, Springer-Verlag: Berlin, 1968). Briefly, whole tobacco plants, of an average age of 38 days, were frozen in liquid nitrogen and ground to a fine powder in a mortar and pestle. 100 mg of frozen powder from one empty vector-transformed control plant line, the five independent transformed plant lines containing the sense construct for OMT and the eight independent transformed plant lines containing the anti-sense construct for OMT were extracted individually with methanol, followed by 10% thioglycolic acid and finally dissolved in 1 M NaOH. The final extracts were assayed for absorbance at 280 nm. The data shown in the column labelled "TGA" in Table 2 shows that the transformed plant lines containing the sense and the anti-sense OMT gene constructs all exhibited significantly decreased levels of lignin, relative to the empty vector-transformed control plant lines.

TABLE 2

| plant line | transgene | orientation | Southern | Northern | Enzyme | TGA |
|---|---|---|---|---|---|---|
| 1 | control | na | + | blank | 100 | 104 |
| 1 | OMT | sense | + | 2.9E + 6 | 86 | 55 |
| 2 | OMT | sense | + | na | 162 | 58 |
| 3 | OMT | sense | + | 4.1E + 6 | na | 63 |
| 4 | OMT | sense | + | 2.3E + 6 | 142 | 66 |
| 5 | OMT | sense | + | 3.6E + 5 | 199 | 75 |
| 1 | OMT | anti-sense | + | 1.6E + 4 | 189 | 66 |
| 2 | OMT | anti-sense | + | 5.7E + 3 | 35 | 70 |
| 3 | OMT | anti-sense | + | 8.0E + 3 | 105 | 73 |
| 4 | OMT | anti-sense | + | 1.4E + 4 | 109 | 74 |
| 5 | OMT | anti-sense | + | 2.5E + 4 | 87 | 78 |
| 6 | OMT | anti-sense | + | 2.5E + 4 | 58 | 84 |
| 7 | OMT | anti-sense | + | 2.5E + 4 | 97 | 92 |
| 8 | OMT | anti-sense | + | 1.1E + 4 | 151 | 94 |

These data clearly indicate that lignin concentration, as measured by the TGA assay, can be directly manipulated by either sense or anti-sense expression of a lignin biosynthetic gene such as OMT.

EXAMPLE 4

Use of a 4-Coumarate:CoA ligase (4CL) Gene to Modify Lignin Biosynthesis a) Transformation of Tobacco Plants with a *Pinus radiata* 4CL Gene Sense and anti-sense constructs containing a polynucleotide including the coding region of 4CL (SEQ ID NO: 56) from *Pinus radiata* were inserted into *Agrobacterium tumefaciens* LBA4301 by direct transformation as described above. The presence and integrity of the transgenic constructs were verified by restriction digestion and DNA sequencing.

Tobacco (*Nicotiana tabacum* cv. *samsun*) leaf sections were transformed as described above. Five independent transformed plant lines were established for the sense construct and eight independent transformed plant lines were established for the anti-sense construct for 4CL. Transformed plants containing the appropriate lignin gene construct were verified using Southern blot experiments. A "+" in the column labeled "Southern" in Table 3 indicates that the transformed plant lines listed were confirmed as independent transformed lines.

b) Expression of Pinus 4CL in Transformed Plants

Total RNA was isolated from each independent transformed plant line created with the 4CL sense and anti-sense constructs. The RNA samples were analysed in Northern blot experiments to determine the level of expression of the transgene in each transformed line. The data shown in the column labelled "Northern" in Table 3 below shows that the transformed plant lines containing the sense and anti-sense constructs for 4CL all exhibit high levels of expression, relative to the background on the Northern blots. 4CL expression in anti-sense plant line number 1 was not measured because the RNA was not available at the time of the experiment. There was no detectable hybridisation to RNA samples from empty vector-transformed control plants.

c) Modulation of 4CL Enzyme Activity in Transformed Plants

The total activity of 4CL enzyme, encoded by the Pinus 4CL gene and by the endogenous tobacco 4CL gene, in transformed tobacco plants was analysed for each transformed plant line created with the 4CL sense and anti-sense constructs. Crude protein extracts were prepared from each transformed plant and assayed using the method of Zhang et al. (*Plant Physiol.*, 113:65–74, 1997). The data contained in the column labeled "Enzyme" in Table 3 shows that the transformed plant lines containing the 4CL sense construct had elevated 4CL enzyme activity, with a maximum of 258%, and the transformed plant lines containing the 4CL anti-sense construct had reduced 4CL enzyme activity, with a minimum of 59%, relative to empty vector-transformed control plants.

d) Effects of Pinus 4CL on Lignin Concentration in Transformed Plants

The concentration of lignin in samples of transformed plant material was determined as described in Example 3. The data shown in the column labelled "TGA" in Table 3 shows that the transformed plant lines containing the sense and the anti-sense 4CL gene constructs all exhibited significantly decreased levels of lignin, relative to the empty vector-transformed control plant lines. These data clearly indicate that lignin concentration, as measured by the TGA assay, can be directly manipulated by either sense or anti-sense expression of a lignin biosynthetic gene such as 4CL.

TABLE 3

| plant line | transgene | orientation | Southern | Northern | Enzyme | TGA |
|---|---|---|---|---|---|---|
| 1 | control | na | + | blank | 100 | 92 |
| 2 | control | na | + | blank | 100 | 104 |
| 1 | 4CL | sense | + | 2.3E + 4 | 169 | 64 |
| 2 | 4CL | sense | + | 4.5E + 4 | 258 | 73 |
| 3 | 4CL | sense | + | 3.1E + 4 | 174 | 77 |
| 4 | 4CL | sense | + | 1.7E + 4 | 164 | 80 |
| 5 | 4CL | sense | + | 1.6E + 4 | 184 | 92 |
| 1 | 4CL | anti-sense | + | na | 59 | 75 |
| 2 | 4CL | anti-sense | + | 1.0E + 4 | 70 | 75 |
| 3 | 4CL | anti-sense | + | 9.6E + 3 | 81 | 80 |
| 4 | 4CL | anti-sense | + | 1.2E + 4 | 90 | 83 |
| 5 | 4CL | anti-sense | + | 4.7E + 3 | 101 | 88 |
| 6 | 4CL | anti-sense | + | 3.9E + 3 | 116 | 89 |
| 7 | 4CL | anti-sense | + | 1.8E + 3 | 125 | 94 |
| 8 | 4CL | anti-sense | + | 1.7E + 4 | 106 | 97 |

EXAMPLE 5

Transformation of Tobacco Using the Inventive Lignin Biosynthetic Genes

Sense and anti-sense constructs containing polynucleotides including the coding regions of C3H (SEQ ID NO: 18), F5H (SEQ ID NO: 19), CCR (SEQ ID NO: 26) and CGT (SEQ ID NO: 31) from *Eucalyptus grandis*, and OMT (SEQ ID NO: 6), PAL (SEQ ID NO: 45 and 47), C4H (SEQ ID NO: 48 and 49), PNL (SEQ ID NO: 81) and LAC (SEQ ID NO: 83) from *Pinus radiata* were inserted into *Agrobacterium tumefaciens* LBA4301 by direct transformation as described above. The presence and integrity of the transgenic constructs were verified by restriction digestion and DNA sequencing.

Tobacco (*Nicotiana tabacum* cv. *samsun*) leaf sections were transformed as described in Example 3. Up to twelve independent transformed plant lines were established for each sense construct and each anti-sense construct listed in the preceding paragraph. Transformed plants containing the appropriate lignin gene construct were verified using Southern blot experiments. All of the transformed plant lines analysed were confirmed as independent transformed lines.

EXAMPLE 6

Manipulation of Lignin Content in Transformed Plants a) Determination of Transgene Expression by Northern Blot Experiments Total RNA was isolated from each independent transformed plant line described in Example 5. The RNA samples were analysed in Northern blot experiments to determine the level of expression of the transgene in each transformed line. The column labelled "Northern" in Table 4 shows the level of transgene expression for all plant lines assayed, relative to the background on the Northern blots. There was no detectable hybridisation to RNA samples from empty vector-transformed control plants.

b) Determination of Lignin Concentration in Transformed Plants

The concentration of lignin in empty vector-transformed control plant lines and in up to twelve independent transformed lines for each sense construct and each anti-sense construct described in Example 5 was determined as described in Example 3. The column labelled "TGA" in Table 4 shows the thioglycolic acid extractable lignins for plant lines transformed with C3H, F5H, CCR, PAL, C4H, PNL and LAC, expressed as the average percentage of TGA extractable lignins in transformed plants versus control plants. The range of variation is shown in parentheses.

TABLE 4

| transgene | orientation | no. of lines | Northern | TGA |
|---|---|---|---|---|
| control | na | 3 | blank | 100 (92–104) |
| C3H | sense | 5 | 3.7E + 4 | 74 (67–85) |
| F5H | sense | 10 | 5.8E + 4 | 70 (63–79) |
| F5H | anti-sense | 9 | 5.8E + 4 | 73 (35–93) |
| CCR | sense | 1 | na | 74 |
| CCR | anti-sense | 2 | na | 74 (62–86) |
| PAL | sense | 5 | 1.9E + 5 | 77 (71–86) |
| PAL | anti-sense | 4 | 1.5E + 4 | 62 (37–77) |
| C4H | anti-sense | 10 | 5.8E + 4 | 86 (52–113) |
| PNL | anti-sense | 6 | 1.2E + 4 | 88 (70–114) |
| LAC | sense | 5 | 1.7E + 5 | na |
| LAC | anti-sense | 12 | 1.7E + 5 | 88 (73–114) |

Figure 5:
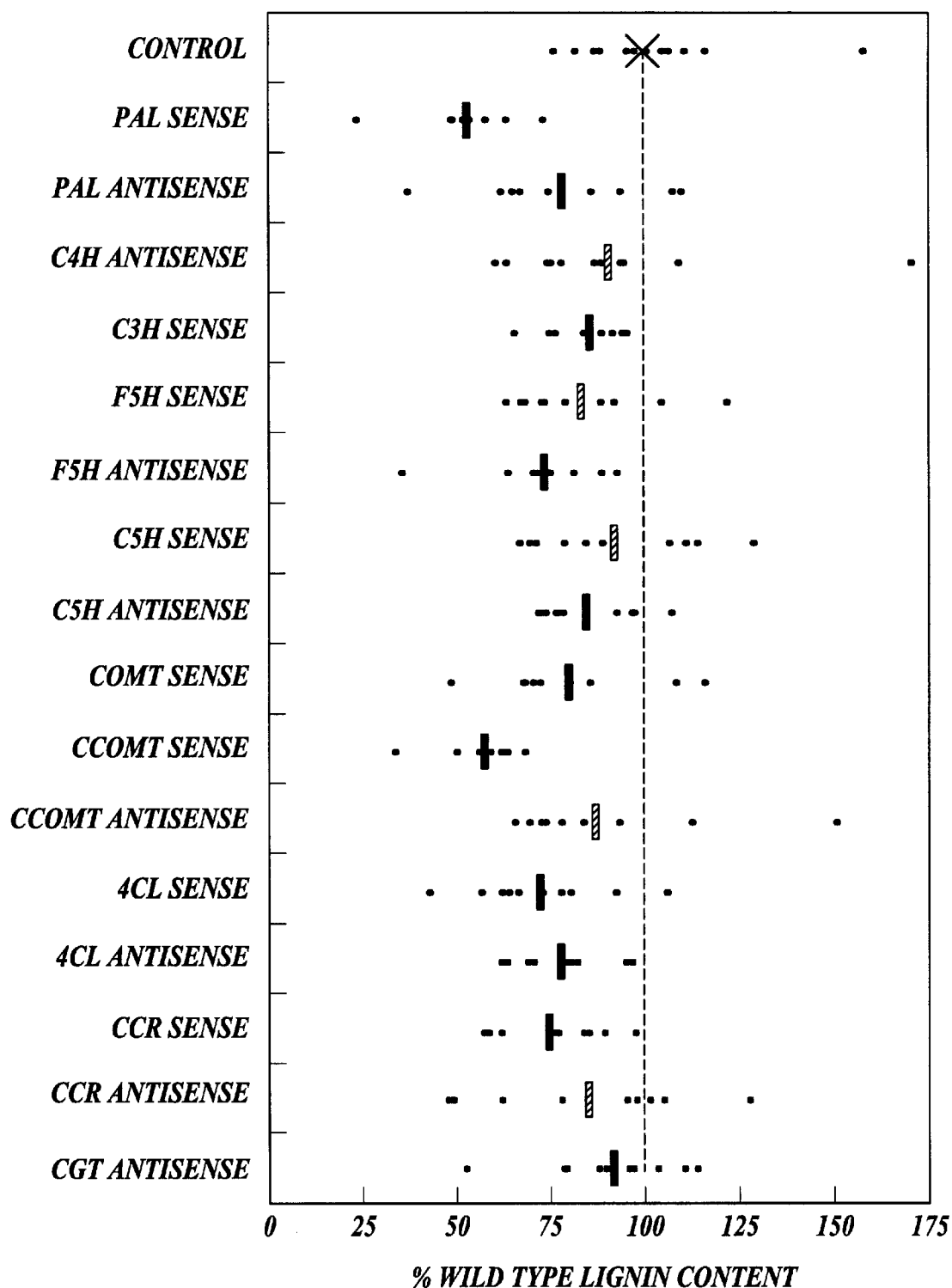
FIG. 5 shows the amount of extractable lignin, as a percentage of wild type lignin content, present in tobacco plants transformed with sense and anti-sense genetic constructs of the present invention.

FIG. 5 illustrates the quantity of extractable lignin, as a percentage of wild type lignin content, in tobacco plants transformed with PAL (sense and anti-sense), C4H (antisense), C3H (sense), F5H (sense and antisense), C5H (sense and antisense) C3H (sense; referred to as COMT in FIG. 5), OMT (sense and antisense; referred to as CCOMT in FIG. 5), 4CL (sense and antisense), CCR (sense and antisense) and CGT (antisense) constructs as described in Example 5. Thioglycolic acid-extractable lignin quantities were measured in transgenic plants, normalized to empty-vector control plants. Three extracts were independently derived from each of approximately 10 independently derived transgenic plants. The average of the three extracts is shown by a black dot, as the lignin value for that plant. The average of ten independent transgenic plants transformed with a given cDNA construct is shown as a bar. The average of empty vector transformed control plants is shown as an X. The value for the controls is extrapolated across the field to facilitate comparison. Black bars indicate means which are significantly reduced (p<0.05) in lignin content with respect to control plants. Grey bars indicate means which are not significantly changed from control plants.

Transformed plant lines containing the sense and the anti-sense lignin biosynthetic gene constructs exhibited a mean level of lignin content that was significantly lower than that of empty vector-transformed control plant lines. The most dramatic effects on lignin concentration were seen in the OMT sense plants, and in the PAL sense plants. These data clearly indicate that lignin concentration, as measured by the TGA assay, can be directly manipulated by conventional anti-sense methodology and also by sense over-expression using the inventive lignin biosynthetic genes.

EXAMPLE 7

Modulation of Lignin Enzyme Activity in Transformed Plants

The activities and substrate specificities of selected lignin biosynthetic enzymes were assayed in crude extracts from transformed tobacco plants containing sense and anti-sense constructs for PAL (SEQ ID NO: 45), PNL (SEQ ID NO: 81) and LAC (SEQ ID NO: 83) from *Pinus radiata*, and CGT (SEQ ID NO: 31) from *Eucalyptus grandis*.

Enzyme assays were performed using published methods for PAL (Southerton S G and Deverall B J, *Plant Path.* 39:223–230, 1990), CGT (Vellekoop P et al., *FEBS*, 330:36–40, 1993), PNL (Espin C J et al., *Phytochemistry* 44:17–22, 1997) and LAC (Bao W et al., *Science*, 260:672–674, 1993). The data shown in the column labelled "Enzyme" in Table 5 shows the average enzyme activity from replicate measures for all plant lines assayed, expressed as a percent of enzyme activity in empty vector-transformed control plants. The range of variation is shown in parentheses.

TABLE 5

| Transgene | orientation | no. of lines | enzyme |
|---|---|---|---|
| control | na | 3 | 100 |
| PAL | sense | 5 | 87 (60–124) |
| PAL | anti-sense | 3 | 53 (38–80) |
| CGT | anti-sense | 1 | 89 |
| PNL | anti-sense | 6 | 144 (41–279) |
| LAC | sense | 5 | 78 (16–240) |
| LAC | anti-sense | 11 | 64 (14–106) |

All of the transformed plant lines, except the PNL antisense transformed plant lines, showed average lignin enzyme activities which were significantly lower than the activities observed in empty vector-transformed control plants. The most dramatic effects on lignin enzyme activities were seen in the PAL anti-sense transformed plant lines in which all of the lines showed reduced PAL activity and in the LAC anti-sense transformed plant lines which showed as little as 14% of the LAC activity in empty vector-transformed control plant lines.

EXAMPLE 8

Functional Identification of Lignin Biosynthetic Genes

Sense constructs containing polynucleotides including the coding regions for PAL (SEQ ID NO: 47), OMT (SEQ ID NO: 53), 4CL (SEQ ID NO: 56 and 57) and POX (SEQ ID NO: 86) from *Pinus radiata*, and OMT (SEQ ID NO: 23 and 24), CCR (SEQ ID NO: 26–28), CGT (SEQ ID NO: 31 and 33) and POX (SEQ ID NO: 42 and 44) from *Eucalyptus grandis* were inserted into the commercially available protein expression vector, pProEX-1 (Gibco BRL). The resultant constructs were transformed into *E. coli* XL1-Blue (Stratagene), which were then induced to produce recombinant protein by the addition of IPTG. Purified proteins were produced for the Pinus OMT and 4CL constructs and the Eucalyptus OMT and POX constructs using Ni column chromatography (Janknecht R et al., *Proc. Natl. Acad. Sci.*, 88:8972–8976, 1991). Enzyme assays for each of the purified proteins conclusively demonstrated the expected substrate specificity and enzymatic activity for the genes tested.

The data for two representative enzyme assay experiments, demonstrating the verification of the enzymatic activity of a *Pinus radiata* 4CL gene (SEQ ID NO: 56) and a *Pinus radiata* OMT gene (SEQ ID NO: 53), are shown in Table 6. For the 4CL enzyme, one unit equals the quantity of protein required to convert the substrate into product at the rate of 0.1 absorbance units per minute. For the OMT enzyme, one unit equals the quantity of protein required to convert 1 pmole of substrate to product per minute.

TABLE 6

| trans-gene | purification step | total ml extract | total mg protein | total units activity | % yield activity | fold purification |
|---|---|---|---|---|---|---|
| 4CL | crude | 10 ml | 51 mg | 4200 | 100 | 1 |
|  | Ni column | 4 ml | 0.84 mg | 3680 | 88 | 53 |
| OMT | crude | 10 ml | 74 mg | 4600 | 100 | 1 |
|  | Ni column | 4 ml | 1.2 mg | 4487 | 98 | 60 |

The data shown in Table 6 indicate that both the purified 4CL enzyme and the purified OMT enzyme show high activity in enzyme assays, confirming the identification of the 4CL and OMT genes described in this application. Crude protein preparations from *E. coli* transformed with empty vector show no activity in either the 4CL or the OMT enzyme assay.

EXAMPLE 9

Demonstration of the Presence/Absence of Unique Sequence Identifiers in Plants

Transgenic tobacco plants were created using unique identifier sequences which are not found in tobacco. The unique identifier sequences inserted were isolated from *Pinus radiata*, SEQ ID NO: 402, and *Eucalyptus grandis*, SEQ ID NO: 403. The unique identifier sequences were inserted into *Agrobacterium tumefaciens* LBA4301 (provided as a gift by Dr. C. Kado, University of California, Davis, Calif.) by direct transformation using published methods (see, An G, Ebert P R, Mitra A, Ha S B, "Binary Vectors," in Gelvin S B, Schilperoort R A, eds., *Plant Molecular Biology Manual*, Kluwer Academic Publishers: Dordrecht, 1988). The presence and integrity of the unique identifier sequences in the Agrobacterium transgenic constructs were verified by restriction digestion and DNA sequencing.

Tobacco (*Nicotiana tabacum* cv. *samsun*) leaf sections were transformed using the method of Horsch et al. (*Science*, 227:1229–1231, 1985). Three independent transformed plant lines were established for each unique sequence identifier used. Two empty-vector control plant lines were established using an empty gene transfer vector which lacked a unique sequence identifier.

The uniqueness of the sequence identifiers was assayed using Southern blot analyses to test for the presence of the sequence identifier in the genome of the plants. If the sequence identifier is unique and therefore useful as a tag, then the sequence identifier should be clearly absent in plants which have not been tagged and it should be clearly present in plants which have been tagged. In the present example, the unique identifiers would be expected to be absent in the empty-vector transformed control plants. The unique identifier would be expected to be present in the transgenic plants transformed with the unique sequence identifiers.

Figure 2:
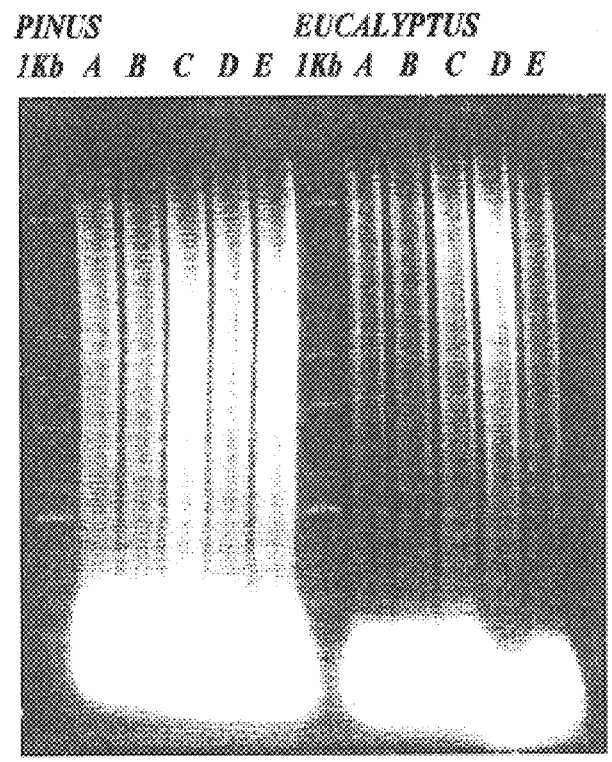
FIG. 2 illustrates genomic DNA samples from tobacco plants created in a tagging experiment using a unique sequence identifier from Pinus (left panel) and a unique sequence identifier from Eucalyptus (right panel). In both panels, lanes A and B contain DNA samples from empty-vector transformed control plants and lanes C–E contain DNA samples from plants transformed with a unique sequence identifier.

Genomic DNA was prepared from empty-vector transformed control plants and plants transformed with unique sequence identifiers using the cetyltrimethyl-ammonium bromide (CTAB) extraction method of Murray and Thompson (*Nucleic Acids Research* 8:4321–4325, 1980). The DNA samples were digested with the restriction enzyme EcoRI in the case of the plants transformed with the Pinus unique sequence identifier (SEQ ID NO: 402) and the restriction enzyme XbaI in the case of the plants transformed with the Eucalyptus unique sequence identifier (SEQ ID NO: 403). The DNA fragments produced in the restriction digests were resolved on a 1% agarose gel; the left panel of FIG. 2 and the right panel of FIG. 2 show the DNA fragment patterns of the DNA samples from the Pinus and Eucalyptus experiments, respectively.

After the agarose gel electrophoresis step, the DNA samples were transferred to Hybond-N+ brand nylon membranes (Amersham Life Science, Little Chalfont, Buckinghamshire, England) using methods established by Southern (*J. Mol. Bio.* 98:503–517). The nylon membranes were probed with radioactively-labeled probes for the unique sequence identifiers identified above and washed at high stringency (final wash: 0.5×salt sodium citrate buffer (SSC) plus 0.1% sodium dodecyl sulfate (SDS), 15 minutes at 65° C.). The hybridisation of the probes to complementary sequences in the genomic DNA samples was detected using auto-radiography. The results are shown in FIGS. 3 and 4.

Figure 3:
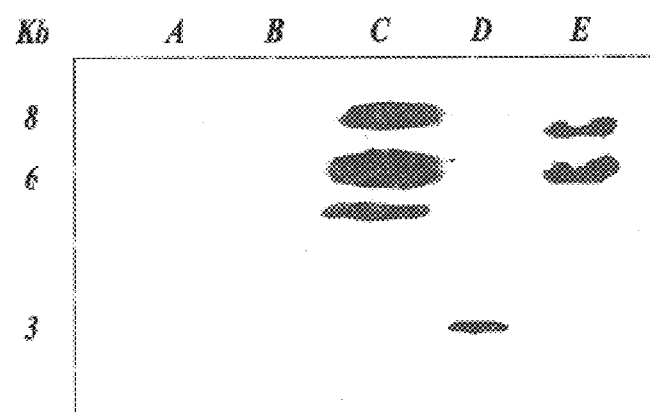
FIG. 3 demonstrates detection of a Pinus unique sequence identifier in transformed S tobacco plants. Lanes A and B show the hybridization of a probe from SEQ ID NO: 402 to the genomic DNA of tobacco plants which lack the Pinus unique sequence identifier (empty-vector transformed control plants). Lanes C–E show the hybridization of the probe to the genomic DNA of tobacco plants containing one to three copies of the Pinus unique sequence identifier.

FIG. 3 (corresponding to the left panel of FIG. 2) shows the hybridisation pattern detected in the Southern blot analysis using a probe derived from the Pinus sequence identifier (SEQ ID NO: 402). Lanes A–B contain DNA samples from empty-vector transformed control plants and lanes C–E contain DNA from plants transformed with SEQ ID NO: 402. There is no hybridization in lanes A–B indicating that SEQ ID NO: 402 is not present in empty-vector transformed tobacco plants; that is, SEQ ID NO: 402 is a unique tag suitable for unambiguous marking of tobacco plants. There is strong hybridisation in lanes C–E indicating that the plants which received SEQ ID NO: 402 via transformation have been clearly and unambiguously tagged with the unique sequence contained in SEQ ID NO: 402.

Figure 4:
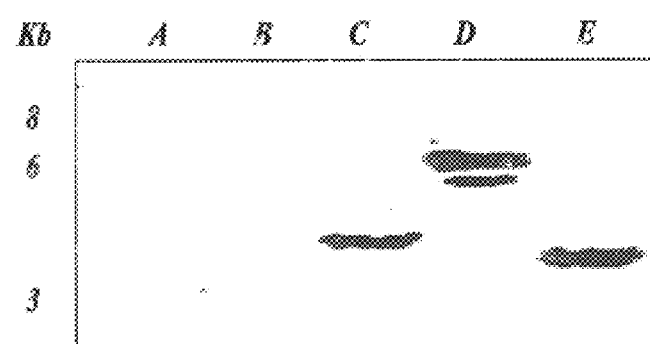
FIG. 4 demonstrates detection of a Eucalyptus unique sequence identifier in transformed tobacco plants. Lanes A and B show the hybridization of a probe from SEQ ID NO: 403 to the genomic DNA of tobacco plants which lack the Eucalyptus unique sequence identifier (empty-vector transformed control plants). Lanes C–E show the hybridization of the probe to the genomic DNA of tobacco plants containing one to two copies of the Eucalyptus unique sequence identifier.

FIG. 4 (corresponding to the right panel of FIG. 2) shows the hybridization pattern detected in the Southern blot analysis using a probe derived from the Eucalyptus sequence identifier (SEQ ID NO: 403). Lanes A–B contain DNA samples from empty-vector transformed control plants and lanes C–E contain DNA from plants transformed with SEQ ID NO: 403. There is no hybridisation in lanes A–B indicating that SEQ ID NO: 403 is not present in empty-vector transformed tobacco plants; that is, SEQ ID NO: 403 is a unique tag suitable for unambiguous marking of tobacco plants. There is strong hybridisation in lanes C–E indicating that the plants which received SEQ ID NO: 403 via transformation have been clearly and unambiguously tagged with the unique sequence contained in SEQ ID NO: 403.

The present example clearly demonstrates the utility of the sequences disclosed in this specification for the purposes of unambiguously tagging transgenic materials. A unique sequence was selected from a large number of potential tags and shown to be absent in the genome of the organism to be tagged. The tag was inserted into the genome of the organism to be tagged and a well-established DNA detection method was used to clearly detect the unique sequence identifier used as the tag.

Because of the sequence-specific detection methods used in the example, a user of the invention disclosed in this specification has both a high likelihood of finding a sequence identifier, among the list which has been disclosed, which will be useful for tagging any given organism and an unequivocal method for demonstrating that a tagged organism could only have acquired a given tag through the deliberate addition of the unique sequence to the genome of the organism to be tagged. If the user of this invention maintains the precise sequence of the tag used in a given organism as a secret, then any disputes as to the origin and history of the organism can be unambiguously resolved using the tag detection techniques demonstrated in the present example. SEQ ID NOS: 1–405 are set out in the attached Sequence Listing. The codes for nucleotide sequences used in the attached Sequence Listing, including the symbol "n," conform to WIPO Standard ST.25 (1998), Appendix 2, Table 1.

All references cited herein, including patent references and non-patent publications, are hereby incorporated by reference in their entireties.

While in the foregoing specification this invention has been described in relation to certain preferred embodiments, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated polynucleotide comprising a nucleotide sequence selected from the group consisting of: (1) the sequence of SEQ ID NO: 266; (2) complements of the sequence of SEQ ID NO: 266; (3) reverse complements of the sequence of SEQ ID NO: 266; and (4) reverse sequences of the sequence of SEQ ID NO: 266.

2. A construct comprising a polynucleotide of claim 1.

3. A construct comprising, in the 5'-3' direction:
   (a) a gene promoter sequence;
   (b) a polynucleotide sequence comprising at least one of the following: (1) a polynucleotide coding for at least a functional portion of a polypeptide encoded by a nucleotide sequence of claim 1; and (2) a polynucleotide comprising a non-coding region of a gene coding for a polypeptide encoded by a nucleotide sequence selected from the group consisting of sequences recited in claim 1; and
   (c) a gene termination sequence.

4. The construct of claim 3 wherein the polynucleotide is in a sense orientation.

5. The construct of claim 3 wherein the polynucleotide is in an antisense orientation.

6. The construct of claim 3, wherein the gene promoter sequence is functional in a plant host to provide for transcription in xylem.

* * * * *